US008252559B2

(12) United States Patent
Fasan et al.

(10) Patent No.: US 8,252,559 B2
(45) Date of Patent: *Aug. 28, 2012

(54) METHODS AND SYSTEMS FOR SELECTIVE FLUORINATION OF ORGANIC MOLECULES

(75) Inventors: Rudi Fasan, Rochester, NY (US); Frances H. Arnold, La Canada, CA (US)

(73) Assignee: The California Institute of Technology, Pasadena, CA (US)

( * ) Notice: Subject to any disclaimer, the term of this patent is extended or adjusted under 35 U.S.C. 154(b) by 724 days.

This patent is subject to a terminal disclaimer.

(21) Appl. No.: 12/365,884

(22) Filed: Feb. 4, 2009

(65) Prior Publication Data

US 2009/0209010 A1 Aug. 20, 2009

Related U.S. Application Data

(63) Continuation-in-part of application No. PCT/US2007/017409, filed on Aug. 4, 2007, and a continuation-in-part of application No. 11/890,218, filed on Aug. 4, 2007, now Pat. No. 8,026,085.

(60) Provisional application No. 61/126,829, filed on May 7, 2008, provisional application No. 60/835,613, filed on Aug. 4, 2006.

(51) Int. Cl.
| C12P 7/00 | (2006.01) |
| C12P 21/04 | (2006.01) |
| C07C 17/00 | (2006.01) |
| C07C 21/00 | (2006.01) |
| C12N 9/02 | (2006.01) |
| C12N 15/00 | (2006.01) |
| C12Q 1/26 | (2006.01) |
| C07H 21/04 | (2006.01) |

(52) U.S. Cl. ........ 435/132; 435/123; 435/246; 435/189; 435/69.1; 435/71.1; 435/440; 435/25; 536/23.2

(58) Field of Classification Search .......................... None
See application file for complete search history.

(56) References Cited

U.S. PATENT DOCUMENTS

| 4,599,342 A | 7/1986 | LaHann |
| 5,198,346 A | 3/1993 | Ladner et al. |
| 5,223,409 A | 6/1993 | Ladner et al. |
| 5,429,939 A | 7/1995 | Misawa et al. |
| 5,602,169 A | 2/1997 | Hewawasam et al. |
| 5,605,793 A | 2/1997 | Stemmer |
| 5,741,691 A | 4/1998 | Arnold et al. |
| 5,785,989 A | 7/1998 | Stanley et al. |
| 5,789,166 A | 8/1998 | Bauer et al. |
| 5,811,238 A | 9/1998 | Stemmer et al. |
| 5,830,721 A | 11/1998 | Stemmer et al. |
| 5,837,458 A | 11/1998 | Minshull et al. |
| 5,945,325 A | 8/1999 | Arnold |
| 5,965,408 A | 10/1999 | Short |
| 6,090,604 A | 7/2000 | Golightly et al. |
| 6,107,073 A | 8/2000 | Chen |
| 6,316,216 B1 | 11/2001 | Ohto et al. |
| 6,361,988 B1 | 3/2002 | Arnold |
| 6,498,026 B2 | 12/2002 | Delagrave et al. |
| 6,524,837 B1 | 2/2003 | Arnold |
| 6,537,746 B2 | 3/2003 | Arnold et al. |
| 6,643,591 B1 | 11/2003 | Korzekwa et al. |
| 6,906,930 B2 | 5/2004 | Arnold et al. |
| 6,794,168 B1 | 9/2004 | Wong et al. |
| 6,902,918 B1 | 6/2005 | Arnold et al. |
| 7,098,010 B1 | 8/2006 | Arnold et al. |
| 7,115,403 B1 | 10/2006 | Arnold et al. |
| 7,226,768 B2 | 6/2007 | Farinas et al. |
| 7,435,570 B2 | 10/2008 | Arnold et al. |
| 7,465,567 B2 | 12/2008 | Cirino et al. |
| 7,524,664 B2 | 4/2009 | Arnold et al. |
| 7,691,616 B2 | 4/2010 | Farinas et al. |
| 2001/0051855 A1 | 12/2001 | Wang et al. |
| 2002/0045175 A1 | 4/2002 | Wang et al. |
| 2002/0168740 A1 | 11/2002 | Chen |
| 2003/0077795 A1 | 4/2003 | Wilson |
| 2003/0077796 A1 | 4/2003 | Crotean |
| 2003/0100744 A1* | 5/2003 | Farinas et al. ................ 536/23.2 |
| 2005/0003389 A1 | 1/2005 | Wang et al. |
| 2005/0037411 A1 | 2/2005 | Arnold et al. |
| 2005/0059045 A1 | 3/2005 | Arnold et al. |
| 2005/0059128 A1 | 3/2005 | Arnold et al. |
| 2005/0202419 A1 | 9/2005 | Cirino et al. |
| 2008/0057577 A1 | 3/2008 | Arnold et al. |
| 2008/0248545 A1 | 10/2008 | Arnold et al. |
| 2008/0268517 A1 | 10/2008 | Arnold et al. |

(Continued)

FOREIGN PATENT DOCUMENTS

EP 0505198 A1 9/1992

(Continued)

OTHER PUBLICATIONS

Branden et al. Introduction to Protein Structure, Garland Publishing Inc., New York, p. 247, 1991.*
Fujisawa et al. Chem Pharm Bull (Tokyo). May 2005;53(5):524-8.*
"Enzymology of cytochrme P450 reductase," printed Apr. 5, 2004 http://www.uky.edu/Pharmacy/ps/porter/CPR_enzymology.htm.
Sequence Alignment, Sep. 10, 1999, Accession Nos. A34286 and S43653.
Fruetel, J., et al., "Relationship of Active Site Topology to Substrate Specificity for Cytochrome P450terp (CYP108)," The Journal of Biological Chemistry, Nov. 18, 1994, pp. 28815-28821, vol. 269, No. 46, The American Society for Biochemistry and Molecular Biology, Inc.
Gahmberg C., et al., "Nonmetabolic Radiolabeling and Taggin of Glycoconjugates," Methods in Enzymology, 1994, pp. 32-44, vol. 230, Academic Press, Inc.

(Continued)

Primary Examiner — Yong Pak
(74) Attorney, Agent, or Firm — Joseph R. Baker, Jr.; Gavrilovich, Dodd & Lindsey, LLP

(57) ABSTRACT

A method and system for selectively fluorinating organic molecules on a target site wherein the target site is activated and then fluorinated are shown together with a method and system for identifying a molecule having a biological activity.

12 Claims, 10 Drawing Sheets

U.S. PATENT DOCUMENTS

| | | | |
|---|---|---|---|
| 2008/0293928 | A1 | 11/2008 | Farinas et al. |
| 2009/0061471 | A1 | 3/2009 | Fasan et al. |
| 2009/0124515 | A1 | 5/2009 | Arnold et al. |
| 2009/0142821 | A1 | 6/2009 | Cirino et al. |
| 2009/0209010 | A1 | 8/2009 | Fasan et al. |
| 2009/0264311 | A1 | 10/2009 | Arnold et al. |
| 2009/0298148 | A1 | 12/2009 | Arnold et al. |

FOREIGN PATENT DOCUMENTS

| | | |
|---|---|---|
| EP | 0752008 B1 | 1/1997 |
| WO | 89/03424 A1 | 4/1989 |
| WO | 95/22625 A1 | 8/1995 |
| WO | 97/16553 A1 | 5/1997 |
| WO | 97/20078 A1 | 6/1997 |
| WO | 97/35957 A1 | 10/1997 |
| WO | 97/35966 A1 | 10/1997 |
| WO | 98/27230 A1 | 6/1998 |
| WO | 98/31837 A1 | 7/1998 |
| WO | 98/41653 | 9/1998 |
| WO | 98/42832 | 10/1998 |
| WO | 99/60096 A2 | 11/1999 |
| WO | 00/00632 A1 | 1/2000 |
| WO | 00/04190 A1 | 1/2000 |
| WO | 00/06718 A2 | 2/2000 |
| WO | 00/09679 A1 | 2/2000 |
| WO | 00/18906 A3 | 4/2000 |
| WO | 00/31273 A2 | 6/2000 |
| WO | 00/42560 A2 | 7/2000 |
| WO | 00/78973 A1 | 12/2000 |
| WO | 01/61344 A1 | 8/2001 |
| WO | 01/62938 A2 | 8/2001 |
| WO | 02/083868 A2 | 10/2002 |
| WO | 03/008563 A2 | 1/2003 |
| WO | 03/091835 A2 | 11/2003 |
| WO | 03/101184 A2 | 12/2003 |
| WO | 2005/017105 A2 | 2/2005 |
| WO | 2005/017106 A2 | 2/2005 |
| WO | 2006/105082 A2 | 10/2006 |
| WO | 2008/016709 A3 | 2/2008 |
| WO | 2008/085900 A2 | 7/2008 |
| WO | 2008/098198 A2 | 8/2008 |
| WO | 2008/115844 A2 | 9/2008 |
| WO | 2008/118545 A2 | 10/2008 |
| WO | 2008/121435 A2 | 10/2008 |

OTHER PUBLICATIONS

Gazaryan, I. G., "Heterologous Expressions of Heme Containing Peroxidases," Plant Peroxidase Newsletter, Sep. 1994, pp. 11-13, No. 4, LABPV Newsletters.

Gillam, E., et al., "Expression of Cytochrome P450 2D6 in *Escherichia coli*, Purification, and Spectral and Catalytic Characterization," Archives of Biochemistry and Biophysics, Jun. 1, 1995, pp. 540-550, vol. 319, No. 2, Academic Press, Inc.

Gleider et al., "Laboratory evolution of a soluble, self-sufficient, highly active alkane hydroxylase," Nature Biotech., 2002, vol. 20, pp. 1135-1139.

Gonzalez et al., "Evolution of the P450 gene superfamily animal-plant 'warfare', molecular drive and human genetic differences in drug oxidation," Trends Genet. 1990, vol. 6, pp. 182-186.

Gonzalez, Frank J., D. W. Nebert, J. P. Hardwick, and C. B. Kasper "Complete cDNA and Protein Sequences of a pregnenolone 16α-Carabonitrile-induced Cytochrome P-450 A Representative of a New Gene Family" J. Biol. Chem. 260 (12):7435-7441, 1985.

Gotoh, Cytochrome P450, 2nd Edition, 1993, pp. 255-272.

Govindaraj and Poulos; "Role of the linker region connecting the reductase and heme domains in cytochrome P450BM-3"; Biochemistry; vol. 34, No. 35, 1995, pp. 11221-11226.

Graham-Lorence, S., et al., "An Active Site Substitution, F87V, Converts Cytochrome P450 BM-3 into a Regio- and Stereoselective (14S,15R)-Arachidonic Acid Epoxygenase," The Journal of Biological Chemistry, Jan. 10, 1997, pp. 1127-1135, vol. 272, No. 2, The American Society for Biochemistry and Molecular Biology, Inc.

Green, J., et al., "Substrate Specificity of Soluble Methane Monooxygenase Mechanistic Implications," The Journal of Biological Chemistry, Oct. 25, 1989, pp. 17698-17703, vol. 264, No. 30, The American Society for Biochemistry and Molecular Biology, Inc.

Groves, John et al., "Models and Mechanisms of Cytochrome P450 Action," Cytochrome P450: Structure, Mechanisms, and Biochemistry, 2nd Edition, New York, 1995, pp. 3-48.

Guengerich, F., et al., "Purification of Functional Recombinant P450s from Bacteria," Methods in Enzymology, 1996, pp. 35-44, vol. 272, Academic Press, Inc.

Haines, Donovan C. et al., "Pivotal Role of Water in the Mechanism of P450BM-3," Biochemistry, 2001, 40, pp. 13456-13465.

Hallinan, E.A. et al., "4-Fluorinated L-lysine analogs as selective i-NOS inhibitors: methodology for introducing fluorine into the lysine side chain", Organic & Biomolecular Chemistry, vol. 1(20), Oct. 21, 2003, pp. 3527-3534.

Hamilton, G.A., et al., "Galactose Oxidase: The Complexities of a Simple Enzyme," Oxidases and Related Redox Systems, 1973, pp. 103-124, vol. 1, University Park Press.

Hartmann, Martin et al., "Selective Oxidations of Linear Alkanes with Molecular Oxygen on Molecular Sieve Catalysts-A Breakthrough?," Journal of the American Chemical Society, 1978, vol. 100, pp. 888-890.

Ito, N. et al., "X-Ray Crystallographic Studies of Cofactors in Galactose Oxidase," Methods in Enzymology, Redox-Active Amino Acids in Biology, 1995, pp. 235-262, vol. 258, Academic Press, Inc.

Ito, N. et al., "Crystal Structure of a Free Radical Enzyme, Galactose Oxidase," Journal of Molecular Biology, 1994, pp. 794-814, vol. 238, No. 5, Academic Press Limited.

Jaeger et al., "Enantioselective biocatalysts optimized by directed evolution," Current Opinion in Biotechnology, 2004, vol. 15, No. 4, pp. 305-313.

Joo, H. et al., "Laboratory evolution of peroxide-mediated cytochrome P450 hydroxylation," Nature, Jun. 17, 1999, pp. 670-673, vol. 399.

Joo, Hyun et al., "A high-throughput digital imaging screen for the discovery and directed evolution of oxygenases." Chemistry and Biology, 1999, pp. 699-706.

Kallis, Russel, International Search Report, Date of Mailing: Feb. 10, 2004, International Application No. PCT/US03/17775.

Kiba, N. et al., "A post-column co-immobilized galactose oxidase/peroxidase reactor for fluorometric detection of saccharides in a liquid chromatographic system," Journal of Chromatography, 1989, pp. 183-187, vol. 463, Elsevier Science Publishes B.V., Amsterdam, The Netherlands.

Kim, J. et al., "Use of 4-(Nitrobenzyl)Pyridine (4-NBP) to Test Mutagenic Potential of Slow-Reacting Epoxides, Their Corresponding Olefins, and Other Alkylating Agents," Bull. Environ. Contam. Toxicol., 1992, pp. 879-885, vol. 49, Springer-Verlag New York Inc.

Kim, Ji Yun, International Search Report, Date of Mailing of Search: Feb. 5, 2008, International Application No. PCT/US07/17409.

Klibanov, A. et al., "Stereospecific Oxidation of Aliphatic Alcohols Catalyzed by Galactose Oxidase," Biochemical and Biophysical Research Communications, 1982, pp. 804-808, vol. 108, No. 2, Academic Press, Inc.

Koroleva, O. et al., "Properties of Fusarium graminearum Galactose Oxidase," 1984, pp. 500-509, Plenum Publishing Corporation.

Koster, R. et al., "Organoboron Monosaccharides; XIII. Quantitative Preparation of D-gluco-Hexodialdose from Sodium D-Glucuronate or D-Glucuronic acid," Synthesis, Aug. 1982, pp. 650-652, No. 8, Georg Thieme Verlag.

Kuhn-Velten, W., "Effects of Compatible Solutes on Mammalian Cytochrome P450 Stability," 1997, pp. 132-135, Verlag der Zeitschrift für Naturforschung.

Landwehr, et al., "Diversification of Catalytic Function in a Synthetic Family of Chimeric Cytochrome P450s", Chemistry and Biology, Current Biology, vol. 14, No. 3, Mar. 23, 2007, pp. 269-278.

Leadbetter, E. R., et al. "Incorporation of Molecular Oxygen in Bacterial Cells Utilizing Hydrocarbons for Growth" Nature, Oct. 31, 1959; vol. 184, pp. 1428-1429.

Lee C et al., "Accurate prediction of the stability and activity effects of site directed mutagenesis on a protein core", Nature, 1991, 352, pp. 448-451.

Lewis, D., "P450 Substrate Specificity and Metabolism," Cytochrome P450: Structure, Function and Mechanism, Aug. 2001, pp. 115-166, Taylor & Francis Publishers.

Lewis, D. F. W., et al., "Molecular modeling of CYP1 family enzymes CYP1A1, CYP1A2, CYP1A6 and CYP1B1 based on sequence homology with CYP102," Toxicology, 139, 1999, pp. 53-79.

Li, Huiying et al., "The Structure of the cytochrome p450BM-3 haem domain complexed with the fatty acid substrate, palmitoleic acid," Nature Structural Biology, 1997, pp. 140-146.

Li, Q. et al., "Rational evolution of a medium chain-specific cytochrome P-450 BM-3 variant," Biochimica et Biophysica Acta, 2001, pp. 114-121, 1545, Elsevier Science B.V.

Li, Qing-Shan, J. Ogawa, R. D. Schmid, and S. Shimizu, "Engineering Cytochrome P450 BM-3 for Oxidation of Polycyclic Aromatic Hydrocarbon" Appl. and Env. Microbiol. Dec. 2001, 67(10): 5735-5739.

Li et al., "Directed evolution of the fatty-acid hydroxylase P450 BM-3 into an indole-hydroxylating catalyst," Chemistry 2000, vol. 6, pp. 1531-1536.

Li et al., "residue size at position 87 of cytochrome P450 BM-3 determines its stereo selectivity in propylbenzene and 3-chlorostyrene oxidation," FEBS Lett 508, 2001, pp. 249-252.

Li, H., et al., "Characterization of Recombinant *Bacillus megaterium* Cytochrome P-450BM-3 and Its Two Functional Domains", Journal of Biological Chemistry, vol. 266, No. 18, 1991:266: pp. 11909-11914.

Li, Q. S., et al.; "Critical Role of the residue size at position 87 in H2O2-dependent substrate hydroxylation activity in H2O2 inactivation of cytochrome P450-BM-3"; Biochem, Biophysics Res Commun. vol. 280, No. 5, Abstract, 2001: pp. 1258-1261.

Li, et al., "Critical Role of the Residue Size at Position 87 in H2O2-Dependent Substrate Hydroxylation Activity and H2O2 Inactivation of Cytochrome P450BM-3", Biochemical and Biophysical Research Communications, 2001, vol. 280, pp. 1258-1261.

Lis, M. et al., "Galactose Oxidase-Glucan Binding Domain Fusion Proteins as Targeting Inhibitors of Dental Plaque Bacteria," Antimicrobial Agents & Chemotherapy, May 1997, pp. 999-1003, vol. 41, No. 5, American Society for Microbiology.

Liu, C. et al., "Sugar-containing Polyamines Prepared Using Galactose Oxidase Coupled with Chemical Reduction," J. Am. Chem. Soc., Jan. 20, 1999, pp. 466-467, vol. 121, No. 2, American Chemical Society.

Lundglen, Jeffrey S. International Search Report, Date of Mailing of Search: Jul. 16, 2001, International Application No. PCT/US01/05043.

Ly, Cheyrie D., International Search Report, Date of Mailing of Search: Aug. 18, 2004, International Application No. PCT/US02/34342.

Maradufu, A. et al., "A Non-Hydrogen-Bonding Role for the 4-Hydroxyl Group of D-Galactose in its Reaction with D-Galactose Oxidase," Carbohydrate Research, 1974, pp. 93-99, 32, Elsevier Scientific Publishing Company, Amsterdam, The Netherlands.

Martinez, C. et al., "Cytochrome P450's: Potential Catalysts for Asymmetric Olefin Epoxidations," Current Organic Chemistry, 2000, pp. 263-282, vol. 4, No. 3, Bentham Science Publishers B.V.

Matson, R. et al., "Characteristics of a Cytochrome P-450-Dependent Fatty Acid ω-2 Hydroxylase From *Bacillus megaterium*," Biochimica et Biophysica Acta, 1977, pp. 487-494, 487, Elsevier/North Holland Biomedical Press.

Matsunaga, I., et al., "Fatty Acid-Specific, Regiospecific, and Stereospecific Hydroxylation by Cyctochrome P450 (CYP152B1) from *Sphingomonas paucimobilis*: Substrate Structure Required for a α-Hydroxylation", Lipids 2000; 35, pp. 365-371.

Mazur, A., "Chapter 8, Galactose Oxidase," ACS Symposium Series 466—Enzymes in Carbohydrate Synthesis, 1991, pp. 99-110, American Chemical Society, Washington, DC, USA.

McPherson, M. et al., "Galactose Oxidase of Dactylium dendroides," Apr. 1992, pp. 8146-8152, The Journal of Biological Chemistry, vol. 267, No. 12, The American Society for Biochemistry and Molecular Biology, Inc.

McPherson, M. et al., "Galactose oxidase: Molecular analysis and mutagenesis studies," Biochemical Society Transactions, 646th Meeting Leeds, 1993, pp. 1992-1994, vol. 21, The Biochemical Society, Portland Press.

Meah, Mohammad Y., International Search Report and Written Opinion, Date of Mailing: Sep. 10, 2008, International Application No. PCT/US06/11273.

Meinhold, P. et al., "Direct Conversion of Ethane to Ethanol by Engineered Cytochrome P450 BM3," ChemBioChem, 2005, pp. 1-4, vol. 6, Wiley-VCH Verlag GmbH & Co. Weinheim, Germany.

Mendonca, M. et al., "Purification and Characterization of Intracellular Galactose Oxidase from *Dactylium dendroides*," Archives of Biochemistry and Biophysics, Feb 1987, pp. 507-514, vol. 252, No. 2, Academic Press, Inc.

Mendonca, M. et al., "Role of Carbohydrate Content on the Properties of Galactose Oxidase from *Dactylium dendroides*," Archives of Biochemistry and Biophysics, Nov 1988, pp. 427-434, vol. 266, No. 2, Academic Press, Inc.

Meyer et al., "Library analysis of SCHEMA-guided protein recombination," Prot. Sci., 2003, vol. 12, No. 8, pp. 1686-1693.

Miles, Caroline S. et al., "Protein engineering of cytochromes P-450," Biochimica et Biophysica Acta 1543, 2000, pp. 383-407.

Miura, Yoshiro, et al., "ω-1, ω-2 and ω-3 hydroxylation of long-chain fatty acids, amides and alcohols by a soluble enzyme system from *Bacillus megaterium*," Biochimica et Biophysica Acta 388, 1975, pp. 305-317.

Modi, S. et al., "NMR Studies of Substrate Binding to Cytochrome P450 BM3: Comparisons to Cytochrome P450 cam," Biochemistry, 1995, pp. 8982-8988, vol. 34, No. 28, American Chemical Society.

Moyse, Ellen, International Preliminary Report on Patentability and Written Opinion, Date of Issuance of Report: Feb. 10, 2009, International Application No. PCT/US07/17409.

Munro, A. et al., "Alkane Metabolism by Cytochrome P450 BM3," Biochemical Society Transactions, 1993, p. 412S, 21.

Munro, A. et al., "Probing electronic transfer in flavocytochrome P-450 BM3 and its component domains," Eur. J. Biochem., 1996, pp. 403-409, FEBS.

Munro et al., "P450 BM3: The very model of a modern flavocyteochrome," TRENDS Biochem. Sci., 2002, vol. 27, pp. 250-257.

Murrell, J. et al., "Molecular biology and regulation of methane monooxygenase," Arch. Microbiol., 2000, pp. 325-332, 173o.

Narhi, L. et al., "Identification and Characterization of Two Functional Domains in Cytochrome P-450BM-3, a Catalytically Self-sufficient Monooxygenase Induced by Barbiturates in *Bacillus megaterium*," The Journal of Biological Chemistry, May 1987, pp. 6683-6690, vol. 262, No. 14, The American Society of Biological Chemists, Inc.

Narhi, L. et al., "Characterization of a Catalytically Self-sufficient 199,000-Dalton Cytochrome P-450 Monooxygenase Induced by Barbiturates in *Bacillus megaterium*," The Journal of Biological Chemistry, Jun. 1986, pp. 7160-7169, vol. 261, No. 16, The American Society of Biological Chemists, Inc.

Nashed, Nashaat, Transmittal of International Search Report and Written Opinion, International Search Report, and Written Opinion, PCT/US08/00135, Sep. 3, 2008.

Nashed, Nashaat, International Search Report and Written Opinion, Date of Mailing of Report: Sep. 26, 2008, International Application No. PCT/US08/53472.

Nelson, D., "Appendix A—Cytochrome P450 Nomenclature and Alignment of Selected Sequences," Cytochrome P450: Structure, Mechanism, and Biochemistry, Second Ed., 1995, pp. 575-606, Plenum Press, NY.

Ness, J. et al., "DNA shuffling of subgenomic sequences of subtilisin," Nature Biotechnology, Sep. 1999, pp. 893-896, vol. 17, No. 9, Nature Publishing Group.

Nickitas-Etienne, Athina, International Preliminary Report on Patentability and Written Opinion, Date of Issuance of Report: Jul. 7, 2009, International Application No. PCT/US08/00135.

Nickitas-Etienne, Athina, International Preliminary Report on Patentability and Written Opinion, Date of Issuance of Report: Nov. 17, 2009, International Application No. PCT/US08/53344.

Noble, M. et al., "Roles of key active-site residues in flavocytochrome P450 BM3," Biochem. J., 1999, pp. 371-379, 339, Biochemical Society.

Ohkuma et al., "Cyp52 (Cytochrome-P450alk) multigene family in candida-maltose—Identification and characterization of 8 members," DNA and Cell Biology, 1995, vol. 14, No. 2, pp. 163-173.

Oliver, C. et al., "Engineering the substrate specificity of *Bacillus megaterium* cytochrome P-450 BM3: hydroxylation of alkyl trimethylammonium compounds," Biochem. J., 1997, pp. 537-544, 327, The Biochemical Society, London, England.

Oliver, C. F., et al., "A single Mutation in Cytochrome P450 BM3 Changes Substrate Orientation in a Catalytic Intermediate and the Regiospecificity of Hydroxylation", Biochemistry 1997; 36:1567-72.

Ortlepp, S. et al., "Expression and characterization of a protein specified by a synthetic horseradish peroxidase gene in *Escherichia coli*," Journal of Biotechnology, 1989, pp. 353-364, 11, Elsevier Science Publishers B.V.

Osman, Ahmed M. et al. "Microperoxidase /H-20-2-catalyzed aromatic hydroxylation proceeds by a cytochrome-P-450-type oxygen-transfer reaction mechanism", Eurpoean Journal of Biochemistry, vol. 240, No. 1, 1996, pp. 232-238, XP002187778.

Ost, T. et al., "Rational re-design of the substrate binding site of flavocytochrome P450 BM3," FEBS Letters, 2000, pp. 173-177, 486, Elsevier Science B.V.

Ost, T. W., et al. "Rational re-design of the substrate binding site of flavocytochrome P450 BM3"; FEBS Lett., vol. 486, No. 2, Abstract 2000.

Otey, Christopher R. et al., "Structure-guided recombination creates an artificial family of cytochromes P450", PLOS Biology, vol. 4, No. 5, May 2006, pp. 789-798.

Otey, et al., "Functional evolution and structural conservation in chimeric cytochromes P450: Calibrating a structure-guided approach", Chemistry & Biology (Cambridge), vol. 11, No. 3, Mar. 2004, pp. 309-318, XP002570369.

Patten, P. et al., "Applications of DNA shuffling to pharmaceuticals and vaccines," Biotechnology, 1997, pp. 724-733, vol. 8, Elsevier Science Ltd.

Paulsen, M. et al., "Dramatic Differences in the Motions of the Mouth of Open and Closed Cytochrome P450BM-3 by Molecular Dynamics Simulations," PROTEINS: Structure, Function and Genetics, 1995, pp. 237-243, Wiley-Liss, Inc.

Peters, Matthew W., "Regio- and Enantioselective Alkane Hydroxylation with Engineered Cytochromes P450 BM-3," J. Am. Chem. Soc., vol. 125, 2003, pp. 13442-13450.

Peterson, J. et al., "Chapter 5—"Bacterial P450s—Structural Similarities and Functional Differences, Cytochrome P450: Structure, Mechanism, and Biochemistry, Second Ed., 1995, pp. 151-180.

Peterson et al., "The many faces of P450s and their structural and functional implications," Sixth International Symposium on Cytrochrome P450 Biodiversity: University of California, Los Angels, 2002, p. 26.

Petrounia, Ioanna and F. H. Arnold "Designed evolution of enzymatic properties," Current Opinion in Biotech., 11 (4): 325-330, Aug. 2000.

Pompon, et al., "Protein engineering by cDNA recombination in yeasts: shuffling of mammalian cytochrome P-450 functions," Gene, 1989, vol. 83, pp. 15-24.

Ramarao et al., "Identification by in vitro mutagenesis of the interaction of two segments of C2MstC1, a chimera of cytochromes P450 2C2 and P450 2C1," The Journal of Biological Chemistry, Jan. 27, 1995, vol. 270, No. 4, pp. 1873-1880.

Rao, Manjunath N., International Preliminary Report on Patentability, Date of Completion of Search: Mar. 7, 2003, International Application No. PCT/US99/11460.

Reynolds, M., et al., "Structure and Mechanism of Galactose Oxidase: Catalytic Role of Tyrosine 495," JBIC, 1997, pp. 327-335, vol. 2.

Roberts, "The power of evolution: accessing the synthetic potential of P450s", Chemistry & Biology, 1999, vol. 6, No. 10, pp. R269-R272.

Rodriguez-Lopez, J., et al., "Role of Arginine 38 in Horseradish Peroxidase—A Critical Residue for Substrate Binding and Cataly-sis," The Journal of Biological Chemistry, Feb. 23, 1996, pp. 4023-4030, vol. 271, No. 8, The American Society for Biochemistry and Molecular Biology.

Abecassis et al., Nucleic Acids Res., 2000, vol. 28, E88.

Abecassis et al., "Design and characterization of a novel family-shuffling" technology adapted to membrane enzyme: application to P450s involved in xenobiotic metabolism, adv. Exp. Med. Biol. 500, 2001, pp. 319-322.

Abecassis et al., "Exploration of natural and artificial sequence spaces: Towards a functional remodeling of membrane- bound cytochome P450," Biocatal. Biotransform, 2003, vol. 21, No. 2, pp. 55-66.

Adam et al., "Microbial Asymmetric CH Oxidations of Simple Hydrocarbons: A Novel Monooxygenase Activity of the Topsoil Microorganism *Bacillus megaterium*," Eur. J. Org. Chem., 2000, pp. 2923-2926, Wiley-VCH Verlag GmbH, Weinheim, Germany.

Aisaka et al., "Production of Galactose Oxidase by *Gibberella fujikuroi*," Agric. Biol. Chem., 1981, pp. 2311-2316, 45 (10).

Amaral et al., "Galactose Oxidase of *Polyporus circinatus*1-4," Methods in Enzymology, Carbohydrate Metabolism, 1966, pp. 87-92, vol. 9, Academic Press Inc., New York, NY, USA.

Appel et al., "A P450 BM-3 mutant hydroxylates alkanes, cycloalkanes, arenas and heteroarenes," Journal of Biotechnology, 2001, pp. 167-171, Elsevier Science B.V.

Arnold et al., "Optimizing Industrial Enzymes by Directed Evolution," Advances in Biochemical Engineering/Biotechnology, 1997, pp. 1-14, vol. 58, Springer-Verlag, Berlin, Germany.

Arnold & Wintrode, Enzymes, Directed Evolution, in Encyclopedia of bioprocess technology: fermentation, biocatalysis, and bioseparation, 1999, 2, 971.

Arts et al., "Hydrogen Peroxide and Oxygen in Catalytic Oxidation of Carbohydrates and Related Compounds," Synthesis Journal of Synthetic Organic Chemistry, Jun. 1997, pp. 597-613.

Ashraf et al., "Bacterial oxidation of propane," FEMS Microbiology Letters, 1994, pp. 1-6, Federation of European Microbiological Societies, Elsevier.

Assis et al., "Hydrocarbon oxidation with iodosylbenzene catalyzed by the sterically hindered iron (iii)5-(pentafluorophenyl)-10, 15, 20-tris(2,6-dichlorophenyl) porphyrin in homogenous solution and covalently bound to silica," Journal of the Chemical Society-Perkin Transactions 2, 1998, vol. 10, pp. 2221-2226.

Aust, S. D., "Commentary—Laboratory evolution of peroxide-mediated cytochrome P450 Hydroxylation," Redox Report, 1999, 4:195-7.

Avigad, "Oxidation Rates of Some Desialylated Glycoproteins by Galactose Oxidase," Archives of Biochemistry and Biophysics, Jun. 1985, pp. 531-537, vol. 239, No. 2, Academic Press, Inc.

Avigad, "An NADH Coupled Assay System for Galactose Oxidase," Analytical Biochemistry, 1978, pp. 470-476, 86, Academic Press, Inc.

Avigad et al., "The D-Galactose Oxidase of *Polyporus circinatus*," Journal of Biological Chemistry, Sep. 1962, pp. 2736-2743, vol. 237, No. 9, American Society of Biological Chemists, Baltimore, MD, USA.

Ayala, et al., "Enzymatic Activation of alkanes: constraints and prospective," Applied Catalysts A: General, 2004, pp. 1-13, vol. 272.

Barnes, "Maximizing Expression of Eukaryotic Cytochrome P450s in *Escherichia coli*," Methods in Enzymology, Cytochrome P450, Part B, 1996, pp. 3-14, vol. 272, Academic Press, Inc., San Diego, CA, USA.

Barnes, H. J., et al., "Expression and enzymatic activity of recombinant cytochrome P450 17 a-hydroxylase in *Escherichia coli*, " Proce. Natl Acad. Sci USA 1991; 88:5597-601.

Baron et al., "Structure and Mechanism of Galactose Oxidase," The Journal of Biological Chemistry, Sep. 23, 1994, pp. 25095-25105, vol. 269, No. 38, American Soc for Biochemistry and Molecular Biology.

Bell et al., "Butane and propane oxidation by engineered cytochromes P450(cam)," Chemical Communications, 2002, vol. 5, pp. 490-491.

Bell et al., "Engineering Cytochrome P450cam into an alkane hydroxylase," Dalton Transactions, 2003, vol. 11, pp. 2133-2140.

Beratan, D. N. T., "The protein bridge between redox centres," Protein Electron Transfer, 1996, Oxford: Bios Scientific Publishers, pp. 23-42.

Blay et al., "Alkane oxidation by a carbonxylate-bridged dimanganese (III) complex," Chemical Communications, 2001, vol. 20, pp. 2102-2103.

Boddupalli et al., "Fatty Acid Monooxygenation by P450BM-3: Product Identification and Proposed Mechanisms for the Sequential Hydroxylation Reactions," Archives of Biochemistry and Biophysics, Jan. 1992, pp. 20-28, vol. 292, No. 1, Academic Press, Inc.

Boddupalli et al., "Fatty Acid Monooxygenation by Cytochrome P-450BM-3," The Journal of Biological Chemistry, 1990, pp. 4233-4239, The American Society for Biochemistry and Molecular Biology.

Borman et al., "Kinetic studies on the reactions of Fusarium galactose oxidase with five different substrates in the presence of dioxygen," Journal of Biological Inorganic Chemistry, 1997, pp. 480-487, Society of Biological Inorganic Chemistry.

Brenner, et al., Protein Science, vol. 3, pp. 1871-1882, 1994.

Brooks B.R. et al., "CHARMM: A Program for Macromolecular Energy, Minimization, and Dynamics Calculations", J. Comp. Chem., 1983, 4, pp. 187-217.

Capdevila, J. et al., "The Highly Stereoselective Oxidation of Polyunsaturated Fatty Acids by Cytochrome P450BM-3," The Journal of Biological Chemistry, Sep. 13, 1996, pp. 22663-22671, vol. 271, No. 37, The American Society for Biochemistry and Molecular Biology, Inc.

Carmichael, A. et al., "Protein engineering of *Bacillus megaterium* CYP102," Eur. J. Biochem., 2001, pp. 3117-3125, vol. 268, FEBS.

Chang, Yan-Tyang et al., "Homology Modeling, Molecular Dynamics Simulations, and Analysis of CYP119, a P450 Enzyme from Extreme Acidothermophilic Archaeon Sulfolobus solfataricus," Biochemistry, 2000, 39, pp. 2484-2498.

Chavez et al., "Syntheses, structures, and reactivities of cobalt (III)-alkylperoxo complexes and their role in stoichiometric and catalytic oxidation of hydrocarbons," Journal of the American Chemical Society, 1998, vol. 120, No. 35, pp. 9015-9027.

Chen, H. et al., "Thermal, Catalytic, Regiospecific Functionalization of Alkanes," Science, 2000, vol. 287, pp. 1995-1997.

Chen et al., "Stereospecific alkane hydroxylation by non-heme iron catalysts: mechanistic evidence for an Fe-V = O active species," Journal of the American Chemical Society, 2001, vol. 123, No. 26, pp. 6327-6337.

Cherry, J. et al., "Directed evolution of a fungal peroxidase," Nature Biotechnology, Apr. 1999, pp. 379-384, vol. 17, Nature America Inc., New York, NY, USA.

Cirino et al. "A self-sufficient peroxide-driven hydroxylation biocatalyst," Angewandte Chemie International Edition, 2003, vol. 42, No. 28, pp. 3299-3301.

Cirino et al., "Exploring the diversity of heme enzymes through directed evolution," In Directed Molecular Evolution of Proteins, 2002, pp. 215-243, S. Brakmann and K. Johnsson, eds., (Germany: Wiley-VCH).

Cirino, Patrick C., and R. Georgescu "Screening for Thermostability," Methods in Molecular Biology, May 2003, pp. 117-125, vol. 230.

Cussac, Yolaine, International Preliminary Report on Patentability and Written Opinion, Date of Issuance of Report: Oct. 9, 2007 International Application No: PCT/US04/18832.

Dahlhoff, W. et al., "L-Glucose or D-gluco-Hexadialdose from D-Glucurono-6,3-lactone by Controlled Reductions," Angew. Chem. Int. Ed. Engl., 1980, pp. 546-547, 19 No. 7, Verlag Chemie, GmbH, Weinheim, Germany.

De Visser et al., "Hydrogen bonding modulates the slectivity of enzymatic oxidation by P450: Chameleon oxidant behavior by compound I," Angewandte Chemie-International Edition, 2002, vol. 41, No. 11, pp. 1947.

De Visser et al., "What factors affect the regioselectivity of oxidation by cytochrome P450? A DFT study of allylic hydroxylation and double bond epoxidation in a model reaction," Journal of the American Chemical Society, 2002, vol. 124, No. 39, pp. 11809-11826.

Deacon, S. et al., "Enhanced Fructose Oxidase Activity in a Galactose Oxidase Variant," ChemBioChem: A European Journal of Chemical Biology, 2004, pp. 971-979, 5, Wiley-VCH Verlag GmbH & Co., Weinheim, Germany.

Elliot et al., "Regio- and stereoselectivity of particulate methane monoxygenanse from Methylococcus capsulates (Bath)," Journal of the American Chemical Society, 1997, vol. 199, No. 42, pp. 9949-9955.

Farinas, E., et al., "Directed Evolution of a Cytochrome P450 Monooxygenase for Alkane Oxidation," Adv. Synth. Catal., 2001, pp. 601-606, vol. 343, No. 6-7.

Ferreira, S.B., "Diethylaminosulfur trifluoride (DAST)", Synlett, No. 7, Apr. 24, 2006, pp. 1130-1131.

Fisher, M., et al., "Positional Specificity of Rabbit CYP4B1 for ω-Hydroxylation of Short-Medium Chain Fatty Acids and Hydrocarbons," Biochemical and Biophysical Research Communications, 1998, pp. 352-355, vol. 248, No. RC988842.

Fox, B., et al., "Methane Monooxygenase from Methylosinus trichosporium OB3b," Methods in Enzymology, 1990, pp. 191-202, vol. 188, Academic Press, Inc.

Root, R., et al., "Enzymatic Synthesis of Unusual Sugars: Galactose Oxidase Catalyzed Stereospecific Oxidation of Polyols," Journal of the American Chemical Society, 1985, pp. 2997-2999, vol. 107, No. 10, American Chemical Society.

Ruettinger, R., et al., "Coding Nucleotide, 5' Regulatory, and Deduced Amino Acid Sequences of P-450BM-3, a Single Peptide Cytochrome P-450:NADPH-P-450 Reductase from *Bacillus megaterium*," The Journal of Biological Chemistry, Jul. 5, 1989, pp. 10987-10995, vol. 264, No. 19, The American Society for Biochemistry and Molecular Biology, Inc.

Ruettinger, R., et al., "Epoxidation of Unsaturated Fatty Acids by a Soluble Cytochrome P-450-dependent System from *Bacillus megaterium*," The Journal of Biological Chemistry, Jun. 10, 1981, pp. 5728-5734, vol. 256, No. 11.

Salazar, Oriana, P. C. Cirino, F. H. Arnold "Thermostability of a Cytochrome P450 Peroxygenase," Chembiochem, 4 (9):891-893, Sep. 2003.

Sasai, "Conformation, energy, and folding ability of selected amino acid sequences", Proc. Natl. Acad. Sci. USA, 1995, 92, pp. 8438-8442.

Savenkova, M., et al. "Improvement of Peroxygenase Activity by Relocation of a Catalytic Histidine within the Active Site of Horseradish Peroxidase," Biochemistry, 1998, pp. 10828-10836, vol. 37, American Chemical Society.

Saysell, C., et al., "Properties of the Trp290His Variant of Fusarium NRRL 2903 Galactose Oxidase: Interactions of the GOasesemi State with Different Buffers, Its Redox Activity and Ability to Bind Azide," JBIC, 1997, pp. 702-709, vol. 2.

Scheller, U., et al., "Characterization of the n-Alkane and Fatty Acid Hydroxylating Cytochrome P450 Forms 52A3 and 52A4," Archives of Biochemistry and Biophysics, Apr. 15, 1996, pp. 245-254, vol. 328, No. 2, Academic Press, Inc.

Schlegel, R., et al., "Substrate Specificity of D-Galactose Oxidase," Carbohydrate Research, Jun. 1968, pp. 193-199, vol. 7, No. 2, Elsevier Publishing Company, Amsterdam.

Schmid, A., et al., "Industrial Biocatalysis Today and Tomorrow," Nature, Jan. 11, 2001, pp. 258-268, vol. 409, Macmillian Magazines Ltd.

Schneider, S., et al., "Controlled Regioelectivity of Fatty Acid Oxidation by Whole Cells Producing Cytochrome P450BM-3 Monooxygenase Under Varied Dissolved Oxygen Concentrations," Biotechnology and Bioengineering, Aug. 5, 1999, pp. 333-341, vol. 64, No. 3, John Wiley & Sons, Inc.

Schneider, et al., "Production of chiral hydroxyl long chain fatty acids by whole cells producing cytochrome P450 (BM-3) monoxygenase," Tetrahedron Asymetry, 1998, Vool. 9, No. 16, pp. 2833-2844.

Schwaneberg, U., et al., "A Continuous Spectrophotometric Assay for P450 BM-3, a Fatty Acid Hydroxylating Enzyme, and Its Mutant F87A," Analytical Biochemistry, 1999, pp. 359-366, vol. 269, Academic Press.

Schwaneberg, U., et al., "Cost-Effective Whole-Cell Assay for Laboratory Evolution of Hydroxylases in *Escherichia coli*," Journal of Biomolecular Screening, 2001, pp. 111-117, vol. 6, No. 2, The Society for Biomolecular Screening.

Schwaneberg, U., et al., "P450 Monooxygenase in Biotechnology—Single-Step, Large-Scale Purification Method for Cytochrome P450 BM-3 by Anion-Exchange Chromatography," Journal of Chromatography, 1999, pp. 149-159, vol. 848, Elsevier Science B.V.

Seghezzi et al., "Identification of characterization of additional members of the cytochrome-P450 multigene family Cyp52 of candida-tropicalis," DNA and Cell Biology, 1992, vol. 11, No. 10, pp. 767-780.

Shanklin, J., et al., "Mössbauer Studies of Alkane ω-Hydroxylase: Evidence for a Diiron Cluster in an Integral-Membrane Enzyme," Proc. Natl. Acad. Sci. USA, Apr. 1997, pp. 2981-2986, vol. 94.

Shilov, A., et al., "Activation of C-H Bonds by Metal Complexes," Chem. Rev., 1997, pp. 2879-2932, vol. 97, American Chemical Society.

Smith, A., et al., "Substrate Binding and Catalysis in Herne Peroxidases," Current Opinion in Chemical Biology, (1998), pp. 269-278, vol. 2.

Sonnenschmidt-Rogge, Sandra, International Search Report and Written Opinion, Date of Mailing of Search: Mar. 19, 2009, International Application No: PCT/US08/057174.

Sono et al., "Heme-containing oxygenases," Chemical Reviews, 1996, vol. 96, No. 7, pp. 2841-2887.

Sprinks, Matthew, Supplementary European Search Report, Date of Completion of Search: Oct. 13, 2009, Application No: EP 06748800.

Staijen, I., et al., "Expression, Stability and Performance of the Three-Component Alkane Mono-oxygenase of *Pseudomonas oleovorans* in *Escherichia coli*," Eur. J. Biochem., 2000, pp. 1957-1965, vol. 267.

Stevenson, J., et al., "The Catalytic Oxidation of Linear and Branched Alkanes by Cytochrome P450cam," J. Am. Chem. Soc., 1996, pp. 12846-12847, vol. 118, No. 50, American Chemical Society.

Straatmann, M. G. et al., "Fluorine-18-labeled diethylaminosulfur trifluoride (DAST): An F-for-OH fluorinating agent", Journal of Nuclear Medicine, vol. 18(2), 1977, pp. 151-158.

Sun, L., et al., "Expression and Stabilization of Galactose Oxidase in *Escherichia coli* by Directed Evolution," Protein Engineering, Sep. 2001, pp. 699-704, vol. 14, No. 9, Oxford University Press.

Sun, L., et al., "Modification of Galactose Oxidase to Introduce Glucose 6-Oxidase Activity," ChemBioChem: A European Journal of Chemical Biology, Aug. 2, 2002, pp. 781-783, vol. 3, No. 8, Wiley-VCH-Vertag GmbH, Weinheim, Germany.

Taly et al., "A combinatorial approach to substrate discrimination in the P450 CYP1A subfamily," Biochimica et Biophysica Acta, 2007, vol. 1770, pp. 446-457.

Thomas, J. M., et al., "Molecular Sieve Catalysts for the Regioselective and shape-Selective Oxyfunctionalization of Alkanes in Air", Acc Chem Res 2001; 34:191-200.

Tonge, G., et al., "Purification and Properties of the Methane Monooxygenase enzyme System from *Methylosinus trichosporium* OB3b," Biochem. J., 1977, pp. 333-344, vol. 161.

Tressel, P., et al., "A Simplified Purification Procedure for Galactose Oxidase," Analytical Biochemistry, Jun. 1980, pp. 150-153, vol. 105, No. 1, Academic Press, Inc.

Tressel, P., et al., "Galactose Oxidase from *Dactylium dendroides*," Methods in Enzymology, 1982, pp. 163-171, vol. 89, Academic Press.

Truan, G., et al., "Thr268 in Substrate Binding and Catalysis in P450BM-3," Archives of iochemistry and Biophysics, Jan. 1, 1998, pp. 53-64, vol. 349, No. 1, Academic Press.

Tsotsou et al., "High throughput assay for chytochroms P450BM3 for screening libraries of substrates and combinatorial mutants," Biosensors and Bioelectronics, 2002, vol. 17, No. 1-2, pp. 119-131.

Tuyman, A. International Search Report and Written Opinion, Date of Mailing of Search: Feb. 26, 2002, International Application No: PCT/US99111460.

Urlacher et al., "Biotransformations using prokaryotic P450 monooxygenases," Current Opinion in Biotechnology, 2002, vol. 13, pp. 557-564.

Urlacher et al., "Protein Engineering of cytochrome P450 monooxygenase from *Bacillus megaterium*." Methods in Enzymology, pp. 208-224, vol. 388, 2004.

Van Deurzen M. P. J., et al., "Selective Oxidations Catalyzed by Peroxidases", Tetrahedron Report No. 427, vol. 53, No. 39, 1997; pp. 13183-13220.

Wachter, R., et al., "Molecular Modeling Studies on Oxidation of Hexopyranoses by Galactose Oxidase. An Active Site Topology Apparently Designed to Catalyze Radical Reactions, Either Concerted or Stepwise," Journal of the American Chemical Society, Mar. 9, 1996, pp. 2782-2789, vol. 118, No. 9.

Whittaker, M., et al., "The Active Site of Galactose Oxidase," The Journal of Biological Chemistry, 1988, pp. 6074-6080, vol. 263, No. 13, The American Society for Biochemistry and Molecular Biology, Inc.

Whittaker, M., et al., "Kinetic Isotope Effects as probes of the Mechanism of Galactose Oxidase," Biochemistry, 1998, pp. 8426-8436, vol. 37, American Chemical Society.

Wilkinson, D., et al., "Structural and Kinetic Studies of a Series of Mutants of Galactose Oxidase Identified by Directed Evolution," Protein Engineering, Design & Selection, Jan. 12, 2004, pp. 141-148, vol. 17, No. 2, Oxford University Press.

Wubbolts, et al., "Enantioselective oxidation by non-heme iron monoxygenases from *Pseudomonas*," CHIMIA, 1996, vol. 16, pp. 436-437.

Yeom, H., et al., "Oxygen Activation by Cytochrome P450BM-3: Effects of Mutating an Active Site Acidic Residue," Archieves of Biochemistry and Biophysics, Jan. 15, 1997, pp. 209-216, vol. 337, No. 2, Academic Press.

Yeom, Sligar H., et al., "The role of Thr268 in oxygen activation of cytochrome P450BM-3" Biochemistry, vol. 34, No. 45., Abstract 1995.

Young, Lee W., International Search Report and Written Opinion, Date of Mailing of Search: Feb. 11, 2009, International Application No: PCT/US08/52795.

Young, Lee W., International Search Report and Written Opinion, Date of Mailing of Search: Apr. 17, 2009, International Application No: PCT/US08/53344.

Zhang, J., et al., "Directed Evolution of a Fucosidase from a Galactosidase by DNA Shuffling and Screening," Proc. Natl. Acad. Sci. USA, Apr. 1997, pp. 4504-4509, vol. 94.

Zhao, H. et al., "Methods for Optimizing Industrial Enzymes by Directed Evolution", Manual of Industrial Microbiology and Biotechnology, 2nd Edition, 1999, pp. 597-604.

Zimmer, T., et al., "The CYP52 Multigene Family of *Candida maltosa* Encodes Functionally Diverse n-Alkane-Inducible Cytochromes P450," Biochemical and Biophysical Research Communications, 1996, pp. 784-789, vol. 224, No. 3, Academic Press, Inc.

* cited by examiner

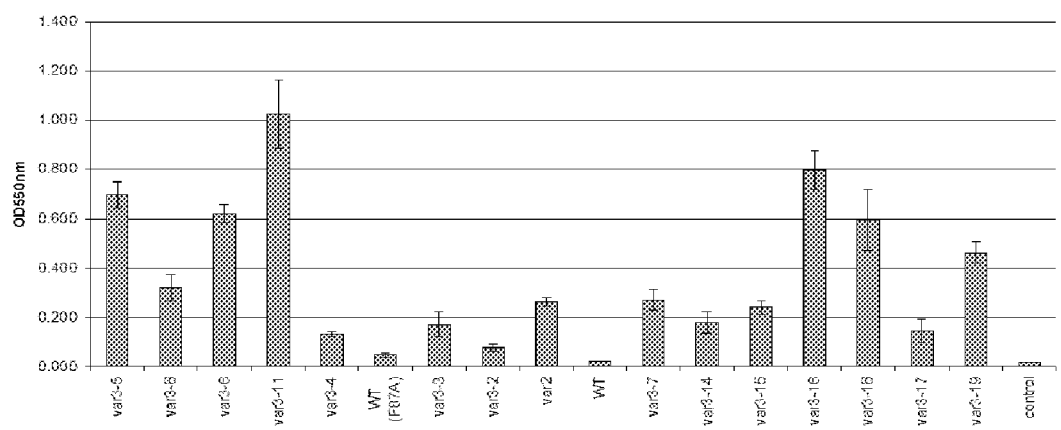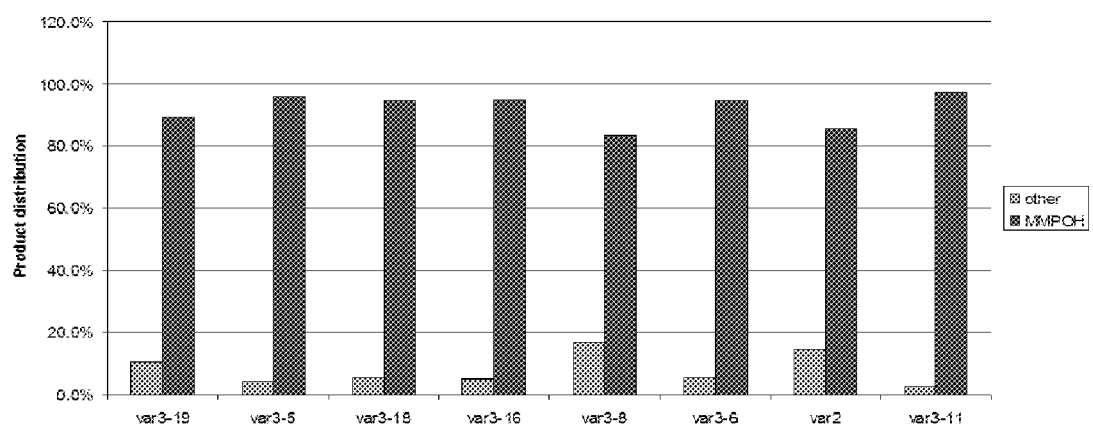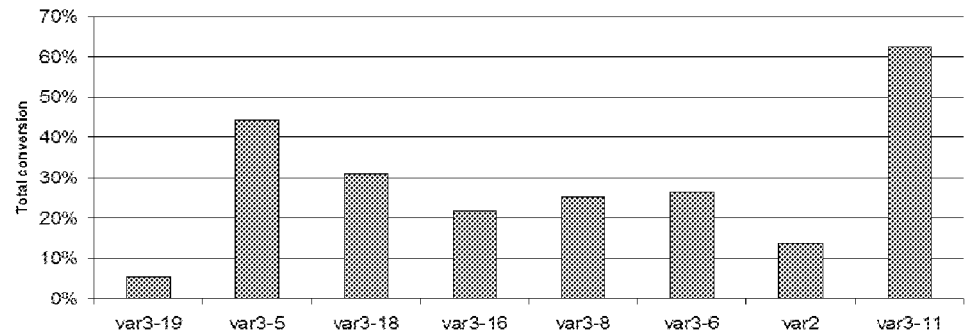
FIG. 7

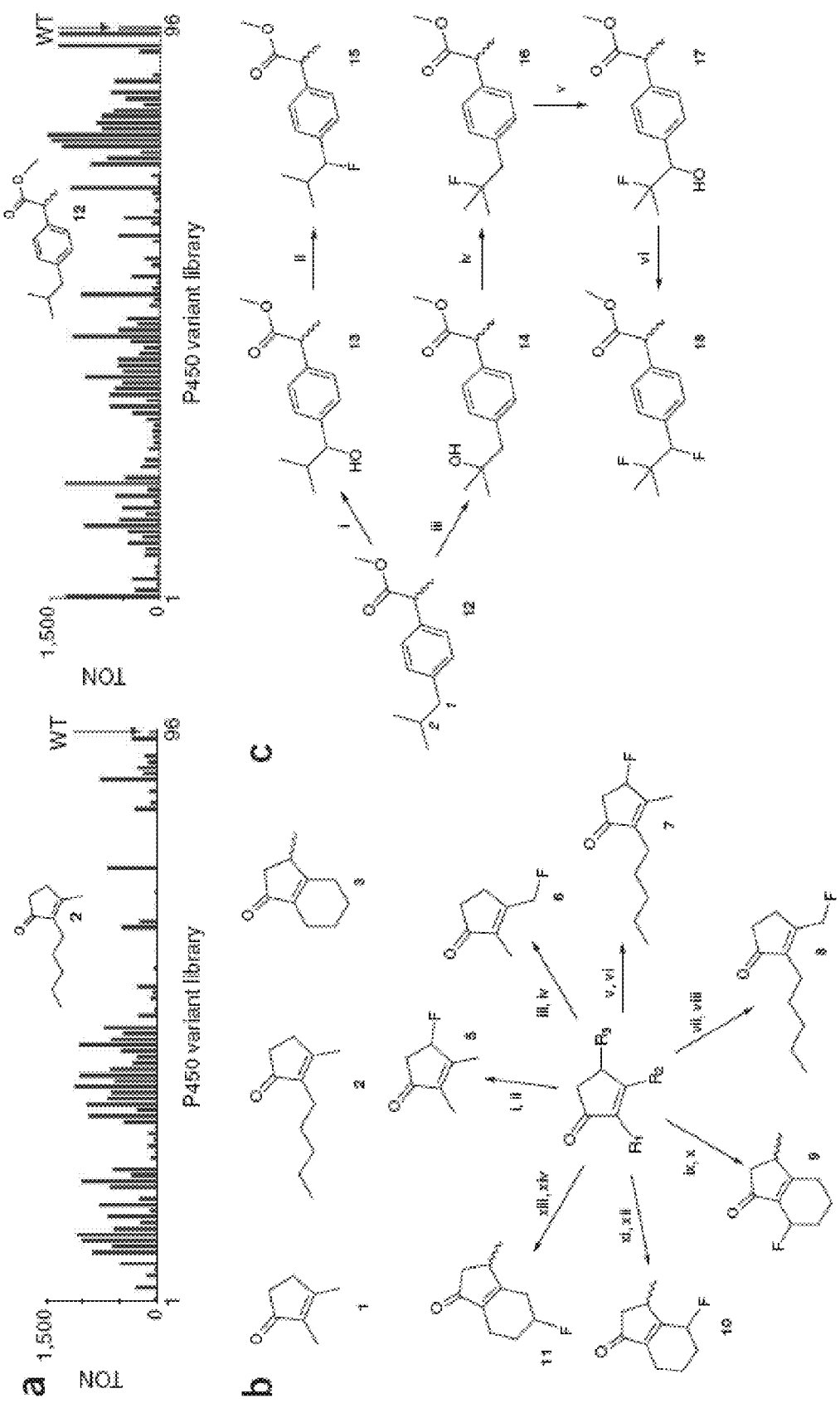
FIG. 10A-C

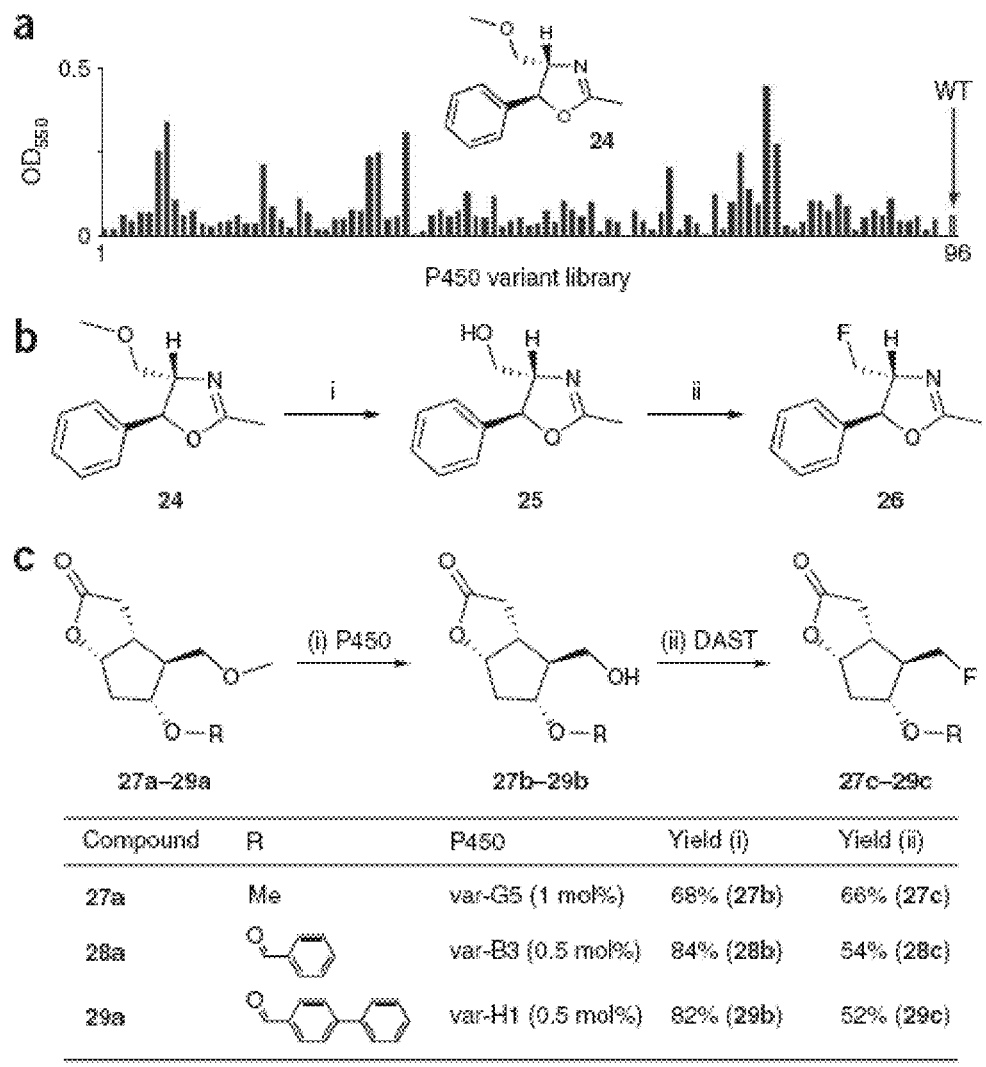
FIG. 11A-C
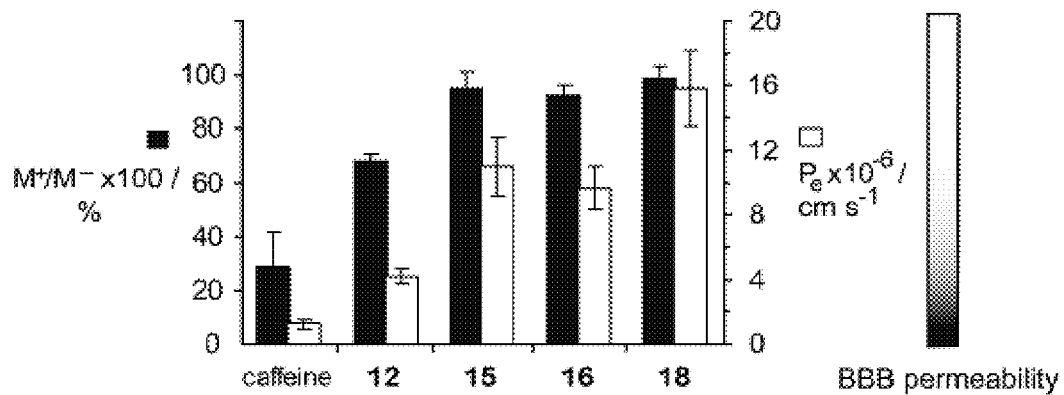
FIG. 12

METHODS AND SYSTEMS FOR SELECTIVE FLUORINATION OF ORGANIC MOLECULES

CROSS REFERENCE TO RELATED APPLICATIONS

This application claims priority to and is a continuation-in-part of International Application No. PCT/US07/17409, filed Aug. 4, 2007, and a continuation-in-part of U.S. patent application Ser. No. 11/890,218, filed Aug. 4, 2007, which applications claim priority to U.S. Provisional Application Ser. No. 60/835,613 filed on Aug. 4, 2006. This application also claims priority to U.S. Provisional Application No. 61/126,829, filed May 7, 2008. The disclosures of each of the foregoing application are incorporated herein by reference in their entirety.

TECHNICAL FIELD

The present disclosure generally relates to the fields of synthetic organic chemistry and pharmaceutical chemistry. In particular, the present disclosure relates to methods and systems for the selective fluorination of organic molecules.

BACKGROUND

The importance of fluorine in altering the physicochemical properties of organic molecules and its exploitation in medicinal chemistry has been highlighted in recent reviews (Bohm, Banner et al. 2004). Although similar in size to hydrogen, HOOF substitutions can cause dramatic effects on several properties of organic molecules, including the lipophilicity, dipole moment, and pKa thereof. In addition, fluorine substitutions can dramatically alter the reactivity of the fluorinated site as well as that of neighboring functional groups.

In particular, in medicinal chemistry, there is a growing interest towards incorporating fluorine atoms in building blocks, lead compounds and drugs in that this may increase by many-fold the chances of turning these molecules into marketable drugs. Several studies have shown that potent drugs can be obtained through fluorination of much less active precursors. Some representative examples include anticholesterolemic Ezetimib (Clader 2004), anticancer CF3-taxanes (Ojima 2004), fluoro-steroids, and antibacterial fluoroquinolones.

The improved pharmacological properties of fluoro-containing drugs are often due to their improved pharmacokinetic properties (biodistribution, clearance) and enhanced metabolic stability (Park, Kitteringham et al. 2001). Primary metabolism of drugs in humans generally occurs through P450-dependent systems, and the introduction of fluorine atoms at or near the sites of metabolic attack has often proven successful in increasing the half-life of a compound (Bohm, Banner et al. 2004). A comprehensive review covering the influence of fluorination on drug metabolism (especially P450-dependent) is presented. (Park, Kitteringham et al. 2001).

In other cases, the introduction of fluorine substituents leads to improvements in the pharmacological properties as a result of enhanced binding affinity of the molecule to biological receptors. Examples of the effect of fluorine on binding affinity are provided by recent results in the preparation of NK1 antagonists (Swain and Rupniak 1999), 5HT1D agonists (van Niel, Collins et al. 1999), and PTB1B antagonists (Burke, Ye et al. 1996).

Over the past years, fluorination has been covering an increasingly important role in drug discovery, as exemplified by the development of fluorinated derivatives of the anticancer drugs paclitaxel and docetaxel (Ojima 2004).

However, only a handful of organofluorine compounds occur in nature and even those only in very small amounts (Harper and O'Hagan 1994). Consequently, any fluorine-containing substance selected for research, pharmaceutical, or agrochemical application has to be man-made.

Despite a few reports on the application of molecular fluorine ($F_2$) for direct fluorination of organic compounds (Chambers, Skinner et al. 1996; Chambers, Hutchinson et al. 2000), this method typically suffers from poor selectivity and requires handling of a highly toxic and gaseous reagent. Several chemical strategies have been developed over the past decades to afford selective fluorination of organic compounds under friendlier conditions. These have been recently reviewed by Togni (Togni, Mezzetti et al. 2001), Cahard (Ma and Cahard 2004), Sodeoka (Hamashima and Sodeoka 2006), and Gouverneur (Bobbio and Gouverneur 2006). These strategies involve catalytic as well as non-catalytic methods. The latter comprise substrate-controlled fluorination methods, which generally make use of a chiral auxiliary, and reagent-controlled fluorination methods, which generally make use of chiral electrophilic N—F or nucleophilic fluorinating reagents.

These fluorination methods, however, need several chemical steps to prepare the chiral substrates (Davis and Han 1992; Enders, Potthoff et al. 1997) or the chiral reagents (Davis, Zhou et al. 1998; Taylor, Kotoris et al. 1999; Nyffeler, Duron et al. 2005) and have an applicability restricted to reactive C—H bonds (Cahard, Audouard et al. 2000; Shibata, Suzuki et al. 2000; Kim and Park 2002; Beeson and MacMillan 2005; Marigo, Fielenbach et al. 2005) in specific classes of compounds such as aldehydes (Beeson and MacMillan 2005; Marigo, Fielenbach et al. 2005) or di-carbonyls (Hintermann and Togni 2000; Ma and Cahard 2004; Shibata, Ishimaru et al. 2004; Hamashima and Sodeoka 2006).

Despite much progress in the field of organofluorine chemistry, the number of available methods for direct or indirect asymmetric synthesis of organofluorine compounds remains limited and additional tools are desirable. In particular, a general method to afford mono- or poly-fluorination of organic compounds at reactive and unreactive sites of their molecular scaffold is desirable.

SUMMARY

Provided herein are methods and systems for the selective fluorination of a target site of an organic molecule, which include the activation and subsequent fluorination of the target site. In the methods and systems herein disclosed, the target site is an oxidizable carbon atom of the organic molecule, the activation is performed by introducing an oxygen-containing functional group on the target site, and the fluorination of the activated site is performed by replacing the functional group introduced on the target site with fluorine The introduction of the oxygen-containing functional group and the replacement of the functional group with a fluorine can be performed by suitable agents.

Fluorination covers an increasingly important role in drug discovery and development. The disclosure provides a versatile strategy that combines cytochrome P450-catalyzed oxygenation with deoxofluorination to achieve mono- and poly-fluorination of non-reactive sites in a variety of organic scaffolds. This procedure was applied for the rapid identification of fluorinated drug derivatives with enhanced membrane permeability.

The disclosure provides a method for fluorinating an organic molecule is disclosed, the method comprising providing an organic molecule comprising a target site; providing an Oxidizing agent that oxidizes the organic molecule by introducing an oxygen containing functional group on the target site, contacting the Oxidizing agent with the organic molecule for a time and under condition to allow introduction of the oxygen-containing functional group on the target site thus providing an oxygenated organic molecule, providing a fluorinating agent and contacting the fluorinating agent with the oxygenated organic molecule, for a time and under condition to allow replacement of the oxygen-containing functional group with fluorine.

The disclosure also provides a system for the fluorination of an organic molecule is disclosed, the system comprising an Oxidizing agent for introducing an oxygen-containing functional group in an organic molecule and a fluorinating agent for replacing the oxygen-containing functional group in the organic molecule with fluorine or a fluorine group. An oxygen-providing compound and/or fluorine-providing compound can also be included in the system.

The methods and systems of the disclosure allow the fluorination of organic molecules in one or more specific and predetermined target sites, including one or more target sites of interest, thus allowing a regioselective mono- and poly-fluorination.

The disclosure further allows introduction of fluorine in an fluorine unreactive site of a molecule, e.g. a site that, in absence of the oxygen-containing functional group is unlikely to undergo a chemical transformation such as a fluorination, as long as said site is oxidizable.

An advantage of the methods and systems herein disclosed is that by using a suitable agent, in particular a suitable oxidizing agent, it is possible to control the chirality of the final product and therefore produce a product molecule having a desired chirality (stereoselective fluorination).

Another advantage of the methods and systems herein disclosed is that the methods and system can provide fluorinated compounds wherein the fluorine is introduced in a predetermined site expected to be associated with a biological activity, which are therefore candidate compounds to be screened for the activity.

The disclosure provides a method for the identification of a molecule having a biological activity is disclosed, the method comprising, providing an organic molecule comprising a target site; providing an Oxidizing agent, contacting the Oxidizing agent with the organic molecule for a time and under condition to allow introduction of an oxygen-containing functional group on the target site thus providing an oxygenated organic molecule, providing a fluorinating agent; contacting the fluorinating agent with the oxygenated organic molecule, for a time and under condition to allow replacement of the oxygen-containing functional group with fluorine and testing the fluorinated organic molecule for the biological activity.

The disclosure also provides a system for identifying a molecule having a biological activity is disclosed. The system comprises an oxidizing agent capable of introducing an oxygen-containing functional group in a target site of an organic molecule, a fluorinating agent capable of replacing the oxygen-containing functional group in the organic molecule with fluorine, and an agent for testing the biological activity. An oxygen-providing agent and/or fluorine-providing-agent can also be included in the system.

A further advantage of the methods and systems for the identification of a molecule having a biological activity is the possibility to produce a broad spectrum of molecules that in view of the selected insertion of fluorine, already constitute promising candidates, thus shortening and improving the selection process.

An additional advantage of the methods and systems for the identification of a molecule having a biological activity is the possibility to confer new activities to a molecule that is already biologically active and/or to improve the biological activity of the original molecule by selective insertion of fluorine.

A still further advantage of the methods and systems of the identification of a molecule having a biological activity, is the possibility to derive molecules that have a biological activity that is pharmacologically relevant, or to improve the pharmacologically activity of a molecule that is already pharmacologically active. This in view of the known ability of fluorine to improve the pharmacological profile of drugs.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description, serve to explain the principles and implementations of the disclosure.

FIG. 7 illustrates exemplary results from the screening of a subset of pre-selected oxygenases for the identification of a suitable Oxidizing agent for the selective activation of the organic molecule dihydro-4-methoxymethyl-2-methyl-5-phenyl-2-oxazoline (MMPO). In particular, Panel (A) is a diagram showing the results from HTS screening of Oxidizing agent pool using calorimetric reagent Purpald; Panel (B) is a diagram showing the results from the re-screen of the positive hits identified with calorimetric HTS, where the regioselectivity of each oxygenase is determined by GC analysis (MMPOH is dihydro-4-hydroxymethyl-2-methyl-5-phenyl-2-oxazoline, that is the desired activated product); Panel (C) is a diagram showing the conversion ratios for the activation reactions of MMPO with each of the tested Oxidizing agents, as determined by GC analysis.

FIG. 10A-C shows chemo-enzymatic fluorination of organic molecules. (a) Screening of P450 library in 96-well format. Reactions were carried out in the presence of the substrate, P450 enzyme from cell lysate, and a glucose-6-phosphate dehydrogenase-based NADPH regeneration system. TON: turnover number. Standard error is within 15%. WT=wild-type P450BM3. (b) Selective fluorination of cyclopentenone derivatives. Reagents and conditions: i) 1, 0.04 mol % var-H3, 88%; ii) DAST (1.2 equiv), $CH_2Cl_2$, 78° C., 12 h, 90% (20% ee); iii) 1, 0.04 mol % var-G6, 45%; iv) DAST (1.2 equiv), $CH_2Cl_2$, 78° C., 12 h, 85%; v) 2, 0.05 mol % var-H3, 85%; vi) DAST (1.3 equiv), $CH_2Cl_2$, 78° C., 12 h, 92% (78% ee); vii) 2, 0.05 mol % var-G4, 42%; viii) DAST (1.5 equiv), $CH_2Cl_2$, 78° C., 12 h, 89%; ix) 3, 0.05 mol % var-D10, 69%; x) DAST (1.2 equiv), $CH_2Cl_2$, 78° C., 3 h, 88% (dr 1:8.5, major: 5% ee, minor: 71% ee); xi) 3, 0.05 mol % var-G4, 62%; xii) DAST (1.2 equiv), $CH_2Cl_2$, 78° C., 5 h, 92% (dr 4:96, major: 0% ee, minor: 57% ee); xiii) 3, 0.07 mol % var-G5, 32%; xiv) DAST (1.2 equiv), $CH_2Cl_2$, 78° C., 5 h, 90% (dr not measurable). (c) Selective mono- and difluorination of prodrug ibuprofen methyl ester. Reagents and conditions: i) 0.1 mol % var-B4, 72%; ii) DAST (1.4 equiv), $CH_2Cl_2$, 78° C., 12 h, 86% (dr 1:3.2, major: 19% ee, minor: 44% ee); iii) 0.05 mol % var-G4, 88%; iv) DAST (1.4 equiv), $CH_2Cl_2$, 78° C., 12 h, 95%; v) 0.06 mol % var-B2, 93%; vi) DAST (1.2 equiv), $CH_2Cl_2$, 78° C., 12 h, 98% (dr 1:3.7, major: 9% ee, minor: 9% ee). The sequences of the P450 variants are described in a table below. Yields refer to the isolated products. Enantiomeric excess values were determined by chiral GC analysis.

FIG. 11A-C shows chemo-enzymatic —$OCH_3$→—F transformation. (a) Screening of P450 demethylation activities using a Purpald-based assay for detection of formaldehyde formation in 96-well plate format. Standard error is within 15%. WT=wild-type P450BM3. (b) —$OCH_3$→—F transformation in a 5-phenyl oxazoline derivative. Reagents and conditions: i) 0.1 mol % var-H1, KPi pH 8.0, room temperature, 48 h, 92%; ii) DAST (1.0 equiv), $CH_2Cl_2$, 0° C., 12 h, 40%. (c) —$OCH3$→—F transformation in Corey lactone derivatives. Yields refer to the isolated products.

FIG. 12 shows membrane permeability properties of 12 and its fluorinated derivatives. Effective permeability values (Pe) are calculated by monitoring accumulation of the organic molecule in a cross-membrane compartment. The correlation between Pe value and BBB-permeability in the absence of active transport has been previously established using a wide set of commercial drugs and is illustrated by the graded bar (black=not BBB-permeable; white=BBB-permeable). Caffeine served as control for assay validation (literature: $1.30 \times 10^6$ cm s−1; experimental: $1.24 \times 10^{-6}$ cm s−1). M+/M− refers to the fraction of compound that crossed the BBB-mimic membrane as compared to system with no membrane after 16 hour incubation at room temperature. Values are means of three replicates.

DETAILED DESCRIPTION

As used herein and in the appended claims, the singular forms "a," "and," and "the" include plural referents unless the context clearly dictates otherwise. Thus, for example, reference to "a species" includes a plurality of such species and reference to "the enzyme" includes reference to one or more enzymes and equivalents thereof, and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure.

Figure 1:
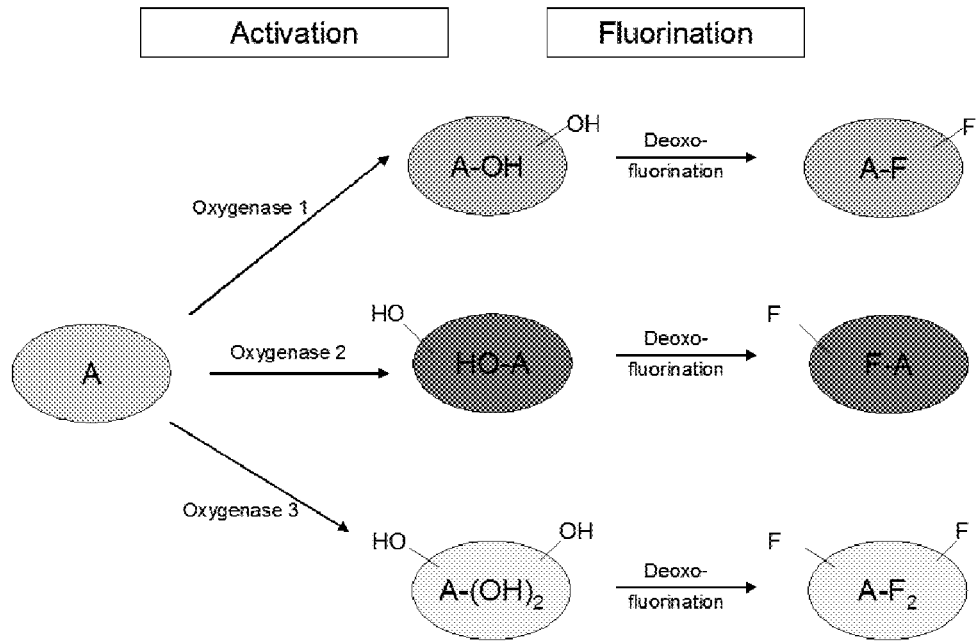
FIG. 1 is a schematic representation of the methods and systems for the selective fluorination of an organic molecule A according to an embodiment of herein disclosed.
Figure 2:
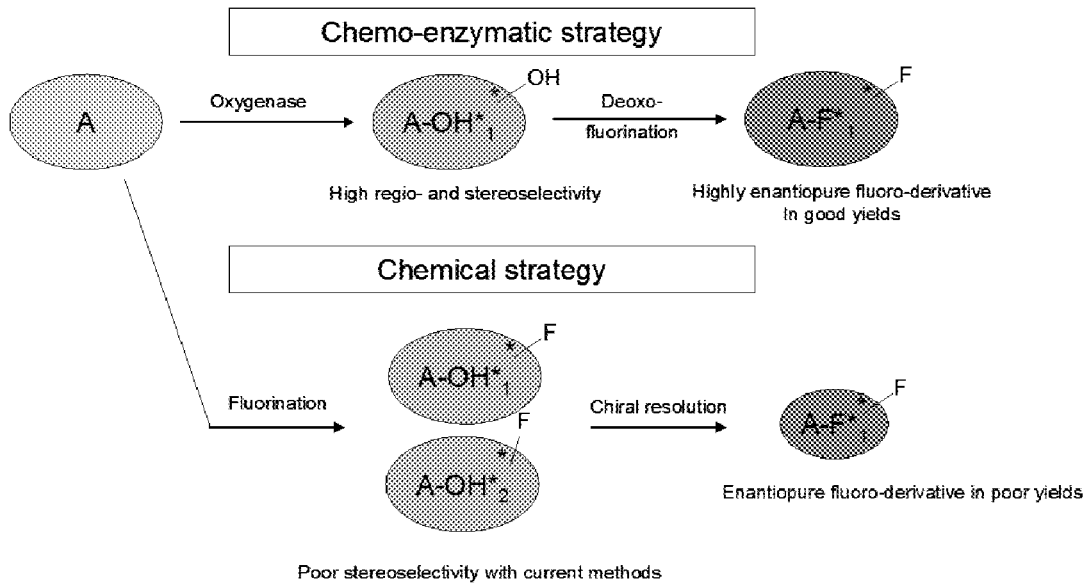
FIG. 2 is a schematic representation of methods and systems for stereoselective fluorination of an organic molecule A according to an embodiment of what herein disclosed (chemo-enzymatic strategy), illustrated in comparison with methods and systems of the art (chemical strategy)

Methods and systems for the selective fluorination of a predetermined target site of an organic molecule are herein disclosed. In these methods and systems, the predetermined target site is first activated by an Oxidizing agent that introduces an oxygen-containing functional group in the target site, and then fluorinated by a fluorinating agent that replaces the oxygen-containing functional group with fluorine or a fluorine group. In particular, activation and fluorination of an organic molecule can be performed as schematically illustrated in FIGS. 1 and 2, FIG. 2 also showing activation and fluorination of an organic molecule performed according to some embodiments herein disclosed, in comparison with chemical methods and systems of the art.

The term "target site" as used herein refers to an oxidizable C atom, i.e. a C atom in the organic molecule that bears an oxidizable bond. Examples of oxidizable bonds include but are not limited to a C—H bond, a C—C double bond, and a C—X bond, single or double, where X is an heteroatom independently selected from the group consisting of B (boron), O, (oxygen), P (phosphorous), N (nitrogen), S (sulphur), Si (silicium), Se (selenium), F (fluorine), Cl (chlorine), Br (bromine), and I (iodine).

The terms "activate" and "activation" as used herein with reference to a target site indicate a chemical reaction resulting in an enhanced reactivity of the C atom that forms the site, so that said C atom acquires or improves its ability to undergo a chemical transformation, more specifically a fluorination reaction. For example, the insertion of an oxygen atom in a target site bearing a C—H bond and resulting in the formation of a hydroxyl group (C—OH) on the site activates the target site for a deoxofluorination reaction. A further example is the insertion of an oxygen atom in a target site bearing a C=C double bond and resulting in the formation of an epoxy group activates the site for a ring-opening fluorination reaction. Accordingly, the wording "activated site" as used herein refers to a C atom of an organic molecule that, following activation, has acquired or improved its ability to undergo a chemical transformation and in particular a fluorination reaction when contacted with a fluorine.

The term "contact" as used herein with reference to interactions of chemical units indicates that the chemical units are at a distance that allows short range non-covalent interactions (such as Van der Waals forces, hydrogen bonding, hydrophobic interactions, electrostatic interactions, dipole-dipole interactions) to dominate the interaction of the chemical units. For example, when an oxygenase enzyme is 'contacted' with a target molecule, the enzyme is allowed to interact with and bind to the organic molecule through non-covalent interactions so that a reaction between the enzyme and the target molecule can occur.

The wording "chemical unit" identifies single atoms as well as groups of atoms connected by a chemical bond. Exemplary chemical units herein described include, but are not limited to fluorine atom, chemical groups such as oxygen-containing chemical group and fluorine-containing groups, organic molecules or portions thereof including target sites, chemical agents, including Oxidizing agents and fluorinating agents.

The term "agent" as used herein refers to a chemical unit that is capable to cause a chemical reaction specified in the identifier accompanying the term. Accordingly, an "Oxidizing agent" is an agent capable of causing an oxygenation reaction of a suitable substrate and a "fluorinating agent" is an agent capable of causing a fluorination reaction of a suitable substrate. An oxygenation reaction is a chemical reaction in which one or more oxygen atoms are inserted into one or more pre-existing chemical bonds of said substrate. A fluorination reaction is a chemical reaction in which a substituent connected to an atom in said substrate is substituted for fluorine.

The term "introducing" as used herein with reference to the interaction between two chemical units, such as a functional groups and a target site, indicates a reaction resulting in the formation of a bond between the two chemical units, e.g. the functional group and the target site.

The term "functional group" as used herein refers to a chemical unit within a molecule that is responsible for a characteristic chemical reaction of that molecule. An "oxygen-containing functional group" is a functional group that comprises an oxygen atom. Exemplary oxygen-containing functional groups include but are not limited to a hydroxyl group (—OH), ether group (—OR), carbonyl oxygen (=O), hydroperoxy group (—OOH), and peroxy group (—OOR).

The terms "replace" and "replacement" as used herein with reference to chemical units indicates formation of a chemical bond between the chemical units in place of a pre-existing bond in at least one of said chemical unit. In particular, replacing an oxygen-containing functional group on the target site with a fluorine or fluorine group indicates the formation of a bond between the target site and the fluorine or fluorine group in place of the bond between the target site and the oxygen-containing functional group.

Any organic molecule that includes at least one target site, i.e. at least one oxidizable C atom, and is a substrate of at least one Oxidizing agent, can be used as an organic molecule to be fluorinated according to the methods and systems herein disclosed.

In some embodiments, the Oxidizing agent is an enzyme such as an oxygenase or Oxidizing enzymes that is able to introduce an oxygen-containing functional group in the target site of the organic molecule using an oxygen source such as molecular oxygen ($O_2$), hydrogen peroxide ($H_2O_2$), a hydroperoxide (R—OOH), or a peroxide (R—O—O—R'), including the oxidoreductases with an Enzyme Classification (EC) number typically corresponding to EC 1.13 or EC 1.14. Suitable oxygenases for the systems and methods herein described include but are not limited to monooxygenases, dioxygenases, peroxygenases, and peroxidases. In particular, monooxygenases and peroxygenase can be used to introduce on the target site an oxygen-containing functional group that comprises one oxygen atom, dioxygenases can be used to introduce on the target site an oxygen-containing functional group that comprises two oxygen atoms, and peroxydases can be used to introduce on the target site an oxygen-containing functional group that comprises one or two oxygen atoms.

In some embodiments, the oxygenases are wild-type oxygenases and in some embodiments the oxygenase is a mutant or variant. An oxygenase is wild-type if it has the structure and function of an oxygenase as it exists in nature. An oxygenase is a mutant or variant if it has been mutated from the oxygenase as it exists in nature and provides an oxygenase enzymatic activity.

In some embodiments, the variant oxygenase provides an enhanced oxygenase enzymatic activity compared to the corresponding wild-type oxygenase. In some embodiments, the variant oxygenases maintain the binding specificity of the corresponding wild-type oxygenase, in other embodiments the variant oxygenases disclosed herein are instead bindingly distinguishable from the corresponding wild-type and bindingly distinguishable from another. The wording "bindingly distinguishable" as used herein with reference to molecules, indicates molecules that are distinguishable based on their ability to specifically bind to, and are thereby defined as complementary to a specific molecule. Accordingly, a first oxygenase is bindingly distinguishable from a second oxygenase if the first oxygenase specifically binds and is thereby defined as complementary to a first substrate and the second oxygenase specifically binds and is thereby defined as complementary to a second substrate, with the first substrate distinct from the second substrate. In some embodiments, the variant oxygenase herein disclosed, has an increased enzyme half-time in vivo, a reduced antigenicity, and/or an increased storage stability when compared to the corresponding wild-type oxygenase.

In some embodiments, the oxygenase is a heme-containing oxygenase or a variant thereof. The wording "heme" or "heme domain" as used herein refers to an amino acid sequence within an oxygenase, which is capable of binding an iron-complexing structure such as a porphyrin. Compounds of iron are typically complexed in a porphyrin (tetrapyrrole) ring that may differ in side chain composition. Heme groups can be the prosthetic groups of cytochromes and are found in most oxygen carrier proteins. Exemplary heme domains include that of P450$_{BM3}$ as well as truncated or mutated versions of these that retain the capability to bind the iron-complexing structure. A skilled person can identify the heme domain of a specific protein using methods known in the art. Exemplary organic molecules that can be oxidized by heme-containing oxygenases include $C_5$-$C_{22}$ alkanes, fatty acids, steroids, terpenes, aromatic hydrocarbons, polyketides, prostaglandins, terpenes, statins, amino acids, flavonoids, and stilbenes.

Figure 3:
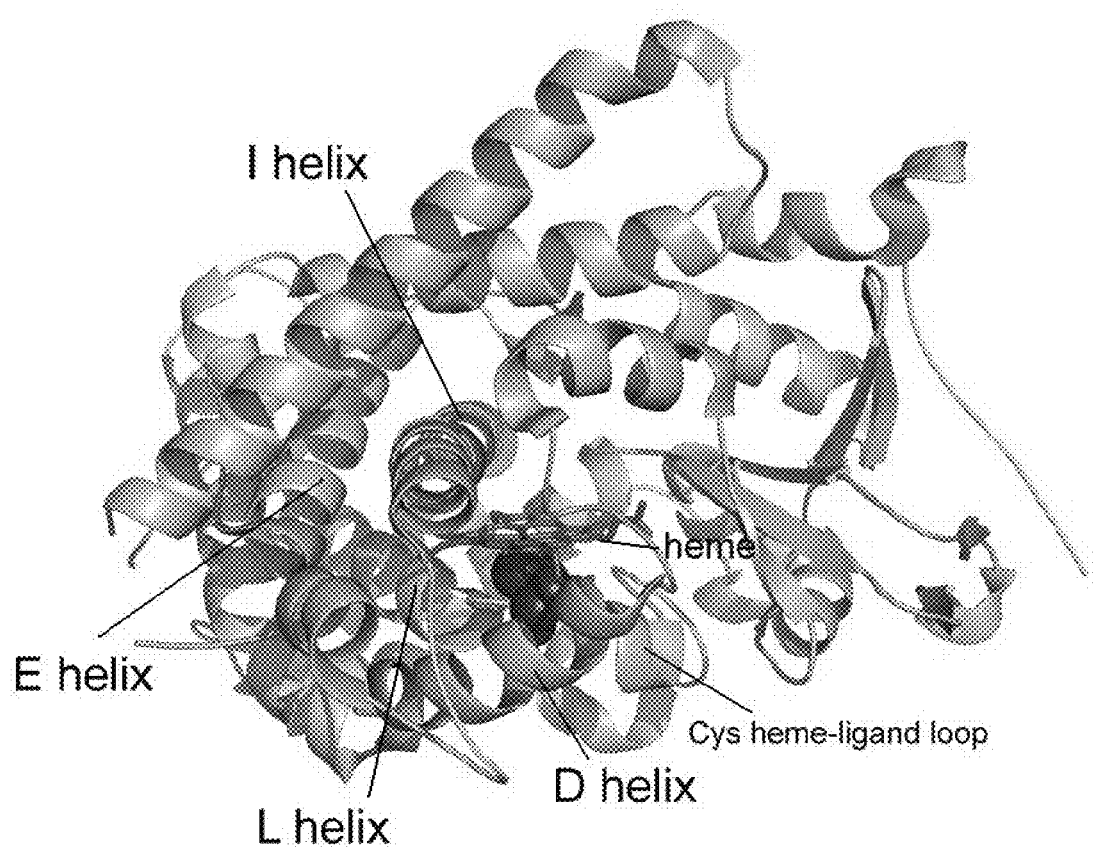
FIG. 3 is a graphic representation of the crystal structure of a P450 heme domain; helixes D, L, I and E in the domain are also indicated; the heme prosthetic group in the domain is indicated as "heme"; the cysteine in the heme-ligand loop is displayed in spheres (black).

In particular, in some embodiments the "heme-containing oxygenase" is a cytochrome P450 enzyme (herein also indicates as CYPs or P450s) or a variant thereof. The wording "P450 enzymes" indicates a group of heme-containing oxygenases that share a common overall fold and topology despite less than 20% sequence identity across the corresponding gene superfamily (Denisov, Makris et al. 2005). In particular, the P450 enzymes share a conserved P450 structural core, which binds to the heme group and comprises a P450 signature sequence. The conserved P450 structural core is formed by a four-helix bundle composed of three parallel helices (usually labeled D, L, and I), and one antiparallel helix (usually labeled as helix E) (Presnell and Cohen 1989) and by a Cys heme-ligand loop which includes a conserved cysteine that binds to the heme group and the P450 signature. In particular, the conserved cysteine that binds to the heme group is the proximal or "fifth" ligand to the heme iron and the relevant ligand group (a thiolate) is the origin of the characteristic name giving 450-nm Soret absorbance observed for the ferrous-CO complex (Pylypenko and Schlichting 2004). The P450 signature sequence is the sequence indicated in the enclosed sequence listing as SEQ ID NO:1. FIG. 3 is a representation of the P450 structural core of bacterial P450$_{BM3}$. In the illustration of FIG. 3, the prosthetic heme group ('heme') is located between the distal I helix ('helix I') and proximal L helix ('helix L') and is bound to the adjacent Cys heme-ligand loop containing the P450 signature sequence SEQ ID NO: 1. Helices D and E are also indicated in FIG. 3.

P450 enzymes are known to be involved in metabolism of exogenous and endogenous compounds. In particular, P450 enzymes can act as terminal oxidases in multicomponent electron transfer chains, called here P450-containing systems. Reactions catalyzed by cytochrome P450 enzymes include hydroxylation, epoxidation, N-dealkylation, O-dealkylation, S-oxidation and other less common transformations. The most common reaction catalyzed by P450 enzymes is the monooxygenase reaction using molecular oxygen ($O_2$), where one atom of oxygen is inserted into a substrate while the other is reduced to water.

P450 monooxygenases can catalyze the monooxygenation of a variety of structurally diverse substrates. Exemplary substrates, that can be oxidized by naturally-occurring P450s include $C_5$-$C_{22}$ alkanes, cyclic alkanes, cyclic alkenes, alkane derivatives, alkene derivatives, $C_{10}$-$C_{20}$ fatty acids, steroids, terpenes, aromatic hydrocarbons, natural products and natural product analogues such as polyketides, prostaglandines, thromboxanes, leukotrienes, anthraquinones, tetracyclines, anthracyclines, polyenes, statins, amino acids, flavonoids, stilbenes, alkaloids (e.g. lysine-derived, nicotinic acid-derived, tyrosine-derived, tryptophan-derived, anthranilic acid-derived, histidine-derived, purine-derived alkaloids), beta-lactams, aminoglycosides, polymyxins, quinolones, synthetic derivatives such as aromatic heterocyclic derivatives (e.g. phenyl-, pyrimidine-, pyridine-, piperidine-, pyrrole-, furan-, triazol-, thiophene-, pyrazole-, imidazole-, tetrazole-, oxazole-, isoxazole-, thiazole-, isothiazole-, pyran-, pyridazine-, pyrazine-, piperazine-, thiazine-, and oxazine-derivatives), and the like.

Naturally-occurring P450 monooxygenases have been also mutated in their primary sequence to favor their activity towards other non-native substrates such as short-chain fatty acids, 8- and 12-pNCA, indole, aniline, p-nitrophenol, polycyclic hydrocarbons (e.g. indole, naphthalene), styrene, medium- and short-chain alkanes, alkenes (e.g. cyclohexene, 1-hexene, styrene, benzene), quinoline, steroid derivatives, and various drugs (e.g. chlorzoxazone, propranolol, amodiaquine, dextromethorphan, acetaminophen, ifosfamide, cyclophosphamide, benzphetamine, buspirone, MDMA).

P450 monooxygenases suitable in the methods and systems herein disclosed include cytochrome P450 monooxygenases (EC 1.14.14.1) from different sources (bacterial, fungi, yeast, plant, mammalian, and human), and variants thereof. Exemplary P450 monooxygenases suitable in the methods and systems herein disclosed include members of CYP102A subfamily (e.g. CYP102A1, CYP102A2, CYP102A3, CYP102A5), members of CYP101A subfamily (e.g. CYP101A1), members of CYP102e subfamily (e.g. CYP102E1), members of CYP1A subfamily (e.g. CYP1A1, CYP1A2), members of CYP2A subfamily (e.g. CYP2A3, CYP2A4, CYP2A5, CYP2A6, CYP2A12, CYP2A13), members of CYP1B subfamily (e.g. CYP1B1), members of CYP2B subfamily (e.g. CYP2B6), members of CYP2C subfamily (e.g. CYP2C8, CYP2C9, CYP2C10, CYP2C18, CYP2C19) members of CYP2D subfamily (e.g. CYP2D6), members of CYP3A subfamily (e.g. CYP3A4, CYP3A5, CYP3A7, CYP3A43), members of CYP107A subfamily (e.g. CYP107A1), and members of CYP153 family (e.g. CYP153A1, CYP153A2, CYP153A6, CYP153A7, CYP153A8, CYP153A11, CYP153D3, and CYP153D2, (van Beilen and Funhoff 2007)). Exemplary organic molecules oxidizable by P450 monooxygenases include $C_5$-$C_{22}$ alkanes, cyclic alkanes, cyclic alkenes, alkane derivatives, alkene derivatives, $C_{10}$-$C_{20}$ fatty acids, steroids, terpenes, aromatic hydrocarbons, natural products and natural product analogues such as polyketides, prostaglandines, thromboxanes, leukotrienes, anthraquinones, tetracyclines, anthracyclines, polyenes, statins, amino acids, flavonoids, stilbenes, alkaloids (e.g. lysine-derived, nicotinic acid-derived, tyrosine-derived, tryptophan-derived, anthranilic acid-derived, histidine-derived, purine-derived alkaloids), beta-lactams, aminoglycosides, polymyxins, quinolones, synthetic derivatives such as aromatic heterocyclic derivatives (e.g. phenyl-, pyrimidine-, pyridine-, piperidine-, pyrrole-, furan-, triazol-, thiophene-, pyrazole-, imidazole-, tetrazole-, oxazole-, isoxazole-, thiazole-, isothiazole-, pyran-, pyridazine-, pyrazine-, piperazine-, thiazine-, and oxazine-derivatives), and the like.

Other exemplary P450 monooxygenases suitable in the methods and systems herein disclosed include CYP106A2, CYP2F1, CYP2J2, CYP2R1, CYP2S1, CYP2U1, CYP2W1, CYP4A11, CYP4A22, CYP4B1, CYP4F2, CYP4F3, CYP4F8, CYP4F11, CYP4F12, CYP4F22, CYP4V2, CYP4X1, CYP4Z1, CYP5A1, CYP7A1, CYP7B1, CYP8A1, CYP8B1, CYP11A1, CYP1B1, CYP11B2, CYP17A1, CYP19A1, CYP20A1, CYP21A2, CYP24A1, CYP26A1, CYP26B1, CYP26C1, CYP27A1, CYP27C1, CYP39A1, CYP46A1, CYP51A1.

In particular, in some embodiments P450 monooxygenases suitable in the methods and systems herein disclosed include CYP102A1 (also called P450$_{BM3}$) from *Bacillus megaterium* (SEQ ID NO: 2), CYP102A2 from *Bacillus subtilis* (SEQ ID NO: 3), CYP102A3 from *Bacillus subtilis* (SEQ ID NO: 4), CYP102A5 from *Bacillus cereus* (SEQ ID NO: 5), CYP102E1 from *Ralstonia metallidurans* (SEQ ID NO: 6), CYP102A6 from *Bradyrhizobium japonicum* (SEQ ID NO:

7), CYP101A1 (also called P450cam) from *Pseudomonas putida* (SEQ ID NO: 8), CYP106A2 (also called P450meg) from *Bacillus megaterium* (SEQ ID NO: 9), CYP153A6 (SEQ ID NO: 54), CYP153A7 (SEQ ID NO: 55), CYP153A8 (SEQ ID NO: 56), CYP153A11 (SEQ ID NO: 57), CYP153D2 (SEQ ID NO: 58), CYP153D3 (SEQ ID NO: 59), P450cin from *Citrobacter brakii* (SEQ ID NO: 10), P450terp from *Pseudomonas* sp. (SEQ ID NO: 11), P450eryF from *Saccharopolyspora erythreae* (SEQ ID NO: 12), CYP1A2 (SEQ ID NO: 13), CYP2C8 (SEQ ID NO: 14), CYP2C9 (SEQ ID NO: 15), CYP2C19 (SEQ ID NO: 16), CYP2D6 (SEQ ID NO: 17), CYP2E1 (SEQ ID NO: 18), CYP2F1 (SEQ ID NO: 19), CYP3A4 (SEQ ID NO: 20), CYP153-AlkBurk from *Alcanivorax borkumensis* (SEQ ID NO: 60), CYP153-EB104 from *Acinetobacter* sp. EB104 (SEQ ID NO: 61), CYP153-OC4 from *Acinetobacter* sp. OC4 (SEQ ID NO: 62), and variants thereof. Exemplary organic molecules that can be oxidized by these P450 monooxygenases include branched and linear $C_{10}$-$C_{20}$ fatty acids, $C_6$-$C_{20}$ alkanes, cyclic alkanes, cyclic alkenes, alkane derivatives, alkene derivatives, steroids, terpenes, aromatic hydrocarbons, natural products and natural product analogues such as polyketides, prostaglandines, thromboxanes, leukotrienes, anthraquinones, tetracyclines, anthracyclines, polyenes, statins, amino acids, flavonoids, stilbenes, alkaloids (e.g. lysine-derived, nicotinic acid-derived, tyrosine-derived, tryptophan-derived, anthranilic acid-derived, histidine-derived, purine-derived alkaloids), beta-lactams, aminoglycosides, polymyxins, quinolones, synthetic derivatives such as aromatic heterocyclic derivatives (e.g. phenyl-, pyrimidine-, pyridine-, piperidine-, pyrrole-, furan-, triazol-, thiophene-, pyrazole-, imidazole-, tetrazole-, oxazole-, isoxazole-, thiazole-, isothiazole-, pyran-, pyridazine-, pyrazine-, piperazine-, thiazine-, and oxazine-derivatives), and the like.

In particular, in some embodiments P450 monooxygenases suitable for the methods and systems herein disclosed include CYP102A1 (SEQ ID NO: 2) and variants thereof, wherein none, one or more of the amino acids that are located within 50 Å from the heme iron are mutated to any other of the natural amino acids or mutated to an unnatural amino acid or modified in some way so to alter the properties of the enzyme. Examples of amino acid positions that can be modified in CYP102A1 to produce a P450 monooxygenase suitable in the methods and systems herein disclosed include without limitations: 25, 26, 42, 47, 51, 52, 58, 74, 75, 78, 81, 82, 87, 88, 90, 94, 96, 102, 106, 107, 108, 118, 135, 138, 142, 145, 152, 172, 173, 175, 178, 180, 181, 184, 185, 188, 197, 199, 205, 214, 226, 231, 236, 237, 239, 252, 255, 260, 263, 264, 265, 268, 273, 274, 275, 290, 295, 306, 324, 328, 353, 354, 366, 398, 401, 430, 433, 434, 437, 438, 442, 443, 444, and 446.

In particular, in some embodiments, P450 monooxygenases suitable in the methods and system herein disclosed are selected from the group consisting of CYP102A1 (SEQ ID NO:2) and variants thereof including CYP102A1var1 (SEQ ID NO: 21), CYP102A1var2 (SEQ ID NO: 22), CYP102A1var3 (SEQ ID NO: 23), CYP102A1var3-2 (SEQ ID NO:24), CYP102A1var3-3 (SEQ ID NO: 25), CYP102A1var3-4 (SEQ ID NO: 26), CYP102A1var3-5 (SEQ ID NO: 27), CYP102A1var3-6 (SEQ ID NO: 28), CYP102A1var3-7 (SEQ ID NO: 29), CYP102A1var3-8 (SEQ ID NO: 30), CYP102A1var3-9 (SEQ ID NO: 31), CYP102A1var3-5 (SEQ ID NO: 32), CYP102A1var3-6 (SEQ ID NO: 33), CYP102A1var3-12 (SEQ ID NO: 34), CYP102A1var3-13 (SEQ ID NO: 35), CYP102A1var3-14 (SEQ ID NO: 36), CYP102A1var3-15 (SEQ ID NO: 37), CYP102A1var3-16 (SEQ ID NO: 38), CYP102A1var3-17 (SEQ ID NO: 39), CYP102A1var3-18 (SEQ ID NO: 40), CYP102A1var3-19 (SEQ ID NO: 41), CYP102A1var3-20 (SEQ ID NO: 42) CYP102A1var3-21 (SEQ ID NO: 43), CYP102A1var3-22 (SEQ ID NO: 44), CYP102A1var3-23 (SEQ ID NO: 45), CYP102A1var4 (SEQ ID NO: 46) CYP102A1var5 (SEQ ID NO:47), CYP102A1var6 (SEQ ID NO: 48), CYP102A1var7 (SEQ ID NO: 49), CYP102A1var8 (SEQ ID NO:50), CYP102A1var9 (SEQ ID NO: 51), CYP102A1var9-1 (SEQ ID NO: 52)

The above variants are illustrated in particular in the following Table 1 wherein the respective sequences reporting in the enclosed Sequence Listing and the mutations of each variant with respect to the wild type (SEQ ID NO: 2) are listed.

TABLE 1

| Name | Sequence | Mutation(s) with respect to CYP102A1 |
| --- | --- | --- |
| CYP102A1 | SEQ ID NO: 2 | — |
| CYP102A1var1 | SEQ ID NO: 21 | V78A, H138Y, T175I, V178I, A184V, H236Q, E252G, R255S, A290V, A295T, L353V |
| CYP102A1var2 | SEQ ID NO: 22 | V78A, T175I, A184V, F205C, S226R, H236Q, E252G, R255S, A290V, L353V |
| CYP102A1var3 | SEQ ID NO: 23 | R47C, V78A, K94I, P142S, T175I, A184V, F205C, S226R, H236Q, E252G, R255S, A290V, L353V |
| CYP102A1var3-2 | SEQ ID NO: 24 | V78A, F81P, A82L, F87A, P142S, T175I, A180T, A184V, A197V, F205C, S226R, H236Q, E252G, R255S, A290V, L353V |
| CYP102A1var3-3 | SEQ ID NO: 25 | V78A, F81C, A82P, F87A, P142S, T175I, A180T, A184V, A197V, F205C, S226R, H236Q, E252G, R255S, A290V, L353V |
| CYP102A1var3-4 | SEQ ID NO. 26 | V78A, F81W, A82I, F87A, P142S, T175I, A180T, A184V, A197V, F205C, S226R, H236Q, E252G, R255S, A290V, L353V |
| CYP102A1var3-5 | SEQ ID NO: 27 | V78A, A82G, F87V, P142S, T175I, A184V, F205C, S226R, H236Q, E252G, R255S, A290V, A328V, L353V |
| CYP102A1var3-6 | SEQ ID NO: 28 | R47C, V78A, F87I, K94I, P142S, T175I, A184V, F205C, S226R, H236Q, E252G, R255S, A290V, L353V |
| CYP102A1var3-7 | SEQ ID NO: 29 | R47C, V78A, F87A, K94I, P142S, T175I, A184V, F205C, S226R, H236Q, E252G, R255S, A290V, L353V |

TABLE 1-continued

| Name | Sequence | Mutation(s) with respect to CYP102A1 |
|---|---|---|
| CYP102A1var3-8 | SEQ ID NO: 30 | R47C, V78A, A82L, K94I, P142S, T175I, A184V, F205C, S226R, H236Q, E252G, R255S, A290V, L353V |
| CYP102A1var3-9 | SEQ ID NO: 31 | R47C, V78T, A82G, F87V, K94I, P142S, T175I, A184V, F205C, S226R, H236Q, E252G, R255S, A290V, A328L, L353V |
| CYP102A1var3-10 | SEQ ID NO: 32 | R47C, L52I, V78F, A82S, K94I, P142S, T175I, A184V, F205C, S226R, H236Q, E252G, R255S, A290V, A328F, I366V, L353V, E464G, I710T |
| CYP102A1var3-11 | SEQ ID NO: 33 | R47C, L52I, V78F, A82S, K94I, P142S, T175I, A184V, F205C, S226R, H236Q, E252G, R255S, A290V, A328L, K349N, L353V, I366V, E464G, I710T |
| CYP102A1var3-12 | SEQ ID NO: 34 | R47C, L52I, V78F, A82S, K94I, P142S, T175I, A184V, L188P, F205C, S226R, H236Q, E252G, R255S, A290V, A328L, I366V, L353V, E464G, I710T |
| CYP102A1var3-13 | SEQ ID NO. 35 | R47C, V78T, A82G, K94I, P142S, T175I, A184V, F205C, S226R, H236Q, E252G, R255S, A290V, A328L, L353V |
| CYP102A1var3-14 | SEQ ID NO: 36 | V78A, A82V, F81R, F87A, P142S, T175I, A180T, A184V, A197V, F205C, S226R, H236Q, E252G, R255S, A290V, L353V |
| CYP102A1var3-15 | SEQ ID NO: 37 | V78A, F81W, A82S, F87A, P142S, T175I, A184V, A197V, F205C, S226R, H236Q, E252G, R255S, A290V, L353V |
| CYP102A1var3-16 | SEQ ID NO: 38 | R47C, V78F, A82S, K94I, P142S, T175I, A184V, F205C, S226R, H236Q, E252G, R255S, A290V, A328F, L353V, E464G, I710T |
| CYP102A1var3-17 | SEQ ID NO: 39 | V78A, F81V, A82T, F87A, P142S, T175I, A180T, A184V, A197V, F205C, S226R, H236Q, E252G, R255S, A290V, L353V |
| CYP102A1var3-18 | SEQ ID NO: 40 | R47C, L52I, V78F, A82S, K94I, P142S, T175I, A184V, L188P, F205C, S226R, H236Q, E252G, R255S, A290V, A328F, I366V, L353V, E464G, I710T |
| CYP102A1var3-19 | SEQ ID NO. 41 | R47C, L52I, A74S, V78F, A82S, K94I, P142S, T175I, L188P, F205C, S226R, H236Q, E252G, R255S, A290V, A328F, I366V, L353V, E464G, I710T |
| CYP102A1var3-20 | SEQ ID NO: 42 | R47C, V78A, A82V, K94I, P142S, T175I, A184V, F205C, S226R, H236Q, E252G, R255S, A290V, A328V, L353V |
| CYP102A1var3-21 | SEQ ID NO: 43 | R47C, V78A, F87V, K94I, P142S, T175I, A184V, F205C, S226R, H236Q, E252G, R255S, I263A, A290V, L353V |
| CYP102A1var3-22 | SEQ ID NO: 44 | R47C, V78A, A82F, K94I, P142S, T175I, A184V, F205C, S226R, I263A, H236Q, E252G, R255S, A290V, A328V, L353V |
| CYP102A1var3-23 | SEQ ID NO: 45 | R47C, V78A, K94I, P142S, T175I, A184V, F205C, S226R, H236Q, E252G, R255S, A290V, A328V, L353V |
| CYP102A1var4 | SEQ ID NO: 46 | F87A |
| CYP102A1var5 | SEQ ID NO: 47 | F87V |
| CYP102A1var6 | SEQ ID NO: 48 | F87V, L188Q |
| CYP102A1var7 | SEQ ID NO: 49 | A74G, F87V, L188Q |
| CYP102A1var8 | SEQ ID NO: 50 | R47L, F87V, L188Q |
| CYP102A1var9 | SEQ ID NO: 51 | F87A, T235A, R471A, E494K, S1024E |
| CYP102A1var9-1 | SEQ ID NO: 52 | F87A, A184K, T235A, R471A, E494K, S1024E |

In some embodiments, the P450 monooxygenases listed in Table 1 or 6 are provided as oxygenating agents for the methods and systems herein disclosed, wherein the organic molecules, include branched and linear $C_6$-$C_{20}$ fatty acids, $C_2$-$C_{20}$ alkanes, cyclic alkanes, cyclic alkenes, alkane derivatives, alkene derivatives, steroids, terpenes, aromatic hydrocarbons, prostaglandins, aromatic heterocyclic derivatives such as phenyl-, pyrimidine-, pyridine-, piperidine-, pyrrole-, furan-, triazol-, thiophene-, pyrazole-, imidazole-, tetrazole-, oxazole-, isoxazole-, thiazole-, isothiazole-, pyran-, pyridazine-, pyrazine-, piperazine-, thiazine-, and oxazine- derivatives.

In some embodiments P450 monooxygenases suitable in the methods and systems herein disclosed include CYP102A2 from *Bacillus subtilis* (SEQ ID NO: 3), and variants thereof, wherein none, one or more of the amino acids that are located within 50 Å from the heme iron are mutated to any other of the natural aminoacids or mutated to an unnatural amino acid or modified in some way so to alter the properties of the enzyme.

In particular, in some embodiments, P450 monooxygenases suitable in the methods and system herein disclosed are selected from the group consisting of CYP102A2 (SEQ ID NO:3) and variants thereof including CYP102A2var1 (SEQ ID NO:63). The above variants are illustrated in particular in the following Table 2 wherein the mutations of each variant with respect to the wild type (SEQ ID NO: 3) are listed.

TABLE 2

| Name | Sequence | Mutation(s) with respect to CYP101A1 |
|---|---|---|
| CYP102A2 | SEQ ID NO: 3 | — |
| CYP102A2var1 | SEQ ID NO: 63 | F88A |

In some embodiments P450 monooxygenases suitable for the methods and systems herein disclosed include CYP102A3 from *Bacillus subtilis* (SEQ ID NO: 4), and variants thereof, wherein none, one or more of the amino acids that are located within 50 Å from the heme iron are mutated to any other of the natural amino acids or mutated to an unnatural amino acid or modified in some way so to alter the properties of the enzyme.

In particular, in some embodiments P450 monooxygenases suitable in the methods and systems herein disclosed are selected from the group consisting of CYP102A3 (SEQ ID NO:4) and variants thereof including CYP102A3var1 (SEQ ID NO: 64). The above variants are illustrated in particular in the following Table 3 wherein the mutations of each variant with respect to the wild type (SEQ ID NO: 4) are listed.

TABLE 3

| Name | Sequence | Mutation(s) with respect to CYP101A1 |
|---|---|---|
| CYP102A3 | SEQ ID NO: 4 | — |
| CYP102A3var1 | SEQ ID NO: 64 | F88A |

In particular, in some embodiments P450 monooxygenases suitable in the methods and systems herein disclosed include CYP101A1 (also called P450cam) from *Pseudomonas putida* (SEQ ID NO: 8) and variants thereof, wherein none, one or more of the amino acids that are located within 50 Å from the heme iron are mutated to any other of the natural aminoacids or mutated to an unnatural amino acid or modified in some way so to alter the properties of the enzyme.

In particular, in some embodiments, P450 monooxygenases suitable in the methods and system herein disclosed are selected from the group consisting of CYP101A1 (SEQ ID NO:8) and variants thereof including CYP101A1var1 (SEQ ID NO:65), CYP101A1var2 (SEQ ID NO:66), CYP101A1var2-1 (SEQ ID NO:67), CYP101A1var2-2 (SEQ ID NO:68), and CYP101A1 var2-3 (SEQ ID NO:69).

The above variants are illustrated in particular in the following Table 4 wherein the mutations of each variant with respect to the wild type (SEQ ID NO: 8) are listed.

TABLE 4

| Name | Sequence | Mutation(s) with respect to CYP101A1 |
|---|---|---|
| CYP101A1 | SEQ ID NO: 8 | — |
| CYP101Avar1 | SEQ ID NO: 65 | Y96A |
| CYP101A1var2 | SEQ ID NO: 66 | Y96F |
| CYP101A1var2-1 | SEQ ID NO: 67 | Y96F, F87W |
| CYP101A1var2-2 | SEQ ID NO: 68 | Y96F, V247L |
| CYP101A1var2-3 | SEQ ID NO: 69 | F87W, Y96F, V247L |

In some embodiments, the P450 enzyme is included in a P450-containing system, a system including a P450 enzyme and one or more proteins that deliver one or more electrons to the heme iron in the P450 enzyme. Natural P450-containing systems occur according to the following general schemes:

CYP reductase (CPR)/cytochrome b5 (cyb5)/P450 systems: typically employed by eukaryotic microsomal (i.e., not mitochondrial) CYPs, they involve the reduction of cytochrome P450 reductase (variously CPR, POR, or CYPOR) by NADPH, and the transfer of reducing power as electrons to the CYP. Cytochrome b5 (cyb5) can also contribute reducing power to this system after being reduced by cytochrome b5 reductase (CYB5R);

Ferrodoxin Reductase (FdxR) or Putidaredoxin Reductase (PdxR)/Ferrodoxin (Fdx) or Putidaredoxin (Pdx)/P450 systems, typically employed by mitochondrial and some bacterial CYPs. Reducing electrons from a soluble cofactor, typically NADPH or NADH, are transferred through the reductase to electron carrier, Fdx or Pdx, and transferred from the electron carrier to the P450 component;

P450-CPR fusion systems, where the CYP domain is naturally fused to the electron donating partners. An example of these systems is represented by cytochrome $P450_{BM3}$ (CYP102A1) from the soil bacterium *Bacillus megaterium;*

CYB5R/cyb5/P450 systems, where both electrons required by the CYP derive from cytochrome b5;

FMN/Fd/P450 systems, where a FMN-domain-containing reductase is fused to the CYP. This type of system was originally found in *Rhodococcus* sp;

P450 only systems, which do not require external reducing power. These include CYP5 (thromboxane synthase), CYP8, prostacyclin synthase, and CYP74A (allene oxide synthase).

In some embodiments, the oxidizing agent is a non-heme containing monooxygenases i.e. a monooxygenases that is able to function without a heme prosthetic group. These monooxygenases include, but are not limited to, flavin monooxygenases, pterin-dependent non-heme monooxygenases, non-heme diiron monooxygenases, and diiron hydroxylases. In these enzymes, oxygen activation occurs at a site in the enzyme's structural fold that is covalently or non-covalently bound to a flavin cofactor, a pterin cofactor, or a diiron cluster. Examples of non-heme containing monooxygenases include but are not limited to ω-hydroxylases (n-octane ω-hydroxylase, n-decane ω-hydroxylases, 9-α-hydroxylase, and AlkB), styrene monooxygenase, butane monooxygenases, propane monooxygenases, and methane monooxygenases. Non-heme containing monooxygenases catalyze the monooxygenation of a variety of structurally diverse substrates. Exemplary substrates accepted by progesterone 9-α-hydroxylase from *Nocardia* sp. include steroid derivatives. Exemplary substrates accepted by non-heme monooxygenases such as integral membrane di-iron alkane hydroxylases (e.g. AlkB), soluble di-iron methane monooxygenases (sMMO), di-iron propane monooxygenases, di-iron butane monooxygenases, membrane-bound copper-containing methane monooxygenases, styrene monooxygenase, xylene monooxygenase include $C_1$-$C_{24}$ linear and branched alkanes, alkenes, and aromatic hydrocarbons.

In some embodiments, the oxidizing agent is a dioxygenase or a variant thereof and in particular a dioxygenase involved in the catabolism of aromatic hydrocarbons. Dioxygenases are a class of oxygenase enzymes that incorporate both atoms of molecular oxygen ($O_2$) onto the substrate according to the general scheme of reaction:

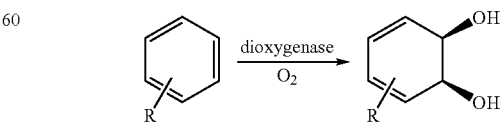

Dioxygenases are metalloprotein and activation of molecular oxygen is carried out in a site within the structural fold of the enzyme that is covalently or non-covalently bound to one or more metal atoms. The metal is typically iron, manganese, or copper. Example of dioxygenases are catechol dioxygenases, toluene dioxygenases, biphenyl dioxygenases. Catechol dioxygenases catalyze the oxidative cleavage of catechols and have different substrate specificities, including catechol 1,2-dioxygenase (EC 1.13.11.1), catechol 2,3-dioxygenase (EC 1.13.11.2), and protocatechuate 3,4-dioxygenase (EC 1.13.11.3). Toluene dioxygenase and biphenyl dioxygenases are involved in the natural degradation of aromatic compounds and typically introduce two oxygen atoms across a double bond in aromatic or non-aromatic compounds. Diooxygenases, e.g. toluene dioxygenase, can be engineered to accept substrates for which the wild-type enzyme shows only basal or no activity, e.g. 4-picoline (Sakamoto, Joern et al. 2001). Potentially suitable substrates for dioxygenase enzymes include but are not restricted to substituted or non-substituted monocyclic, polycyclic, and heterocyclic aromatic compounds. On these substrates, the diooxygenase can introduce one or more cis dihydrodiol functional group.

In some embodiments, the oxidizing agent is a peroxygenase. Natural peroxygenases are heme-dependent oxidases that are distinct from cytochrome P450 enzymes and peroxidases and that accept only peroxides, in particular hydrogen peroxide, as the source of oxidant. Natural peroxygenases are typically membrane-bound and can catalyze hydroxylation reactions of aromatics, sulfoxidations of xenobiotics, or epoxidations of unsaturated fatty acids. In contrast to cytochrome P450 monooxygenases, peroxygenases' activity does not require any cofactor such as NAD(P)H and does not use molecular oxygen. Examples are the plant peroxygenase (PXG) (Hanano, Burcklen et al. 2006), soybean peroxygenase (Blee, Wilcox et al. 1993), and oat seed peroxygenase.

In some embodiments, the peroxygenase is a cytochrome P450s can also use peroxides as oxygen donors. This constitutes the so-called 'peroxide shunt pathway' and the enzyme does not need a reductase and NAD(P)H to carry out catalysis. Normally, this peroxide-driven reaction in P450s is not significant. However, mutations in the heme domain of P450 enzymes can enhance their latent peroxygenase activity, as in the case of P450cam (Joo, Lin et al. 1999) and P450$_{BM3}$ (Cirino and Arnold 2003). Using three engineered P450 enzymes, namely CYP102A1, CYP102A2 and CYP102A3, that are capable of peroxygenase activity, a library of ~6000 members peroxygenase chimeras was created by site-directed recombination (Otey, Landwehr et al. 2006).

Naturally-occurring P450 peroxygenases also exist. P450$_{BS\beta}$ (CYP152A1) and P450$_{SP\alpha}$ (CYP152B1), recently isolated from *Bacillus subtilis* and *Sphingomonas paucimobilis* (Matsunaga, Sumimoto et al. 2002; Matsunaga, Yamada et al. 2002), efficiently utilize $H_2O_2$ to hydroxylate fatty acids, prevalently in α and β positions.

Exemplary peroxygenases suitable in the methods and system herein disclosed include but are not limited to natural heme-containing peroxygenases, natural P450 peroxygenases, engineered P450s with peroxygenase activity, and P450 peroxygenase chimeras described in more details in the work of Arnold and co-workers (Otey, Landwehr et al. 2006). These peroxygenases show activity on a variety of substrates including fatty acids, 8- and 12-pNCA, indole, aniline, p-nitrophenol, heterocyclic derivatives (e.g. chlorzoxazone, buspirone), statins, naphtyl derivatives.

Other suitable Oxidizing agents for the systems and methods herein disclosed are peroxidases (EC number 1.11.1.x). Sequences of the peroxidase enzymes identified so far can be found in the PeroxiBase database. Peroxidases typically catalyze a reaction of the form: ROOR'+electron donor (2 e$^-$)+ 2H$^+$→ROH+R'OH. For most peroxidases the optimal oxygen providing compound is hydrogen peroxide, but others are more active with organic hydroperoxides such as lipid peroxides. Peroxidases can contain a heme cofactor in their active sites, or redox-active cysteine or selenocysteine residues. The nature of the electron donor is very dependent on the structure of the enzyme. For example, horseradish peroxidase can use a variety of organic compounds as electron donors and acceptors. Horseradish peroxidase has an accessible active site and many compounds can reach the site of the reaction. In contrast, cytochrome c peroxidase has a much more restricted active site, and the electron-donating compounds are very specific. Glutathione peroxidase is a peroxidase found in humans, which contains selenocysteine. It uses glutathione as an electron donor and is active with both hydrogen peroxide and organic hydroperoxide substrates.

In some embodiments the organic molecule has the structure of formula (I)

in which X═C atom is the target site, and $R_1$, $R_2$, and $R_3$ are independently selected from the group consisting of hydrogen, aliphatic, aryl, substituted aliphatic, substituted aryl, heteroatom-containing aliphatic, heteroatom-containing aryl, substituted heteroatom-containing aliphatic, substituted heteroatom-containing aryl, alkoxy, aryloxy, and functional groups (FG) or are taken together to form a ring, such that the carbon atom is a secondary or tertiary carbon atom.

The term "aliphatic" is used in the conventional sense to refer to an open-chain or cyclic, linear or branched, saturated or unsaturated hydrocarbon group, including but not limited to alkyl group, alkenyl group and alkynyl groups. The term "heteroatom-containing aliphatic" as used herein refer to an aliphatic moiety where at least one carbon atom is replaced with a heteroatom.

The term "alkyl" and "alkyl group" as used herein refers to a linear, branched, or cyclic saturated hydrocarbon typically containing 1 to 24 carbon atoms, preferably 1 to 12 carbon atoms, such as methyl, ethyl, n-propyl, isopropyl, n-butyl, isobutyl, t-butyl, octyl, decyl and the like. The term "heteroatom-containing alkyl" as used herein refers to an alkyl moiety where at least one carbon atom is replaced with a heteroatom, e.g. oxygen, nitrogen, sulphur, phosphorus, or silicon, and typically oxygen, nitrogen, or sulphur.

The term "alkenyl" and "alkenyl group" as used herein refers to a linear, branched, or cyclic hydrocarbon group of 2 to 24 carbon atoms, preferably of 2 to 12 carbon atoms, containing at least one double bond, such as ethenyl, n-propenyl, isopropenyl, n-butenyl, isobutenyl, octenyl, decenyl, and the like. The term "heteroatom-containing alkenyl" as used herein refer to an alkenyl moiety where at least one carbon atom is replaced with a heteroatom.

The term "alkynyl" and "alkynyl group" as used herein refers to a linear, branched, or cyclic hydrocarbon group of 2 to 24 carbon atoms, preferably of 2 to 12 carbon atoms, containing at least one triple bond, such as ethynyl, n-propynyl, and the like. The term "heteroatom-containing alkynyl" as used herein refer to an alkynyl moiety where at least one carbon atom is replaced with a heteroatom.

The term "aryl" and "aryl group" as used herein refers to an aromatic substituent containing a single aromatic or multiple aromatic rings that are fused together, directly linked, or indirectly linked (such as linked through a methylene or an ethylene moiety). Preferred aryl groups contain 5 to 24 carbon atoms, and particularly preferred aryl groups contain 5 to 14 carbon atoms. The term "heteroatom-containing aryl" as used herein refer to an aryl moiety where at least one carbon atom is replaced with a heteroatom.

The term "alkoxy" and "alkoxy group" as used herein refers to an aliphatic group or a heteroatom-containing aliphatic group bound through a single, terminal ether linkage. Preferred aryl alkoxy groups contain 1 to 24 carbon atoms, and particularly preferred alkoxy groups contain 1 to 14 carbon atoms.

The term "aryloxy" and "aryloxy group" as used herein refers to an aryl group or a heteroatom-containing aryl group bound through a single, terminal ether linkage. Preferred aryloxy groups contain 5 to 24 carbon atoms, and particularly preferred aryloxy groups contain 5 to 14 carbon atoms.

The terms "halo" and "halogen" are used in the conventional sense to refer to a fluoro, chloro, bromo or iodo substituent.

By "substituted" it is intended that in the alkyl, alkenyl, alkynyl, aryl, or other moiety, at least one hydrogen atom is replaced with one or more non-hydrogen atoms. Examples of such substituents include, without limitation: functional groups referred to herein as "FG", such as alkoxy, aryloxy, alkyl, heteroatom-containing alkyl, alkenyl, heteroatom-containing alkenyl, alkynyl, heteroatom-containing alkynyl, aryl, heteroatom-containing aryl, alkoxy, heteroatom-containing alkoxy, aryloxy, heteroatom-containing aryloxy, halo, hydroxyl (—OH), sulfhydryl (—SH), substituted sulfhydryl, carbonyl (—CO—), thiocarbonyl, (—CS—), carboxy (—COOH), amino (—NH$_2$), substituted amino, nitro (—NO$_2$), nitroso (—NO), sulfo (—SO$_2$—OH), cyano (—C≡N), cyanato (—O—C≡N), thiocyanato (—S—C≡N), formyl (—CO—H), thioformyl (—CS—H), phosphono (—P(O)OH$_2$), substituted phosphono, and phospho (—PO$_2$).

In particular, the substituents $R_1$, $R_2$ and $R_3$ of formula I can be independently selected from hydrogen, $C_1$-$C_{24}$ alkyl, $C_1$-$C_{24}$ substituted alkyl, $C_1$-$C_{24}$ substituted heteroatom-containing alkyl, $C_1$-$C_{24}$ substituted heteroatom-containing alkyl, $C_2$-$C_{24}$ alkenyl, $C_2$-$C_{24}$ substituted alkenyl, $C_2$-$C_{24}$ substituted heteroatom-containing alkenyl, $C_2$-$C_{24}$ substituted heteroatom-containing alkenyl, $C_5$-$C_{24}$ aryl, $C_5$-$C_{24}$ substituted aryl, $C_5$-$C_{24}$ substituted heteroatom-containing aryl, $C_5$-$C_{24}$ substituted heteroatom-containing aryl, $C_1$-$C_{24}$ alkoxy, $C_5$-$C_{24}$ aryloxy, carbonyl, thiocarbonyl, and carboxy. More in particular, $R_1$, $R_2$ and $R_3$ of formula I can be independently selected from hydrogen, $C_1$-$C_{12}$ alkyl, $C_1$-$C_{12}$ substituted alkyl, $C_1$-$C_{12}$ substituted heteroatom-containing alkyl, $C_1$-$C_{12}$ substituted heteroatom-containing alkyl, $C_2$-$C_{12}$ alkenyl, $C_2$-$C_{12}$ substituted alkenyl, $C_2$-$C_{12}$ substituted heteroatom-containing alkenyl, $C_2$-$C_{12}$ substituted heteroatom-containing alkenyl, $C_5$-$C_{14}$ aryl, $C_5$-$C_{14}$ substituted aryl, $C_5$-$C_{14}$ substituted heteroatom-containing aryl, $C_5$-$C_{14}$ substituted heteroatom-containing aryl, $C_2$-$C_{14}$ alkoxy, $C_5$-$C_{14}$ aryloxy, carbonyl, thiocarbonyl, and carboxy.

Oxidizing agents known or expected to react with the target site of a compound of Formula (I) include but are not limited to oxygenases or variants thereof.

In some embodiments, the oxygenase can be a non-heme monooxygenase or a variant thereof, a heme-containing monooxygenase or a variant thereof, a peroxygenase or a variant thereof, such as any of the heme-containing monooxygenase, non heme-containing monooxygenases and peroxygenases herein disclosed. In particular, the oxygenase can be any of the P450 monooxygenases and P450 peroxygenases herein disclosed.

In some embodiments, the oxygenase or variant thereof can be butane monooxygenase, CYP102A1 (SEQ ID NO:2), CYP102A1var4 (SEQ ID NO:46), CYP102A1var8 (SEQ ID NO: 50), CYP102A1var1 (SEQ ID NO:21), CYP102A1var2 (SEQ ID NO:22), CYP102A1var3 (SEQ ID NO:23), CYP102A1var3-20 (SEQ ID NO:42), CYP102A var3-2 (SEQ ID NO:44), CYP102A1var3-3 (SEQ ID NO:25), CYP102A var3-4 (SEQ ID NO:26), CYP102A1var3-5 (SEQ ID NO:27), CYP102A1var3-7 (SEQ ID NO:29), CYP102A1var3-8 (SEQ ID NO:30), CYP102A1var3-9 (SEQ ID NO:31), CYP102A1var3-11 (SEQ ID NO:33), CYP102A1var3-13 (SEQ ID NO:35), CYP102A1var3-14 (SEQ ID NO:36), CYP102A1var3-15 (SEQ ID NO:37), CYP101A1 (SEQ ID NO:8), CYP101A1var1 (SEQ ID NO: 65), CYP101A1var2-3 (SEQ ID NO:69), CYP102A2 (SEQ ID NO:3), CYP102A2var1 (SEQ ID NO:63), CYP102A3 (SEQ ID NO:4), CYP102A3var1 (SEQ ID NO:64) and CYP153A6 (SEQ ID NO:54), CYP153A7 (SEQ ID NO:55), CYP153A8 (SEQ ID NO:56), CYP153A11 (SEQ ID NO:57), CYP153D2 (SEQ ID NO:58), CYP106A2 (SEQ ID NO:9) and/or CYP102A1var2 (SEQ ID NO:22) having mutations at F87 (e.g., F87I), P142 (e.g., P142S) or a combination thereof. In particular, in those embodiments at least one of said oxygenases or variants thereof is expected to activate the target site by introducing an oxygen-containing functional group in the form of a hydroxyl group. In these embodiments, the final products resulting from the application of the systems and methods herein disclosed can be ($R_1R_2R_3CF$), ($R_1R_2CF_2$), ($R_1R_3CF_2$), or ($R_2R_3CF_2$).

In some embodiments of the methods and systems herein disclosed wherein the organic molecule is a compound of Formula (I), in which $R_1$=H, —CH$_3$ or =O, and/or $R_2$ and $R_2$ are connected together through 4, 5, 6, or 7-methylene moiety to form a ring, the oxidizing agent can be an oxygenase, such as a P450 monooxygenase, and in particular CYP102A1var1 (SEQ ID NO:21), CYP102A1var2 (SEQ ID NO:22), CYP102A1var3 (SEQ ID NO:23), CYP102A1var3-7 (SEQ ID: NO:29), CYP101A1 (SEQ ID NO:8), CYP101A1var1 (SEQ ID NO:65), and/or CYP101A1var2-3 (SEQ ID NO:69), and is expected to activate the target site of the corresponding compound of Formula (I) by introducing an oxygen-containing functional group in the form of a hydroxyl group.

In some embodiments of the methods and systems herein disclosed wherein the organic molecule is a compound of Formula (I), in which $R_1$=H, $R_2$=-Me, -Et, —Pr, or -iPr, and/or $R_3$=—(CH$_2$)$_n$COOH with n between 9 and 15, the oxidizing agent can be an oxygenase such as a P450 monooxygenase, in particular CYP102A1 (SEQ ID NO:2), CYP102A1var4 (SEQ ID NO:46), CYP102A 1 var5 (SEQ ID NO:47), CYP102A2 (SEQ ID NO:3), CYP102A2var1 ((SEQ ID NO:63), CYP102A3 (SEQ ID NO:4), and/or CYP102A3var1 (SEQ ID NO:64), which is expected to activate the target site by introducing an oxygen-containing functional group in the form of a hydroxyl group.

In some embodiments of the methods and systems herein disclosed wherein the organic molecule is a compound of Formula (I), in which $R_1$=$R_2$=-Me, $R_3$=—CH$_2$-o-substituted-Ph, activation can be performed by reacting the organic molecule with an oxygenase, such as a P450 monooxygenase, including CYP102A1 (SEQ ID NO:2), CYP102A1var3-4 (SEQ ID NO:26), CYP102A1var3-14 (SEQ ID NO:36), CYP102A1var3-15 (SEQ ID NO:37), CYP102A1var3-3

(SEQ ID NO:25), CYP102A1var3-2 (SEQ ID NO:24), CYP102A1var3 (SEQ ID NO:23), CYP102A1var3-9 (SEQ ID NO:31), CYP102A1var1 (SEQ ID NO:21), and/or CYP102A1var2 (SEQ ID NO:22), which introduce an hydroxyl group in the target site, as exemplified in Examples 11 and illustrated in corresponding scheme 11.

In some embodiments of the methods and systems herein disclosed wherein the organic molecule is a compound of Formula (I), in which $R_1=R_2=H$, activation can be performed by reacting the organic molecule with an oxygenase such as a P450 monooxygenase, including CYP153A6 (SEQ ID NO:54), CYP153A7 (SEQ ID NO:55), CYP153A8 (SEQ ID NO:56), CYP153A11 (SEQ ID NO:57), CYP153D2 (SEQ ID NO:58), and/or CYP153D3 (SEQ ID NO:59), which are expected to introduce an hydroxyl group on the target site In some embodiments of the methods and systems herein disclosed wherein the organic molecule is a compound of Formula (I), in which $R_3=n$-$C_6$-$C_{10}$ alkyl (e.g. linear $C_6$-$C_{10}$ alkanes), activation can be performed by an oxygenase such as a butane monooxygenase, which is expected to introduce an hydroxyl group on the target site.

In some embodiments of the methods and systems herein disclosed wherein the organic molecule is a compound of Formula (I), in which $R_3$=cyclohexenyl (e.g. limonene), the oxidating agent can be an oxygenase, such as a P450 monooxygenase including CYP153A6 (SEQ ID NO:54), CYP153A7 (SEQ ID NO:55), CYP153A8 (SEQ ID NO:56), CYP153A11 (SEQ ID NO:57), CYP153D2 (SEQ ID NO:58), and/or CYP153D3 (SEQ ID NO:59) which are expected to introduce an hydroxyl group on the target site.

In some embodiments of the methods and systems herein disclosed wherein the organic molecule is a compound of Formula (I), in which $R_3=n$-C7, the oxidating agent can be a monooxygenase such as a P450 monooxygenases including CYP102A1var3-13 (SEQ ID NO: 35), which is expected to introduce an hydroxyl group on the target site.

In some embodiments of the methods and systems herein disclosed wherein the organic molecule is a compound of Formula (I), in which $R_1=H$, $R_2$ and $R_3$ are connected through n methylene moieties, activation can be performed by reacting the substrate with monooxygenases such as P450 monooxygenases including CYP102A1var1 (SEQ ID NO: 21), CYP102A1var2 (SEQ ID NO: 22), CYP102A1var3-20 (SEQ ID NO: 42). In particular, when n=5, as in the case of cyclopentanecarboxylic acid derivatives, the compound of formula (I) can be activated with methods and systems herein disclosed wherein the oxidating agent is a monooxygenase CYP102A1var8 (SEQ ID NO: 50). When instead n=6, as in the case of camphor, cyclohexane and cyclohexene, the compound of formula (I) can be activated with methods and systems herein disclosed wherein the oxidating agent is a monooxygenase, such as a P450 monooxygenase including CYP101A1 (SEQ ID NO: 8), CYP153A6 (SEQ ID NO: 54), CYP153A7 (SEQ ID NO:55), CYP153A8 (SEQ ID NO: 56), CYP153A1 (SEQ ID NO: 57), CYP153D3 (SEQ ID NO: 59) or CYP153D2 (SEQ ID NO: 58). In those embodiments, activation is known or expected to result in the introduction of a hydroxyl group in the target site.

In some embodiments of the methods and systems herein disclosed wherein the organic molecule is a compound of Formula (I), wherein $R_1=H$, $R_2$ and $R_3$ are connected through 5 or 6 methylene moieties, so to form a polycyclic unsaturated system, such as in steroids, activation can be performed by reacting the substrate with a monooxygenases such a P450 monooxygenase including CYP106A2 (SEQ ID NO: 9), and the activation is expected to result in the introduction of an hydroxyl group in the target site.

In the compound of formula I, wherein $R_1=H$, $R_2=$—$CH_2COOH$, $R_3=$n-dodecyl, activation can be performed by reacting the substrate with peroxygenase $P450_{BS\beta}$ (CYP152A1) (SEQ ID NO:70), resulting in the introduction of a hydroxyl group in the target site.

In some embodiments, the organic molecule has the structure of formula (II)

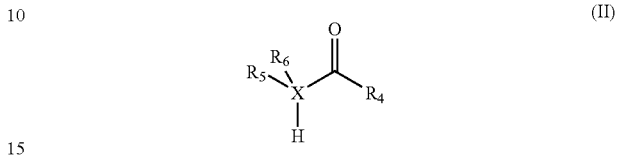

in which X is the target site C atom, and $R_4$, $R_5$, and $R_6$ are independently selected from the group consisting of hydrogen, aliphatic, aryl, substituted aliphatic, substituted aryl, heteroatom-containing aliphatic, heteroatom-containing aryl, substituted heteroatom-containing aliphatic, substituted heteroatom-containing aryl, alkoxy, aryloxy, and functional groups (FG) or are taken together to form a ring, such that the carbon atom is a secondary or tertiary carbon atom.

In particular, the substituents $R_4$, $R_5$ and $R_6$ of Formula (II) can be independently selected from hydrogen, $C_1$-$C_{24}$ alkyl, $C_1$-$C_{24}$ substituted alkyl, $C_1$-$C_{24}$ substituted heteroatom-containing alkyl, $C_1$-$C_{24}$ substituted heteroatom-containing alkyl, $C_2$-$C_{24}$ alkenyl, $C_2$-$C_{24}$ substituted alkenyl, $C_2$-$C_{24}$ substituted heteroatom-containing alkenyl, $C_2$-$C_{24}$ substituted heteroatom-containing alkenyl, $C_5$-$C_{24}$ aryl, $C_5$-$C_{24}$ substituted aryl, $C_5$-$C_{24}$ substituted heteroatom-containing aryl, $C_5$-$C_{24}$ substituted heteroatom-containing aryl, $C_1$-$C_{24}$ alkoxy, $C_5$-$C_{24}$ aryloxy, carbonyl, thiocarbonyl, carboxy, sulfhydryl, amino, substituted amino. More in particular, $R_4$ can be independently selected from hydrogen, $C_2$-$C_{14}$ alkoxy, $C_5$-$C_{14}$ aryloxy, amino, substituted amino, sulfhydryl, substituted sulfhydryl, $C_1$-$C_{12}$ alkyl, $C_1$-$C_{12}$ substituted alkyl, $C_1$-$C_{12}$ substituted heteroatom-containing alkyl, $C_1$-$C_{12}$ substituted heteroatom-containing alkyl, $C_2$-$C_{12}$ alkenyl, $C_2$-$C_{12}$ substituted alkenyl, $C_2$-$C_{12}$ substituted heteroatom-containing alkenyl, $C_2$-$C_{12}$ substituted heteroatom-containing alkenyl, $C_5$-$C_{14}$ aryl, $C_5$-$C_{14}$ substituted aryl, $C_5$-$C_{14}$ substituted heteroatom-containing aryl, and $C_5$-$C_{14}$ substituted heteroatom-containing aryl, while $R_5$ and $R_6$ are independently selected from hydrogen, $C_1$-$C_{12}$ alkyl, $C_1$-$C_{12}$ substituted alkyl, $C_1$-$C_{12}$ substituted heteroatom-containing alkyl, $C_1$-$C_{12}$ substituted heteroatom-containing alkyl, $C_2$-$C_{12}$ alkenyl, $C_2$-$C_{12}$ substituted alkenyl, $C_2$-$C_{12}$ substituted heteroatom-containing alkenyl, $C_2$-$C_{12}$ substituted heteroatom-containing alkenyl, $C_5$-$C_{14}$ aryl, $C_5$-$C_{14}$ substituted aryl, $C_5$-$C_{14}$ substituted heteroatom-containing aryl, $C_5$-$C_{14}$ substituted heteroatom-containing aryl, $C_2$-$C_{14}$ alkoxy, $C_5$-$C_{14}$ aryloxy, carbonyl, thiocarbonyl, and carboxy.

Oxidizing agents known or expected to react with the target site of a compound of Formula (II) include but are not limited to oxygenases or variants thereof.

In some embodiments, the oxygenase can be a non-heme monooxygenase or a variant thereof, a heme-containing monooxygenase or a variant thereof, a peroxygenase or a variant thereof, such as any of the heme-containing monooxygenase, non heme-containing monooxygenases and peroxugenases herein disclosed. In particular, the oxygenase can be any of the P450 monooxygenases and P450 peroxygenases herein disclosed.

In some embodiments, the oxygenase or variant thereof can be a P450 monooxygenase or peroxygenase including CYP102A1 (SEQ ID NO:2), CYP102A1var4 (SEQ ID NO:46), CYP102A1var8 (SEQ ID NO:50), CYP102A1var1 (SEQ ID NO:21), CYP102A1var2 (SEQ ID NO:22), CYP102A1var3 (SEQ ID NO:23), CYP102A1var3-7 (SEQ ID NO:9), CYP102A1var3-5 (SEQ ID NO:27), CYP102A1var3-9 (SEQ ID NO:31), CYP102A1var3-14 (SEQ ID NO:36), CYP102A1var3-15 (SEQ ID NO:37), CYP102A1var3-17 (SEQ ID NO:39), CYP101A1 (SEQ ID NO:8), CYP101A1(Y96F), CYP101A1var2-1 (SEQ ID NO:67), CYP101A1var1 (SEQ ID NO:65), CYP101A1var2-2 (SEQ ID NO:68), CYP1A2 (SEQ ID NO:13), CYP2C9 (SEQ ID NO:15), CYP2C19 (SEQ ID NO:16), CYP2D6 (SEQ ID NO:17), CYP2E1 (SEQ ID NO:18), CYP3A4 (SEQ ID NO:20), P450$_{BSβ}$ (CYP152A1) (SEQ ID NO:70) and/or P450$_{SPα}$ (CYP152B1). In particular, in those embodiments at least one of said oxygenases or variants thereof is expected to activate the target site of a compound of Formula (II) by introducing an oxygen-containing functional group in the form of a hydroxyl group. In these embodiments, the final products resulting from the application of the systems and methods herein disclosed can be (R$_5$R$_6$CF—(CO)—R$_4$), (R$_5$CF$_2$—(CO)—R$_4$), or (R$_6$CF$_2$—(CO)—R).

In some embodiments of the methods and systems herein disclosed wherein the organic molecule is a compound of Formula (II) with R$_4$=—OH, the Oxidizing agent can be a peroxygenase, such as a P450$_{BSβ}$ (CYP152A1) (SEQ ID NO:70) and/or or a peroxygenase P450$_{SPα}$ (CYP152B1), which are most expected activate the target site, in particular by introducing an oxygen-containing functional group in the form of a hydroxyl group.

In some embodiments of the methods and systems herein disclosed wherein the organic molecule is a compound of Formula (II), with R$_4$=—OR, and R=a C$_1$-C$_6$ alkyl, the Oxidizing agent can be an oxygenase and in particular a P450 oxygenase such as CYP102A1(F87A), CYP102A1var3 (SEQ ID NO: 23), CYP102A1var3-7 (SEQ ID NO: 29), CYP102A1var3-14 (SEQ ID NO: 36), CYP102A1var3-15 (SEQ ID NO: 37), and/or CYP102A1var3-5 (SEQ ID NO: 27), which are most expected to activate the target site, in particular by introducing an oxygen-containing functional group in the form of a hydroxyl group.

In some embodiments of the methods and systems herein disclosed wherein the organic molecule is a compound of Formula (II), in which R$_4$ is —OMe, —OEt, —OPr, —OBu, —OtBu, R$_5$ is hydrogen, and R$_6$ is benzyl, o-chloro-phenyl, p-chloro-phenyl, or m-chloro-phenyl, o-methyl-phenyl, p-methyl-phenyl, or m-methyl-phenyl, o-methoxy-phenyl, p-methoxy-phenyl, or m-methoxy-phenyl, the activation can be performed by reacting the substrate with oxygenase CYP102A1var4 (SEQ ID NO: 46), CYP102A1var3 (SEQ ID NO: 23), and CYP102A1var3-7 (SEQ ID NO: 29), as illustrated in Examples 1, 2, 3 and 4 and corresponding schemes 1, 2, 3, and 4.

In some embodiments of the methods and systems herein disclosed wherein the organic molecule is a compound of Formula (II), in which R$_4$ is —OH, R$_5$ is hydrogen, and R$_6$ is a linear C$_{12-16}$ alkyl chain, (for example a myristic acid), the activation can be performed by reacting the substrate with peroxygenases P450$_{BSβ}$ (CYP152A1) and P450$_{SPα}$ (CYP152B1), resulting in the introduction of an hydroxy group in the target site.

In some embodiments of the methods and systems herein disclosed wherein the organic molecule is a compound of Formula (II), in which R$_5$ is -Me, and R$_5$ and R$_6$ are connected through a 6-methylene ring, (for example a α-thujone), the activation can be performed by reacting the substrate with monooxygenases CYP101A1 (SEQ ID NO: 8), CYP102A1 (SEQ ID NO: 2), CYP1A2 (SEQ ID NO: 13), CYP2C9 (SEQ ID NO: 14), CYP2C19 (SEQ ID NO: 16), CYP2D6 (SEQ ID NO: 17), CYP2E (SEQ ID NO: 18), and CYP3A4 (SEQ ID NO: 20), resulting in the introduction of an hydroxyl group in the target site.

In some embodiments, the organic molecule has the structure of formula (III)

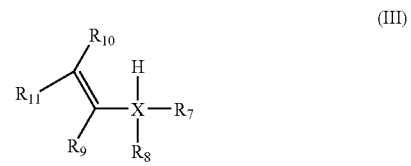

(III)

in which X is the target site C atom, and R$_7$, R$_5$, R$_9$, R$_{10}$ and R$_{11}$ are independently selected from the group consisting of hydrogen, aliphatic, aryl, substituted aliphatic, substituted aryl, heteroatom-containing aliphatic, heteroatom-containing aryl, substituted heteroatom-containing aliphatic, substituted heteroatom-containing aryl, alkoxy, aryloxy, and functional groups (FG) or are taken together to form a ring, such that the carbon atom is a secondary or tertiary carbon atom.

In particular, the substituents R$_7$, R$_8$, R$_9$, R$_{10}$, and R$_{11}$, of Formula (III) can be independently selected from hydrogen, C$_1$-C$_{24}$ alkyl, C$_1$-C$_{24}$ substituted alkyl, C$_1$-C$_{24}$ substituted heteroatom-containing alkyl, C$_1$-C$_{24}$ substituted heteroatom-containing alkyl, C$_2$-C$_{24}$ alkenyl, C$_2$-C$_{24}$ substituted alkenyl, C$_2$-C$_{24}$ substituted heteroatom-containing alkenyl, C$_2$-C$_{24}$ substituted heteroatom-containing alkenyl, C$_5$-C$_{24}$ aryl, C$_5$-C$_{24}$ substituted aryl, C$_5$-C$_{24}$ substituted heteroatom-containing aryl, C$_5$-C$_{24}$ substituted heteroatom-containing aryl, C$_1$-C$_{24}$ alkoxy, C$_5$-C$_{24}$ aryloxy, carbonyl, thiocarbonyl, and carboxy. More in particular, R$_7$, R$_8$, R$_9$, R$_{10}$, and R$_{11}$ are independently selected from hydrogen, C$_1$-C$_{12}$ alkyl, C$_1$-C$_{12}$ substituted alkyl, C$_1$-C$_{12}$ substituted heteroatom-containing alkyl, C$_1$-C$_{12}$ substituted heteroatom-containing alkyl, C$_2$-C$_{12}$ alkenyl, C$_2$-C$_{12}$ substituted alkenyl, C$_2$-C$_{12}$ substituted heteroatom-containing alkenyl, C$_2$-C$_{12}$ substituted heteroatom-containing alkenyl, C$_5$-C$_{14}$ aryl, C$_5$-C$_{14}$ substituted aryl, C$_5$-C$_{14}$ substituted heteroatom-containing aryl, C$_5$-C$_{14}$ substituted heteroatom-containing aryl, C$_2$-C$_{14}$ alkoxy, C$_5$-C$_{14}$ aryloxy, carbonyl, thiocarbonyl, and carboxy.

Oxidizing agents known or expected to react with the target site of a compound of Formula (III) include but are not limited to oxygenases or variants thereof.

In some embodiments, the oxygenase can be a non-heme monooxygenase or a variant thereof, a heme-containing monooxygenase or a variant thereof, a peroxygenase or a variant thereof, such as any of the heme-containing monooxygenase, non heme-containing monooxygenases and peroxygenases herein disclosed. In particular, the oxygenase can be any of the P450 monooxygenases and P450 peroxygenases herein disclosed.

In some embodiments, the oxygenase or variant thereof can be a P450 oxygenase including CYP102A1var1 (SEQ ID NO:21), CYP102A1var2 (SEQ ID NO:22), CYP102A1var3 (SEQ ID NO:23), CYP102A1var3-2 (SEQ ID NO:24), CYP102A1var3-6 (SEQ ID NO:28), CYP102A1var3-5 (SEQ ID NO:27), CYP102A1var3-8 (SEQ ID NO:30), CYP102A1var3-9 (SEQ ID NO:31), CYP102A1var3-11 (SEQ ID NO:33), CYP102A1var3-17 (SEQ ID NO:39), CYP102A1var5 (SEQ ID NO:47), CYP102A1var6 (SEQ ID NO:48), CYP102A1var7 (SEQ ID NO:49), CYP102A1var8 (SEQ ID NO:50), CYP101A1var1 (SEQ ID NO:65), CYP101A1var2-1 (SEQ ID NO:67), CYP101A1var2-3 (SEQ ID NO:69), CYP2C19 (SEQ ID NO:16) and/or CYP2D6 (SEQ ID NO:17). In particular, in those embodiments at least one of said oxygenases or variants thereof is expected to activate the target site of a compound of Formula III by introducing an oxygen-containing functional group in the form of a hydroxyl group. In these embodiments, the final products resulting from the application of the systems and methods herein disclosed can be $(R_7R_8CF\!-\!C(R_9)\!=\!CR_{10}R_{11})$, $(R_7CF_2\!-\!C(R_9)\!=\!CR_{10}R_{11})$ or $(R_8CF_2\!-\!C(R_9)\!=\!CR_{10}R_{11})$.

In some embodiments of the methods and systems herein disclosed wherein the organic molecule is a compound of Formula (III) in which $R_7\!=\!H$, $R_9\!=\!-\!CH_3$, $R_{10}\!=\!-\!n\text{-}C_5H_{11}$, and $R_8$ and $R_{11}$ are linked to form a substituted 5-member ring, activation can be performed by reacting the substrate with oxygenases such as CYP102A1var2 (SEQ ID NO:22), CYP102A1var3 (SEQ ID NO:23), CYP102A1var3-2 (SEQ ID NO:24), CYP102A1var3-6 (SEQ ID NO:28), CYP102A1var3-5 (SEQ ID NO:27), CYP102A1var3-8 (SEQ ID NO:30), CYP102A1var3-9 (SEQ ID NO:31), resulting in the introduction of an hydroxyl group in the target site as illustrated in Examples 5 and corresponding scheme 5.

In some embodiments of the methods and systems herein disclosed wherein the organic molecule is a compound of Formula (III), in which $R_7\!=\!H$, $R_9\!=\!H$, $R_{10}\!=\!-\!CH_3$, $R_8$ and $R_{11}$ are linked to form a substituted 6-member ring, activation can be performed by reacting the substrate with oxygenase CYP101A1var2-3 (SEQ ID NO:69), resulting in the introduction of an hydroxyl group in the target site as in the case of a-pinene.

In some embodiments of the methods and systems herein disclosed wherein the organic molecule is a compound of Formula (III), in which $R_7\!=\!R_8\!=\!R_{10}\!=\!H$, $R_9$ and $R_{11}$ are connected through a substituted 5-member ring, activation can be performed by reacting the organic molecule with an oxygenase such as CYP102A1var3-2 (SEQ ID NO:24), resulting in the introduction of an hydroxyl group in the target site as illustrated by Example 6 and corresponding scheme 6.

In some embodiments of the methods and systems herein disclosed wherein the organic molecule is a compound of Formula (III), in which $R_{10}\!=\!R_{11}\!=\!-\!CH_3$, $R_8\!=\!R_9\!=\!H$, and $R_7\!=$ substituted $C_5$ alkenyl, activation can be performed by reacting the substrate with oxygenases such as CYP2C19 (SEQ ID NO:16) and CYP2D6 (SEQ ID NO:17), as in the case of linalool.

In some embodiments of the methods and systems herein disclosed wherein the organic molecule is a compound of Formula (III), in which $R_7\!=\!H$, $R_9$ and $R_{11}$, are linked together to form a 6-membered aromatic ring, $R_7$ and $R_{10}$ are linked together to form a 5-carbon cyclic alkenyl, activation can be performed by reacting the substrate with oxygenases CYP102A1var5 (SEQ ID NO:47), CYP102A1var6 (SEQ ID NO:48), and/or CYP102A1var7 (SEQ ID NO:49), resulting in the introduction of an hydroxyl group in the target site as in the case of acenaphthene.

In some embodiments, the organic molecule has the structure of formula (IV)

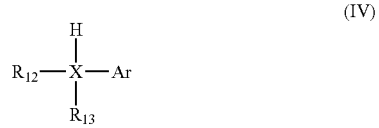

(IV)

in which X is the target site C atom, Ar can be a $C_5\text{-}C_{24}$ aryl, $C_5\text{-}C_{24}$ substituted aryl, $C_5\text{-}C_{24}$ substituted heteroatom-containing aryl or $C_5\text{-}C_{24}$ substituted heteroatom-containing aryl, while $R_{12}$ and $R_{13}$ are independently selected from the group consisting of hydrogen, aliphatic, aryl, substituted aliphatic, substituted aryl, heteroatom-containing aliphatic, heteroatom-containing aryl, substituted heteroatom-containing aliphatic, substituted heteroatom-containing aryl, alkoxy, aryloxy, and functional groups (FG) or are taken together to form a ring, such that the carbon atom is a secondary or tertiary carbon atom.

In particular, the substituent Ar of Formula (IV) can be $C_5\text{-}C_{14}$ aryl, $C_5\text{-}C_{14}$ substituted aryl, $C_5\text{-}C_{14}$ substituted heteroatom-containing aryl, or $C_5\text{-}C_{14}$ substituted heteroatom-containing aryl, while $R_{12}$ and $R_{13}$ are independently selected from hydrogen, $C_1\text{-}C_{12}$ alkyl, $C_1\text{-}C_{12}$ substituted alkyl, $C_1\text{-}C_{12}$ substituted heteroatom-containing alkyl, $C_1\text{-}C_{12}$ substituted heteroatom-containing alkyl, $C_2\text{-}C_{12}$ alkenyl, $C_2\text{-}C_{12}$ substituted alkenyl, $C_2\text{-}C_{12}$ substituted heteroatom-containing alkenyl, $C_2\text{-}C_{12}$ substituted heteroatom-containing alkenyl, $C_5\text{-}C_{14}$ aryl, $C_5\text{-}C_{14}$ substituted aryl, $C_5\text{-}C_{14}$ substituted heteroatom-containing aryl, $C_5\text{-}C_{14}$ substituted heteroatom-containing aryl, $C_2\text{-}C_{14}$ alkoxy, $C_5\text{-}C_{14}$ aryloxy, carbonyl, thiocarbonyl, and carboxy.

Oxidizing agents known or expected to react with the target site of a compound of Formula (IV) include but are not limited to oxygenases or variants thereof.

In some embodiments, the oxygenase can be a non-heme monooxygenase or a variant thereof, a heme-containing monooxygenase or a variant thereof, a peroxygenase or a variant thereof, such as any of the heme-containing monooxygenase, non heme-containing monooxygenases and peroxygenases herein disclosed. In particular, the oxygenase can be any of the P450 monooxygenases and P450 peroxygenases herein disclosed.

In some embodiments, the oxygenase or variant thereof can be such as CYP102A1 (SEQ ID NO:2), CYP102A1var4 (SEQ ID NO:46), CYP102A1var5 (SEQ ID NO:47), CYP102A1var6 (SEQ ID NO:48), CYP102A1var7 (SEQ ID NO:49), CYP102A1var1 (SEQ ID NO:21), CYP102A1var2 (SEQ ID NO:22), CYP102A1var3 (SEQ ID NO:23), CYP102A1var3-2 (SEQ ID NO:24), CYP102A1var3-3 (SEQ ID NO:25), CYP102A1var3-4 (SEQ ID NO:26), CYP102A1var3-5 (SEQ ID NO:27), CYP102A1var3-7 (SEQ ID NO:29), CYP102A1var3-8 (SEQ ID NO:30), CYP102A1var3-9 (SEQ ID NO:31), CYP102A1var3-17 (SEQ ID NO:39), CYP102A1var8 (SEQ ID NO:50), CYP101A1var2-1 (SEQ ID NO:67), and/or CYP101A1var2-3 (SEQ ID NO:69). In particular, in those embodiments at least one of said oxygenases or variants thereof is expected to activate the target site of a compound of Formula IV by introducing an oxygen-containing functional group in the form of a hydroxyl group. In these embodiments, the final products resulting from the application of the systems and methods herein disclosed can be $R_{12}R_{13}ArC\!-\!F$, $R_{12}ArCF_2$, or $R_{13}ArCF_2$ In some embodiments of the methods and systems herein disclosed wherein the organic molecule is a compound of Formula (IV), in which Ar=para-substituted phenyl $R_{13}\!=\!H$, $R_{12}\!=\!\text{-iPr}$, activation can be performed by reacting the organic molecule with an oxygenase such as a P450 monooxygenase including CYP102A1 (SEQ ID NO:2) and CYP102A1var5 (SEQ ID NO:47), which results in the introduction of an hydroxyl group in the target site as illustrated in Examples 10 and corresponding scheme 10.

In some embodiments of the methods and systems herein disclosed wherein the organic molecule is a compound of Formula (IV), in which Ar=para- or ortho or meta substituted phenyl (where substituent is halo, $-CH_3$, or $-OCH_3$), $R_{12}\!=\!H$, $R_{13}\!=\!-\!COOR$, where R is $C_1\text{-}C_6$ n-alkyl, activation can be performed by reacting the substrate with oxygenase CYP102A1var5 (SEQ ID NO:47), CYP102A1var3 (SEQ ID NO:23), and CYP102A1var3-7 (SEQ ID NO:29), as illustrated in Examples 1, 2, 3 and 4 and corresponding schemes 1, 2, 3, and 4.

In some embodiments of the methods and systems herein disclosed wherein the organic molecule is a compound of Formula (IV), in which $R_{12}$=H, Ar is ortho substituted phenyl, $R_{13}$ is linked to Ar through a phenyl moiety, activation can be performed by reacting the substrate with oxygenases CYP102A1var6 (SEQ ID NO:48) and CYP102A1var8 (SEQ ID NO:50), resulting in the introduction of an hydroxyl group in the target site as in the case of fluorene.

In some embodiments of the methods and systems herein disclosed wherein the organic molecule is a compound of Formula (IV), in which $R_{12}$=H, Ar is ortho substituted phenyl, $R_{13}$ is linked to Ar through a 2-methylene bridge, activation can be performed by reacting the substrate with oxygenase CYP102A1var5 (SEQ ID NO:47), resulting in the introduction of an hydroxyl group in the target site as in the case of indan.

In some embodiments the organic molecule has the structure of formula (V),

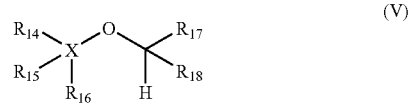

in which X is the target site C atom, $R_{14}, R_{15}, R_{16}, R_{17}, R_{18}$ are independently selected from the group consisting of hydrogen, aliphatic, aryl, substituted aliphatic, substituted aryl, heteroatom-containing aliphatic, heteroatom-containing aryl, substituted heteroatom-containing aliphatic, substituted heteroatom-containing aryl, alkoxy, aryloxy, and functional groups (FG) or are taken together to form a ring, such that the carbon atom is a secondary or tertiary carbon atom.

In particular, the substituents $R_{14}, R_{15}, R_{16}, R_{17},$ and $R_{18}$ of Formula (V) can be independently selected from hydrogen, $C_1$-$C_{24}$ alkyl, $C_1$-$C_{24}$ substituted alkyl, $C_1$-$C_{24}$ substituted heteroatom-containing alkyl, $C_1$-$C_{24}$ substituted heteroatom-containing alkyl, $C_2$-$C_{24}$ alkenyl, $C_2$-$C_{24}$ substituted alkenyl, $C_2$-$C_{24}$ substituted heteroatom-containing alkenyl, $C_2$-$C_{24}$ substituted heteroatom-containing alkenyl, $C_5$-$C_{24}$ aryl, $C_5$-$C_{24}$ substituted aryl, $C_5$-$C_{24}$ substituted heteroatom-containing aryl, $C_5$-$C_{24}$ substituted heteroatom-containing aryl, carbonyl, thiocarbonyl, and carboxy. More in particular, $R_{14}, R_{15}, R_{16}, R_{17},$ and $R_{18}$ is are independently selected from hydrogen, $C_1$-$C_{12}$ alkyl, $C_1$-$C_{12}$ substituted alkyl, $C_1$-$C_{12}$ substituted heteroatom-containing alkyl, $C_1$-$C_{12}$ substituted heteroatom-containing alkyl, $C_2$-$C_{12}$ alkenyl, $C_2$-$C_{12}$ substituted alkenyl, $C_2$-$C_{12}$ substituted heteroatom-containing alkenyl, $C_2$-$C_{12}$ substituted heteroatom-containing alkenyl, $C_5$-$C_{14}$ aryl, $C_5$-$C_{14}$ substituted aryl, $C_5$-$C_{14}$ substituted heteroatom-containing aryl, $C_5$-$C_{14}$ substituted heteroatom-containing aryl, $C_2$-$C_{14}$ alkoxy, $C_5$-$C_{14}$ aryloxy, carbonyl, and carboxy.

Oxidizing agents known or expected to react with the target site of a compound of Formula (V) include but are not limited to oxygenases or variants thereof.

In some embodiments, the oxygenase can be a non-heme monooxygenase or a variant thereof, a heme-containing monooxygenase or a variant thereof, a peroxygenase or a variant thereof, such as any of the heme-containing monooxygenase, non heme-containing monooxygenases and peroxugenases herein disclosed. In particular, the oxygenase can be any of the P450 monooxygenases and P450 peroxygenases herein disclosed.

In some embodiments, the oxygenase or variant thereof can be CYP102A1var8 (SEQ ID NO:50), CYP102A1var3-2 (SEQ ID NO:24), CYP102A1var3-3 (SEQ ID NO:25), CYP102A1var3-5 (SEQ ID NO:27), CYP102A1var3-6 (SEQ ID NO:28), CYP102A1var3-9 (SEQ ID NO:31), CYP102A1var3-11 (SEQ ID NO:33), CYP102A1var3-16 (SEQ ID NO:38), CYP102A1var3-19 (SEQ ID NO:41, CYP102A1var3-18 (SEQ ID NO:40), CYP102A1var3-2 (SEQ ID NO:24), CYP102A1var3-3 (SEQ ID NO:25), CYP102A1var3-14 (SEQ ID NO:36), CYP102A1var3-15 (SEQ ID NO:37), CYP102A1var3-17 (SEQ ID NO:39), CYP102A1var3-9 (SEQ ID NO:31), CYP101A1var2-3 (SEQ ID NO:69), and/or CYP3A4 (SEQ ID NO:20). In particular, in those embodiments, at least one of said oxygenases or variants thereof is expected to activate a compound of Formula V by affording a hydroxyl group at the target site. In these embodiments, the final product resulting from the application of the systems and methods herein disclosed can be $R_{14}R_{15}R_{16}C$—F.

In some embodiments of the methods and systems herein disclosed wherein the organic molecule is a compound of Formula (V), in which $R_{14}, R_{15}, R_{17}, R_{18}$ are hydrogen, and $R_{16}$ is 2-methyl-5-phenyl-4,5-dihydrooxazolyl, activation can be performed by reacting the substrate with oxygenases CYP102A1var3-5 (SEQ ID NO:27), CYP102A1var3-6 (SEQ ID NO:28), CYP102A1var3-11 (SEQ ID NO:33), CYP102A1var3-16 (SEQ ID NO:38), CYP102A1var3-19 (SEQ ID NO:41), CYP102A1var3-18 (SEQ ID NO:40), resulting in a hydroxyl group at the target site as illustrated in Examples 12 and corresponding scheme 12.

In some embodiments of the methods and systems herein disclosed wherein the organic molecule is a compound of Formula (V), in which $R_{14}, R_{15}, R_{17}, R_{18}$ are hydrogen, and $R_{16}$ is 2,3,4,5-tetramethoxy-tetrahydro-2H-pyranyl, activation can be performed by reacting the substrate with oxygenases such as CYP102A1var3-2 (SEQ ID NO:24), CYP102A1var3-3 (SEQ ID NO:25), CYP102A1var3-14 (SEQ ID NO:36), CYP102A1var3-15 (SEQ ID NO:37), CYP102A1var3-17 (SEQ ID NO:39), CYP102A1var3-9 (SEQ ID NO:31), resulting in a hydroxyl group at the target site as illustrated in Examples 13 and corresponding scheme 13.

In some embodiments of the methods and systems herein disclosed wherein the organic molecule is a compound of Formula (V), in which $R_{14}$=CN, $R_{15}$=6-dimethylamino-naphtyl, $R_{16}$=$R_{17}$=H, $R_{18}$=H, or hydrogen, activation can be performed by reacting the substrate with oxygenases such as CYP102A1var8 (SEQ ID NO:50) and CYP3A4 (SEQ ID NO:20), as in the case of α cyano-naphtyl ethers.

In some embodiments the organic molecule has the structure of formula (VI)

in which X is the target site C atom, and $R_{19}, R_{20}, R_{21}, R_{22}$ are independently selected from the group consisting of hydrogen, aliphatic, aryl, substituted aliphatic, substituted aryl, heteroatom-containing aliphatic, heteroatom-containing aryl, substituted heteroatom-containing aliphatic, substituted heteroatom-containing aryl, and functional groups (FG) or are taken together to form a ring representing in this case a cycloalkenyl, substituted cycloalkenyl, heteroatom-containing cycloalkenyl, or a substituted heteroatom-containing cycloalkenyl derivative.

In particular, the substituents $R_{19}$, $R_{20}$, $R_{21}$ and $R_{22}$ of formula VI are independently selected from hydrogen, $C_1$-$C_{24}$ alkyl, $C_1$-$C_{24}$ substituted alkyl, $C_1$-$C_{24}$ substituted heteroatom-containing alkyl, $C_1$-$C_{24}$ substituted heteroatom-containing alkyl, $C_2$-$C_{24}$ alkenyl, $C_2$-$C_{24}$ substituted alkenyl, $C_2$-$C_{24}$ substituted heteroatom-containing alkenyl, $C_2$-$C_{24}$ substituted heteroatom-containing alkenyl, $C_5$-$C_{24}$ aryl, $C_5$-$C_{24}$ substituted aryl, $C_5$-$C_{24}$ substituted heteroatom-containing aryl, $C_5$-$C_{24}$ substituted heteroatom-containing aryl, carbonyl, thiocarbonyl, carboxy, and substituted amino. More in particular, $R_{19}$, $R_{20}$, $R_{21}$ and $R_{22}$ are independently selected from hydrogen, $C_1$-$C_{12}$ alkyl, $C_1$-$C_{12}$ substituted alkyl, $C_1$-$C_{12}$ substituted heteroatom-containing alkyl, $C_1$-$C_{12}$ substituted heteroatom-containing alkyl, $C_2$-$C_{12}$ alkenyl, $C_2$-$C_{12}$ substituted alkenyl, $C_2$-$C_{12}$ substituted heteroatom-containing alkenyl, $C_2$-$C_{12}$ substituted heteroatom-containing alkenyl, $C_5$-$C_{14}$ aryl, $C_5$-$C_{14}$ substituted aryl, $C_5$-$C_{14}$ substituted heteroatom-containing aryl, $C_5$-$C_{14}$ substituted heteroatom-containing aryl, carbonyl, and carboxy.

Oxidizing agents known or expected to react with the target site of a compound of Formula (VI) include but are not limited to oxygenases or variants thereof.

In some embodiments, the oxygenase can be a non-heme monooxygenase or a variant thereof, a heme-containing monooxygenase or a variant thereof, a peroxygenase or a variant thereof, such as any of the heme-containing monooxygenase, non heme-containing monooxygenases and peroxugenases herein disclosed. In particular, the oxygenase can be any of the P450 monooxygenases and P450 peroxygenases herein disclosed.

In some embodiments, the oxygenase or variant thereof can be CYP102A1 (SEQ ID NO:2), CYP102A1var1 (SEQ ID NO:21), CYP102A1var2 (SEQ ID NO:22), CYP102A1var3 (SEQ ID NO:23), CYP102A1var3-18 (SEQ ID NO:40), CYP102A1var5 (SEQ ID NO:47), CYP102A1var4 (SEQ ID NO:46), CYP102A1var3-21 (SEQ ID NO:43), CYP102Avar3-22 (SEQ ID NO:44), CYP102A1var3-23 (SEQ ID NO:45), CYP102Avar9 (SEQ ID NO:51), CYP102A1var9-1 (SEQ ID NO:52), and/or toluene dioxygenase. In particular, in those embodiments at least one of said oxygenases or variants thereof is expected to activate a compound of Formula VI by introducing an oxygen-containing functional group in the form of an epoxy group. In these embodiments, the final products resulting from the application of the systems and methods herein disclosed can be ($R_{19}R_{20}C(OH)$—$CFR_{21}R_{22}$), ($R_{19}R_{20}CF$—$C(OH)R_{21}R_{22}$), or ($R_{19}R_{20}CF$—$CFR_{21}R_{22}$).

Additional Oxidizing agents that are expected to react with the target site of a compound of Formula (VI) include but are not limited to dioxygenases such as toluene dioxygenase. More specifically, dioxidizing agents are expected to activate a compound of Formula (VI) by introducing an oxygen-containing functional group in the form of a vicinal diol. In these embodiments, the final products resulting from the application of the systems and methods herein disclosed can be ($R_{19}R_{20}C(OH)$—$CFR_{21}R_{22}$), ($R_{19}R_{20}CF$—$C(OH)R_{21}R_{22}$), or ($R_{19}R_{20}CF$—$CFR_{21}R_{22}$).

In some embodiments of the methods and systems herein disclosed wherein the organic molecule is a compound of Formula (VI), in which $R_{19}$=$R_{20}$=$R_{21}$=H, $R_{22}$=n-butyl, activation through epoxidation can be performed by reacting the substrate with oxygenases such as CYP102A1var1 (SEQ ID NO; 21), CYP102A1var3-21 (SEQ ID NO; 43), CYP102A1var3-22 (SEQ ID NO; 44), CYP102A1var3-23 (SEQ ID NO; 45), resulting in the introduction of an epoxide functional group at the target site as in the case of 1-hexene.

In some embodiments of the methods and systems herein disclosed wherein the organic molecule is a compound of Formula (VI), in which $R_{19}$=$R_{20}$=$R_{21}$=H, $R_{22}$=phenyl, activation through epoxidation can be performed by reacting the substrate with oxygenases var1, CYP1A2 (SEQ ID NO; 13), CYP102A1var9 (SEQ ID NO; 51) or CYP102A1var9-1 (SEQ ID NO; 52), resulting in the introduction of an epoxide functional group at the target site as in the case of styrene.

In some embodiments of the methods and systems herein disclosed wherein the organic molecule is a compound of Formula (VI), in which $R_{19}$=$R_{21}$=H, $R_{21}$ and $R_{22}$ are connected together through 4 methylene units so to form a 6-membered ring, activation through epoxidation can be performed by reacting the substrate with oxygenases of CYP153 family, such as CYP153A6 (SEQ ID NO; 54), CYP153A7 (SEQ ID NO; 55), CYP153A8 (SEQ ID NO; 56), CYP153A11 (SEQ ID NO; 57), CYP153D2 (SEQ ID NO; 58), resulting in the introduction of an epoxide functional group at the target site as in the case of cyclohexene.

In some embodiments of the methods and systems herein disclosed wherein the organic molecule is a compound of Formula (VI), in which $R_{20}$=$R_{21}$=H, =$R_{19}$=n-pentyl, $R_{22}$=$C_{10}$C-alkenyl, activation through epoxidation can be performed by reacting the substrate with oxygenases CYP102A1 (SEQ ID NO; 2), resulting in the introduction of an epoxide functional group at the target site as in the case of linolenic acid.

In some embodiments of the methods and systems herein disclosed wherein the organic molecule is a compound of Formula (VI), in which $R_{19}$=$R_{21}$=H, $R_{20}$ and $R_{22}$ are linked together to form a 6-membered substituted or non-substituted aromatic ring, activation can be performed by reacting the substrate with toluene dioxygenase, resulting in the introduction of an oxygen-containing functional group in the form of a vicinal diol. In those embodiments, the oxygen-containing functional group will have the form of an epoxy group (C=(O)=C), that is an oxygen atom joined by single bonds to two adjacent carbon atoms so to form a three-membered ring.

In some embodiments, the oxidating agent suitable to activate an organic molecule including a target site with the methods and systems herein disclosed can be identified by (a) providing the organic molecule, (b) providing an Oxidizing agent, (c) contacting the Oxidizing agent with the organic molecule for a time and under condition to allow the introduction of an oxygen-containing functional group on the target site; (d) detecting the oxygen-containing functional group on the target site of the organic molecule resulting from step c), and repeating steps (a) to (d) until an oxygen containing functional group is detected on the target site. In particular, one or more oxidating agents can be provided under step b) of the method herein disclosed.

In particular, in embodiments wherein the organic molecule is a molecule of formula (I), (II), (III), and (IV), detecting the oxygen-containing functional group on the target site can be performed by: e) isolating of the organic molecule resulting from step c), for example by a separation method or a combination of separation methods, including but not limited to extraction, chromatography, distillation, precipitation, sublimation, and crystallization; and f) characterizing the isolated organic molecule resulting from step c) to identify the oxygen containing functional group, for example by a characterization method or a combination of methods, including but not limited to spectroscopic or spectrometric technique, preferably a combination of two or more spectroscopic or spectrometric techniques, including UV-VIS spectroscopy, fluorescence spectroscopy, IR spectroscopy, $^1$H-NMR, $^{13}$C-NMR, 2D-NMR, 3D-NMR, GC-MS, LC-MS, and MS-MS.

In particular, in embodiments wherein the organic molecule is a molecule of formula (V), detecting the oxygen-containing functional group on the target site can be performed by monitoring the removal of the —CHR$_{17}$R$_{18}$ moiety associated with the introduction of an oxygen containing functional group in the target site. In those embodiments, monitoring the removal of the —CHR$_{17}$R$_{18}$ moiety, can be performed by g) contacting the organic molecule resulting from step c) with a reagent that can react with an aldehyde (R—CHO), a ketone (R—C(O)—R), a dicarbonyl (R—C(O)—C(O)—R), or a glyoxal (R—C(O)—CHO) functional group; and h) detecting the formation of an adduct or a complex between an aldehyde, ketone, dicarbonyl, or glyoxal in the organic molecule, the aldehyde, ketone, dicarbonyl, or glyoxal resulting from the removal of the —CHR$_4$R$_5$ moiety.

Detecting the formation of an adduct or complex can be performed by spectroscopic (colorimetric, fluorimetric) or chromatographic methods and additional methods identifiable by a skilled person upon reading of the present disclosure.

Reagents that can react with an aldehyde, ketone, dicarbonyl, or glyoxal and suitable for the methods and systems described herein include but are not limited to 4-amino-3-hydrazino-5-mercapto-1,2,4-triazole-4-amino-5-hydrazino-1,2,4-triazole-3-thiol (Purpald), (pentafluorobenzyl)-hydroxylamine, p-nitrophenyl-hydrazine, 2,4-dinitrophenyl-hydrazine, 3-methylbenzothiazolin-2-one hydrazone, diethyl acetonedicarboxylate and ammonia, cyclohexane-1,3-dione and ammonia, m-phenylenediamine, p-aminophenol, 3,5-diaminobenzoic acid, p-dimethylamino-aniline, m-dinitrobenzene, o-phenylenediamine, and the like.

Figure 5:
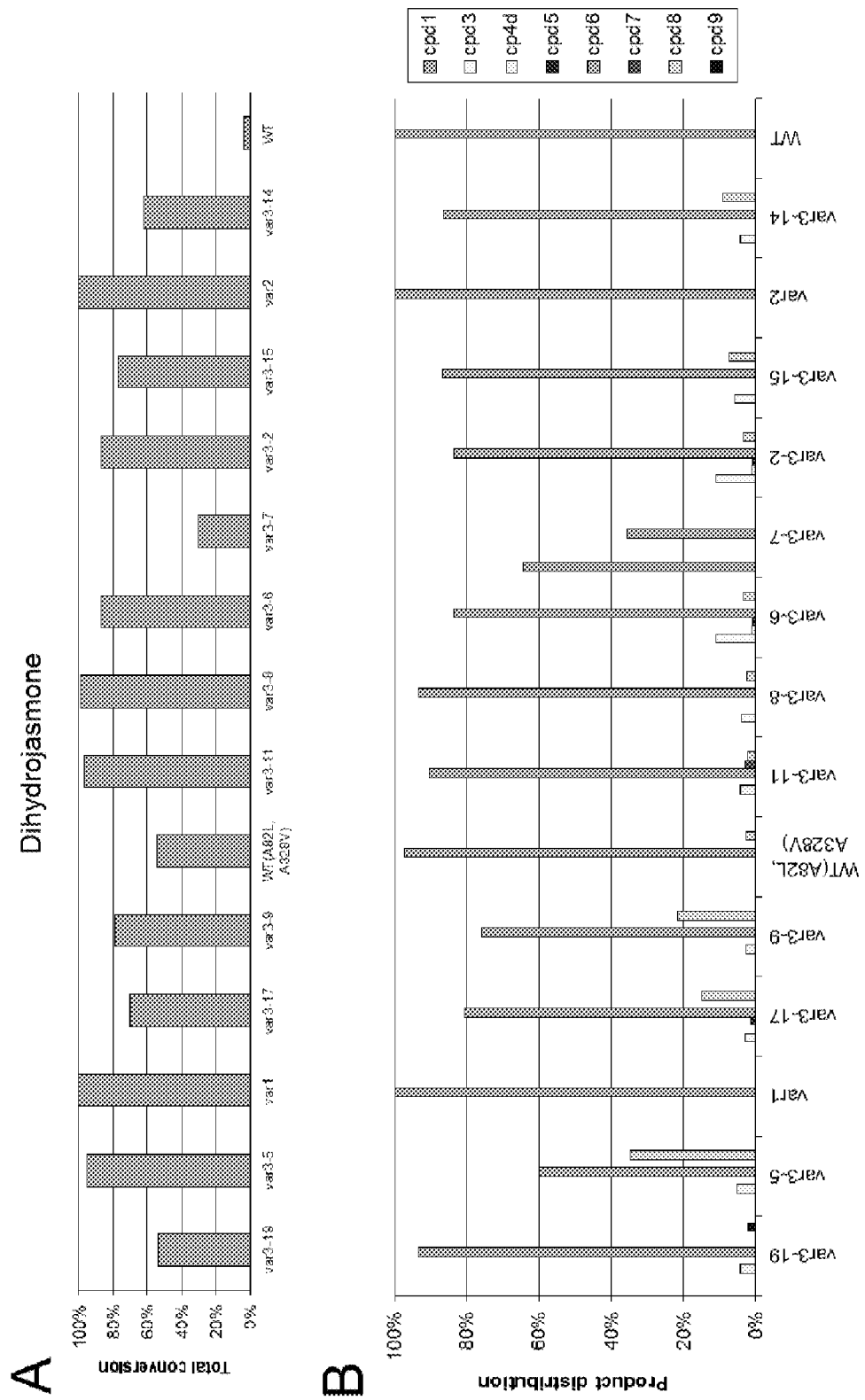
FIG. 5 illustrates exemplary results from the screening of a subset of pre-selected oxygenases for the identification of a suitable Oxidizing agent for the selective activation of the organic molecule dihydrojasmone. Panel A) is a diagram showing the conversion ratios for the reaction of activation of dihydrojasmone with wild-type $P450_{BM3}$ and variants thereof, as determined by GC analysis; Panel B) is a diagram showing the product distribution obtained with wild-type $P450_{BM3}$ and variants thereof in the reaction of activation of dihydrojasmone, as determined by GC analysis. Cpd 1 to cpd 9 indicate activated products 1 to 9.
Figure 6:
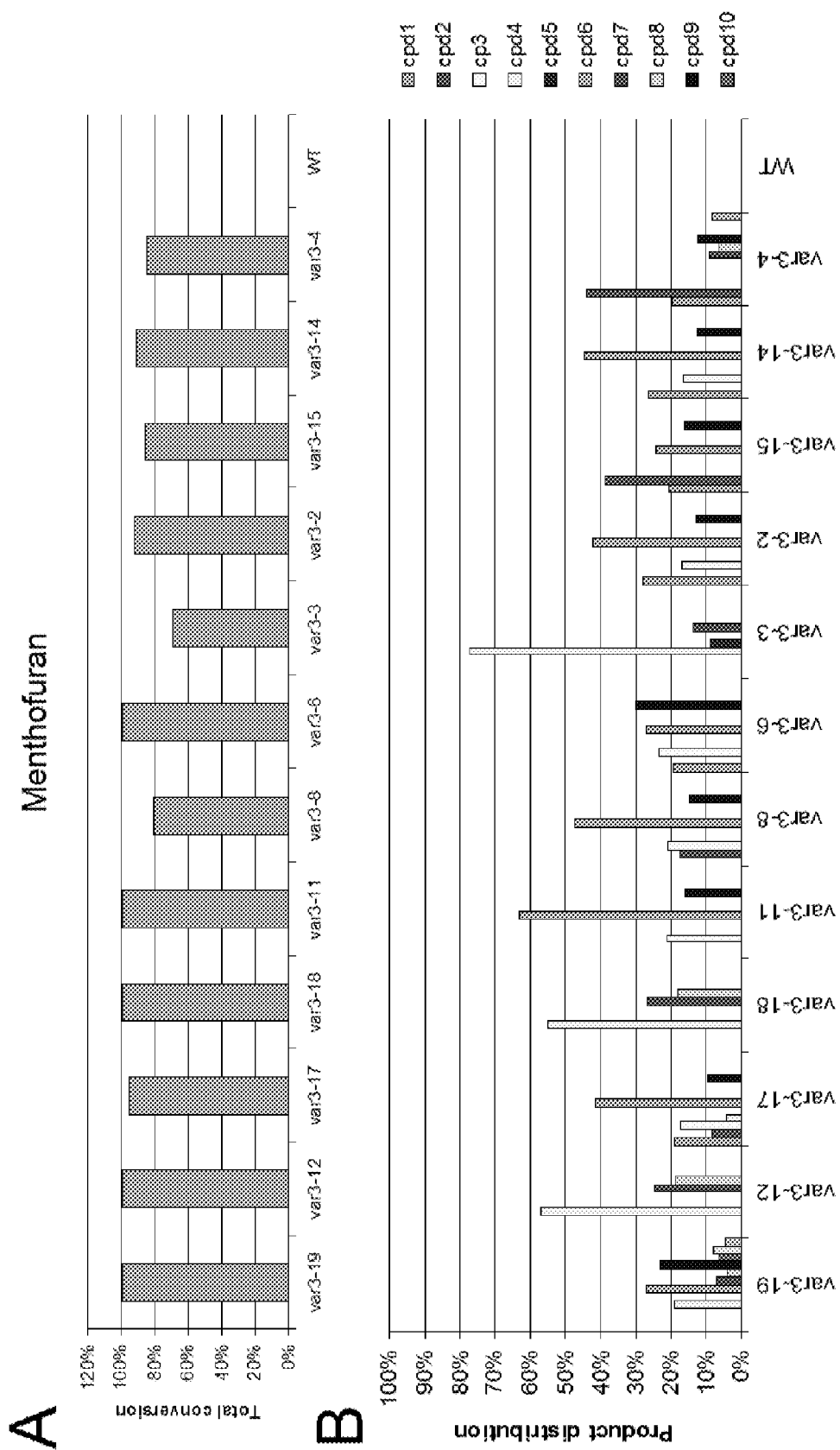
FIG. 6 illustrates exemplary results from the screening of a subset of pre-selected oxygenases for the identification of a suitable Oxidizing agent for the selective activation of the organic molecule Menthofuran; Panel A) is a diagram showing the conversion ratios for the reaction of activation of menthofuran with wild-type $P450_{BM3}$ and variants thereof, as determined by GC analysis. Panel B) is a diagram showing the product distribution obtained with wild-type $P450_{BM3}$ and variants thereof in the reaction of activation of menthofuran, as determined by GC analysis. Cpd 1 to cpd 10 indicate activated products 1 to 10.

In some embodiments, a plurality of oxidating agents can be provided to identify a suitable oxidating agent in the methods and systems herein disclosed. In particular, in some of those embodiments wherein the organic molecule is an organic molecule of general formula (I), (II), (III), (IV) and (V) a pool of Oxidizing agents, for example a library of engineered P450s, e.g. in a 96-well plate, can be provided. In particular, in embodiments wherein the organic molecule is an organic molecule of general formula (I), (II), (III) and (IV), isolating the organic molecule resulting from step c) can be performed by extracting the reaction mixture with organic solvent and characterizing the oxygen containing functional group in the organic molecule can be performed by GC analysis of the extraction solution. In some of those embodiments, selected mixtures of Oxidizing agent, and co-reagents (e.g. cofactors, oxygen) which gave rise to the largest amount of activated products for a given organic molecule, can be repeated at a larger scale. The activated products can be subsequently isolated by suitable technique including liquid chromatography and identified by $^1$H-, $^{13}$C-NMR, and MS and additional techniques identifiable by a skilled person. Examples of those embodiments is provided in the Examples section and illustrated in FIGS. 5 and 6.

In embodiments wherein the organic molecule is an organic molecule of general formula (V) wherein R$_1$ is 2-methyl-5-phenyl-4,5-dihydrooxazolyl and R$_2$=R$_3$=R$_4$=R$_5$=H, upon contacting a library of engineered P450 monooxygenases (Oxidizing agents) the oxygen containing functional group can be detected using colorimetric reagent (e.g. Purpald) and measuring the change in absorbance (e.g. at 550 nm on a microtiter plate reader). In embodiments wherein the organic molecule is an organic molecule of general formula (V) wherein R$_1$ is 2,3,4,5-tetramethoxytetrahydro-2H-pyranyl and R$_2$=R$_3$=R$_4$=R$_5$=H upon contacting a library of engineered P450 monooxygenases, the oxygen containing functional group can also using calorimetric reagent (e.g. Purpald) and measuring the change in absorbance (e.g. at 550 nm on a microtiter plate reader).

In some embodiments, the molecule is a therapeutic drug. For example, a common strategy for improving drugs' in vivo half-life involves blocking the sites in the molecule that are susceptible to attack by human P450s with fluorine substituents. The fluorination of position 2 in 15 and 18 (see below) would prevent one of the major P450-dependent routes of ibuprofen metabolism in humans. An added advantage of this approach is thus to enable fluorination of metabolically vulnerable sites in the target molecule. The methods of the disclosure find utility in the rapid identification of drug or lead compound derivatives with improved chemo-physical/biological properties as well as in the preparation of fluorinated synthons for chemical synthesis or fragment-based drug discovery programs.

In some embodiments, the isolated and characterized organic molecule that includes the oxygen-containing functional group at the target site can be used as authentic standard for high-throughput screening of other, more suitable Oxidizing agents, or improvement of reaction conditions for the activation reaction. In exemplary embodiments, high-throughput screening can be carried out performing the activation reaction in a multi-well plate, typically a 96-well or 384-well plate, each well containing the candidate organic molecule, the Oxidizing agent, and the co-reagents (e.g. cofactors, oxygen) required for the reaction to proceed, and detecting the activation of the target site using one of the following techniques, UV-VIS spectroscopy, fluorimetry, IR, LC, GC, GC-MS, LC-MS, or a combination thereof, according to the nature and properties of the candidate organic molecule and the activated product.

In some embodiments, an oxygenase that oxidizes a pre-determined organic molecule in a target site is provided by (i) providing a candidate oxygenase, (j) mutating the candidate oxygenase to generate a mutant or variant oxygenase, (k) contacting the variant oxygenase with the pre-determined organic molecule for a time and under condition to allow detection of an oxygen containing functional group on the target site, (l) detecting the introduction of the oxygen containing functional group on the target site and repeating steps (i) to (l) until formation of on oxygen containing functional group is detected.

In some embodiments, mutating the candidate oxygenase can be performed by laboratory evolutionary methods and/or rational design methods, using one or a combination of techniques such as random mutagenesis, site-saturation mutagenesis, site-directed mutagenesis, DNA shuffling, DNA recombination, and additional techniques identifiable by a skilled person. In particular, mutating a candidate oxygenase can be performed by targeting one or more of the amino acid residues comprised in the oxygenase's nucleotidic or amino acidic primary sequence to provide a mutant or variant polynucleotide or polypeptide.

In general, the term "mutant" or "variant" as used herein with reference to a molecule such as polynucleotide or polypeptide, indicates that has been mutated from the molecule as it exits in nature. In particular, the term "mutate" and "mutation" as used herein indicates any modification of a nucleic acid and/or polypeptide which results in an altered nucleic acid or polypeptide. Mutations include any process or mechanism resulting in a mutant protein, enzyme, polynucleotide, gene, or cell. This includes any mutation in which a polynucleotide or polypeptide sequence is altered, as well as any detectable change in a cell wherein the mutant polynucleotide or polypeptide is expressed arising from such a mutation. Typically, a mutation occurs in a polynucleotide or gene sequence, by point mutations, deletions, or insertions of single or multiple nucleotide residues. A mutation in a polynucleotide includes mutations arising within a protein-encoding region of a gene as well as mutations in regions outside of a protein-encoding sequence, such as, but not limited to, regulatory or promoter sequences. A mutation in a coding polynucleotide such as a gene can be "silent", i.e., not reflected in an amino acid alteration upon expression, leading to a "sequence-conservative" variant of the gene. A mutation in a polypeptide includes but is not limited to mutation in the polypeptide sequence and mutation resulting in a modified amino acid. Non-limiting examples of a modified amino acid include a glycosylated amino acid, a sulfated amino acid, a prenylated (e.g., farnesylated, geranylgeranylated) amino acid, an acetylated amino acid, an acylated amino acid, a PEGylated amino acid, a biotinylated amino acid, a carboxylated amino acid, a phosphorylated amino acid, and the like. References adequate to guide one of skill in the modification of amino acids are replete throughout the literature. Example protocols are found in Walker (1998) Protein Protocols on CD-ROM (Humana Press, Towata, N.J.).

A mutant or engineered protein or enzyme is usually, although not necessarily, expressed from a mutant polynucleotide or gene. Engineered cells can be obtained by introduction of an engineered gene or part of it in the cell. The terms "engineered cell", "mutant cell" or "recombinant cell" as used herein refer to a cell that has been altered or derived, or is in some way different or changed, from a parent cell, including a wild-type cell. The term "recombinant" as used herein with reference to a cell in alternative to "wild-type" or "native", indicates a cell that has been engineered to modify the genotype and/or the phenotype of the cell as found in nature, e.g., by modifying the polynucleotides and/or polypeptides expressed in the cell as it exists in nature. A "wild-type cell" refers instead to a cell which has not been engineered and displays the genotype and phenotype of said cell as found in nature.

The term "engineer" refers to any manipulation of a molecule or cell that result in a detectable change in the molecule or cell, wherein the manipulation includes but is not limited to inserting a polynucleotide and/or polypeptide heterologous to the cell and mutating a polynucleotide and/or polypeptide native to the cell. Engineered cells can also be obtained by modification of the cell' genetic material, lipid distribution, or protein content. In addition to recombinant production, the enzymes may be produced by direct peptide synthesis using solid-phase techniques, such as Solid-Phase Peptide Synthesis. Peptide synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer Variants of naturally-occurring sequences can be generated by site-directed mutagenesis (Botstein and Shortle 1985; Smith 1985; Carter 1986; Dale and Felix 1996; Ling and Robinson 1997), mutagenesis using uracil containing templates (Kunkel, Roberts et al. 1987; Bass, Sorrells et al. 1988), oligonucleotide-directed mutagenesis (Zoller and Smith 1983; Zoller and Smith 1987; Zoller 1992), phosphorothioate-modified DNA mutagenesis (Taylor, Schmidt et al. 1985; Nakamaye and Eckstein 1986; Sayers, Schmidt et al. 1988), mutagenesis using gapped duplex DNA (Kramer, Drutsa et al. 1984; Kramer and Fritz 1987), point mismatch, mutagenesis using repair-deficient host strains, deletion mutagenesis (Eghtedarzadeh and Henikoff 1986), restriction-selection and restriction-purification (Braxton and Wells 1991), mutagenesis by total gene synthesis (Nambiar, Stackhouse et al. 1984; Grundstrom, Zenke et al. 1985; Wells, Vasser et al. 1985)], double-strand break repair (Mandecki 1986), and the like. Additional details on many of the above methods can be found in Methods in Enzymology Volume 154, which also describes useful controls for trouble-shooting problems with various mutagenesis methods.

Additional details regarding the methods to generate variants of naturally-occurring sequences can be found in the following U.S. patents, PCT publications, and EPO publications: U.S. Pat. No. 5,605,793 to Stemmer (Feb. 25, 1997), "Methods for In vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library Immunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/13487 by Stemmer et al., "Methods for Optimization of Gene Therapy by Recursive Sequence Shuffling and Selection;" WO 00/00632, "Methods for Generating Highly Diverse Libraries;" WO 00/09679, "Methods for Obtaining in vitro Recombined Polynucleotide Sequence Banks and Resulting Sequences;" WO 98/42832 by Arnold et al., "Recombination of Polynucleotide Sequences Using Random or Defined Primers;" WO 99/29902 by Arnold et al., "Method for Creating Polynucleotide and Polypeptide Sequences;" WO 98/41653 by Vind, "An in vitro Method for Construction of a DNA Library;" WO 98/41622 by Borchert et al., "Method for Constructing a Library Using DNA Shuffling;" WO 98/42727 by Pati and Zarling, "Sequence Alterations using Homologous Recombination;" WO 00/18906 by Patten et al., "Shuffling of Codon-Altered Genes;" WO 00/04190 by del Cardayre et al. "Evolution of Whole Cells and Organisms by Recursive Recombination;" WO 00/42561 by Crameri et al., "Oligonucleotide Mediated Nucleic Acid Recombination;" WO 00/42559 by Selifonov and Stemmer "Methods of Populating Data Structures for Use in Evolutionary Simulations;" WO 00/42560 by Selifonov et al., "Methods for Making Character Strings, Polynucleotides & Polypeptides Having Desired Characteristics;" WO 01/23401 by Welch et al., "Use of Codon-Varied Oligonucleotide Synthesis for Synthetic Shuffling;" and WO 01/64864 "Single-Stranded Nucleic Acid Template-Mediated Recombination and Nucleic Acid Fragment Isolation" by Affholter.

In particular, in some embodiments, site-directed mutagenesis can be performed on predetermined residues of the oxygenase. These predetermined sites can be identified using the crystal structure of said Oxidizing agent if available or a crystal structure of a homologous protein that shares at least 20% sequence identity with said Oxidizing agent and an alignment of the polynucleotide or amino acid sequences of the Oxidizing agent and its homologous protein. The predetermined sites are chosen among the amino acid residues that are found within 50 Å, preferably within 35 Å from the oxygen-activating site of said Oxidizing agent. For example, when a cytochrome P450 monooxygenase is to be used as the Oxidizing agent, the predetermined site are chosen among the amino acid residues that are found within 50 Å, preferably within 35 Å from the heme iron. Mutagenesis of the predetermined sites can be performed changing one, two or three of the nucleotides in the codon that encodes for each of the predetermined amino acids. Mutagenesis of the predetermined sites can be performed in the described way so that each of the predetermined amino acid is mutated to any of the other 19 natural amino acids. Substitution of the predetermined sites with unnatural amino acids can be performed using methods established in vivo (Wang, Xie et al. 2006), in vitro (Shimizu, Kuruma et al. 2006), semisynthetic (Schwarzer and Cole 2005) or synthetic methods (Camarero and Mitchell 2005) for incorporation of unnatural amino acids into polypeptides.

In still further embodiments, libraries of engineered variants can be obtained by laboratory evolutionary methods and/or rational design methods, using one or a combination of techniques such as random mutagenesis, site-saturation mutagenesis, site-directed mutagenesis, DNA shuffling, DNA recombination, and the like and targeting one or more of the amino acid residues, one at a time or simultaneously, comprised in the Oxidizing agent's amino acid sequence. Said libraries can be arrayed on multi-well plates and screened for activity on the target molecule using a calorimetric, fluorimetric, enzymatic, or luminescence assay and the like. For example a method for making libraries for directed evolution to obtain P450s with new or altered properties is recombination, or chimeragenesis, in which portions of homologous P450s are swapped to form functional chimeras, can use used. Recombining equivalent segments of homologous proteins generates variants in which every amino acid substitution has already proven to be successful in one of the parents. Therefore, the amino acid mutations made in this way are less disruptive, on average, than random mutations. A structure-based algorithm, such as SCHEMA, can be used to identify fragments of proteins that can be recombined to minimize disruptive interactions that would prevent the protein from folding into its active form.

In some embodiments, activation of a target site in an organic molecule can be performed in a whole-cell system. To prepare the whole-cell system, the encoding sequence of the Oxidizing agent can be introduced into a host cell using a suitable vector, such as a plasmid, a cosmid, a phage, a virus, a bacterial artificial chromosome (BAC), a yeast artificial chromosome (YAC), or the like, into which the said sequence of the disclosure has been inserted, in a forward or reverse orientation. In some embodiments, the construct further comprises regulatory sequences, including, for example, a promoter linked to the sequence. Large numbers of suitable vectors and promoters are known to those of skill in the art, and are commercially available.

Accordingly, in other embodiments, vectors that include a nucleic acid molecule of the disclosure are provided. In other embodiments, host cells transfected with a nucleic acid molecule of the disclosure, or a vector that includes a nucleic acid molecule of the disclosure, are provided. Host cells include eucaryotic cells such as yeast cells, insect cells, or animal cells. Host cells also include procaryotic cells such as bacterial cells.

In other embodiments, methods for producing a cell that converts a target molecule into a pre-determined oxygenated derivative are provided. Such methods generally include: (a) transforming a cell with an isolated nucleic acid molecule encoding a polypeptide comprising an amino acid sequence set forth in SEQ ID NO: 2 to SEQ ID NO: 70; (b) transforming a cell with an isolated nucleic acid molecule encoding a polypeptide of the disclosure; or (c) transforming a cell with an isolated nucleic acid molecule of the disclosure.

The terms "vector", "vector construct" and "expression vector" as used herein refer to a vehicle by which a DNA or RNA sequence (e.g. a foreign gene) can be introduced into a host cell, so as to transform the host and promote expression (e.g. transcription and translation) of the introduced sequence. Vectors typically comprise the DNA of a transmissible agent, into which foreign DNA encoding a protein is inserted by restriction enzyme technology. A common type of vector is a "plasmid", which generally is a self-contained molecule of double-stranded DNA that can readily accept additional (foreign) DNA and which can readily introduced into a suitable host cell. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g., antibiotic resistance, and one or more expression cassettes.

The terms "express" and "expression" refers to allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. A polynucleotide or polypeptide is expressed recombinantly, for example, when it is expressed or produced in a foreign host cell under the control of a foreign or native promoter, or in a native host cell under the control of a foreign promoter.

Polynucleotides provided herein can be incorporated into any one of a variety of expression vectors suitable for expressing a polypeptide. Suitable vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated viruses, retroviruses and many others. Any vector that transduces genetic material into a cell, and, if replication is desired, which is replicable and viable in the relevant host can be used.

Vectors can be employed to transform an appropriate host to permit the host to express a protein or polypeptide. Examples of appropriate expression hosts include: bacterial cells, such as *E. coli, B. subtilis, Streptomyces*, and *Salmonella typhimurium*; fungal cells, such as *Saccharomyces cerevisiae, Pichia pastoris*, and *Neurospora crassa*; insect cells such as *Drosophila* and *Spodoptera frugiperda*; mammalian cells such as CHO, COS, BHK, HEK 293 br Bowes melanoma; or plant cells or explants, etc.

In bacterial systems, a number of expression vectors may be selected. depending upon the use intended for the Oxidizing polypeptide. For example, such vectors include, but are not limited to, multifunctional *E. coli* cloning and expression vectors such as BLUESCRIPT (Stratagene), in which the Oxidizing agent-encoding sequence may be ligated into the vector in-frame with sequences for the amino-terminal Met and the subsequent 7 residues of beta-galactosidase so that a hybrid protein is produced; pIN vectors; pET vectors; and the like.

Similarly, in the yeast *Saccharomyces cerevisiae* a number of vectors containing constitutive or inducible promoters such as alpha factor, alcohol oxidase and PGH may be used for production of the Oxidizing agent.

In some embodiments, the activation of the target site in an organic molecule by an oxidating agent can be performed using an immobilized Oxidizing agent. Immobilization of the Oxidizing agent can be carried out through covalent attachment or physical adsorption to a support, entrapment in a matrix, encapsulation, cross-linking of Oxidizing agent's crystals or aggregates and the like. Several immobilization techniques are known (Bomscheuer 2003; Cao 2005). The type of immobilization and matrix that preserves activity often depends on the nature and physical-chemical properties of the Oxidizing agent.

In any of the above mentioned embodiments, the oxygen-containing functional group introduced on a target site of any of the above molecules is then replaced by fluorine.

In some embodiments, the fluorination is performed by deoxofluorination of the oxygenated organic molecule.

The terms "deoxofluorination" and "deoxofluorination reaction" as used herein refer to a chemical reaction where an oxygen-containing chemical unit is replaced with fluorine. Accordingly, the terms "deoxofluorinating agent", "deoxofluorinating agent", and "deoxofluorination agent" as used herein refer to a chemical agent that is able to carry out a deoxofluorination reaction. The term "reagent" as used herein is equivalent to the term "agent".

In some embodiments, the fluorination can be performed by ring-opening fluorination of the oxygenated organic molecule.

The terms "ring-opening fluorination" and "ring-opening fluorination reaction" as used herein refer to a chemical reaction where an epoxide is reacted with a nucleophile, specifically fluoride ($F^-$) to afford a fluorohydrin (—$CFR_1$—$C(OH)R_2$—) or a vicinal difluoride-(—$CR_1F$—$CR_2F$—) containing derivative. Accordingly, the terms "ring-opening fluorination agent" and "ring-opening fluorinating agent" as used herein refer to a chemical agent that is able to carry out a ring-opening fluorination reaction.

In particular, the deoxofluorination reaction can be performed using commercially available, deoxofluorinating agents such as sulfur tetrachloride ($SF_4$), DAST (diethylaminosulfur trifluoride, (Middleton 1975), U.S. Pat. No. 3,914,265; U.S. Pat. No. 3,976,691), Deoxo-Fluor (bis-(2-methoxyethyl)-aminosulfur trifluoride, (Lal, Pez et al. 1999), U.S. Pat. No. 6,222,064), DFI (2,2-difluoro-1,3-dimethylimidazolidine, (Hayashi, Sonoda et al. 2002), U.S. Pat. No. 6,632,949), or analogues and derivatives thereof. Other deoxofluorinating agents include $XeF_2$, $SiF_4$, and $SeF_4$. The deoxofluorination reaction can be performed in the presence or in the absence of additional chemical agents that facilitate or enable the deoxofluorination to occur. These additional agents include but are not limited to hydrogen fluoride (HF), Lewis acids, fluoride salts (e.g. CsF, KF, NaF, LiF, $BF_3$), crown-ethers, ionic liquids and the like.

In particular, the ring-opening fluorination reaction can be performed using nucleophilic fluoride-containing agents including without limitations metal fluorides (e.g. CsF, KF, NaF, LiF, AgF, $BF_3$), potassium hydrogen difluoride ($KHF_2$), $Bu_4NH_2F_3$, $R_3N.nHF$, $Bu_4NF.nHF$, Py.9 HF (Olah's reagent), and the like. The ring-opening fluorination reaction can be performed in the presence or in the absence of additional chemical agents that facilitate or enable the deoxofluorination to occur. These additional agents include but are not limited to hydrogen fluoride (HF), Lewis acids, fluoride salts (e.g. CsF, KF, NaF, LiF), crown-ethers, ionic liquids and the like Exemplary fluorinations of an organic molecule containing an oxygen-containing group include but are not limited to conversion of a hydroxyl group to a fluoride, a carboxylic acid group to a carbonyl fluoride, an aldehyde group to a gem-difluoride, a keto group to a gem-difluoride, an epoxide group to a fluorohydrin (also called vic-fluoro-alcohol), an epoxide group to a vic-difluoride.

Exemplary products produced by methods and systems herein disclosed comprise fluorinated derivatives of organic molecules which include 2-aryl-acetate esters, dihydrojasmone, menthofuran, guaiol, permethylated mannopyranoside, methyl 2-(4'-(2"-methylpropyl)phenyl)propanoate and a 5-phenyl-2-oxazoline.

Specifically, the methods and systems herein disclosed have been applied to produce methyl 2-fluoro-2-phenylacetate, ethyl 2-fluoro-2-phenylacetate, propyl 2-(3-chlorophenyl)-2-fluoroacetate, propyl 2-fluoro-o-tolylacetate, and propyl 2-fluoro-p-tolylacetate starting from corresponding 2-aryl-acetate esters; 4-fluoro-3-methyl-2-pentylcyclopent-2-enone, 4,4-difluoro-3-methyl-2-pentylcyclopent-2-enone, and 3-(fluoromethyl)-2-pentylcyclopent-2-enone, starting from dihydrojasmone; methyl 2-(4'-(1"-fluoro-2"-methylpropyl)phenyl)propanoate and methyl 2-(4'-(2"-fluoro-2"-methylpropyl)phenyl)propanoate, starting from methyl 2-(4'-(2"-methylpropyl)phenyl)propanoate; 6-fluoro-menthofuran-2-ol from menthofuran; 2-((3S,5S,8S)-4-fluoro-3,8-dimethyl-1,2,3,4,5,6,7,8-octahydroazulen-5-yl) propan-2-ol from (−)-guaiol; 6-fluoro-6-deoxy-1,2,3,4-tetramethyl-mannopyranoside starting from 1,2,3,4,6-pentamethyl-mannpyranoside; (4R,5S)-4-(fluoromethyl)-2-methyl-5-phenyl-4,5-dihydrooxazole, starting from (4S,5S)-4-(methoxymethyl)-2-methyl-5-phenyl-4,5-dihydrooxazole.

More specifically, the methods and systems herein disclosed have been applied to fluorinate a target site, namely a C carbon atom, in a highly regioselective manner despite the presence of other similar moieties in the molecule, as in the case of 1,2,3,4,6-pentamethyl-mannopyranoside.

Even more specifically, the methods and systems herein disclosed have been applied to fluorinate target organic molecules, namely 2-aryl-acetate esters, in a highly stereoselective manner, leading to the formation of the (R)-fluoro enantiomer in considerable excess over the (S)-fluoro enantiomer.

The above mentioned fluorinated products are or can be associated with a biological activity or can be used for the synthesis of chemical compounds that are or can be associated with a biological activity.

2-fluoro-2-phenylacetate derivatives find potential applications in the synthesis of prodrugs, in particular in the preparation of ester-type anticancer prodrugs with different susceptibility to hydrolysis, which can be useful in selective targeting of cancer cells (Yamazaki, Yusa et al. 1996). 2-(4'-(2"-methylpropyl)phenyl)propionate also known as ibuprofen is a marketed drug of the class non-steroidal anti-inflammatory drugs (NSAIDs). This drug has ample application in the treatment of arthritis, primary dysmenorrhoea, fever, and as an analgesic, especially in the presence of inflammation process. Ibuprofen exerts its analgesic, antipyretic, and anti-inflammatory activity through inhibition of cyclooxygenase (COX-2), thus inhibiting prostaglandin synthesis. More recently, ibuprofen was found to be useful in the prophylaxis of Alzheimer's disease (AD) (Townsend and Pratico 2005). The anti-AD activity of ibuprofen is presumably due to its ability to lower the levels of amyloid-beta (A beta) peptides, in particular the longer, highly amyloidogenic isoform A beta 42, which are believed to be the central disease-causing agents in Alzheimer's disease (AD). There is therefore a growing interest towards the discovery of A beta 42-lowering compounds with improved potency and brain permeability (Leuchtenberger, Beher et al. 2006). Unlike other NSAIDs, ibuprofen was also found to be useful in protection against Parkinson's disease, although the underlying mechanism is not yet known (Casper, Yaparpalvi et al. 2000).

Dihydrojasmone incorporates a cyclopentenone structural unit. The cyclopentanone and cyclopentenone scaffolds are present in a wide range of important natural products such as jasmonoids, cyclopentanoid antibiotic, and prostaglandins. This type of compound has a broad spectrum of biological activities and important application in medicinal chemistry as well as in the perfume and cosmetic industry, and agriculture. Despite their relatively simple structures, the synthesis of these scaffolds is not trivial (Mikolajczyk, Mikina et al. 1999). Therefore, novel routes for functionalization (and specifically in the context of the disclosure, fluorination) of these scaffolds and compounds incorporating these scaffolds would be highly desirable.

Guaiol is a sesquiterpene alcohol having the guaiane skeleton, found in many medicinal plants. The essential oils of *Salvia lanigera* and *Helitta longifoliata*, which both contain guaiol as a major component, were found to possess pronounced antibacterial activity (De-Moura, Simionatto et al. 2002). Structural modification of naturally-occurring bioactive substances by conventional chemical methods is very difficult and often not feasible. Accessible methods to produce derivatives of these natural products (and specifically in the context of this disclosure, fluorinated derivatives) would be highly desirable.

Furans and 2-(5H)-furanones are attractive building blocks being present in a large number of natural products that display a wide range of biological activities, and being present in a number of drugs with biologically relevant properties, such as antifungal, antibacterial and anti-inflammatory activities (Knight 1994; De Souza 2005). Many methods are available for their synthesis. However, strategies for post-synthetic functionalization (and specifically in the context of the disclosure, fluorination) of these scaffolds and compounds incorporating these scaffolds would be highly desirable.

Embodiments, wherein methods for selective fluorination of protected hydroxyl groups in the form of $R_1$—O—$CHR_2R_3$ are performed where the resulting product is $R_1$—F is expected to expand our current synthetic capabilities and facilitate the synthesis of fluorinated compounds that bear multiple hydroxyl functional groups as well as the synthesis of compounds that incorporate chemical units or structural features that are uncompatible with the currently available methods for protection/deprotection of hydroxyl groups (Green and Wuts 1999). The protection of hydroxyl groups with alkyl groups different from methoxymethyl (MOM), tetrahydropyranyl (THP), allyl, and benzyl (Bn) is rarely used in practice, if ever, due to the requirement of harsh chemical reagents and conditions for their removal (e.g. strong Lewis acids in the case of a methoxy group). These chemical reagents are poorly chemoselective, reacting with any nucleophilic group of the molecule. Chemical methods for regioselective substitution, and more specifically fluorination, of a single protected hydroxyl functional group in the presence of multiple identically protected hydroxyl groups are not available.

In some embodiments, activation and fluorination of the organic molecules can be performed as it follows.

The activation reaction can be carried out in aqueous solvent containing variable amounts of organic solvents to facilitate dissolution of the organic molecule in the mixture. The co-solvents include but are not limited to alcohols, acetonitrile, dimethyl sulfoxide, dimethylformamide, acetone. The one or more Oxidizing agents can be present as free in solution or inside a cell where its expression has been achieved using a plasmid vector or other strategies as described earlier. The reaction can be carried out in batch, semicontinuously or continuously, in air or using devices to flow air or oxygen through the solution, at autogeneous pressure or higher. The reaction temperature will generally be in the range of 0° C. and 100° C., depending on the nature and stability of the biocatalysts and substrates, preferably in the range of about 4° C. and 30° C. The amount of biocatalyst is generally in the range of about 0.01 mole % to 10 mole %, preferably in the range of about 0.05 mole % to 1 mole %. The cofactor (NADPH) can be added directly, regenerated using an enzyme-coupled system (typically dehydrogenase-based), or provided by the host cell. Reducing equivalent to the biocatalysts can be provided though the use of an electrode or chemical reagents. Superoxide dismutase, catalase or other reactive oxygen species-scavenging agents, can be used to prevent biocatalyst inactivation and improve the yields of the activation reaction. Glycerol, bovine serum albumine or other stabilizing agents can be used to prevent biocatalyst aggregation and improve the yields of the activation reaction.

After the activation reaction, the activated products may or may not be isolated through any of the following methods or combination thereof: extraction, distillation, precipitation, sublimation, chromatography, crystallization with optional seeding and/or co-crystallization aids.

The activated products are then contacted with the fluorinating agent in the presence or the absence of an organic solvent under inert atmosphere. The activated products can be reacted in the form of isolated compound, purified compound, partially-purified mixtures or crude mixtures. No particular restriction is imposed upon the solvent of the reaction as long as the solvent does not react with the fluorination reagent, enzymatic product, or reaction product.

Solvents that can be used in the fluorination reaction include, but are not restricted to, dichloromethane, pyridine, acetonitrile, chloroform, ethylene dichloride, 1,2-dimethoxyethane, diethylene glycol dimethyl ether, N-methylpyrrolidone, dimethylformamide, and 1,3-dimethyl-2-imidazolidinone, preferably dichloromethane or pyridine. The reaction temperature will generally be in the range of −80° C. to 150°

C., preferably in the range of about −78° C. and 30° C. The amount of the fluorination reagent is preferably 1 equivalent or more for oxygen atom introduced in the molecular scaffold of the organic molecule during the enzymatic reaction. After completion of the reaction, the fluorinated products are isolated through any of the following methods or combination thereof: extraction, distillation, precipitation, sublimation, chromatography, crystallization with optional seeding and/or co-crystallization aids.

An advantage of the methods and systems is the possibility to perform fluorination of predetermined target sites in a candidate organic molecule. A further advantage is that subjecting the activated product or the fluorinated derivative to the action of the same Oxidizing agent used for its preparation or another Oxidizing agent, polyfluorination of the molecule at the same or another predetermined target site can be achieved. A further advantage is that the mono- and/or poly fluorination of predetermined target sites in a candidate organic molecule can be carried out under mild conditions (room temperature and pressure), with limited use of hazardous chemical and toxic solvents, in a chemoselective, regioselective, and stereoselective manner.

An additional advantage of the methods and systems herein disclosed is the possibility to carry out fluorination of nonreactive sites of a candidate organic molecule, that is sites that would could not be easily functionalized using chemical reagents or would react only after or concurrently to other, more reactive sites of the molecule.

A further advantage of the methods and systems herein disclosed is the possibility to produce fluorinated derivatives of candidate organic molecules with an established or potentially relevant biological activity in only two steps. This "post-synthetic" transformation represents a considerable advantage compared to synthesis of the same derivative or derivatives starting from fluorine-containing building blocks which may or may not be available, thus requiring numerous additional synthetic steps. For example, the described methyl 2-(4'-(1"-fluoro-2"-methylpropyl)phenyl)propanoate, methyl 2-(4'-(2"-fluoro-2"-methylpropyl)phenyl)propanoate, and methyl 2-(4'-(1",1"-difluoro-2"-methylpropyl)phenyl)propanoate prepared according to the methods and systems herein disclosed could be conceivably synthesized using (1-fluoro-2-methylpropyl)benzyl, (2-fluoro-2-methylpropyl)benzyl, (1,1-difluoro-2-methylpropyl)benzyl derivatives, which however are not commercially available and therefore need to be prepared from row material through several chemical steps.

A further advantage of the methods and systems herein disclosed is the possibility to produce fluorinated derivatives of a candidate organic molecule at a preparative scale, obtaining from a minimum of 10 up to hundreds milligrams of the final fluorinated product with overall yields (after isolation) of up to 80%. These quantities and yields enable the evaluation of the biological, pharmacological, and pharmacokinetic properties of said products as well as their use in further synthesis of more complex molecules.

An additional advantage of the methods and systems herein disclosed is the possibility to substitute protected hydroxyl groups in the form of $R_1$—O—$CHR_2R_3$ for fluorine. A further advantage is that the substitution of protected hydroxyl group for fluorine can be carried out under mild conditions (room temperature and pressure), with limited use of hazardous chemical and toxic solvents, in a chemoselective and regioselective manner.

Classes of molecules that can be potentially obtained using the methods and systems herein disclosed include but are not limited to α-fluoro acid derivatives, fluoro-alkyl derivatives, fluoro-allyl derivatives, fluorohydrins, vic- and gem-difluoride derivatives.

Classes of molecules that can be potentially obtained in enantiopure form using the methods and systems herein disclosed include but are not limited to α-fluoro acid derivatives, fluoro-alkyl derivatives, fluoro-allyl derivatives, and fluorohydrins.

In general, the methods and systems herein disclosed, in contrast to previously known synthetic methods, provide a simple, environmentally benign, two-step procedure for regio- and stereospecific incorporation of fluorine in a wide variety of organic compounds both at reactive and non-reactive sites of their molecular scaffold. Particularly, it will be appreciated that methods and systems herein disclosed procedure gives access to organofluorine derivatives, whose preparation through alternative routes would require many more synthetic steps and much higher amounts of toxic reagents and organic solvents.

Accordingly, the methods and systems herein disclosed have utility in the field of organic chemistry for preparation of fluorinated building blocks and in medicinal chemistry for the preparation or discovery of fluorinated derivatives of drugs, drug-like molecules, drug precursors, and chemical building blocks with altered or improved physical, chemical, pharmacokinetic, or pharmacological properties.

In particular, in some embodiment of the methods and systems herein disclosed, the organic molecules are pre-selected among molecules of interest, such as drugs, drug precursors, lead compounds, and synthetic building blocks. The term "drug" as used herein refer to a synthetic or non-synthetic chemical entity with established biological and/or pharmacological activity, which is used to treat a disease, cure a disfunction, or alter in some way a physiological or non-physiological function of a living organism. Lists of drugs can be easily found in online databases such as www.accessdata.fda.gov, www.drugs.com, www.rxlist.com, and the like. The term "drug precursor" as used herein refers to a synthetic or non-synthetic chemical entity which can be converted into a drug through a chemical or biochemical transformation. The conversion of a drug precursor into a drug can also occur after administration, in which case the drug precursor is typically referred to as "prodrug". Accordingly, any synthetic or semi-synthetic intermediate in the preparation of a drug can be considered a drug precursor. The term "lead compound" as used herein refers to a synthetic or non-synthetic chemical entity that has pharmacological or biological activity and whose chemical structure is used as a starting point for chemical modifications in order to improve potency, selectivity, or pharmacokinetic parameters. Lead compounds are often found in high-throughput screenings ("hits") or are secondary metabolites from natural sources. Reports on the discovery and/or identification of lead compounds for various applications are widespread in the scientific literature and in particular in specialized journals such as *Journal of medicinal chemistry, Bioorganic & medicinal chemistry, Current medicinal chemistry, Current topics in medicinal chemistry, European Journal of Medicinal Chemistry, Mini reviews in medicinal chemistry*, and the like. The term "synthetic building blocks" as used herein refer to any synthetic or non-synthetic chemical entity that is used for the preparation of a structurally more complex molecule.

Upon fluorination of the target site of the pre-selected molecule, the fluorinated organic molecules produced can be further used in the synthesis of more complex molecules, or, in addition, or in alternative, being tested for biological activities.

Figure 4A:
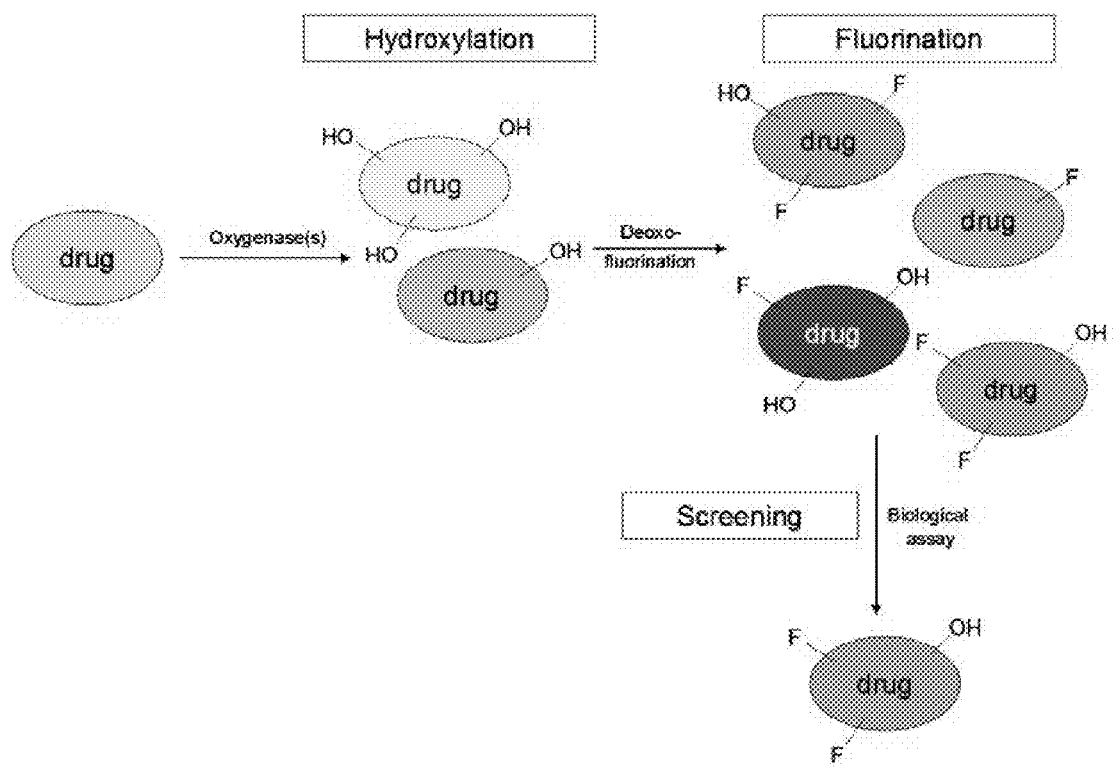
FIG. 4 is a schematic representation of methods and system for identifying a molecule having a biological activity according to an embodiment disclosed in the present specification.
Figure 4B:
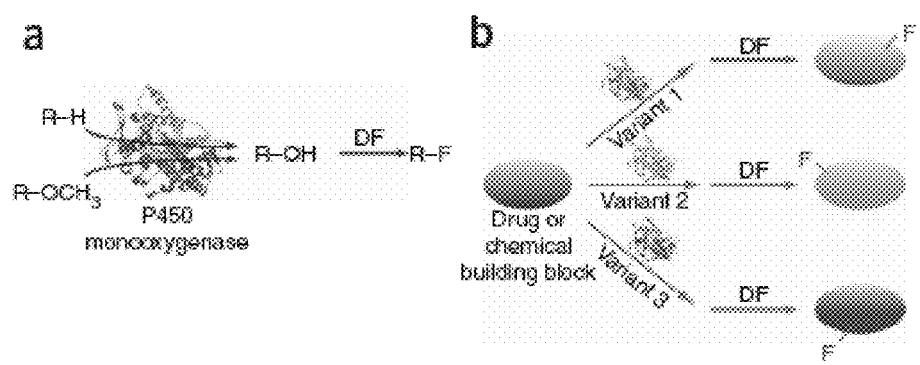

In particular, in any embodiment, wherein identification of a an organic molecule having a predetermined biological activity is desired, the methods and systems herein disclosed further comprise testing the fluorinated organic molecule for the desired biological activity. Testing can in particular be performed by screening the products of the reaction by the methods and systems illustrated in FIG. 4 in form of mixture or as isolated compound for altered or improved metabolic stability, biological activity, pharmacological potency, and pharmacokinetic properties. This approach couples the exceptional ability of cytochrome P450 monooxygenases to selectively insert oxygen into non reactive C—H bonds with a deoxofluorination (DF) reaction in which the newly generated hydroxyl group is substituted by fluorine by means of a nucleophilic fluorinating reagent (FIG. 4B).

The wording "biological activity" as used herein refers to any activity that can affect the status of a biological molecule or biological entity. A biological molecule can be a protein or a polynucleotide. A biological entity can be a cell, an organ, or a living organism. The wording "pharmacological activity" as used herein refers to any activity that can affect and, generally but not necessarily, improve the status of a living organism.

In embodiments where identification of a molecule having pharmacological activity is desired, use of P450 as Oxidizing agents is particularly preferred, since Phase I drug metabolism in humans is mainly dependent on P450s. In this connection, one clear advantage of the methods and systems herein disclosed is that they allow for protection through fluorination of sites in the molecule that are sensitive to P450 hydroxylation attack.

A further advantage of the methods and systems herein described for the identification of a molecule having biological activity compared to corresponding strategies known in the art for producing fluorinated drugs (which mainly rely on the use of fluorinated building blocks), is that the methods herein disclosed can be carried out post-synthetically. As a consequence, the method herein disclosed can be broadly applied to produce oxygenated/fluorinated derivatives starting from marketed drugs, drugs in advanced testing phase, lead compounds, or screening hits.

Additionally, a pre-selection of organic molecules of interest and/or related fluorinated products can be made on the basis of the ability of fluorine atoms to improve dramatically the pharmacological profile of drugs. In particular, this can be done in view of several studies have shown that potent drugs can be obtained through fluorination of much less active precursors. Anticholesterolemic Ezetimib (Clader 2004), anticancer $CF_3$-taxanes (Ojima 2004), fluoro-steroids, and antibacterial fluoroquinolones are only some representative examples. The improved pharmacological properties of fluoro-containing drugs are due mainly to enhanced metabolic stability (Park, Kitteringham et al. 2001). Primary metabolism of drugs in humans generally occurs through P450-dependent systems, and the introduction of fluorine atoms at or near the sites of metabolic attack has often proven successful in increasing the half-life of a compound (Bohm, Banner et al. 2004).

In some cases, the introduction of fluorine substituents leads to improvements in the pharmacological properties as a result of enhanced binding affinity of the molecule to biological receptors. Examples of the effect of fluorine on binding affinity are provided by recent results in the preparation of NK1 antagonists (Swain and Rupniak 1999), $5HT_{1D}$ agonists (van Niel, Collins et al. 1999), and PTB1B antagonists (Burke, Ye et al. 1996).

Accordingly, with the methods and system herein disclosed production of various oxygenated/fluorinated products was expected starting from a given drug or a drug-like molecule, for example a 'lead' compound identified in a drug-discovery program.

In an embodiment of the methods and systems, an array of oxygenases (P450 monooxygenases, non-heme iron monooxygenases, dioxygenases and peroxygenases) can be used to produce various mono- and poly-oxygenated compounds. Some of these products can be isolated and subjected to fluorination, e.g. deoxo-fluorination, where all or a subset of the introduced oxygen-containing functional groups are substituted for fluorine. The resulting products can then be separated and tested for improved biological properties.

EXAMPLES

The present disclosure is further illustrated in the following examples, which are provided by way of illustration and are not intended to be limiting.

The following experiments have been carried out to perform chemo-enzymatic fluorination approach according to embodiments of the methods and systems herein disclosed.

First, a set of organic molecules has been selected, from which potentially useful fluorinated products can be obtained.

These compounds include: (a) 2-aryl acetic acid derivatives, as demonstrative examples of useful synthetic blocks, for example in the preparation of prodrugs with different susceptibility to hydrolysis. With the systems and methods herein described, stereoselective fluorination of the alpha position of these target molecules was achieved, affording 2-fluoro-2-aryl acetic acid derivatives in considerable enantiomeric excess; (b) ibuprofen methyl ester, as demonstrative example of a marketed drug, of which more potent and BBB (blood-brain-barrier)-penetrating derivatives are sought after for treatment of Alzheimer's and Parkinson's diseases. With the systems and methods herein described, regioselective fluorination of weakly reactive sites of this target molecule was achieved, affording various C—F derivatives; (c) dihydrojasmone, menthofuran, and guaiol, as demonstrative examples of various molecular scaffolds that are present in several natural, synthetic, and semisynthetic biologically active molecules. With the systems and methods herein described, regioselective fluorination of weakly reactive sites of these target molecules was achieved, affording various C—F derivatives; (d) dihydro-4-methoxymethyl-2-methyl-5-phenyl-2-oxazoline, as demonstrative example for chemoselective substitution of methoxygroup for fluorine. With the systems and methods herein described, fluorination of the methoxy protected group in the target molecules was achieved, affording a demethoxy-fluoro derivative; (e) permethylated mannopyranoside as demonstrative example for regioselective substitution of a specific methoxy group for fluorine in the presence of several other identical groups in the molecule. With the systems and methods herein described, regioselective fluorination of the methoxy protected group in position 6 of the target molecule was achieved, affording a 6-demethoxy-fluoro derivative.

A pool of Oxidizing agents, comprising wild-type $P450_{BM3}$ (CYP102A1), variants of wild-type $P450_{BM3}$ carrying one or more mutations at the positions 25, 26, 42, 47, 51, 52, 58, 64, 74, 75, 78, 81, 82, 87, 88, 90, 94, 96, 102, 106, 107, 108, 118, 135, 138, 142, 143, 145, 152, 172, 173, 175, 178, 180, 181, 184, 185, 188, 197, 199, 205, 214, 226, 231, 236, 237, 239, 252, 255, 260, 263, 264, 265, 267, 268, 273, 274, 275, 290, 295, 306, 324, 328, 354, 366, 398, 401, 430, 433, 434, 437, 438, 442, 443, 444, and 446, and a selection of the most active P450 chimera peroxygenases and monooxygenases from the libraries described in Otey et al. (Otey, Landwehr et al. 2006) and Landwehr et al. (Landwehr, Carbone et al. 2007) were arrayed on 96-well plates. Arrays were prepared by growing recombinant *E. coli* transformed with an expression plasmid encoding for the P450 sequence, inducing protein expression with IPTG, and preparing a cell lysate.

The activation reaction of the pre-selected organic molecules ibuprofen methyl ester, menthofuran, dihydrojasmone, and guaiol with the pool of pre-selected Oxidizing agents was tested at a 1-mL scale dissolving the organic molecule in phosphate buffer (1% ethanol) at a final concentration of 2 mM. The Oxidizing agent was then added to the solution at a final concentration of about 200-400 nM. The reaction was started by adding NADPH and a glucose-6-phosphate dehydrogenase cofactor regeneration system to the mixture. After 20 hrs incubation at room temperature, the reactions were extracted with chloroform and analyzed by gas chromatography. Total conversion ratios were calculated including in the experiment a sample containing no enzyme and adding an internal standard to the samples. The 20-30% most promising Oxidizing agents were re-tested at a larger scale (3 mL) to identify false positives and determine regioselectivity and product distribution. Exemplary results from the screening of the pool of P450s on dihydrojasmone and menthofuran are reported on FIGS. 5 and 6.

A group of about 5 to 10 most interesting Oxidizing agents were then selected based on the results from the re-screen, in particular based on their regioselectivity, conversion efficiency, or ability to produce "rare" activated product. Using the selected Oxidizing agents, conditions for the activation reaction were optimized, testing different co-solvents (e.g. ethanol, ethylacetate), additives (e.g. BSA, glycerol), ROS (Reactive oxygen species) scavengers (e.g. SOD, catalase), temperature, and target molecule:Oxidizing agent ratios. Once optimized, the activation reaction was scaled up to 100-300 mL reaction scale, where the Oxidizing agent concentration typically ranged from 0.5 to 15 µM, the target molecule concentration from 5 to 20 mM, and a cofactor regeneration system was used. The co-solvent was usually ethanol, typically at a final concentration of 0.5% to 2%.

Large scale reactions were incubated under stirring at room temperature for a period of time of up to 56 hours, during which target molecule conversion was monitored by extracting small aliquots of the reaction mixture and analyzing them by gas chromatography.

As the desired amount of activated product was produced, the reaction mixture was extracted with an organic solvent, typically chloroform, and the activated product was isolated by silica gel chromatography using hexane:ethyl acetate gradient. Purified products were identified using GC-MS, $^1$H-, and $^{13}$C-NMR.

Once the product with the activated target site was identified, the activated product was subjected to fluorination using the deoxo-fluorinating agent DAST in dichloromethane. Different reaction conditions were typically tested to optimize yield and possibly achieve quantitative conversion. During these tests, the conversion of the activated product to the corresponding fluorinated derivative was typically monitored by GC-MS.

After the fluorination reaction, the fluorinated product was isolated by silica gel chromatography using a hexane:ethyl acetate gradient. The identity of the purified product was confirmed by GC-MS, HR-MS, $^1$H-, $^{13}$C-, and $^{19}$F-NMR.

The pool of pre-selected Oxidizing agents and other selected variants from mutagenesis libraries of var3-10—i.e. libraries where positions 74, 82, 87, 88, and 328 position of var3-10 were subjected to saturation mutagenesis—were screened for activity towards activation of the pre-selected organic molecules dihydro-4-methoxymethyl-2-methyl-5-phenyl-2-oxazoline (MMPO) and 1,2,3,4,6-pentamethyl mannopyranoside using a calorimetric assay on a 96-well plate format. In the case of MMPO, for example, different Oxidizing agents were arrayed on a 96-well plate, each well containing about 150 µL phosphate buffer and about 1 µM Oxidizing agent. The target molecule was added to the solution from an ethanol stock to a final concentration of 2 mM (and 1% ethanol). After addition of 1 mM NADPH, the reaction mixture was incubated for 30 minutes at room temperature. After incubation, MMPO activation activity was determined using the calorimetric reagent Purpald (Sigma), which reacts with formaldehyde and serves in this case to detect the demethylation of the methoxy group in the target molecule. Positive 'hits' were re-tested on a 1-mL scale using 1 mM MMPO, 0.5 µM Oxidizing agent, 1 mM NADPH, and a cofactor regeneration system. After incubation at room temperature, the reaction mixtures were extracted with chloroform and analyzed by gas chromatography. In this way, the regioselectivity and conversion efficiency of each Oxidizing agent was established. The identity of the activated product was also confirmed by GC-MS. Most promising Oxidizing agents, that is those showing highest regioselectivity and/or conversion efficiency, were used for scale-up tests and for producing larger quantities of activated product for the fluorination reaction as described above. Representative results from the screening of the P450 pool for MMPO activation activity are reported on FIG. 7.

Figure 8:
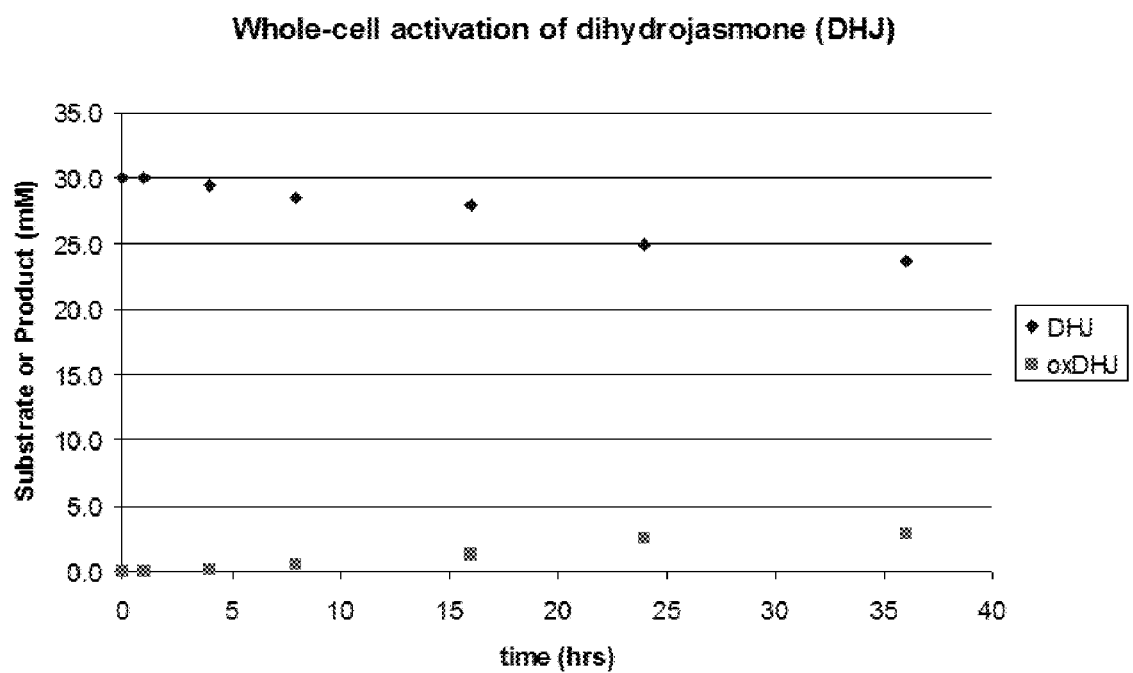
FIG. 8 shows a diagram illustrating the time course for whole-cell activation of the organic molecule dihydrojasmone (DHJ) using batch culture of var3-expressing *E. coli* DH5α cells (0.5 L). The consumption of substrate (DHJ) and the accumulation of the desired activated product (oxDHJ) were monitored over time by GC analysis of aliquots of the cell culture.

The activation of the target molecule dihydrojasmone was also carried out using a whole-cell system (FIG. 8). Specifically, the whole-cell system consisted of *E. coli* DH5a cells transformed with a pCWori vector that contains the sequence for var3. The whole-cell activation reaction was carried out growing a 0.5 L culture of the recombinant cells in TB medium, inducing the intracellular expression of var3 during mid-log phase by adding 0.5 mM IPTG, and growing the cells at 30° C. for further 12 hours. After that, 15 mL dodecane were added to the culture. Dihydrojasmone was then added to the culture at a final concentration of 30 mM. Formation of the activated product and consumption of the target molecule were monitored by gas chromatography for up to 36 hours. Conversion ratio at the end of the 36 hours amounted to ~10%. Higher conversion ratios (>90-95%) were achieved in vitro with the same variant using a cofactor regeneration system. The lower efficiency of the whole-cell system in the case of dihydrojasmone may be attributed to potential toxicity of this molecule or its activated product to the cells as well as their low membrane permeability. Nevertheless, this experiment demonstrates that the activation of the target molecule for the scope of the systems and methods herein described can also be performed using a whole-cell, especially in cases where the chemo-physical properties of the candidate molecule may make this option more favorable.

Chemical reagents, substrates and solvents were purchased from Sigma, Aldrich, and Fluka. Silica gel chromatography purifications were carried out using AMD Silica Gel 60 230-400 mesh. Gas chromatography (GC) analyses were carried out using a Shimadzu GC-17A gas chromatograph, a FID detector, and an Agilent HP5 column (30 m×0.32 mm×0.1 µm film). Chiral GC analyses were carried out using a Shimadzu GC-17A gas chromatograph, a FID detector, and an Agilent Cyclosilb column (30 m×0.52 mm×0.25 µm film). GC-MS analyses were carried out on a Hewlett-Packard 5970B MSD with 5890 GC and a DB-5 capillary column. $^1$H, $^{13}$C, and $^{19}$F NMR spectra were recorded on a Varian Mercury 300 spectrometer (300 MHz, 75 MHz, and 282 MHz, respectively), and are internally referenced to residual protio solvent signal. Data for $^1$H NMR are reported in the conventional form: chemical shift (δ ppm), multiplicity (s=singlet, d=doublet, t=triplet, q=quartet, m=multiplet, br=broad), coupling constant (Hz), integration, and assignment). Data for $^{13}$C NMR are reported in the terms of chemical shift (δ ppm). Data for $^{19}$F NMR are reported in the terms of chemical shift (δ ppm) and multiplicity. High-resolution mass spectra were obtained with a JEOL JMS-600H High Resolution Mass Spectrometer at the California Institute of Technology Mass Spectral facility.

Example 1

Stereoselective fluorination of methyl 2-phenyl acetate

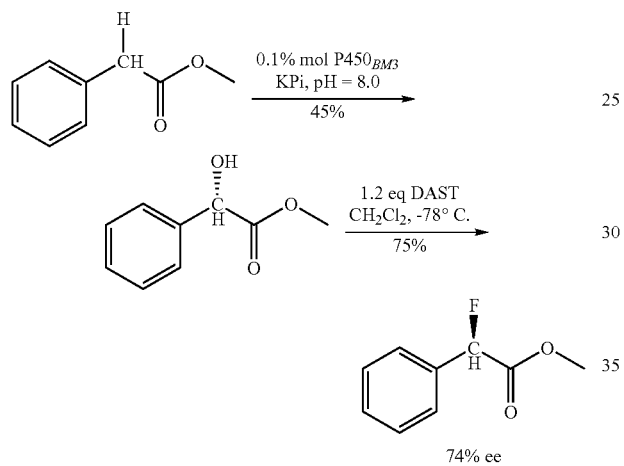

Scheme 1.

74% ee

Methyl 2-phenyl acetate was subjected to selective fluorination of the target site C (alpha position) according to the systems and methods herein disclosed and, more specifically, according to the general procedure described above.

Experimental description: 90 mg methyl 2-phenyl acetate were dissolved in 500 µL ethanol and added to 240 mL potassium phosphate buffer pH 8.0. P450$_{BM3}$ was added to the mixture at a final concentration of 2 µM. The mixture was split in 4 mL aliquots into 15 mL scintillation vials equipped with a stir bar. 500 µL of a 5 mM NADPH solution were added to each vial and stirred for 2 minutes. 500 µL of a cofactor regeneration solution containing 300 mM glucose-6-phosphate and 10 units/mL glucose-6-phosphate dehydrogenase were then added to each vial. The resulting mixtures were stirred at room temperature. After 4 hours, the reaction mixtures were joined together and extracted with chloroform (3×100 mL). The organic phase was then dried over magnesium sulfate (MgSO$_4$) and evaporated in vacuo. Purification of the resulting oil by silica gel chromatography (5% ethyl acetate:95% hexane) afforded the activated product ((S)-methyl 2-hydroxy-2-phenylacetate, 40.5 mg). 40 mg (0.24 mmol) of activated product were dissolved in 2 mL dry dichloromethane (CH$_2$Cl$_2$) and a catalytic amount (4 drops) of ethanol was added to the solution. The solution was cooled to −78° C. (dry ice) and added with 41 µL DAST (0.29 mmol). The reaction was stirred in dry ice for 12 hours. The reaction mixture was then added with 5 mL saturated sodium bicarbonate (NaHCO$_3$) and extracted with dichloromethane (3×15 mL). The organic phase was then dried over magnesium sulfate (MgSO$_4$) and evaporated in vacuo. Purification of the resulting oil by silica gel chromatography (5% ethyl acetate: 95% hexane) afforded the fluorinated product ((R)-methyl 2-fluoro-2-phenylacetate) (30 mg, 75% yield, pale yellow oil) in 74% ee, as determined by chiral GC analysis. $^1$H-NMR (300 MHz, CDCl$_3$): δ 3.75 (s, 3H, —OCH$_3$), δ 5.77 (d, J=48 Hz, 1H, —CHF), δ 7.37-7.46 (m, 5H); $^{13}$C-NMR (75 MHz, CDCl$_3$): δ2.8, 89.5 (d, J=184.5 Hz), 126.8, 126.9, 129.0, δ 129.9, δ 134.4 (d, J=34.5 Hz), δ 169.0. $^{19}$F-NMR (282 MHz, CDCl$_3$): δ −180.29 (d, J=48.7 Hz). HRMS (EI+): exact mass calculated for C$_9$H$_9$FO$_2$ requires m/z 168.0587, found 168.0594.

Example 2

Stereoselective fluorination of ethyl 2-phenyl acetate

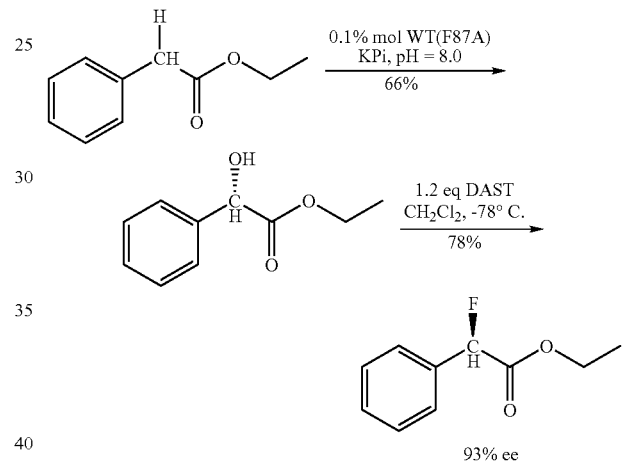

Scheme 2.

93% ee

Ethyl 2-phenyl acetate was subjected to selective fluorination of the target site C (alpha position) according to the systems and methods herein disclosed and, more specifically, according to the general procedure described above.

Experimental description: 100 mg ethyl 2-phenyl acetate were dissolved in 500 µL ethanol and added to 250 mL potassium phosphate buffer pH 8.0. WT(F87A) was added to the mixture at a final concentration of 2 µM. The mixture was split in 4 mL aliquots into 15 mL scintillation vials equipped with a stir bar. 500 µL of a 5 mM NADPH solution were added to each vial and stirred for 2 minutes. 500 µL of a cofactor regeneration solution containing 300 mM glucose-6-phosphate and 10 units/mL glucose-6-phosphate dehydrogenase were then added to each vial. The resulting mixtures were stirred at room temperature. After 3 hours, the reaction mixtures were joined together and extracted with chloroform (3×100 mL). The organic phase was then dried over magnesium sulfate (MgSO$_4$) and evaporated in vacuo. Purification of the resulting oil by silica gel chromatography (5% ethyl acetate:95% hexane) afforded the activated product ((S)-ethyl 2-hydroxy-2-phenylacetate, 66 mg). 66 mg (0.36 mmol) of activated product were dissolved in 2 mL dry dichloromethane (CH$_2$Cl$_2$) and a catalytic amount (4 drops) of ethanol was added to the solution. The solution was cooled to −78° C. (dry ice) and added with 61 µL DAST (0.43 mmol).

The reaction was stirred in dry ice for 12 hours. The reaction mixture was then added with 5 mL saturated sodium bicarbonate (NaHCO$_3$) and extracted with dichloromethane (3×15 mL). The organic phase was then dried over magnesium sulfate (MgSO$_4$) and evaporated in vacuo. Purification of the resulting oil by silica gel chromatography (5% ethyl acetate: 95% hexane) afforded the fluorinated product ((R)-ethyl 2-fluoro-2-phenylacetate) (51 mg, 78% yield, pale yellow oil) in 93% ee, as determined by chiral GC analysis. $^1$H-NMR (300 MHz, CDCl$_3$): δ 1.24 (t, J=7.2 Hz, 3H, —CH$_3$), δ 4.16-4.27 (m, 2H, —OCH$_2$), δ 5.75 (d, J=48 Hz, 1H, —CHF), δ 7.37-7.46 (m, 5H); $^{13}$C-NMR (75 MHz, CDCl$_3$): 14.2, 62.0, 81.2, 89.6 (d, J=184.5 Hz), 126.8, 126.9, 128.9, 129.8, 134.4 (d, J=34.5 Hz), δ 169.0. $^{19}$F-NMR (282 MHz, CDCl$_3$): δ −180.27 (d, J=48.7 Hz). HRMS (EI+): exact mass calculated for C$_{10}$H$_{11}$FO$_2$ requires m/z 182.0743, found 182.0750.

Example 3

Stereoselective fluorination of propyl 2-(3-chlorophenyl)acetate

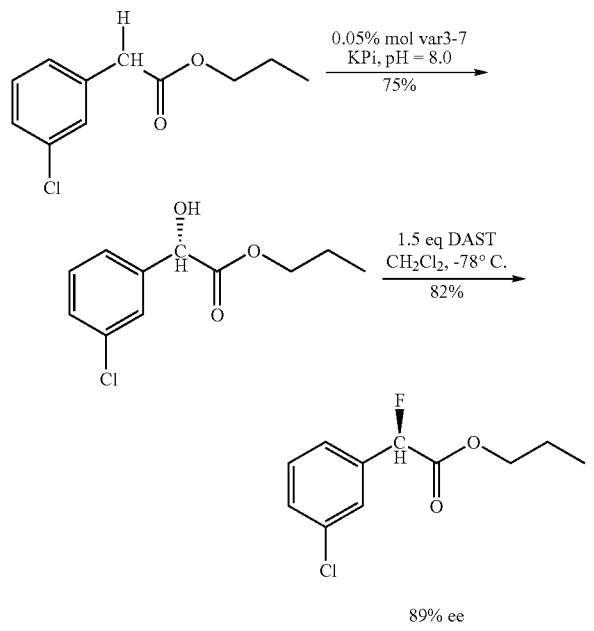

Propyl 2-(3-chlorophenyl)acetate was subjected to selective fluorination of the target site C (alpha position) according to the systems and methods herein disclosed and, more specifically, according to the general procedure described above.

Experimental description: 95 mg propyl 2-(3-chlorophenyl)acetate were dissolved in 500 μL ethanol and added to 250 mL potassium phosphate buffer pH 8.0. Var3-7 was added to the mixture at a final concentration of 1 μM. The mixture was split in 4 mL aliquots into 15 mL scintillation vials equipped with a stir bar. 500 μL of a 5 mM NADPH solution were added to each vial and stirred for 2 minutes. 500 μL of a cofactor regeneration solution containing 300 mM glucose-6-phosphate and 10 units/mL glucose-6-phosphate dehydrogenase were then added to each vial. The resulting mixtures were stirred at room temperature. After 4 hours, the reaction mixtures were joined together and extracted with chloroform (3×100 mL). The organic phase was then dried over magnesium sulfate (MgSO$_4$) and evaporated in vacuo. Purification of the resulting oil by silica gel chromatography (5% ethyl acetate:95% hexane) afforded the activated product ((S)-propyl 2-hydroxy-2-(3-chlorophenyl)acetate, 71 mg). 70 mg (0.3 mmol) of activated product were dissolved in 2 mL dry dichloromethane (CH$_2$Cl$_2$) and a catalytic amount (4 drops) of ethanol was added to the solution. The solution was cooled to −78° C. (dry ice) and added with 64 μL DAST (0.45 mmol). The reaction was stirred in dry ice for 12 hours. The reaction mixture was then added with 5 mL saturated sodium bicarbonate (NaHCO$_3$) and extracted with dichloromethane (3×15 mL). The organic phase was then dried over magnesium sulfate (MgSO$_4$) and evaporated in vacuo. Purification of the resulting oil by silica gel chromatography (5% ethyl acetate:95% hexane) afforded the fluorinated product ((R)-propyl 2-fluoro-2-(3-chlorophenyl)acetate) (57 mg, 82% yield, colorless oil) in 89% ee, as determined by chiral GC analysis. $^1$H-NMR (300 MHz, CDCl$_3$): δ 0.85 (t, J=7 Hz, 3H, —CH$_3$), δ 1.56-1.68 (m, 2H, CH$_2$), δ 4.12 (t, J=6 Hz, 2H, —O—(CH$_2$), δ 5.72 (d, J=48 Hz, 1H, —CHF), δ 7.32 (br, 3H), δ 7.44 (br, 1H); $^{13}$C-NMR (75 MHz, CDCl$_3$): 10.3, 21.9, 67.7, δ 88.7 (d, J=186.5 Hz), 124.8, 126.9, 129.9, 130.3, 134.9. $^{19}$F-NMR (282 MHz, CDCl$_3$): δ −182.8 (d, J=48.7 Hz). HRMS (EI+): exact mass calculated for C$_{11}$H$_{12}$ClFO$_2$ requires m/z 230.0510, found 230.0502.

Example 4

Stereoselective fluorination of propyl 2-(4-methylphenyl)acetate and propyl 2-(2-methylphenyl)acetate

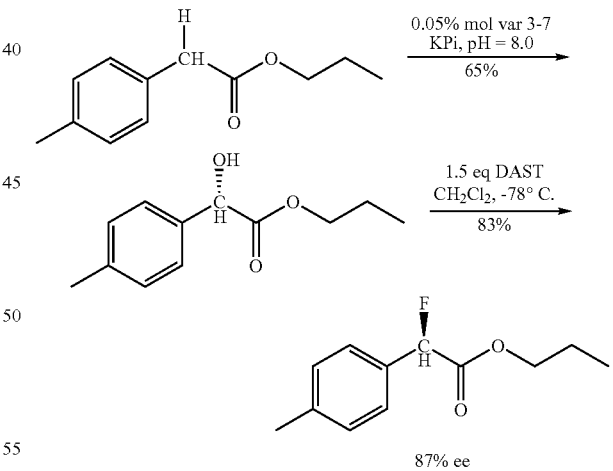

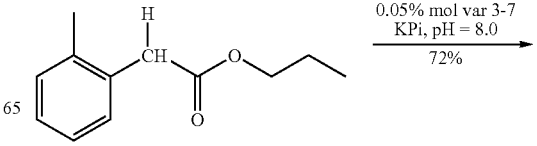

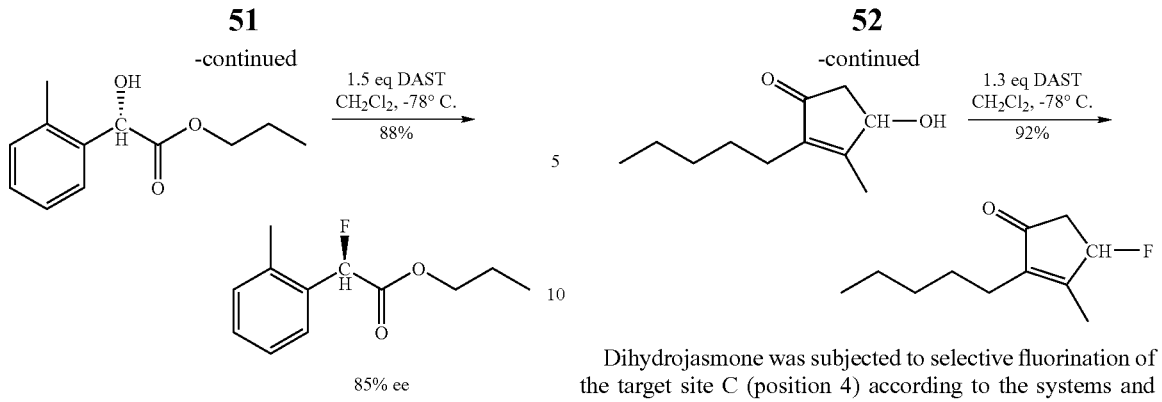

Propyl 2-(4-methylphenyl)acetate and propyl 2-(2-methylphenyl)acetate were subjected to selective fluorination of the target site C (alpha position) according to the systems and methods herein disclosed and, more specifically, according to the general procedure described above.

Experimental description: stereoselective activation and fluorination of 2-(4-methylphenyl)acetate and propyl 2-(2-methylphenyl)acetate were carried out starting from 100 mg substrate according to the experimental protocol described in Example 3. The fluorinated product (R)-propyl 2-fluoro-2-(4-methylphenyl)acetate was obtained in 87% ee (54 mg, colorless oil). $^1$H-NMR (300 MHz, CDCl$_3$): δ 0.84-0.91 (m, 3H, —CH$_3$), δ 1.57-1.68 (m, 2H, CH$_2$), δ 2.37 (s, 3H, —CH$_3$), δ 4.08-4.16 (m, 2H, —O—(CH$_2$), δ 5.75 (d, J=48 Hz, 1H, —CHF), δ 7.18-7.27 (m, 2H), δ 7.27-7.44 (m, 2H); $^{13}$C-NMR (75 MHz, CDCl$_3$): 10.40, 19.41, 22.08, 67.47, 126.57, 131.10. $^{19}$F-NMR (282 MHz, CDCl$_3$): δ −178.5 (d, J=48.7 Hz). HRMS (EI+): exact mass calculated for C$_{12}$H$_{15}$FO$_2$ requires m/z 210.1056, found 210.1062. The fluorinated product (R)-propyl 2-fluoro-2-(2-methylphenyl)acetate was obtained in 87% ee (54 mg, colorless oil). $^1$H-NMR (300 MHz, CDCl$_3$): δ 0.83 (t, J=7.5 Hz, 3H, —CH$_3$), δ 1.52-1.68 (m, 2H, CH$_2$), δ 2.43 (s, 3H, —CH$_3$), δ 4.12 (m, 2H, —O—(CH$_2$), δ 5.96 (d, J=48 Hz, 1H, —CHF), δ 7.16-7.30 (m, 4H); $^{13}$C-NMR (75 MHz, CDCl$_3$): 10.3, 19.3, 22.0, 29.9, 67.4, 87.4 (d, J=183 Hz), δ 126.5, δ 127.5, δ 129.8, δ 131.0. $^{19}$F-NMR (282 MHz, CDCl$_3$): δ −180.1 (d, J=48.7 Hz). HRMS (EI+): exact mass calculated for C$_{12}$H$_{15}$FO$_2$ requires m/z 210.1056, found 210.1070.

Examples 1, 2, 3, and 4 illustrate the application of the systems and methods of the disclosure for stereoselective fluorination of a chemical building block, exemplified by 2-aryl acetic acid derivatives (Schemes 1-4).

Example 5

Regioselective fluorination of 3-methyl-2-pentylcyclopent-2-enone (dihydrojasmone) in position 4

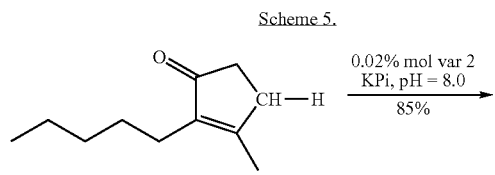

Dihydrojasmone was subjected to selective fluorination of the target site C (position 4) according to the systems and methods herein disclosed and, more specifically, according to the general procedure described above.

Experimental description: 270 µL dihydrojasmone were dissolved in 1.2 mL ethanol and added to 150 mL potassium phosphate buffer pH 8.0. Var2 was added to the mixture at a final concentration of 2 µM. The mixture was split in 4.8 mL aliquots into 15 mL scintillation vials equipped with a stir bar. 600 µL 10 mM NADPH in KPi buffer were added to each vial and stirred for 2 minutes. 600 µL cofactor regeneration solution containing 500 mM glucose-6-phosphate and 10 units/mL glucose-6-phosphate dehydrogenase were then added to each vial. The resulting mixtures were stirred at room temperature. After 36 hours, the reaction mixtures were joined together and extracted with chloroform (3×50 mL). The organic phase was then dried over magnesium sulfate (MgSO$_4$) and evaporated in vacuo. Purification of the resulting oil by silica gel chromatography (0-30% ethyl acetate/hexane) afforded the activated product (4-hydroxy-3-methyl-2-pentylcyclopent-2-enone, 222 mg). 210 mg (1.15 mmol) of activated product were dissolved in 2 mL dry dichloromethane (CH$_2$Cl$_2$) and a catalytic amount (4 drops) of ethanol was added to the solution. The solution was cooled to −78° C. (dry ice) and added with 215 µL DAST (1.5 mmol). The reaction was stirred in dry ice for 12 hours. The reaction mixture was then added with 5 mL saturated sodium bicarbonate (NaHCO$_3$) and extracted with dichloromethane (3×15 mL). The organic phase was then dried over magnesium sulfate (MgSO$_4$) and evaporated in vacuo. Purification of the resulting oil by silica gel chromatography (0-30% ethyl acetate/hexane) afforded the fluorinated product, 4-fluoro-3-methyl-2-pentylcyclopent-2-enone (193 mg, 92% yield, yellow oil). $^1$H-NMR (300 MHz, CDCl$_3$): δ 0.88 (t, J=6.6 Hz, 3H, CH$_3$), δ 1.25-1.40 (m, 6H, CH$_2$), δ 2.10 (d, J=2.1 Hz, 2H, CH$_3$), δ 2.20 (t, J=7.1 Hz, 2H), δ 2.44-2.60 (m, 1H), δ 2.70-2.82 (m, 1H), δ 5.47 (dd, J=54.2 Hz, J=5.8, 1H); $^{13}$C-NMR (75 MHz, CDCl$_3$): δ 13.7, 14.2, 22.6, 23.1, 27.9, 29.9, 31.9, 41.4 (d, J=19.6 Hz), δ 91.2 (d, J=174 Hz): $^{19}$F-NMR (282 MHz, CDCl$_3$): δ −179.08 (ddd, J=51.88 Hz, J=21.43 Hz, J=9.3 Hz). HRMS (EI+): exact mass calculated for C$_{11}$H$_{17}$FO requires m/z 184.1263, found 184.1255.

Example 6

Regioselective fluorination of 3-methyl-2-pentylcyclopent-2-enone (dihydroiasmone) in position 11

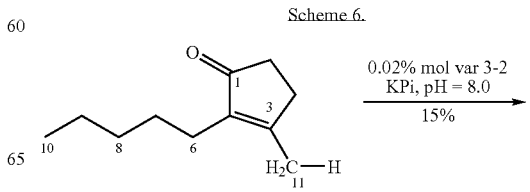

-continued

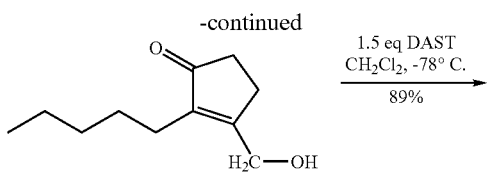

Dihydrojasmone was subjected to selective fluorination of the target site C (position 11) according to the systems and methods herein disclosed and, more specifically, according to the general procedure described above.

Experimental description: 240 µL dihydrojasmone were dissolved in 1.1 mL ethanol and added to 130 mL potassium phosphate buffer pH 8.0. Var2 was added to the mixture at a final concentration of 2 µM. The mixture was split in 4.8 mL aliquots into 15 mL scintillation vials equipped with a stir bar. 600 µL 10 mM NADPH in KPi buffer were added to each vial and stirred for 2 minutes. 600 µL cofactor regeneration solution containing 500 mM glucose-6-phosphate and 10 units/mL glucose-6-phosphate dehydrogenase were then added to each vial. The resulting mixtures were stirred at room temperature. After 36 hours, the reaction mixtures were joined together and extracted with chloroform (3×50 mL). The organic phase was then dried over magnesium sulfate ($MgSO_4$) and evaporated in vacuo. Purification of the resulting oil by silica gel chromatography (0-30% ethyl acetate/hexane) afforded the activated product (11-hydroxy-3-methyl-2-pentylcyclopent-2-enone, 35 mg). 30 mg (0.16 mmol) of activated product were dissolved in 2 mL dry dichloromethane ($CH_2Cl_2$) and a catalytic amount (4 drops) of ethanol was added to the solution. The solution was cooled to −78° C. (dry ice) and added with 35 µL DAST (0.25 mmol). The reaction was stirred in dry ice for 12 hours. The reaction mixture was then added with 5 mL saturated sodium bicarbonate ($NaHCO_3$) and extracted with dichloromethane (3×15 mL). The organic phase was then dried over magnesium sulfate ($MgSO_4$) and evaporated in vacuo. Purification of the resulting oil by silica gel chromatography (0-30% ethyl acetate/hexane) afforded the fluorinated product, 11-fluoro-3-methyl-2-pentylcyclopent-2-enone (27 mg, 89% yield, yellow oil). $^1$H-NMR (300 MHz, $CDCl_3$): δ 0.88 (t, J=6.6 Hz, 3H, $CH_3$), δ 1.25-1.40 (m, 6H, $CH_2$), δ 2.10 (d, J=2.1 Hz, 2H, $CH_3$), δ 2.17 (t, J=7.6 Hz, 2H), δ 2.38-2.44 (m, 1H), δ 2.59-2.64 (m, 1H), δ 5.20 (d, J=48.8 Hz, 1H); $^{13}$C-NMR (75 MHz, $CDCl_3$): δ 14.3, 22.8, 23.3, 28.4, 31.8, 29.9, 31.9, 34.8, 60.6, 80.3 (d, J=164 Hz), 87.9; $^{19}$F-NMR (282 MHz, $CDCl_3$): δ −48.80 (d, J=48.7 Hz). HRMS (EI+): exact mass calculated for $C_{11}H_{17}FO$ requires m/z 184.1263, found 184.1263.

Examples 5 and 6 illustrate the application of the systems and methods of the disclosure for regioselective fluorination of an organic molecule at weakly reactive sites, exemplified by dihydrojasmone (Schemes 5 and 6).

Example 7

Regioselective difluorination of 3-methyl-2-pentylcyclopent-2-enone (dihydrojasmone) in position 4

Scheme 7.

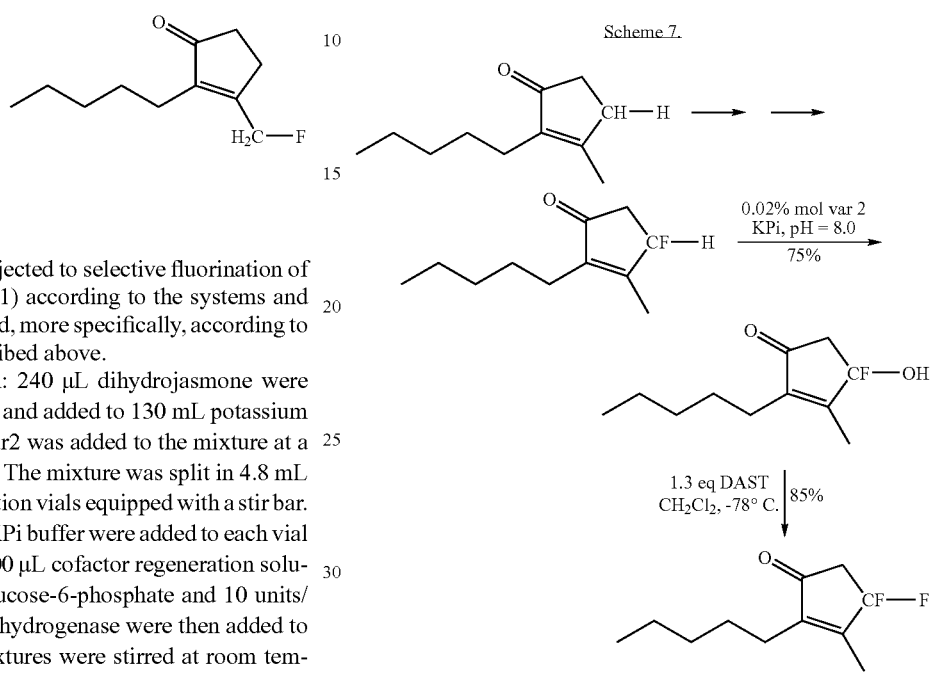

Dihydrojasmone was subjected to selective difluorination of the target site C (position 4) according to the systems and methods herein disclosed and, more specifically, according to the general procedure described above.

Experimental description: 4-fluoro-3-methyl-2-pentylcyclopent-2-enone was obtained according to the experimental described in Example 5. 180 mg 4-fluoro-3-methyl-2-pentylcyclopent-2-enone were dissolved in 900 µL ethanol and added to 120 mL potassium phosphate buffer pH 8.0. Var2 was added to the mixture at a final concentration of 2 µM. The mixture was split in 4.8 mL aliquots into 15 mL scintillation vials equipped with a stir bar. 600 µL 10 mM NADPH in KPi buffer were added to each vial and stirred for 2 minutes. 600 µL cofactor regeneration solution containing 500 mM glucose-6-phosphate and 10 units/mL glucose-6-phosphate dehydrogenase were then added to each vial. The resulting mixtures were stirred at room temperature. After 36 hours, the reaction mixtures were joined together and extracted with chloroform (3×50 mL). The organic phase was then dried over magnesium sulfate ($MgSO_4$) and evaporated in vacuo. Purification of the resulting oil by silica gel chromatography (0-30% ethyl acetate/hexane) afforded the activated product (4-hydroxy-4-fluoro-3-methyl-2-pentylcyclopent-2-enone, 135 mg). 100 mg (0.54 mmol) of activated product were dissolved in 2 mL dry dichloromethane ($CH_2Cl_2$) and a catalytic amount (4 drops) of ethanol was added to the solution. The solution was cooled to −78° C. (dry ice) and added with 100 µL DAST (0.7 mmol). The reaction was stirred in dry ice for 12 hours. The reaction mixture was then added with 5 mL saturated sodium bicarbonate ($NaHCO_3$) and extracted with dichloromethane (3×15 mL). The organic phase was then dried over magnesium sulfate (MgSO₄) and evaporated in vacuo. Purification of the resulting oil by silica gel chromatography (0-30% ethyl acetate/hexane) afforded the fluorinated product, 4,4-difluoro-3-methyl-2-pentylcyclopent-2-enone (85 mg, 85% yield, yellow oil). MS (EI+): m/z 202. Mw for $C_{11}H_{16}F_2O$: 202.24.

Example 7 illustrates the application of the systems and methods of the disclosure for regioselective polyfluorination of an organic molecule at a weakly reactive site, exemplified by dihydrojasmone (Scheme 7).

Example 8

Regioselective Fluorination of Menthofuran

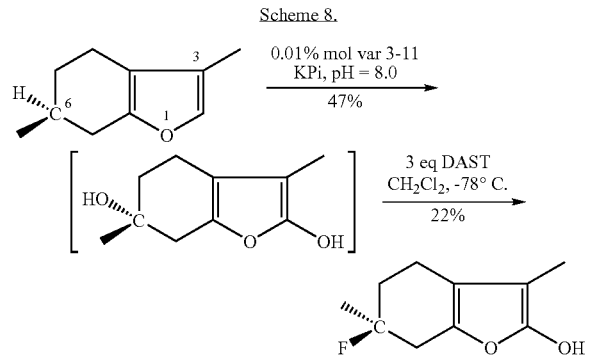

Menthofuran was subjected to selective fluorination of the target site C (position 6) according to the systems and methods herein disclosed and, more specifically, according to the general procedure described above.

Experimental description: 112 mg menthofuran were dissolved in 0.6 mL ethanol and added to 125 mL potassium phosphate buffer pH 8.0. Var3-11 was added to the mixture at a final concentration of 0.7 µM. The mixture was split in 4 mL aliquots into 15 mL scintillation vials equipped with a stir bar. 500 µL 10 mM NADPH in KPi buffer were added to each vial and stirred for 2 minutes. 500 µL cofactor regeneration solution containing 500 mM glucose-6-phosphate and 10 units/mL glucose-6-phosphate dehydrogenase were then added to each vial. The resulting mixtures were stirred at room temperature. After 24 hours, the reaction nearly reached completion (95% substrate conversion). The reaction mixtures were joined together and extracted with chloroform (3×50 mL). The organic phase was then dried over magnesium sulfate (MgSO₄) and evaporated in vacuo. The resulting oil (53 mg) was subjected directly to deoxo-fluorination without purification of the activated product. 53 mg of the activation mixture (~0.32 mmol) were dissolved in 2 mL dry dichloromethane (CH₂Cl₂) and a catalytic amount (4 drops) of ethanol was added to the solution. The solution was cooled to −78° C. (dry ice) and added with 150 µL DAST (1 mmol). The reaction was stirred in dry ice for 16 hours. The reaction mixture was then added with 5 mL saturated sodium bicarbonate (NaHCO₃) and extracted with dichloromethane (3×15 mL). The organic phase was then dried over magnesium sulfate (MgSO₄) and evaporated in vacuo. Purification of the resulting oil by silica gel chromatography (0-10% ethyl acetate/hexane) afforded the fluorinated product, 6-fluoromenthofuran-2-ol (12 mg, 22% yield, yellow oil). ¹H-NMR (300 MHz, CDCl₃): δ 1.13 (d, J: 75.6 Hz, 3H, —CH₃), δ 1.2-1.3 (m, 2H, —CH₂—), δ 1.84 (s, 3H, —CH₃), 1.95-2.4 (dm, 2H, —CH₂—), 2.4-2.6 (dm, 2H, —CH₂—); ¹³C-NMR (75 MHz, CDCl₃): δ 22.7 (d, J=209 Hz), 43.08, 45.36, 91.7 (d, J=215 Hz), 114.9, 127.1. ¹⁹F-NMR (282 MHz, CDCl₃): δ −114.4 (m). HRMS (EI+): exact mass calculated for $C_{10}H_{13}FO_2$ requires m/z 184.0909, found 184.0899.

Example 8 illustrates the application of the systems and methods of the disclosure for regioselective fluorination of an organic molecule at a weakly reactive site, exemplified by menthofuran (Scheme 8).

Example 9

Regioselective Fluorination of (−)-Guaiol

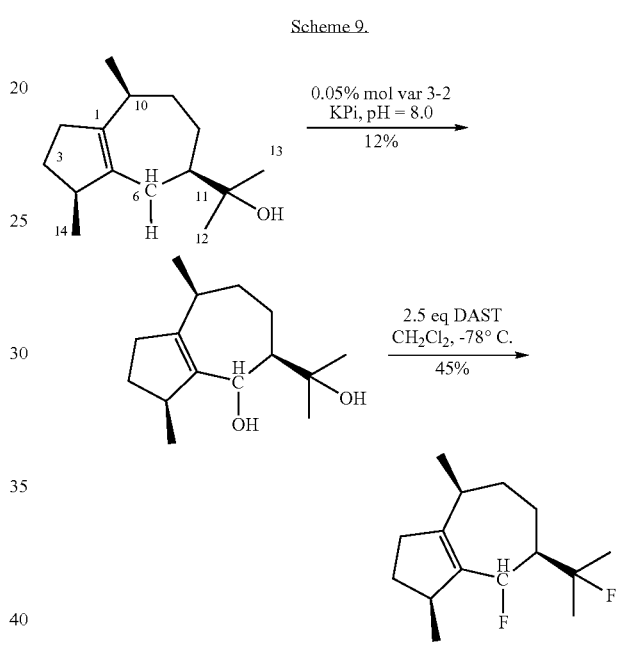

(−)-Guaiol was subjected to selective fluorination of the target site C (position 6) according to the systems and methods herein disclosed and, more specifically, according to the general procedure described above.

Experimental description: 250 mg guaiol were dissolved in 2 mL ethanol and added to 210 mL potassium phosphate buffer pH 8.0. Var3-2 was added to the mixture at a final concentration of 3 µM. The mixture was split in 4.8 mL aliquots into 15 mL scintillation vials equipped with a stir bar. 600 µL 10 mM NADPH in KPi buffer were added to each vial and stirred for 2 minutes. 600 µL cofactor regeneration solution containing 500 mM glucose-6-phosphate and 10 units/mL glucose-6-phosphate dehydrogenase were then added to each vial. The resulting mixtures were stirred at room temperature. After 48 hours, the reaction mixtures were joined together and extracted with chloroform (3×50 mL). The organic phase was then dried over magnesium sulfate (MgSO₄) and evaporated in vacuo. Purification of the resulting oil by silica gel chromatography (0-30% ethyl acetate/hexane) afforded the activated product (6-hydroxy-guaiol, 30 mg, colorless oil). ¹H-NMR (300 MHz, CDCl₃): δ 1.01 (d, J=6.9 Hz, 3H, —CH₃), δ 1.22 (s, 3H, CH₃), δ 1.28 (s, 3H, CH₃), δ 1.25 (d, J=9 Hz, 3H, CH₃), δ 1.42-1.45 (m, 2H,), δ 1.685 (bs, 2H), δ 1.74-1.183 (m, 2H), δ 1.95-2.03 (m, 2H), δ 2.15-2.24 (m, 2H), δ 2.54-2.72 (m, 3H), δ 2.97-3.06 (m, 1H), δ 3.67 (d, J=9 Hz, 1H); $^{13}$C-NMR (75 MHz, CDCl$_3$): δ 11.20, 19.41, 26.08, 28.32, 31.07, 34.13, 35.33, 38.08, 42.42, 48.01, 72.12, 73.15, 178.94. 15 mg of the activated product (~0.06 mmol) were dissolved in 1 mL dry dichloromethane (CH$_2$Cl$_2$) and a catalytic amount (3 drops) of ethanol was added to the solution. The solution was cooled to −78° C. (dry ice) and added with 18 μL DAST (0.12 mmol). The reaction was stirred in dry ice for 16 hours. The reaction mixture was then added with 5 mL saturated sodium bicarbonate (NaHCO$_3$) and extracted with dichloromethane (3×15 mL). The organic phase was then dried over magnesium sulfate (MgSO$_4$) and evaporated in vacuo. Purification of the resulting oil by silica gel chromatography (0-30% ethyl acetate/hexane) afforded the fluorinated product, 6-fluoro-guaiol (7 mg, 45% yield, pale yellow oil). MS (EI+): m/z 242. Mw for C$_{15}$H$_{25}$FO: 242.35.

Example 9 illustrates the application of the systems and methods of the disclosure for regioselective fluorination of an organic molecule at a weakly reactive site, exemplified by (−)-guaiol (Scheme 9).

Example 10

Regioselective fluorination of ibuprofen methyl ester (methyl 2-(4'-(2"-methylpropyl)phenyl)propanoate) in 1" position

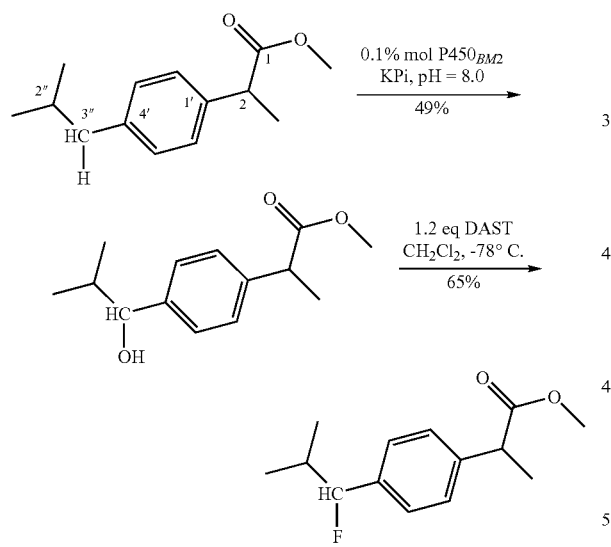

Scheme 10.

Ibuprofen methyl ester was subjected to selective fluorination of the target site C (position 1") according to the systems and methods herein disclosed and, more specifically, according to the general procedure described above.

Experimental description: 150 mg ibuprofen methyl ester were dissolved in 1.4 mL ethanol and added to 150 mL potassium phosphate buffer pH 8.0. P450$_{BM3}$ was added to the mixture at a final concentration of 10 μM. The mixture was split in 4 mL-aliquots into 15 mL scintillation vials equipped with a stir bar. 500 μL 10 mM NADPH in KPi buffer were added to each vial and stirred for 2 minutes. 500 μL cofactor regeneration solution containing 500 mM glucose-6-phosphate and 10 units/mL glucose-6-phosphate dehydrogenase were then added to each vial. The resulting mixtures were stirred at room temperature. After 48 hours, the reaction mixtures were joined together and extracted with chloroform (3×50 mL). The organic phase was then dried over magnesium sulfate (MgSO$_4$) and evaporated in vacuo. Purification of the resulting oil by silica gel chromatography (5-40% ethyl acetate/hexane) afforded the activated product (methyl 2-(4'-(1"-hydroxy-2"-methylpropyl)phenyl)propanoate, 73 mg). 15 mg (0.06 mmol) of activated product were dissolved in 2 mL dry dichloromethane (CH$_2$Cl$_2$) and a catalytic amount (4 drops) of ethanol was added to the solution. The solution was cooled to −78° C. (dry ice) and added with 11 μL DAST (0.72 mmol). The reaction was stirred in dry ice for 16 hours. The reaction mixture was then added with 5 mL saturated sodium bicarbonate (NaHCO$_3$) and extracted with dichloromethane (3×15 mL). The organic phase was then dried over magnesium sulfate (MgSO$_4$) and evaporated in vacuo. Purification of the resulting oil by silica gel chromatography (0-30% ethyl acetate/hexane) afforded the fluorinated product, methyl 2-(4'-(1"-fluoro-2"-methylpropyl)phenyl)propanoate (10 mg, 65% yield, colorless oil). $^1$H-NMR (300 MHz, CDCl$_3$): δ 0.84 (d, J=6.9 Hz, 3H, CH$_3$), δ 1.01 (d, J=6.9 Hz, 3H, —CH$_3$), δ 1.49 (d, J=8.7 Hz, 3H, CH$_3$), δ 2.05-2.08 (m, 1H), δ 3.66 (s, 3H, OCH$_3$), δ 3.73 (q, J=7.5 Hz, 1H), δ 5.07 (dd, J=40.0, J=6.9 Hz, 1H, CHF), δ 7.25 (m, 4H); $^{13}$C-NMR (75 MHz, CDCl$_3$): δ 15.5, 17.82 (d), 18.54 (d), 34.48 (d, J: 85.7 Hz), 45.37, 52.31, 99.3 (d, J=174 Hz), 175.6; $^{19}$F-NMR (282 MHz, CDCl$_3$): δ −179.8 (m). HRMS (EI+): exact mass calculated for C$_{14}$H$_{19}$FO$_2$ requires m/z 238.1369, found 238.1367.

Example 11

Regioselective fluorination of ibuprofen methyl ester (methyl 2-(4'-(2"-methylpropyl)phenyl)propanoate) in 2" position

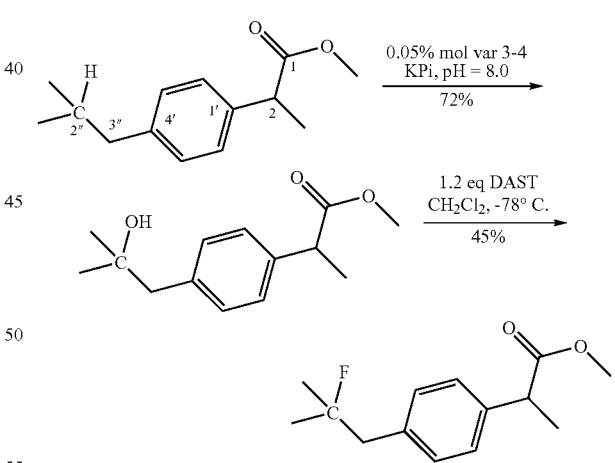

Scheme 11.

Ibuprofen methyl ester was subjected to selective fluorination of the target site C (position 2") according to the systems and methods herein disclosed and, more specifically, according to the general procedure described above.

Experimental description: 150 mg ibuprofen methyl ester were dissolved in 1.4 mL ethanol and added to 150 mL potassium phosphate buffer pH 8.0. Var3-4 was added to the mixture at a final concentration of 3 μM. The mixture was split in 4 mL-aliquots into 15 mL scintillation vials equipped with a stir bar. 500 μL 10 mM NADPH in KPi buffer were added to each vial and stirred for 2 minutes. 500 μL cofactor regeneration solution containing 500 mM glucose-6-phosphate and 10 units/mL glucose-6-phosphate dehydrogenase were then added to each vial. The resulting mixtures were stirred at room temperature. After 48 hours, the reaction mixtures were joined together and extracted with chloroform (3×50 mL). The organic phase was then dried over magnesium sulfate (MgSO$_4$) and evaporated in vacuo. Purification of the resulting oil by silica gel chromatography (5-40% ethyl acetate/hexane) afforded the activated product (methyl 2-(4'-(2"-hydroxy-2"-methylpropyl)phenyl)propanoate, 81 mg). 15 mg (0.06 mmol) of activated product were dissolved in 2 mL dry dichloromethane (CH$_2$Cl$_2$) and a catalytic amount (4 drops) of ethanol was added to the solution. The solution was cooled to −78° C. (dry ice) and added with 11 μL DAST (0.72 mmol). The reaction was stirred in dry ice for 16 hours. The reaction mixture was then added with 5 mL saturated sodium bicarbonate (NaHCO$_3$) and extracted with dichloromethane (3×15 mL). The organic phase was then dried over magnesium sulfate (MgSO$_4$) and evaporated in vacuo. Purification of the resulting oil by silica gel chromatography (0-30% ethyl acetate/hexane) afforded the fluorinated product, methyl 2-(4'-(1"-fluoro-2"-methylpropyl)phenyl)propanoate (7 mg, 45% yield, colorless oil). $^1$H-NMR (300 MHz, CDCl$_3$): δ 1.28 (s, 3H, CH$_3$), δ 1.35 (s, 3H, CH$_3$), δ 1.48 (d, J=6.9 Hz, 3H, CH$_3$), δ 2.87 (d, J: 20.4 Hz, 2H), δ 3.65 (s, 3H, OCH$_3$), δ 3.70 (q, J=7.15 Hz, 1H), δ 7.17 (m, 4H); $^{13}$C-NMR (75 MHz, CDCl$_3$): δ 18.80, 26.83 (d, J: 24.2 Hz), 45.24, 47.37 (d, J: 22.8 Hz), 52.25, 129.12 (d, J: 258.8 Hz), ca. 130, ca. 132, ca. 139, ca. 173; $^{19}$F-NMR (282 MHz, CDCl$_3$): δ −137.7 (m). HRMS (EI+): exact mass calculated for C$_{14}$H$_{19}$FO$_2$ requires m/z 238.1369, found 238.1370.

Example 10 and 11 illustrate the application of the systems and methods of the disclosure for regioselective fluorination of an organic molecule at weakly and non-reactive site, such as positions 1" and 2" of ibuprofen methyl ester (Schemes 10 and 11).

Example 12

Regioselective fluorination of dihydro-4-methoxymethyl-2-methyl-5-phenyl-2-oxazoline

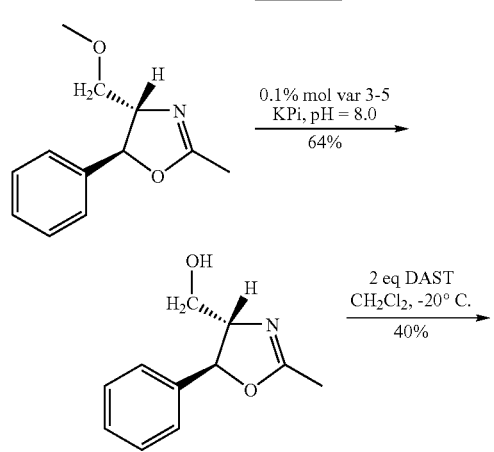

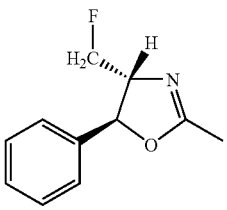

Dihydro-4-methoxymethyl-2-methyl-5-phenyl-2-oxazoline was subjected to selective fluorination of the target site C atom carrying a methoxy group, according to the systems and methods herein disclosed and, more specifically, according to the general procedure described above.

Experimental description: 100 mg dihydro-4-methoxymethyl-2-methyl-5-phenyl-2-oxazoline ibuprofen methyl ester were dissolved in 1.2 mL ethanol and added to 160 mL potassium phosphate buffer pH 8.0. Var3-5 was added to the mixture at a final concentration of 3 μM. The mixture was split in 4 mL-aliquots into 15 mL scintillation vials equipped with a stir bar. 500 μL 10 mM NADPH in KPi buffer were added to each vial and stirred for 2 minutes. 500 μL cofactor regeneration solution containing 500 mM glucose-6-phosphate and 10 units/mL glucose-6-phosphate dehydrogenase were then added to each vial. The resulting mixtures were stirred at room temperature. After 48 hours, the reaction mixtures were joined together and extracted with chloroform (3×50 mL). The organic phase was then dried over magnesium sulfate (MgSO$_4$) and evaporated in vacuo. Purification of the resulting oil by silica gel chromatography (20% ethyl acetate/hexane) afforded the activated product (dihydro-4-hydroxymethyl-2-methyl-5-phenyl-2-oxazoline, 64 mg). 30 mg (0.16 mmol) of activated product were dissolved in 2 mL dry dichloromethane (CH$_2$Cl$_2$) and a catalytic amount (4 drops) of ethanol was added to the solution. The solution was cooled to −78° C. (dry ice) and added with 22 μL DAST (0.32 mmol). The reaction was stirred in dry ice for 2 hours and then at −20° C. for 16 hours. The reaction mixture was then added with 5 mL saturated sodium bicarbonate (NaHCO$_3$) and extracted with dichloromethane (3×15 mL). The organic phase was then dried over magnesium sulfate (MgSO$_4$) and evaporated in vacuo. Purification of the resulting oil by silica gel chromatography (20% ethyl acetate/hexane) afforded the fluorinated product, dihydro-4-fluoromethyl-2-methyl-5-phenyl-2-oxazoline (12 mg, 40% yield, colorless oil). $^1$H-NMR (300 MHz, CDCl$_3$): δ 1.59 (s, 3H, CH$_3$), δ 2.09 (dm, 1H, CH), δ 4.15-4.35 (m, 1H, CH), δ 5.66 (tm, 1H, CH), δ 7.37 (m, 5H, Ph); $^{19}$F-NMR (282 MHz, CDCl$_3$): δ −114.14 (m). HRMS (EI+): exact mass calculated for C$_{11}$H$_{12}$FNO requires m/z 193.0903, found 193.0917.

In another aspect, example 12 illustrates the application of the systems and methods of the disclosure for selective fluorination of an organic molecule at a site carrying a protected hydroxyl group, such as in dihydro-4-methoxymethyl-2-methyl-5-phenyl-2-oxazoline (Scheme 12).

Example 13

Regioselective fluorination of 1,2,3,4,6-pentamethyl-α-D-mannopyranoside

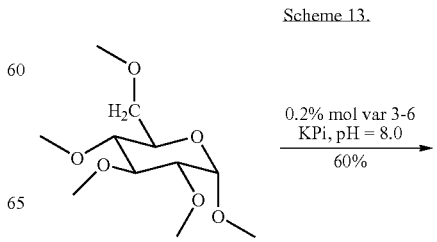

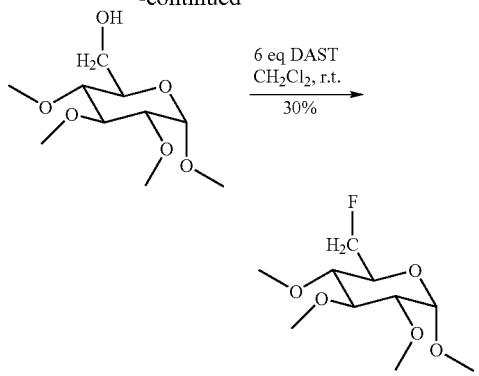

1,2,3,4,6-pentamethyl-α-D-mannopyranoside was subjected to regioselective fluorination of the target site C in position 6, according to the systems and methods herein disclosed and, more specifically, according to the general procedure described above.

Experimental description: 50 mg of 1,2,3,4,6-pentamethyl-α-D-mannopyranoside were dissolved in 0.5 mL ethanol and added to 100 mL potassium phosphate buffer pH 8.0. Var3-6 was added to the mixture at a final concentration of 4 μM. The mixture was split in 4 mL-aliquots into 15 mL scintillation vials equipped with a stir bar. 500 μL 10 mM NADPH in KPi buffer were added to each vial and stirred for 2 minutes. 500 μL cofactor regeneration solution containing 500 mM glucose-6-phosphate and 10 units/mL glucose-6-phosphate dehydrogenase were then added to each vial. The resulting mixtures were stirred at room temperature. After 36 hours, the reaction mixtures were joined together and extracted with chloroform (3×50 mL). The organic phase was then dried over magnesium sulfate ($MgSO_4$) and evaporated in vacuo. Purification of the resulting oil by silica gel chromatography (10% ethyl acetate/hexane) afforded the activated product (1,2,3,4-tetramethyl-α-D-mannopyranoside, 30 mg). 15 mg (0.1 mmol) of activated product were dissolved in 2 mL dry dichloromethane ($CH_2Cl_2$) and a catalytic amount (4 drops) of ethanol was added to the solution. The solution was cooled to −78° C. (dry ice) and added with 85 μL DAST (0.6 mmol). The reaction was stirred in dry ice for 2 hours and then at room temperature for 16 hours. The reaction mixture was then added with 5 mL saturated sodium bicarbonate ($NaHCO_3$) and extracted with dichloromethane (3×15 mL). The organic phase was then dried over magnesium sulfate ($MgSO_4$) and evaporated in vacuo. Purification of the resulting oil by silica gel chromatography (10% ethyl acetate/hexane) afforded the fluorinated product, 6-deoxy-6-fluoro-1,2,3,4-tetramethyl-α-D-mannopyranoside (4.5 mg, 30% yield, colorless oil). $^1$H-NMR (300 MHz, $CDCl_3$): δ 3.35 (s, 3H, $OCH_3$), 3.48 (s, 6H, $OCH_3$), 3.53 (s, 3H, $OCH_3$), 4.0-4.2 (m, 4H), 4.6 (dm, J: 47.5 Hz, 2H, $CH_2F$); $^{13}$C-NMR (75 MHz, $CDCl_3$): δ 55.24, 57.94, 59.24, 61.02, 71.12 (d, J: 18.4 Hz), 73.2, 75.5, 82.49 (d, J: 192 Hz), 98.26. $^{19}$F-NMR (282 MHz, $CDCl_3$): δ −235.2 (m). ESI-MS: m/z calculated for Mw $C_{10}H_{19}FO_5$: 238.2533, found 238.28.

In another aspect, example 13 illustrates the application of the systems and methods of the disclosure for regioselective fluorination of an organic molecule at a defined site carrying a protected hydroxyl group in the presence of other identical functional groups, such as in 1,2,3,4,6-pentamethyl-α-D-mannopyranoside (Scheme 13).

Example 14

Chemo-Enzymatic Fluorination of Unactivated Organic Compounds

Figure 9:
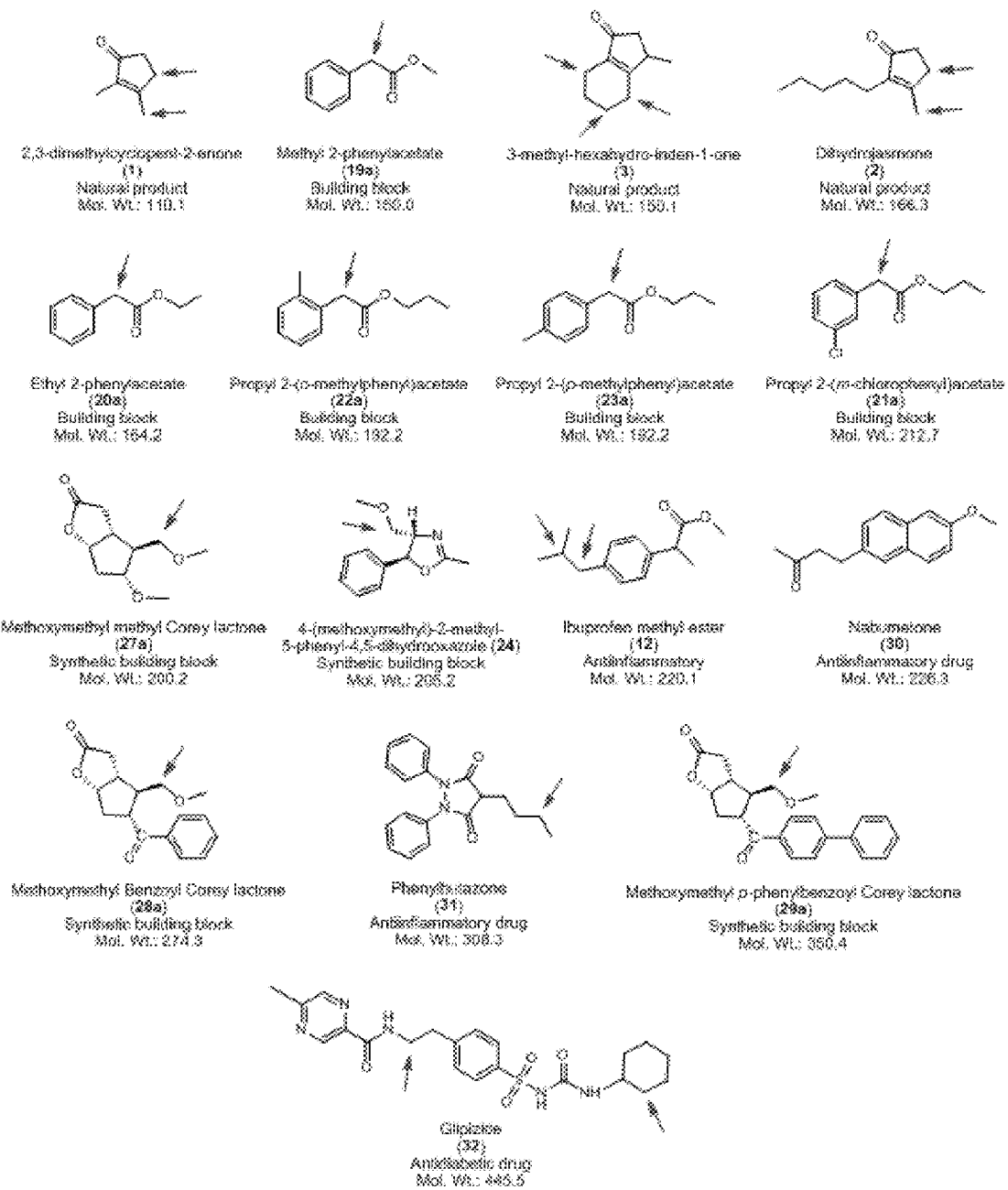
FIG. 9 show test molecules (ordered according to their molecular weight) used in the methods of the disclosure. Arrows indicate the site(s) targeted by chemo-enzymatic fluorination.

To further test the validity of the methods and compositions of the disclosure, various classes of small molecules were targeted, including marketed pharmaceuticals (FIG. 9). For the enzymatic step, variants of the bacterial long-chain fatty acid hydroxylase P450BM3 from *Bacillus megaterium* were used. A panel of 96 P450s derived from a catalytically-promiscuous P450BM3 variant identified in the early stages of the directed evolution of a proficient alkane monooxygenase were used. These variants were found to exhibit good activity and various degrees of selectivity on alkanes and non-alkane substrates.

Enzyme Library Screening. Expression of $P450_{BM3}$ variants in 96-well plates and preparation of cell lysates were performed as described.[1] Screening of enzyme activity on cyclopentenone derivatives (1, 2, and 3) and ibuprofen derivatives (12 and 16) was carried out in 96-well microtiter plates mixing 700 μL KPi (100 mM, pH 8.0), 200 μL cell lysate, 10 μL 200 mM substrate in EtOH, and 100 μL of a cofactor regeneration solution containing 4 mM NADPH, 100 mM glucose-6-phosphate, and 10 U/mL glucose-6-phosphate dehydrogenase. After incubation for 16 hours at room temperature in orbital shaker, reactions were extracted with chloroform and analyzed by gas chromatography on a Shimadzu GC-17A GC using an Agilent HP5 column (30 m×0.32 mm×0.1 μm film), 1 μL injection, FID detector, and the following separation method: 300° C. inlet, 300° C. detector, 70° C. oven, 10° C./min gradient to 210° C., 50° C./min gradient to 260° C., and 260° C. for 2 min. Screening of enzyme activity on dihydro-4-methoxymethyl-2-methyl-5-phenyl-2-oxazoline (24) was carried out on microtiter plates by mixing 100 μL KPi (100 mM, pH 8.0), 50 μL cell lysate, 2 μL 200 mM 24 in DMSO, and 50 μL KPi 4 mM NADPH. Reaction mixtures were incubated for 30 minutes at room temperature and then added with 50 μL 150 mM Purpald in 2 M NaOH. Absorbance at 550 nm was recorded after 30 minutes. The most active variants identified in the colorimetric screen were re-tested for selectivity towards demethylation. 1-mL scale reactions were carried out using 1 mM 24, 0.5 μM P450, 400 μM NADPH, 10 mM glucose-6-phosphate and 1 U/mL glucose-6-phosphate dehydrogenase. After stirring for 16 hours at room temperature, the reaction mixtures were extracted with chloroform and analyzed by GC-MS on a Hewlett-Packard 5970B MSD with 5890 GC using a DB-5 capillary column, 1 μL injection, 250° C. inlet, and the following separation program: 80° C. oven, 10° C./min gradient to 250° C., 250° C. for 3 min. Enzyme activity on 27a, 28a, and 29a was screened by mixing 50 μL cell lysate, 100 μL 100 mM KPi buffer (pH 8.0) containing 1 mM substrate (1% DMSO), and 50 μL 4 mM NADPH in microtiter plates. After 30 min, 50 μL 150 mM Purpald (Sigma) in 2 M NaOH were added to each well. Absorbance at 550 nm was measured after 60 minutes. The most active variants were re-tested at 1-mL scale using 1 mM substrate, 0.5 μM purified P450, and the cofactor regeneration system described above. After overnight incubation at 4° C., reactions were analyzed by HPLC-MS using an Agilent 1100 Series LC/MSD device and Kromasil 100, 5 μm-$C_{18}$ column.

Membrane permeability assay. The membrane permeability assays were carried out adapting a described procedure and using 96-well MultiScreen-IP plates from Millipore. Filter plates were rinsed with 70% EtOH and double-distilled water prior to use. BBB-mimic membranes were prepared by coating filter wells with 5 μL porcine brain lipids (PBL, Avanti Polar Lipids) in dodecane (20 mg/mL). Control wells (PBL-free) were primed in the same way but not coated with PBL. Working solutions contained 0.5 mg/mL fluorinated compound in PBS pH 7.4 (5% EtOH). Assembled plates contained 150 μL working solution in the PBL-coated (or PBL-free) well, 300 μL PBS (5% EtOH) in the acceptor well, and were incubated at room temperature and 100% humidity. The change in organic compound concentration in the donor and acceptor wells was monitored over time by HPLC. Membrane permeability values ($P_e$) were calculated. All measurements were performed in triplicates. The assay was validated by comparing the experimental $P_e$ value for caffeine with that reported in the art.

Synthetic Procedures:

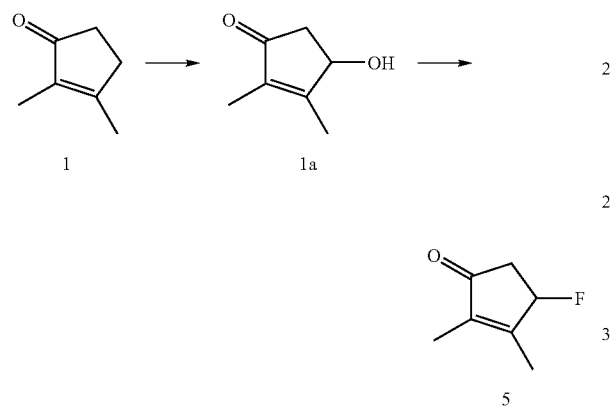

Conversion of 1 to 5. 130 mg (1.18 mmol) 1 were dissolved in 1.5 mL ethanol and added to 200 mL potassium phosphate buffer pH 8.0. The solution was added with var-H3 (final conc.: 2.5 μM) and a cofactor regeneration system (final conc.: 500 μM NADPH, 30 mM glucose-6-phosphate, 1 unit/mL glucose-6-phosphate dehydrogenase) and stirred at room temperature. After 48 hours, the reaction mixture was extracted with dichloromethane (4×50 mL). The combined organic phases were dried over anhydrous $Na_2SO_4$ and evaporated under reduced pressure. The residue was purified by flash chromatography (gradient 0 to 20% ethyl acetate in hexane) to afford 1a (130 mg, 88%, colorless oil). $^1$H-NMR (300 MHz, $CDCl_3$): δ 1.71 (m, 3H, $CH_3$), δ 2.08 (m, 3H, $CH_3$), δ 2.27 (dd, J=18.3, 1.8 Hz, 1H), δ 2.77 (dd, J=18.3, 6.3 Hz, 1H), δ 4.73 (m, 1H). $^{13}$C-NMR (75 MHz, $CDCl_3$): δ 8.18, δ 13.91, δ 44.44, δ 71.85, δ 138.37, δ 168.50, δ 205.96. HRMS (EI+): exact mass calculated for $C_7H_{10}O_2$ requires m/z 126.0681, found 126.0687. Under argon, 50 mg (0.22 mmol) 1a and a catalytic amount (3 drops) of ethanol were dissolved in 3 mL dry dichloromethane. The solution was cooled to −78° C. and added with 38 μL DAST (0.26 mmol, 1.2 eq) in two aliquots. The reaction was stirred in dry ice for 12 hours. The reaction mixture was added with 5 mL saturated sodium bicarbonate and extracted with dichloromethane (3×15 mL). The organic phase was then dried over anhydrous magnesium sulfate and evaporated under reduced pressure. The residue was purified by flash chromatography (gradient 10% to 50% dichloromethane in pentane) to afford 5 (25 mg, 90% yield, colorless oil). $^1$H-NMR (300 MHz, $CD_2Cl_2$): δ 1.68 (dm, J=4.2 Hz, 3H, $CH_3$), δ 2.04 (m, 3H, $CH_3$), δ 2.41 (tm, J=20.71H), δ 2.63-2.76 (m, 1H), δ 5.48 (dm, J=30.6 Hz, 1H). $^{13}$C-NMR (75 MHz, $CD_2Cl_2$): δ 7.83, δ 13.40, δ 41.21 (d, J=19.9 Hz), δ 91.59 (d, J=173.7 Hz), δ 128.03. $^{19}$F-NMR (282 MHz, $CD_2Cl_2$): δ −179.4 (dd, J=51.6, 24.2 Hz). HRMS (EI+): exact mass calculated for $C_7H_9FO$ requires m/z 128.0637, found 128.0642. Chiral GC analyses were carried out using a Shimadzu GC-17A gas chromatograph, FID detector, Agilent Cyclosilb column (30 m×0.52 mm×0.25 μm film) and the following separation program: 300° C. inlet, 300° C. detector, 60° C. oven, 0.5° C./min gradient to 200° C., 50° C./min gradient to 250° C., and 250° C. for 2 min. An enantiomeric excess of 22% was estimated based on peak areas.

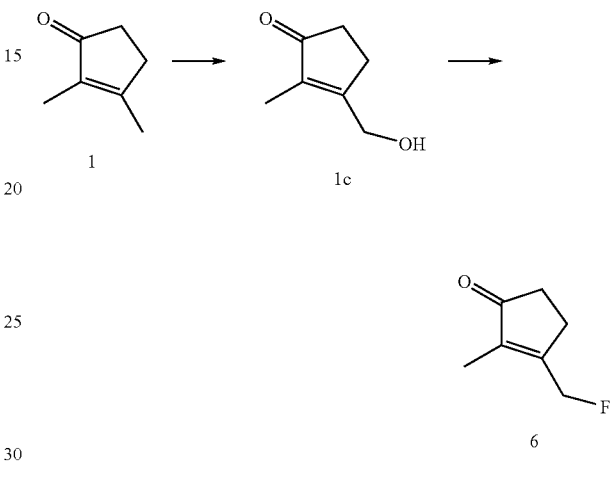

Conversion of 1 to 6. 130 mg (1.18 mmol) 1 were dissolved in 1.5 mL ethanol and added to 200 mL potassium phosphate buffer pH 8.0. The solution was added with var-G6 (final conc.: 2.5 μM) and a cofactor regeneration system (final conc.: 500 μM NADPH, 30 mM glucose-6-phosphate, 1 unit/mL glucose-6-phosphate dehydrogenase) and stirred at room temperature. After 48 hours, the reaction mixture was extracted with dichloromethane (4×50 mL). The combined organic phases were dried over anhydrous $Na_2SO_4$ and evaporated under reduced pressure. The residue was purified by flash chromatography (gradient 0 to 20% ethyl acetate in hexane) to afford 1c (66 mg, 45%, colorless oil). $^1$H-NMR (300 MHz, $CDCl_3$): δ 1.71 (m, 3H, $CH_3$), δ 2.4 (dm, J=4.5 Hz, 2H), δ 2.65 (m, 2H), δ 4.58 (s, 2H). $^{13}$C-NMR (75 MHz, $CDCl_3$): δ 8.23, δ 27.18, δ 34.10, δ 61.05, δ 136.15, δ 170.05, δ 210.61. HRMS (EI+): exact mass calculated for $C_7H_{10}O_2$ requires m/z 126.0681, found 126.0685. Under argon, 50 mg (0.22 mmol) 1c and a catalytic amount (3 drops) of ethanol were dissolved in 3 mL dry dichloromethane. The solution was cooled to −78° C. and added with 38 μL DAST (0.26 mmol, 1.2 eq) in two aliquots. The reaction was stirred in dry ice for 12 hours. The reaction mixture was added with 5 mL saturated sodium bicarbonate and extracted with dichloromethane (3×15 mL). The organic phase was then dried over anhydrous magnesium sulfate and evaporated under reduced pressure. The residue was purified by flash chromatography (gradient 10% to 50% dichloromethane in pentane) to afford 6 (24 mg, 85% yield, colorless oil). $^1$H-NMR (300 MHz, $CD_2Cl_2$): δ 1.67 (m, 3H, $CH_3$), δ 2.36 (m, 2H), δ 2.56 (m, 2H), δ 5.23 (d, J=34.2 Hz, 2H). $^{13}$C-NMR (75 MHz, $CD_2Cl_2$): δ 7.95, δ 26.41 (d, J=4.3 Hz), δ 80.83 (d, J=164.0 Hz). $^{19}$F-NMR (282 MHz, $CD_2Cl_2$): δ −226.9 (t, J=42.3 Hz). HRMS (EI+): exact mass calculated for $C_7H_9FO$ requires m/z 128.0637, found 128.0643.

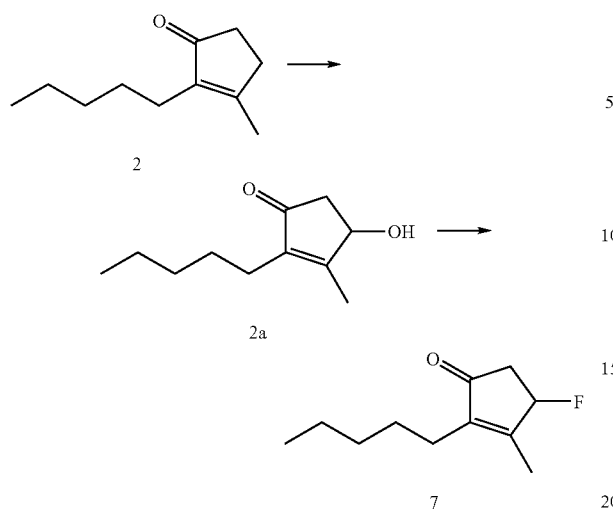

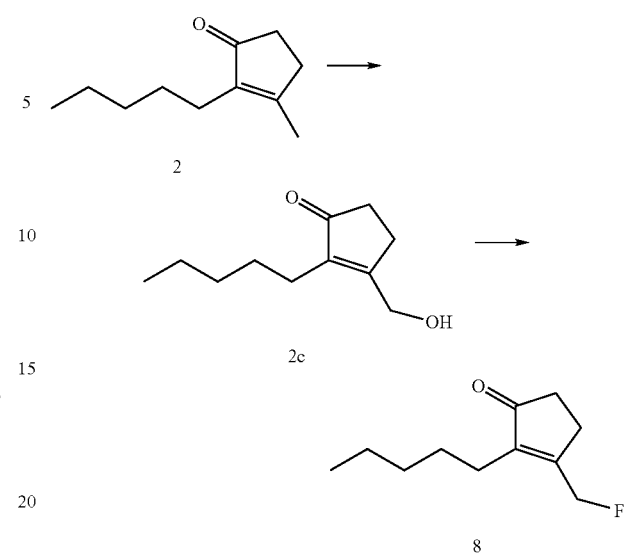

Conversion of 2 to 7. 270 mg (1.62 mmol) 2 were dissolved in 2.5 mL ethanol and added to 250 mL potassium phosphate buffer pH 8.0. The solution was added with var-H3 (final conc.: 3 μM) and a cofactor regeneration system (final conc.: 500 μM NADPH, 30 mM glucose-6-phosphate, 1 unit/mL glucose-6-phosphate dehydrogenase) and stirred at room temperature. After 48 hours, the reaction mixture was extracted with dichloromethane (4×50 mL). The combined organic phases were dried over anhydrous $Na_2SO_4$ and evaporated under reduced pressure. The residue was purified by flash chromatography (gradient 0 to 30% ethyl acetate in hexane) to afford 2a (250 mg, 85%, pale yellow oil). $^1$H-NMR (300 MHz, $CDCl_3$): δ 0.87 (t, J=6.9 Hz, 3H, $CH_3$), δ 1.25-1.39 (m, 6H), δ 2.08 (s, 3H, $CH_3$), δ 2.17 (t, J=8.1 Hz, 2H), δ 2.27 (dd, J=18.3, 2.1 Hz, 1H), δ 2.77 (dd, J=18.3, 6.3 Hz, 1H), δ 4.72 (dm, J=5.1 Hz, 1H). $^{13}$C-NMR (75 MHz, $CDCl_3$): δ 13.83, δ 14.22, δ 22.68, δ 23.16, δ 28.06, δ 28.06, δ 31.99, δ 44.60, δ 71.87, δ 142.73, δ 168.32, δ 205.59. HRMS (EI+): exact mass calculated for $C_{11}H_{18}O_2$ requires m/z 182.1307, found 182.1311. Under argon, 200 mg (1.09 mmol) 2a and a catalytic amount (4 drops) of ethanol were dissolved in 5 mL dry dichloromethane. The solution was cooled to −78° C. and added with 200 μL DAST (1.4 mmol, 1.3 eq) in four aliquots. The reaction was stirred in dry ice for 12 hours. The reaction mixture was added with 7 mL saturated sodium bicarbonate and extracted with dichloromethane (3×20 mL). The organic phase was then dried over anhydrous magnesium sulfate and evaporated under reduced pressure. The residue was purified by flash chromatography (gradient 0 to 30% ethyl acetate in hexane) to afford 7 (193 mg, 92% yield, pale yellow oil). $^1$H-NMR (300 MHz, $CDCl_3$): δ 0.88 (t, J=6.6 Hz, 3H, $CH_3$), δ 1.25-1.40 (m, 6H), δ 2.10 (d, J=2.1 Hz, 2H, $CH_3$), δ 2.20 (t, J=7.1 Hz, 2H), δ 2.51 (tm, J=22.5 Hz, 1H), δ 2.70-2.82 (m, 1H), δ 5.47 (dd, J=53.7, 6.0, 1H). $^{13}$C-NMR (75 MHz, $CDCl_3$): δ 13.75, δ 14.21, δ 22.66, δ 23.13, δ 27.90, δ 29.94, δ 31.96, δ 41.46 (d, J=19.6 Hz), δ 91.42 (d, J=174.9 Hz), δ 167.62. $^{19}$F-NMR (282 MHz, $CDCl_3$): δ −179.1 (ddd, J=51.8, 21.4, 9.3 Hz). HRMS (EI+): exact mass calculated for $C_{11}H_{17}FO$ requires m/z 184.1263, found 184.1255. Chiral GC analyses were carried out using a Shimadzu GC-17A gas chromatograph, FID detector, Agilent Cyclosilb column (30 m×0.52 mm×0.25 μm film) and the following separation program: 300° C. inlet, 300° C. detector, 70° C. oven, 1° C./min gradient to 200° C., 50° C./min gradient to 250° C., and 250° C. for 2 min. An enantiomeric excess of 78% was estimated based on peak areas.

Conversion of 2 to 8. 100 mg (0.60 mmol) 2 were dissolved in 1 mL ethanol and added to 150 mL potassium phosphate buffer pH 8.0. The solution was added with var-G4 (final conc.: 2 μM) and a cofactor regeneration system (final conc.: 500 □M NADPH, 30 mM glucose-6-phosphate, 1 unit/mL glucose-6-phosphate dehydrogenase) and stirred at room temperature. After 48 hours, the reaction mixture was extracted with dichloromethane (3×50 mL). The combined organic phases were dried over anhydrous $Na_2SO_4$ and evaporated under reduced pressure. The residue was purified by flash chromatography (gradient 0 to 30% ethyl acetate in hexane) to afford 2c (46 mg, 42%, pale yellow oil). GC-MS (EI+): m/z 182. Under argon, 46 mg (0.25 mmol) 2c and a catalytic amount (2 drops) of ethanol were dissolved in 2.5 mL dry dichloromethane. The solution was cooled to −78° C. and added with 54 μL DAST (0.38 mmol, 1.5 eq) in two aliquots. The reaction was stirred in dry ice for 12 hours. The reaction mixture was added with 5 mL saturated sodium bicarbonate and extracted with dichloromethane (3×15 mL). The organic phase was then dried over anhydrous magnesium sulfate and evaporated under reduced pressure. The residue was purified by flash chromatography (gradient 0 to 30% ethyl acetate in hexane) to afford 8 (62 mg, 89% yield, pale yellow oil). $^1$H-NMR (300 MHz, $CDCl_3$): δ 0.87 (t, J=6.5 Hz, 3H, $CH_3$), δ 1.23-1.38 (m, 6H), δ 2.17 (t, J=7.5 Hz, 2H), δ 2.41 (m, 1H), δ 2.60 (m, 1H), δ 5.26 (d, J=47.1, 1H). $^{13}$C-NMR (75 MHz, $CDCl_3$): δ 14.32, δ 22.86, δ 23.33, δ 28.46, δ 31.80, δ 31.93, δ 34.87, δ 80.37 (d, J=164.8 Hz). $^{19}$F-NMR (282 MHz, $CDCl_3$): δ −227.9 (t, J=48.2 Hz). HRMS (EI+): exact mass calculated for $C_{11}H_{17}FO$ requires m/z 184.1263, found 184.1263.

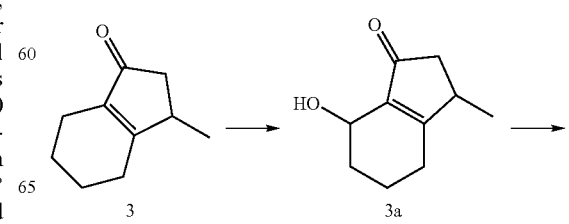

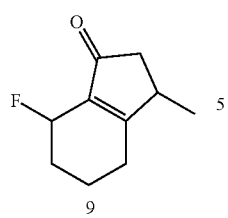

9

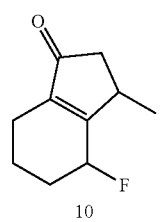

10

Conversion of 3 to 9. 230 mg (1.53 mmol) 3 were dissolved in 2 mL ethanol and added to 300 mL potassium phosphate buffer pH 8.0. The solution was added with var-D10 (final conc.: 2.5 μM) and a cofactor regeneration system (final conc.: 500 μM NADPH, 30 mM glucose-6-phosphate, 1 unit/mL glucose-6-phosphate dehydrogenase) and stirred at room temperature. After 48 hours, the reaction mixture was extracted with dichloromethane (4×80 mL). The combined organic phases were dried over anhydrous $Na_2SO_4$ and evaporated under reduced pressure. The residue was purified by flash chromatography (gradient 0 to 20% ethyl acetate in hexane) to afford 3a (175 mg, 69%, colorless oil). GC-MS (EI+): m/z 166. Under argon, 100 mg (0.60 mmol) 3a and a catalytic amount (3 drops) of ethanol were dissolved in 5 mL dry dichloromethane. The solution was cooled to −78° C. and added with 103 μL DAST (0.72 mmol, 1.2 eq) in two aliquots. The reaction was stirred in dry ice for 3 hours. The reaction mixture was added with 5 mL saturated sodium bicarbonate and extracted with dichloromethane (3×20 mL). The organic phase was then dried over anhydrous magnesium sulfate and evaporated under reduced pressure. The residue was purified by flash chromatography (10% ethyl acetate:90% hexane) to afford 9 (89 mg, 88% yield, colorless oil). $^1$H-NMR (300 MHz, $CDCl_3$): δ 1.84 (d, J=6.6 Hz), δ 1.45-1.75 (m, 2H), δ 1.80-1.86 (m, 2H), δ 2.03 (m, 1H), δ 2.06 (dd, J=18.4, 1.8 Hz, 1H), δ 2.13-2.21 (m, 1H), δ 2.65 (dd, J=18.4, 6.9 Hz, 1H), δ 2.80 (m, 1H), δ 5.28 (dbr, J=50.1 Hz, 1H). $^{13}$C-NMR (75 MHz, $CDCl_3$): δ 14.47, δ 18.78, δ 25.89, δ 28.67 (d, J=21.9 Hz), δ 36.29, δ 43.89, δ 79.93 (d, J=164.2 Hz), δ 135.71 (d, J=17.9 Hz), δ 183.76 (d, J=5.6 Hz), δ 206.26. $^{19}$F-NMR (282 MHz, $CDCl_3$): δ −171.4 (m). HRMS (EI+): exact mass calculated for $C_{10}H_{13}FO$ requires m/z 168.0950, found 168.0908. Chiral GC analyses were carried out using a Shimadzu GC-17A gas chromatograph, FID detector, Agilent Cyclosilb column (30 m×0.52 mm×0.25 μm film) and the following separation program: 300° C. inlet, 300° C. detector, 70° C. oven, 1° C./min gradient to 200° C., 50° C./min gradient to 250° C., and 250° C. for 2 min. A diasteromeric ratio (dr) of 1:8.5, an enantiomeric excess of 5% for the major product, and an enantiomeric excess of 71% for the minor product were estimated based on peak areas.

Conversion of 3 to 10. 200 mg (1.33 mmol) 3 were dissolved in 1.5 mL ethanol and added to 200 mL potassium phosphate buffer pH 8.0. The solution was added with var-G4 (final conc.: 3.5 μM) and a cofactor regeneration system (final conc.: 500 μM NADPH, 30 mM glucose-6-phosphate, 1 unit/mL glucose-6-phosphate dehydrogenase) and stirred at room temperature. After 36 hours, the reaction mixture was extracted with dichloromethane (4×80 mL). The combined organic phases were dried over anhydrous $Na_2SO_4$ and evaporated under reduced pressure. The residue was purified by flash chromatography (30% ethyl acetate in hexane) to afford 3b (137 mg, 62%, colorless oil). GC-MS (EI+): m/z 166. Under argon, 50 mg (0.30 mmol) 3b and a catalytic amount (3 drops) of ethanol were dissolved in 3 mL dry dichloromethane. The solution was cooled to −78° C. and added with 51 μL DAST (0.36 mmol, 1.2 eq) in two aliquots. The reaction was stirred in dry ice for 5 hours. The reaction mixture was added with 5 mL saturated sodium bicarbonate and extracted with dichloromethane (3×15 mL). The organic phase was then dried over anhydrous magnesium sulfate and evaporated under reduced pressure. The residue was purified by flash chromatography (10% ethyl acetate:90% hexane) to afford 10 (46 mg, 92% yield, colorless oil). $^1$H-NMR (300 MHz, $CDCl_3$): δ 1.27 (d, J=6.9 Hz, 3H), δ 1.71-1.79 (m, 3H), δ 2.02 (dbr, J=18.6, 1H), δ 2.03 (br, 1H), δ 2.10-2.13 (m, 1H), δ 2.23-2.35 (m, 1H), δ 2.67 (dd, J=18.6, 6.3 Hz, 1H), δ 2.92 (br, 1H), δ 5.20 (dbr, J=46.2 Hz, 1H). $^{13}$C-NMR (75 MHz, $CDCl_3$): δ 17.55, δ 19.96, δ 20.18 (d, J=2.8 Hz), δ 29.80 (d, J=21.3 Hz), δ 36.12, δ 44.32, δ 86.48 (d, J=166.5 Hz), δ 142.79, δ 168.15 (d, J=13.9 Hz), δ 208.86. $^{19}$F-NMR (282 MHz, $CDCl_3$): δ −174.8 (m). HRMS (EI+): exact mass calculated for $C_{10}H_{13}FO$ requires m/z 168.0950, found 168.0913. Chiral GC analyses were carried out using a Shimadzu GC-17A gas chromatograph, FID detector, Agilent Cyclosilb column (30 m×0.52 mm×0.25 μm film) and the following separation program: 300° C. inlet, 300° C. detector, 70° C. oven, 1° C./min gradient to 200° C., 50° C./min gradient to 250° C., and 250° C. for 2 min. A diasteromeric ratio (dr) of 4:96 and an enantiomeric excess of 57% for minor product were estimated based on peak areas.

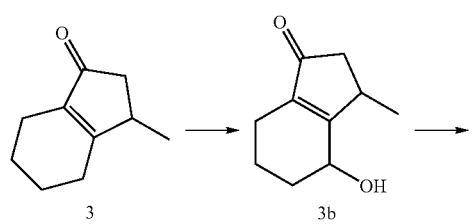

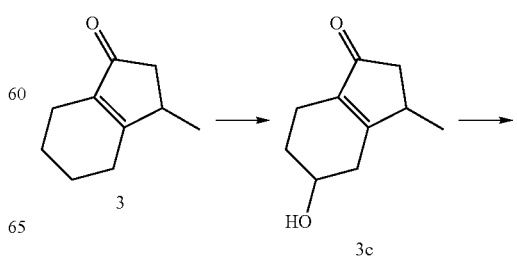

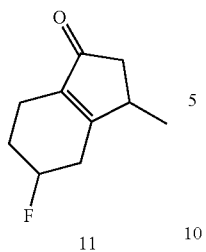

11

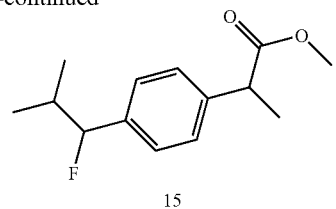

15

Conversion of 3 to 11. 150 mg (1.0 mmol) 3 were dissolved in 1.5 mL ethanol and added to 200 mL potassium phosphate buffer pH 8.0. The solution was added with var-G5 (final conc.: 3.5 µM) and a cofactor regeneration system (final conc.: 500 µM NADPH, 30 mM glucose-6-phosphate, 1 unit/mL glucose-6-phosphate dehydrogenase) and stirred at room temperature. After 36 hours, the reaction mixture was extracted with dichloromethane (4×80 mL). The combined organic phases were dried over anhydrous Na$_2$SO$_4$ and evaporated under reduced pressure. The residue was purified by flash chromatography (30% ethyl acetate in hexane) to afford 3c (53 mg, 32%, colorless oil). GC-MS (EI$^+$): m/z 166. Under argon, 53 mg (0.32 mmol) 3c and a catalytic amount (3 drops) of ethanol were dissolved in 3 mL dry dichloromethane. The solution was cooled to −78° C. and added with 51 µL DAST (0.36 mmol, 1.2 eq) in two aliquots. The reaction was stirred in dry ice for 5 hours. The reaction mixture was added with 5 mL saturated sodium bicarbonate and extracted with dichloromethane (3×15 mL). The organic phase was then dried over anhydrous magnesium sulfate and evaporated under reduced pressure. The residue was purified by flash chromatography (10% ethyl acetate:90% hexane) to afford 11 (48 mg, 90% yield, colorless oil). $^1$H-NMR (300 MHz, CDCl$_3$): δ 1.18 (d, J=7.2 Hz, 3H), δ 1.45-1.64 (m, 1H), δ 1.79-1.86 (m, 2H), δ 2.00 (dd, J=18.6, 3.9 Hz, 1H), δ 2.11-2.24 (m, 1H), δ 2.33-2.37 (m, 1H), δ 2.67 (dd, J=18.6, 6.3 Hz, 1H), δ 2.86 (m, 1H), δ 5.29 (dm, J=50.1 Hz, 1H). $^{13}$C-NMR (75 MHz, CDCl$_3$): δ 17.36, δ 18.62, δ 26.58, δ 28.74 (d, J=20.7 Hz), δ 37.08, δ 43.67, δ 79.82 (d, J=164.2 Hz), δ 135.65, δ 208.57. $^{19}$F-NMR (282 MHz, CDCl$_3$): δ −170.5 (m). HRMS (EI+): exact mass calculated for C$_{10}$H$_{13}$FO requires m/z 168.0950, found 168.0923. Chiral GC analyses were carried out using a Shimadzu GC-17A gas chromatograph, FID detector, Agilent Cyclosilb column (30 m×0.52 mm×0.25 µm film). Complete separation of all four diasteromers was not possible.

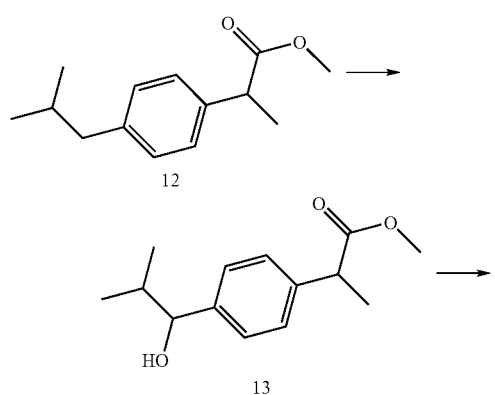

Conversion of 12 to 15. 1.4 mL DMSO containing 150 mg (0.68 mmol) 12 were dissolved in 150 mL 100 mM KPi pH 8.0. The solution was added with var-B4 (final conc.: 4.5 µM) and a cofactor regeneration system (final conc.: 1 mM NADPH, 30 mM glucose-6-phosphate, 1 unit/mL glucose-6-phosphate dehydrogenase) and stirred at room temperature. After 48 hours, the reaction mixture was extracted with dichloromethane (4×50 mL). The combined organic phases were dried over anhydrous Na$_2$SO$_4$ and evaporated under reduced pressure. The residue was purified by flash chromatography (gradient from 5 to 40% ethyl acetate in hexane) to afford 13 (114 mg, 72%, colorless oil). $^1$H-NMR (300 MHz, CDCl$_3$): δ 0.78 (d, J=6.9 Hz, 3H, CH$_3$), δ 0.98 (d, J=6.9 Hz, 3H, CH$_3$), δ 1.48 (d, J=6.9 Hz, 3H, CH$_3$), δ 1.85-2.00 (m, 1H, CH), δ 3.65 (s, 3H, OCH$_3$), δ 3.72 (q, J=6.9 Hz, 1H, CH), δ 4.33 (d, J=6.9 Hz, 1H, CH), δ 7.25 (m, 4H, CH). $^{13}$C-NMR (75 MHz, CDCl$_3$): δ 18.43, δ 18.81, δ 19.26, δ 35.42, δ 45.32, δ 52.27, δ 79.99, δ 127.09, δ 127.52, δ 139.86, δ 142.77, δ 175.27. HRMS (EI$^+$): exact mass calculated for C$_{14}$H$_{20}$O$_3$ requires m/z 236.1412, found 236.1415. Under argon, 40 mg (0.17 mmol) 13 and a catalytic amount of ethanol were dissolved in 4 mL dry dichloromethane. The solution was cooled to −78° C. After 5 minutes, 29 µL DAST (0.24 mmol, 1.4 eq) were added to the mixture. The reaction was stirred in dry ice overnight. The reaction was then added with 5 mL saturated sodium bicarbonate and extracted with dichloromethane (3×15 mL). The organic phase was then dried over anhydrous Na$_2$SO$_4$ and evaporated under reduced pressure. The residue was purified by flash chromatography (5% ethyl acetate:95% hexane) to afford 15 (35 mg, 86% yield, colorless oil). $^1$H-NMR (300 MHz, CDCl$_3$): δ 0.84 (d, J=6.3 Hz, 3H, CH$_3$), δ 1.01 (d, J=5.7 Hz, 3H, CH$_3$), δ 1.48 (d, J=6.9 Hz, 3H, CH$_3$), δ 2.05-2.18 (m, 1H, CH), δ 3.66 (s, 3H, OCH$_3$), δ 3.72 (q, J=7.5 Hz, 1H, CH), 5.07 (dd, J=40.0, J=6.9 Hz, 1H, CHF), δ 7.25 (m, 4H, CH). $^{13}$C-NMR (75 MHz, CDCl$_3$): δ 17.78 (d, J=5.1 Hz), δ 18.58 (d, J=6.0 Hz), δ 18.81, δ 34.48 (d, J: 85.7 Hz), δ 45.37, δ 52.31, δ 99.3 (d, J=174 Hz), δ 126.65, δ 126.75, δ 127.56, δ 138.37, δ 140.6, δ 175.16. $^{19}$F-NMR (282 MHz, CDCl$_3$): δ −179.8 (m). HRMS (EI+): exact mass calculated for C$_{14}$H$_{19}$FO$_2$ requires m/z 238.1369, found 238.1367. Chiral GC analyses were carried out using a Shimadzu GC-17A gas chromatograph, FID detector, Agilent Cyclosilb column (30 m×0.52 mm×0.25 µm film) and the following separation program: 300° C. inlet, 300° C. detector, 70° C. oven, 1° C./min gradient to 200° C., 50° C./min gradient to 250° C., and 250° C. for 2 min. A diasteromeric ratio (dr) of 1:3.2, an enantiomeric excess of 19% for the major product, and an enantiomeric excess of 44% for the minor product were estimated based on peak areas.

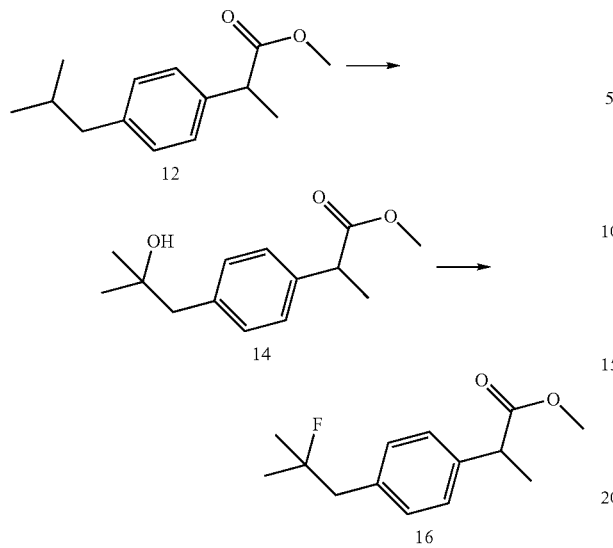

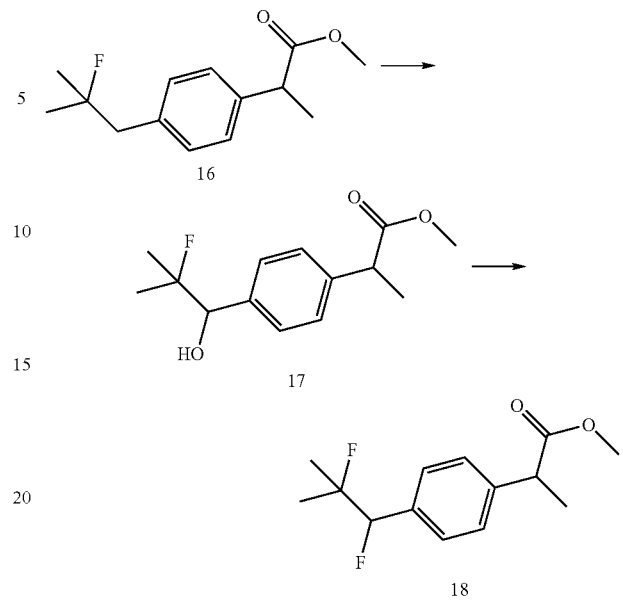

Conversion of 12 to 16. 2.5 mL DMSO containing 220 mg (1 mmol) 12 were dissolved in 250 mL 100 mM KPi pH 8.0. The solution was added with var-G4 (final conc.: 2 μM) and a cofactor regeneration system (final conc.: 500 μM NADPH, 30 mM glucose-6-phosphate, 1 unit/mL glucose-6-phosphate dehydrogenase) and stirred at room temperature. After 48 hours, the reaction mixture was extracted with dichloromethane (4×80 mL). The combined organic phases were dried over anhydrous $Na_2SO_4$ and evaporated under reduced pressure. The residue was purified by flash chromatography (gradient from 5 to 40% ethyl acetate in hexane) to afford 14 (208 mg, 88%, colorless oil). $^1$H-NMR (300 MHz, $CDCl_3$): δ 1.21 (s, 6H, $CH_3$), δ 1.48 (d, J=7.2 Hz, 3H, $CH_3$), δ 2.73 (s, 2H, CH), δ 3.65 (s, 3H, $OCH_3$), δ 3.70 (q, J=7.2 Hz, 1H, CH), δ 7.15 (d, J=8.1 Hz, 2H, CH), δ 7.23 (d, J=8.1 Hz, 2H, CH). $^{13}$C-NMR (75 MHz, $CDCl_3$): δ 18.84, δ 29.41 (2C), δ 45.26, δ 49.51, δ 52.29, δ 71.00, δ 127.53 (2C), δ 130.98 (2C), δ 136.82, δ 138.92, δ 175.33. HRMS ($EI^+$): exact mass calculated for $C_{14}H_{20}O_3$ requires m/z 236.1412, found 236.1413. Under argon, 120 mg (0.51 mmol) 14 and a catalytic amount of ethanol (3 drops) were dissolved in 6 mL dry dichloromethane. The solution was cooled to −78° C. After 5 minutes, 87 μL DAST (0.61 mmol, 1.4 eq) were added to the mixture in three aliquots. The reaction was stirred in dry ice overnight. The reaction was then added with 8 mL saturated sodium bicarbonate and extracted with dichloromethane (3×20 mL). The organic phase was then dried over anhydrous $Na_2SO_4$ and evaporated under reduced pressure. The residue was purified by flash chromatography (5% ethyl acetate: 95% hexane) to afford 16 (114 mg, 95% yield, colorless oil). $^1$H-NMR (300 MHz, $CDCl_3$): δ 1.32 (d, J=23.6 Hz, 6H, $CH_3$), δ 1.48 (d, J=6.9 Hz, 3H, $CH_3$), δ 2.87 (d, J: 20.4 Hz, 2H), δ 3.65 (s, 3H, $OCH_3$), δ 3.70 (q, J=7.1 Hz, 1H), δ 7.15 (d, J=8.1 Hz, 2H, CH), δ 7.21 (d, J=8.1 Hz, 2H, CH). $^{13}$C-NMR (75 MHz, $CDCl_3$): δ 18.80, δ 26.83 (d, J: 24.2 Hz), δ 45.24, δ 47.37 (d, J: 22.8 Hz), δ 52.25, δ 98.37 (d, J=264 Hz), δ 129.12 (d, J: 258.8 Hz), δ 127.39, δ 130.85, δ 136.07, δ 138.92, δ 175.31. $^{19}$F-NMR (282 MHz, $CDCl_3$): δ −137.7 (m). HRMS ($EI^+$): exact mass calculated for $C_{14}H_{19}FO_2$ requires m/z 238.1369, found 238.1370.

Conversion of 16 to 18. 2 mL DMSO containing 80 mg (0.33 mmol) 16 were dissolved in 200 mL 100 mM KPi pH 8.0. The solution was added with var-B2 (final conc.: 1 μM) and a cofactor regeneration system (final conc.: 500 μM NADPH, 30 mM glucose-6-phosphate, 1 unit/mL glucose-6-phosphate dehydrogenase) and stirred at room temperature. After 48 hours, the reaction mixture was extracted with dichloromethane (4×80 mL). The combined organic phases were dried over anhydrous $Na_2SO_4$ and evaporated under reduced pressure. The residue was purified by flash chromatography (5% ethyl acetate: 95% hexane) to afford 17 (78 mg, 93%, colorless oil). $^1$H-NMR (300 MHz, $CDCl_3$): δ 1.31 (d, J=22.5 Hz, 3H, $CH_3$), δ 1.32 (d, J=22.5 Hz, 3H, $CH_3$), δ 1.48 (d, J=7.2 Hz, 3H, $CH_3$), δ 3.65 (s, 3H, $OCH_3$), δ 3.72 (q, J=7.2 Hz, 1H, CH), δ 4.69 (d, J=11.7 Hz, 1H, CH), δ 7.26 (d, J=8.1 Hz, 2H, CH), δ 7.34 (d, J=8.1 Hz, 2H, CH). $^{13}$C-NMR (75 MHz, $CDCl_3$): δ 18.79, δ 21.55 (d, J=23.1 Hz), δ 24.08 (d, J=23.7 Hz), δ 45.31, δ 52.28, δ 79.29 (d, J=23.6 Hz), δ 98.14 (d, J=168 Hz), δ 127.42, δ 127.91, δ 138.28 (d, J=5.7 Hz), δ 140.55, δ 175.12. $^{19}$F-NMR (282 MHz, $CDCl_3$): δ −146.8 (m). HRMS ($EI^+$): exact mass calculated for $C_{14}H_{20}FO_3$ requires m/z 255.1396, found 255.1394. Under argon, 30 mg (0.12 mmol) 17 and a catalytic amount of ethanol were dissolved in 3 mL dry dichloromethane. The solution was cooled to −78° C. After 5 minutes, 20 μL DAST (0.14 mmol, 1.2 eq) were added to the mixture. The reaction was stirred in dry ice overnight. The reaction was then added with 5 mL saturated sodium bicarbonate and extracted with dichloromethane (3×15 mL). The organic phase was then dried over anhydrous $Na_2SO_4$ and evaporated under reduced pressure. The residue was purified by flash chromatography (5% ethyl acetate:95% hexane) to afford 18 (30 mg, 98% yield, colorless oil). $^1$H-NMR (300 MHz, $CDCl_3$): δ 1.32 (m, 6H, $CH_3$), δ 1.51 (d, J=7.2 Hz, 3H, $CH_3$), δ 3.66 (s, 3H, $OCH_3$), δ 3.74 (q, J=7.2 Hz, 1H, CH), δ 5.29 (dd, J=45.0, 13.8 Hz, 1H, CHF), δ 7.31 (s, 4H, CH). $^{13}$C-NMR (75 MHz, $CDCl_3$): δ 18.80, δ 23.01 (m), δ 45.38, δ 52.34, δ 96.80 (d, J=179 Hz), δ 96.52 (d, J=179 Hz), δ 127.50, δ 127.59, δ 134.8 (d, J=22.5), δ 141.28, δ 175.03. $^{19}$F-NMR (282 MHz, $CDCl_3$): δ −150.7 (m), δ −187.8 (dd, J=45.6, 9.0 Hz). HRMS ($EI^+$): exact mass calculated for $C_{14}H_{19}F_2O_2$ requires m/z 257.1353, found 257.1356. Chiral GC analyses were carried out using a Shimadzu GC-17A gas chromatograph, FID detector, Agilent Cyclosilb column (30 m×0.52 mm×0.25 μm film) and the following separation program: 300° C. inlet, 300° C. detector, 70° C. oven, 0.5° C./min gradient to 200° C., 50° C./min gradient to 250° C., and 250° C. for 2 min. A diasteromeric ratio (dr) of 1:3.7, an enantiomeric excess of 9% for the major product, and an enantiomeric excess of 9% for the minor product were estimated based on peak areas.

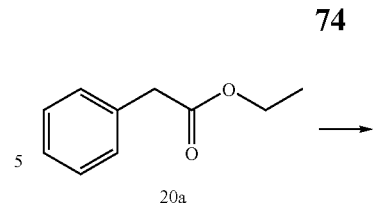

20a

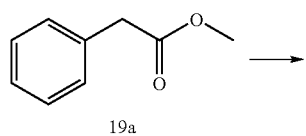

19a

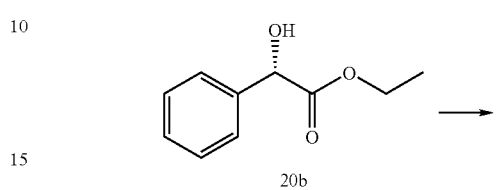

20b

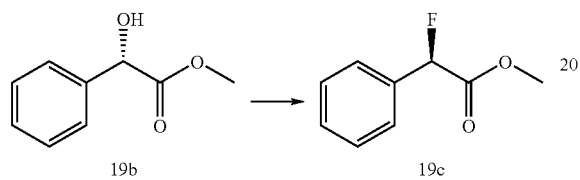

19b  19c

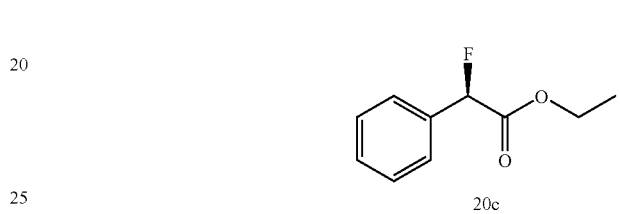

20c

Conversion of 19a to 19c. 90 mg (0.6 mmol) 19a were dissolved in 500 μL ethanol and added to 240 mL 100 mM KPi buffer pH 8.0. Var-A3 was added to the mixture at a final concentration of 2 μM. The mixture was added with a cofactor regeneration solution containing 0.5 mM NADPH, 30 mM glucose-6-phosphate and 1 U/mL glucose-6-phosphate dehydrogenase (final concentrations). The reaction mixtures were stirred at room temperature and extracted with chloroform (3×100 mL) after 4 hours. The organic phase was then dried over anhydrous $MgSO_4$ and evaporated under reduced pressure. Purification of the resulting oil by silica gel chromatography (5% ethyl acetate:95% hexane) afforded 19b (45 mg). 45 mg (0.27 mmol) of 19b and a catalytic amount (3 drops) of ethanol were dissolved in 2 mL dry dichloromethane under argon. The solution was cooled to −78° C. and added with 43 μL DAST (0.30 mmol, 1.2 eq). The reaction was stirred in dry ice for 12 hours. The reaction mixture was then added with 5 mL saturated sodium bicarbonate and extracted with dichloromethane (3×15 mL). The organic phases were then dried over anhydrous $MgSO_4$ and evaporated under reduced pressure. Purification of the resulting oil by silica gel chromatography (5% ethyl acetate:95% hexane) afforded 19c (34 mg, 75% yield, pale yellow oil) in 74% ee, as determined by chiral GC analysis. $^1$H-NMR (300 MHz, $CDCl_3$): δ 3.75 (s, 3H), δ 5.77 (d, J=48 Hz, 1H, —CHF), δ 7.37-7.46 (m, 5H); $^{13}$C-NMR (75 MHz, $CDCl_3$): δ 52.8, δ 89.5 (d, J=184.5 Hz), δ 126.8, δ 126.9, δ 129.0, δ 129.9, δ 134.4 (d, J=34.5 Hz), δ 169.0. $^{19}$F-NMR (282 MHz, $CDCl_3$): δ −180.29 (d, J=48.7 Hz). HRMS (EI+): exact mass calculated for $C_9H_9FO_2$ requires m/z 168.0587, found 168.0594. Chiral GC analyses were carried out using a Shimadzu GC-17A gas chromatograph, FID detector, Agilent Cyclosilb column (30 m×0.52 mm×0.25 μm film) and the following separation program: 300° C. inlet, 300° C. detector, 100° C. oven, 2° C./min gradient to 200° C., 50° C./min gradient to 250° C., and 250° C. for 2 min. An enantiomeric excess of 74% was estimated based on peak areas.

Conversion of 20a to 20c. 100 mg (0.61 mmol) 20a were dissolved in 500 μL ethanol and added to 250 mL 100 mM KPi buffer pH 8.0. var-B4 was added to the mixture at a final concentration of 2 μM. The mixture was added with a cofactor regeneration solution containing 0.5 mM NADPH, 30 mM glucose-6-phosphate and 1 U/mL glucose-6-phosphate dehydrogenase (final concentrations). The reaction mixtures were stirred at room temperature and extracted with chloroform (3×100 mL) after 3 hours. The organic phases were collected, dried over anhydrous $MgSO_4$, and evaporated under reduced pressure. Purification of the resulting oil by silica gel chromatography (5% ethyl acetate:95% hexane) afforded 20b (72 mg, 66%). 72 mg (0.4 mmol) of 20b and a catalytic amount (3 drops) of ethanol were dissolved in 2 mL dry dichloromethane under argon. The solution was cooled to −78° C. and added with 61 μL DAST (0.43 mmol, 1.2 eq). The reaction was stirred in dry ice for 12 hours. The reaction mixture was then added with 5 mL saturated sodium bicarbonate and extracted with dichloromethane (3×15 mL). The organic phases were collected, dried over anhydrous $MgSO_4$ and evaporated under reduced pressure. Purification of the resulting oil by silica gel chromatography (5% ethyl acetate:95% hexane) afforded 20c (57 mg, 78% yield, pale yellow oil) in 72% ee, as determined by chiral GC analysis. $^1$H-NMR (300 MHz, $CDCl_3$): δ 1.24 (t, J=7.2 Hz, 3H, —$CH_3$), δ 4.16-4.27 (m, 2H, —$OCH_2$), δ 5.75 (d, J=48 Hz, 1H, —CHF), δ 7.37-7.46 (m, 5H); $^{13}$C-NMR (75 MHz, $CDCl_3$): δ 14.2, δ 62.0, δ 81.2, δ 89.6 (d, J=184.5 Hz) δ 126.8 δ 126.9 δ 128.9 δ 129.8 δ 134.4 (d, J=34.5 Hz), δ 169.0. $^{19}$F-NMR (282 MHz, $CDCl_3$): δ −180.27 (d, J=48.7 Hz). HRMS (EI+): exact mass calculated for $C_{10}H_{11}FO_2$ requires m/z 182.0743, found 182.0750. Chiral GC analyses were carried out using a Shimadzu GC-17A gas chromatograph, FID detector, Agilent Cyclosilb column (30 m×0.52 mm×0.25 μm film) and the following separation program: 300° C. inlet, 300° C. detector, 100° C. oven, 2° C./min gradient to 200° C., 50° C./min gradient to 250° C., and 250° C. for 2 min. An enantiomeric excess of 72% was estimated based on peak areas.

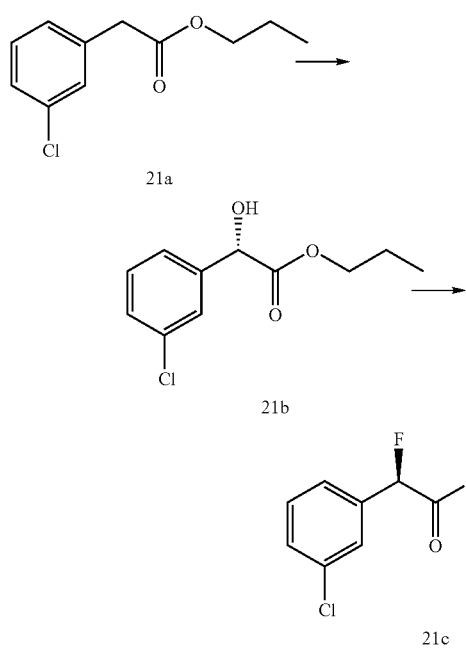

21a

21b

21c

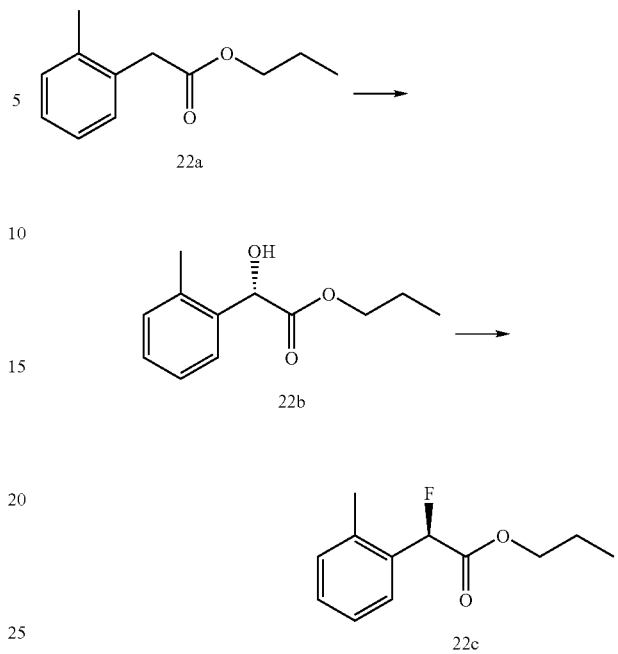

22a

22b

22c

Conversion of 21a to 21c. 95 mg (0.45 mmol) 21a were dissolved in 500 μL ethanol and added to 250 mL 100 mM KPi buffer pH 8.0. Var-C12 was added to the mixture at a final concentration of 1 μM. The mixture was added with a cofactor regeneration solution containing 0.5 mM NADPH, 30 mM glucose-6-phosphate and 1 U/mL glucose-6-phosphate dehydrogenase (final concentrations). The reaction mixtures were stirred at room temperature and extracted with chloroform (3×100 mL) after 4 hours. The organic phases were collected, dried over anhydrous $MgSO_4$, and evaporated under reduced pressure. Purification of the resulting oil by silica gel chromatography (5% ethyl acetate:95% hexane) afforded 21b (71 mg, 75%). 70 mg (0.34 mmol) of 21b and a catalytic amount (3 drops) of ethanol were dissolved in 2 mL dry dichloromethane under argon. The solution was cooled to −78° C. and added with 64 μL DAST (0.45 mmol, 1.5 eq). The reaction was stirred in dry ice for 12 hours. The reaction mixture was then added with 5 mL saturated sodium bicarbonate and extracted with dichloromethane (3×15 mL). The organic phases were collected, dried over anhydrous $MgSO_4$, and evaporated under reduced pressure. Purification of the resulting oil by flash chromatography (5% ethyl acetate:95% hexane) afforded 21c (63 mg, 82% yield, colorless oil) in 89% ee, as determined by chiral GC analysis. $^1$H-NMR (300 MHz, $CDCl_3$): δ 0.85 (t, J=7 Hz, 3H, —$CH_3$), δ 1.56-1.68 (m, 2H, $CH_2$), δ 4.12 (t, J=6 Hz, 2H, —$OCH_2$), δ 5.72 (d, J=48 Hz, 1H, —CHF), δ 7.32 (br, 3H), δ 7.44 (br, 1H). $^{13}$C-NMR (75 MHz, $CDCl_3$): δ 10.3, δ 21.9, δ 67.7, δ 88.7 (d, J=186.5 Hz) δ 124.8 δ 126.9 δ 129.9 δ 130.3 δ 134.9. $^{19}$F-NMR (282 MHz, $CDCl_3$): δ −182.8 (d, J=48.7 Hz). HRMS (EI+): exact mass calculated for $C_{11}H_{12}ClFO_2$ requires m/z 230.0510, found 230.0502. Chiral GC analyses were carried out using a Shimadzu GC-17A gas chromatograph, FID detector, Agilent Cyclosilb column (30 m×0.52 mm×0.25 μm film) and the following separation program: 300° C. inlet, 300° C. detector, 100° C. oven, 2° C./min gradient to 200° C., 50° C./min gradient to 250° C., and 250° C. for 2 min. An enantiomeric excess of 89% was estimated based on peak areas.

Conversion of 22a to 22c. 100 mg (0.52 mmol) of 22a were dissolved in 500 μL ethanol and added to 250 mL 100 mM KPi buffer pH 8.0. Var-C12 was added to the mixture at a final concentration of 1 μM. The mixture was added with a cofactor regeneration solution containing 0.5 mM NADPH, 30 mM glucose-6-phosphate and 1 U/mL glucose-6-phosphate dehydrogenase (final concentrations). The reaction mixtures were stirred at room temperature and extracted with chloroform (3×100 mL) after 4 hours. The organic phases were collected, dried over anhydrous $MgSO_4$, and evaporated under reduced pressure. Purification of the resulting oil by silica gel chromatography (5% ethyl acetate:95% hexane) afforded 22b (78 mg, 65%). 78 mg (0.37 mmol) of 22b and a catalytic amount (3 drops) of ethanol were dissolved in 4 mL dry dichloromethane under argon. The solution was cooled to −78° C. and added with 63 μL DAST (0.44 mmol, 1.5 eq). The reaction was stirred in dry ice for 12 hours. The reaction mixture was then added with 5 mL saturated sodium bicarbonate and extracted with dichloromethane (3×15 mL). The organic phases were collected, dried over anhydrous $MgSO_4$, and evaporated under reduced pressure. Purification of the resulting oil by flash chromatography (5% ethyl acetate:95% hexane) afforded 22c (68 mg, 88%, colorless oil) in 85% ee, as determined by chiral GC analysis. $^1$H-NMR (300 MHz, $CDCl_3$): δ 0.83 (t, J=7.5 Hz, 3H, —$CH_3$), δ 1.52-1.68 (m, 2H, $CH_2$), δ 2.43 (s, 3H, —$CH_3$), δ 4.12 (m, 2H, —$OCH_2$), δ 5.96 (d, J=48 Hz, 1H, —CHF), δ 7.16-7.30 (m, 4H); $^{13}$C-NMR (75 MHz, $CDCl_3$): δ 10.3, δ 19.3, δ 22.0, δ 29.9, δ 67.4, δ 87.4 (d, J=183 Hz) δ 126.5 δ 127.5 δ 129.8 δ 131.0. $^{19}$F-NMR (282 MHz, $CDCl_3$): δ −180.1 (d, J=48.7 Hz). HRMS (EI+): exact mass calculated for $C_{12}H_{15}FO_2$ requires m/z 210.1056, found 210.1070. Chiral GC analyses were carried out using a Shimadzu GC-17A gas chromatograph, FID detector, Agilent Cyclosilb column (30 m×0.52 mm×0.25 μm film) and the following separation program: 300° C. inlet, 300° C. detector, 100° C. oven, 2° C./min gradient to 200° C., 50° C./min gradient to 250° C., and 250° C. for 2 min. An enantiomeric excess of 85% was estimated based on peak areas.

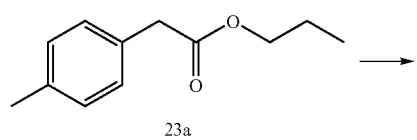

23a

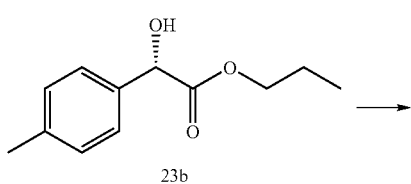

23b

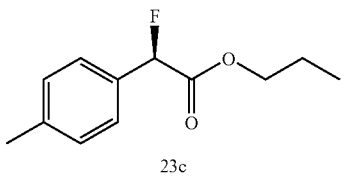

23c

Conversion of 23a to 23c. 100 mg (0.52 mmol) of 23a were dissolved in 500 μL ethanol and added to 250 mL 100 mM KPi buffer pH 8.0. Var-C12 was added to the mixture at a final concentration of 1 μM. The mixture was added with a cofactor regeneration solution containing 0.5 mM NADPH, 30 mM glucose-6-phosphate and 1 U/mL glucose-6-phosphate dehydrogenase (final concentrations). The reaction mixtures were stirred at room temperature and extracted with chloroform (3×100 mL) after 4 hours. The organic phases were collected, dried over anhydrous MgSO$_4$, and evaporated under reduced pressure. Purification of the resulting oil by silica gel chromatography (5% ethyl acetate:95% hexane) afforded 23b (70 mg, 65%). 70 mg (0.34 mmol) of 23b and a catalytic amount (3 drops) of ethanol were dissolved in 4 mL dry dichloromethane under argon. The solution was cooled to −78° C. and added with 58 μL DAST (0.4 mmol, 1.5 eq). The reaction was stirred in dry ice for 12 hours. The reaction mixture was then added with 5 mL saturated sodium bicarbonate and extracted with dichloromethane (3×15 mL). The organic phases were collected, dried over anhydrous MgSO$_4$, and evaporated under reduced pressure. Purification of the resulting oil by flash chromatography (5% ethyl acetate:95% hexane) afforded 23c (59 mg, 83%, colorless oil) in 87% ee, as determined by chiral GC analysis. $^1$H-NMR (300 MHz, CDCl$_3$): δ 0.84-0.91 (m, 3H, —CH$_3$), δ 1.57-1.68 (m, 2H, CH$_2$), δ 2.37 (s, 3H, —CH$_3$), δ 4.08-4.16 (m, 2H, —OCH$_2$), δ 5.75 (d, J=48 Hz, 1H, —CHF), δ 7.18-7.27 (m, 2H), δ 7.27-7.44 (m, 2H); $^{13}$C-NMR (75 MHz, CDCl$_3$): δ 10.4, δ 19.4, δ 22.1, δ 29.9, δ 67.5, δ 87.2 (d, J=185 Hz) δ 126.5 δ 131.1. $^{19}$F-NMR (282 MHz, CDCl$_3$): δ −178.5 (d, J=48.7 Hz). HRMS (EI+): exact mass calculated for C$_{12}$H$_{15}$FO$_2$ requires m/z 210.1056, found 210.1062. Chiral GC analyses were carried out using a Shimadzu GC-17A gas chromatograph, FID detector, Agilent Cyclosilb column (30 m×0.52 mm×0.25 μm film) and the following separation program: 300° C. inlet, 300° C. detector, 100° C. oven, 2° C./min gradient to 200° C., 50° C./min gradient to 250° C., and 250° C. for 2 min. An enantiomeric excess of 87% was estimated based on peak areas.

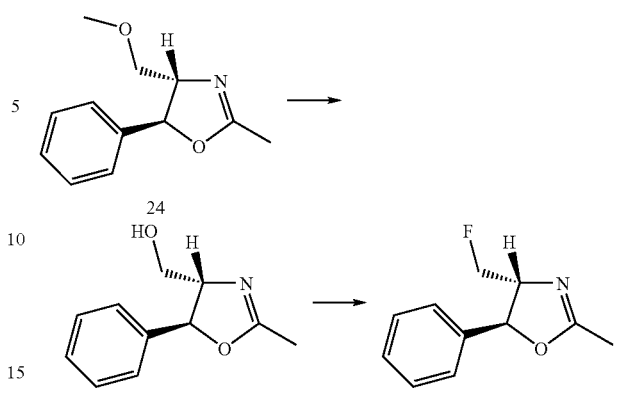

24

25    26

Conversion of 24 to 26. 103 mg (0.5 mmol) 24 were dissolved in 2 mL DMSO and added to 200 mL potassium phosphate buffer pH 8.0. The solution was added with var-H1 (final conc.: 2.5 μM) and a cofactor regeneration system (final conc.: 500 μM NADPH, 30 mM glucose-6-phosphate, 2 units/mL glucose-6-phosphate dehydrogenase) and stirred at room temperature. After 48 hours, the reaction mixture was extracted with dichloromethane (4×70 mL). The combined organic phases were dried over anhydrous Na$_2$SO$_4$ and evaporated under reduced pressure. The residue was purified by flash chromatography (20% ethyl acetate: 80% hexane) to afford 25 (88 mg, 92%, colorless oil). $^1$H-NMR (300 MHz, CDCl$_3$): δ 2.08 (s, 3H, CH$_3$), δ 3.65 (dt, J=11.7, 3.6 Hz, 1H), δ 3.85-3.92 (m, 2H), δ 5.34 (d, J=7.8 Hz, 1H), δ 7.26-7.40 (m, 5H). $^{13}$C-NMR (75 MHz, CDCl$_3$): δ 14.22, δ 56.83, δ 63.18, δ 83.27, δ 125.99, δ 128.50, δ 129.12, δ 140.58, δ 166.60. HRMS (EI$^+$): exact mass calculated for C$_{11}$H$_{13}$NO$_2$ requires m/z 191.0946, found 191.0943. 88 mg (0.46 mmol) 25 and a catalytic amount (3 drops) of ethanol were dissolved in 3 mL dry dichloromethane under argon. The solution was placed in ice. After ten minutes, 66 μL DAST (0.46 mmol, 1 eq) were added to the mixture in aliquots of 22 μL every 30 minutes. The reaction was stirred in ice overnight. The reaction mixture was added with 5 mL saturated sodium bicarbonate and extracted with dichloromethane (3×15 mL). The organic phase was then dried over anhydrous magnesium sulfate and evaporated under reduced pressure. The residue was purified by flash chromatography (gradient 10 to 30% ethyl acetate in hexane) to afford 26 (35 mg, 40% yield, colorless oil). $^1$H-NMR (300 MHz, CDCl$_3$): δ 2.12 (s, 3H, CH$_3$), δ 4.2 (m, 1H), δ 4.57 (dm, J=47.4 Hz, 2H), δ 5.35 (d, J=7.2 Hz, 1H), δ 7.25-7.40 (m, 5H). $^{13}$C-NMR (75 MHz, CDCl$_3$): δ 14.39, δ 60.64, δ 82.34 (d, J=19.6 Hz), δ 83.92 (d, J=155.7 Hz) δ 125.74 (2C), δ 128.72, δ 129.14 (2C), δ 140.34, δ 166.50. $^{19}$F-NMR (282 MHz, CDCl$_3$): δ −230.8 (dt, J=24.2, 45.1 Hz). HRMS (EI+): exact mass calculated for C$_{11}$H$_{12}$FNO requires m/z 193.0903, found 193.0917.

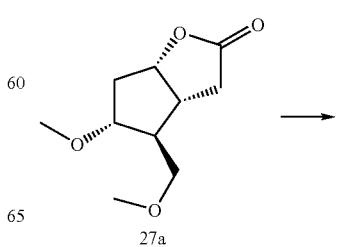

27a

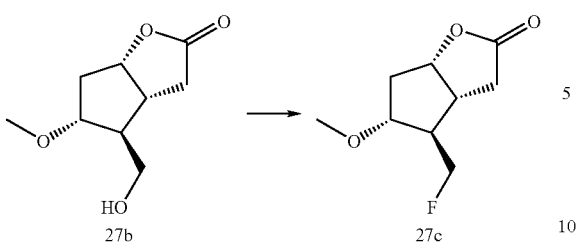

Conversion of 27a to 27c. To a solution containing potassium phosphate buffer pH 8.0 and 0.5 mM 27a in 1% DMSO was added with var-G5 (final conc.: 5 μM), 1 mg/mL bovine serum albumin (BSA), 1000 U/mL catalase, 4.1 U/mL superoxide dismutase (SOD) and a cofactor regeneration system (final conc.: 500 μM NADPH, 30 mM glucose-6-phosphate, 2 units/mL glucose-6-phosphate dehydrogenase). The reaction was stirred for 48 hours at 4° C. then worked-up as described above (e.g. compound 16). The residue was purified by flash chromatography (33% ethyl acetate:67% hexanes, then 50% ethyl acetate:50% hexanes) to afford 27b (60%, colorless oil). $^1$H-NMR (300 MHz, CDCl$_3$): δ 2.2 (m, 3H), δ 2.51 (d J=17.1, 1H), δ 2.76 (m, 2H), δ 3.30 (s, 3H), δ 3.60 (d, J=5.7, 2H), δ 3.75 (q, J=4.8 Hz, 1H), δ 4.96 (m, 1H). $^{13}$C-NMR (75 MHz, CDCl$_3$): δ 26.14, δ 27.4, δ 30.8, δ 48.73, δ 52.09, δ 60.40, δ 73.24, δ 85.57, δ 200.18. HRMS (EI+): exact mass calculated for C$_9$H$_{14}$O$_4$ requires m/z 186.0892, found 186.0885. 14 mg (0.075 mmol) 27b were dissolved in 3 mL of dry dichloromethane and 2.5 μL of dry ethanol were added. The mixture was cooled to −80° C. and 15 μL DAST (0.11 mmol, 1.5 eq) were added. The reaction was allowed to come to room temperature slowly (16 h) and then quenched by addition of 3 mL of saturated NaHCO$_3$ solution. The mixture was extracted with dichloromethane (4×15 mL), the organic phases were collected, dried over anhydrous magnesium sulfate, and evaporated under reduced pressure. The residue was purified by flash chromatography (20% ethyl acetate:80% hexanes, then 33% ethyl acetate: 67% hexanes) to afford 27c (9.4 mg, 66% yield, colorless oil). $^1$H-NMR (300 MHz, CDCl$_3$): δ 2.21 (m, 2H), δ 2.52 (m, 1H), δ 2.81 (m, 2H), δ 3.30 (s, 3H), δ 3.78 (q, J=7.2, 1H), δ 4.40 (ddd, J=47.4, 24.6, 9.6 Hz, 1H, CHF), δ 4.41 (ddd, J=47.4, 24.6, 9.6 Hz, 1H, CHF), δ 5.00 (m, 1H). $^{13}$C-NMR (75 MHz, CDCl$_3$): δ 27.05, δ 35.68, δ 36.85, δ 39.28, δ 52.98 (d, J=18.3 Hz), δ 56.83, δ 83.18 (d, J=139 Hz), δ 84.51, δ 179.29. $^{19}$F-NMR (282 MHz, CDCl$_3$): δ −225.8 (td, J=48.2, 27.1 Hz). HRMS (EI$^+$): exact mass calculated for C$_9$H$_{13}$FO$_3$ requires m/z 188.0849, found 188.0817.

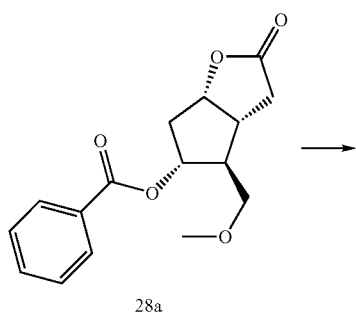

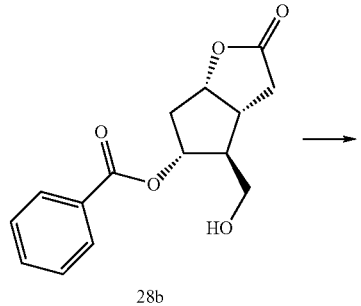

Conversion of 28a to 28c. To a solution containing potassium phosphate buffer pH 8.0 and 1 mM 28a in 1% DMSO was added with var-B3 (final conc.: 5 μM) and a cofactor regeneration system (final conc.: 500 μM NADPH, 30 mM glucose-6-phosphate, 2 units/mL glucose-6-phosphate dehydrogenase). The reaction was stirred for 48 hours at room temperature, then worked-up as described above. The residue was purified by flash chromatography (25% ethyl acetate: 75% hexanes, then 33% ethyl acetate:67% hexanes) to afford 28b (75%, white powder). LC-MS (m/z): [M+H]$^+$ 279.0. $^1$H and $^{13}$C NMR data were identical to those of the authentic standard. Two reaction vessels were prepared dissolving, under argon, 30 mg (0.11 mmol) 28b in 3 mL dry dichloromethane in each vessel. 18.5 μL DAST (0.13 mmol, 1.2 eq) were added each vessel in aliquots of 6 μL aliquots every 30 minutes. The reaction was stirred at room temperature. After 4 hours, the reaction mixture was added with 5 mL saturated sodium bicarbonate and extracted with dichloromethane (3×15 mL). The organic phases were collected, dried over anhydrous magnesium sulfate, and evaporated under reduced pressure. The residue was purified by flash chromatography (20% ethyl acetate:80% hexane) to afford 28c (33 mg, 55% yield, white powder). $^1$H-NMR (300 MHz, CDCl$_3$): δ 2.50 (m, 4H), δ 2.96 (m, 2H), δ 4.54 (ddd, J=47.4, 21.0, 9.6 Hz, 1H, CHF), δ 4.55 (ddd, J=47.4, 21.0, 9.6 Hz, 1H, CHF), δ 5.12 (m, 1H), δ 5.41 (m, 1H), δ 7.44 (m, 2H), δ 7.56 (m, 1H), δ 8.01 (m, 2H). $^{13}$C-NMR (75 MHz, CDCl$_3$): δ 36.20, δ 38.97, δ 40.30, δ 53.66 (d, J=18.5 Hz), δ 73.16, δ 83.62 (d, J=170 Hz), δ 84.92, δ 128.79, δ 129.89, δ 133.66, δ 166.22, δ 176.46. $^{19}$F-NMR (282 MHz, CDCl$_3$): δ −226.7 (td, J=48.0, 30.1 Hz). HRMS (EI$^+$): exact mass calculated for C$_{15}$H$_{16}$FO$_4$ requires m/z 279.1033, found 279.1041.

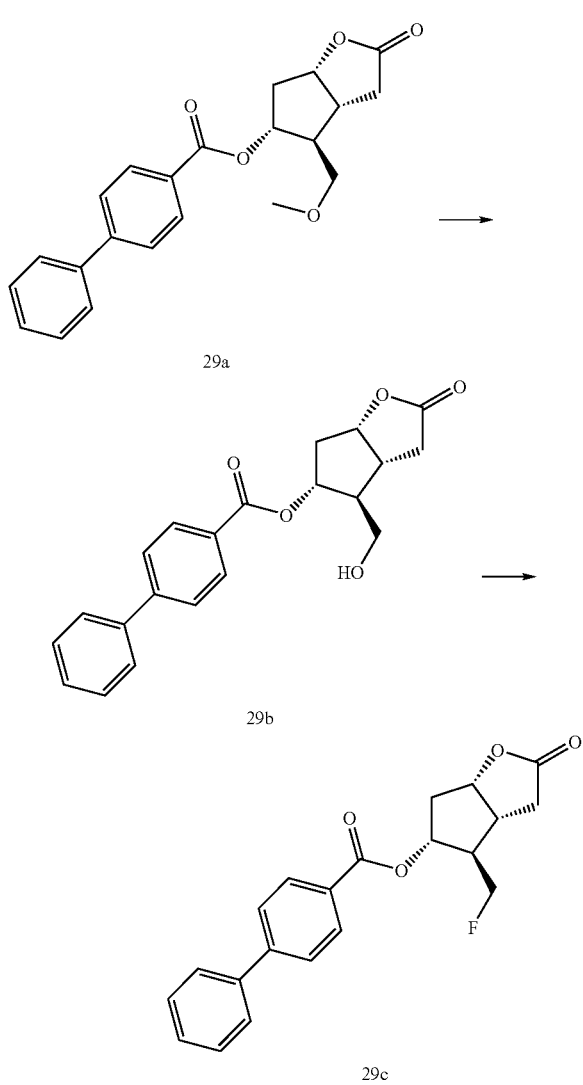

29a

29b

29c

Conversion of 29a to 29c. To a solution containing potassium phosphate buffer pH 8.0 and 0.5 mM 29a in 1% DMSO was added var-H1 (final conc.: 5 µM), 1 mg/mL BSA, 1000 U/mL catalase, 4.1 U/mL SOD and a cofactor regeneration system (final conc.: 500 µM NADPH, 30 mM glucose-6-phosphate, 2 units/mL glucose-6-phosphate dehydrogenase). The reaction was stirred for 48 hours at room temperature, then worked-up as described above (e.g. compound 16). The residue was purified by flash chromatography (25% ethyl acetate: 75% hexanes, then 50% ethyl acetate: 50% hexanes) to afford 29b (60%, colorless oil). LC-MS (m/z): [M+H]+ 355.0. $^1$H and $^{13}$C NMR data were identical to those of the authentic standard. Two reaction vessels were prepared dissolving, under argon, 20 mg (0.05 mmol) 29b in 2 mL dry dichloromethane in each vessel. 10 µL DAST (0.07 mmol, 1.2 eq) were added to each vessel in aliquots of 3 □L aliquots every 30 minutes. The reaction was stirred at room temperature. After 6 hours, the reaction mixture was added with 5 mL saturated sodium bicarbonate and extracted with dichloromethane (3×15 mL). The organic phases were collected, dried over anhydrous magnesium sulfate, and evaporated under reduced pressure. The residue was purified by flash chromatography (20% ethyl acetate:80% hexane) to afford 29c (18 mg, 52% yield, white powder). $^1$H-NMR (300 MHz, CDCl$_3$): δ 2.44 (m, 2H), δ 2.50-2.61 (m, 2H), δ 2.95-3.02 (m, 2H), δ 4.48 (ddd, J=47.1, 21.3, 11.7 Hz, 1H, CHF), δ 4.64 (ddd, J=47.1, 21.3, 11.7 Hz, 1H, CHF), δ 5.15 (m, 1H), δ 5.44 (m, 1H), δ 7.35-7.50 (m, 3H), δ 7.55-7.69 (m, 4H), δ 8.02-8.08 (m, 2H). $^{13}$C-NMR (75 MHz, CDCl$_3$): δ 36.26, δ 39.00, δ 40.28 (d, J=4.27 Hz), δ 53.76 (d, J=18.2 Hz), 83.77 (d, J=183.9 Hz), δ 84.81, δ 127.45 (2C), δ 127.52 (2C), δ 128.35, δ 128.45, δ 129.17 (2C), δ 130.44 (2C), δ 140.08, δ 146.35, δ 166.11, δ 176.55. $^{19}$F-NMR (282 MHz, CDCl$_3$): δ −226.6 (td, J=45.4, 30.2 Hz). HRMS (EI+): exact mass calculated for C$_{21}$H$_{20}$FO$_4$ requires m/z 355.1346, found 355.1332.

P450 expression and purification. For the chemo-enzymatic transformations, P450 enzymes were used in purified form. Enzyme batches were prepared as follows. Two liters Terrific Broth medium were inoculated with an overnight culture (10 mL) of recombinant E. coli DH5α cells harboring a pCWori plasmid encoding for the P450 variant under the control of Plac promoter. At OD$_{600}$=1-1, cultures were added with 0.5 mM IPTG and 0.5 mM δ-aminolevulinic acid (ALA) and transferred to 25° C. Cells were harvested after 24 hours. The cell pellet was resuspended in 25 mM TRIS (pH 8.0) and cell membranes were disrupted by sonication. Cell lysate was loaded onto a Q resin and the column was washed with 3 column volumes of 25 mM TRIS (pH 8.0), 150 mM NaCl. Bound protein was eluted with 25 mM TRIS (pH 8.0), 340 mM NaCl and concentrated using Millipore Centricon. After buffer exchange with 100 mM KPi (pH 8.0), protein samples were frozen and stored at ~80° C. Protein concentration was determined in duplicate from CO-difference spectra. Yields typically ranged between 100 and 500 mg protein per liter depending on the variant.

The first group of test molecules (1-3; FIG. 10a,b) contains a cyclopentenone moiety found in several natural products (e.g. jasmonoids, cyclopentanoid antibiotic, and prostaglandins). The synthesis and functionalization of these scaffolds is not trivial. The activities of the enzymes towards these substrates were probed in multi-well format using GC and GC-MS (FIG. 10a). Depending on the substrate, approximately 30 to 50% of the 96 enzyme variants displayed useful activity (>800 turnovers), while 30 to 50% of this active subset showed moderate to excellent regioselectivity (50-100%). The most active and selective variants were applied in preparative scale reactions (100-300 mg) using ~0.05 mol % catalyst. Compared to 96-well plate reactions, three to four times higher turnover numbers could be obtained using purified enzyme and longer reaction times (24-48 hours). After flash chromatography purification, the hydroxylated products were subjected to deoxofluorination using the common nucleophilic fluorinating agent diethylaminosulfur trifluoride (DAST, 4). The identities and purities of the fluorinated products were established by GC-MS, HRMS, and 1H-, 13C- and $^{19}$F-NMR. Using this strategy, two to three different sites on each substrate were targeted with good to excellent regioselectivity (55-100%), affording the fluorinated derivatives 5-11 with yields of up to 80% over the two steps.

This fluorination strategy was then tested on a methyl ester pro drug of the anti-inflammatory drug ibuprofen (12; FIG. 10a,c). While preparation of α fluoro derivatives of this compound is straightforward, incorporating fluorine atoms in the poorly reactive isobutyl group is not. The methods above identified two chemo-enzymatic routes to achieve this goal in a selective (position 1: 75%; position 2: 100%) and efficient manner (yields over two steps for 15 and 16 were 62% and 84%, respectively) and at preparative scales (150-200 mg).

Two sequential chemo-enzymatic transformations were tested to fluorinate multiple sites of the same molecule. P450 variant B4 (var-B4)—which was used to convert 12 to 13—was found to retain comparable activity on 16, providing a possible route to the desired 17 intermediate. Re-screening of 12-active variants on 16, however, led to the identification of a more suitable candidate, var-B2, with higher activity than var-B4 towards 16 and excellent (100%) 2 regioselectivity. Using var-B2, the synthesis of fluoro-hydroxy derivative 17 was afforded in higher yields (93% vs. 72% for 1213) and required less catalyst (0.06 mol % vs. 0.1 mol % for 1213). 17 was then converted quantitatively to the desired difluoro-derivative 18.

The value of the present approach as synthetic tool for asymmetric fluorination was also examined. In the absence of anchimeric group participation, the DF reaction generally preserves the enantiopurity of the enzymatic products through inversion of configuration. Chiral GC analysis showed appreciable stereoselectivity during preparation of 7 (78% ee), 9 (dr 1:8.5), 10 (dr 4:96), 15 (dr 1:3.2), and 18 (dr 1:3.7). The previous investigations on 2 phenyl acetic acid esters were extended, carrying out the asymmetric synthesis of the corresponding 2 fluoro-2-aryl acetic acid derivatives at 100 mg-scale (19a-23a; Table 5). In this case, up to 89% ee in up to 60% yield (two steps) were achieved.

TABLE 5

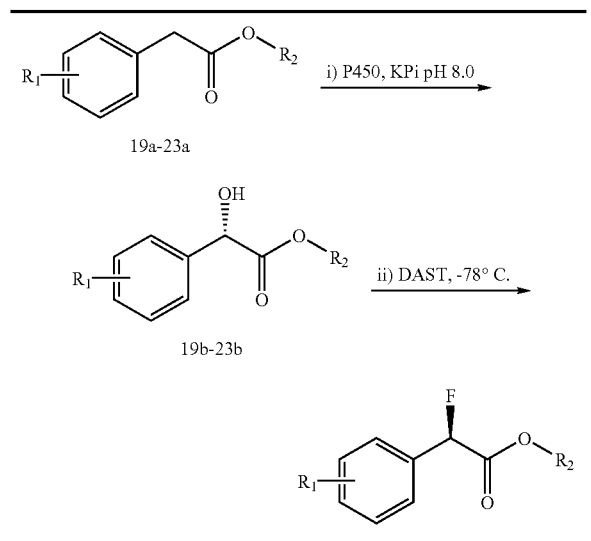

Stereoselective fluorination of substituted 2-aryl acetic acid esters.

| Compound | R₁ | R₂ | P450[a] | mol % | Yield (i)[b] | Yield (ii)[b] | ee[c] |
|---|---|---|---|---|---|---|---|
| 19a | H | Me | var-A3 | 0.1 | 45% (19b) | 75% (19c) | 74% |
| 20a | H | Et | var-B4 | 0.1 | 66% (20b) | 78% (20c) | 72% |
| 21a | m-Cl | Pr | var-C12 | 0.05 | 75% (21b) | 82% (21c) | 89% |

TABLE 5-continued

| 22a | o-Me | Pr | var-C12 | 0.05 | 65% (22b) | 83% (22c) | 85% |
| 23a | p-Me | Pr | var-C12 | 0.05 | 72% (23b) | 88% (23c) | 87% |

[a]The sequences of the P450 variants are reported in Table 6.
[b]Yields refer to the isolated product.
[c]Enantiomeric excess determined by chiral GC analysis.

TABLE 6

Sequences of the P450$_{BM3}$ variants.

| Enzyme | Amino acid mutations compared to wildtype P450$_{BM3}$ |
|---|---|
| var-B2 | V78A, H138Y, T175I, V178I, A184V, H236Q, E252G, R255S, A290V, A295T, L353V |
| var-B3 | R47C, V78A, K94I, P142S, T175I, A184V, F205C, S226R, H236Q, E252G, R255S, A290V, L353V |
| var-B4 | F87A |
| var-C12 | R47C, V78A, F87A, K94I, P142S, T175I, A184V, F205C, S226R, H236Q, E252G, R255S, A290V, L353V |
| var-D10 | R47C, V78A, A82L, K94I, P142S, T175I, A184V, F205C, S226R, H236Q, E252G, R255S, A290V, A328V, L353V |
| var-G4 | V78A, A82G, F87V, P142S, T175I, A184V, F205C, S226R, H236Q, E252G, R255S, A290V, A328V, L353V |
| var-G5 | V78A, F87I, P142S, T175I, A184V, F205C, S226R, H236Q, E252G, R255S, A290V, L353V |
| var-G6 | V78A, F81P, A82L, F87A, P142S, T175I, A180T, A184V, A197V, F205C, S226R, H236Q, E252G, R255S, A290V, L353V |
| var-H1 | R47C, L52I, V78F, A82S, K94I, P142S, T175I, A184V, F205C, S226R, H236Q, E252G, R255S, A290V, A328L, K349N, L353V, I366V, E464G, I710T |
| var-H3 | V78A, T175I, A184V, F205C, S226R, H236Q, E252G, R255S, A290V, L353V |

P450-catalyzed hydroxylation of methoxy groups leads to exposure of a free hydroxyl group through decomposition of the hemi-acetal produced and release of formaldehyde. This chemo-enzymatic strategy could be extended to substitute a methoxy group for fluorine, a challenging transformation for traditional chemical methods. This approach was first tested on the 5-phenyl oxazoline derivative 24 (FIG. 11a,b). The demethylation activities of the P450 variants could be easily assessed using a calorimetric screen (FIG. 11a). The most active variants from the screen were further analyzed with respect to the regioselectivity of oxidation using GC-MS. The highly selective P450 variant var-H1 (95%) was thus applied in combination to DF to afford the desired fluorine-containing compound 26.

The same approach was tested on a set of derivatives of the synthetically important building block Corey lactone (CL) (FIG. 11c). The use of various CLs (27a-29a) enabled investigation of the tolerance of the enzymatic transformation to structural variations within the target scaffold. Based on the colorimetric screen, 30 variants displayed activity on at least one CL (12 on 27a, 17 on 28a, 5 on 29a). Twelve variants were found to accept both 27a and 28a, five 28a and 29a, and five 27a and 29a. Interestingly, four variants (~10% of the CL-active variants) could be used to activate the substrate for subsequent fluorination, regardless of the size of the variable substituent. Using the most active and selective enzymes towards each of the CLs, the desired fluorine-containing compounds 27c, 28c, and 29c were synthesized and isolated.

Ibuprofen has recently shown promising activity against amyloidogenic diseases. Anti-amyloidogenic drugs with high brain permeability are intensively sought after. Compounds 15, 16 and 18 were tested in a membrane permeability assay that mimics the composition of the blood-brain barrier (BBB). While 12 has only modest BBB-crossing potential, monofluorinated 15 and 16 and difluorinated 18 exhibit, respectively, very good and excellent membrane permeability properties (effective permeability value>10×10$^{-6}$ cm s−1, FIG. 12), demonstrating how this procedure could be applied to rapidly screen various H→F substitutions in a target molecule for improvement in chemo-physical or biological properties.

The chemo-enzymatic approach of the disclosure has proven useful for fluorinating 13 of the 16 molecules tested (see FIG. 9). The molecular weight of these compounds ranges between 110 and 450 Da. About 75% of commercial drugs fall within this window. As the P450BM3 active site is largely hydrophobic, highly polar compounds may also be poor substrates. Difficulties were mostly associated with solubilisation of the substrate in aqueous media (30) or with the occurrence of side reactions—in particular elimination—during the deoxofluorination transformation (hydroxylated 31 and 32), which prevented isolation of the enzymatic and fluorinated products, respectively, in satisfactory yields. These issues could be addressed, however, by using P450BM3 variants with increased activity in the presence of organic co-solvent and applying milder nucleophilic fluorination methods.

The disclosure also provides compounds generated by the methods of the disclosure. Compounds developed by the methods include a set from Table 7 below.

TABLE 7

| Compound number | name |
| --- | --- |
| 1 | 2,3-Dimethyl-cyclopent-2-enone |
| 1a | 4-Hydroxy-2,3-dimethyl-cyclopent-2-enone |
| 1c | 3-Hydroxymethyl-2-methyl-cyclopent-2-enone |
| 2 | 3-Methyl-2-pentyl-cyclopent-2-enone |
| 2a | 4-Hydroxy-3-methyl-2-pentyl-cyclopent-2-enone |
| 2c | 3-Hydroxymethyl-2-pentyl-cyclopent-2-enone |
| 3 | 3-Methyl-2,3,4,5,6,7-hexahydro-1H-inden-1-one |
| 3a | 7-Hydroxy-3-methyl-2,3,4,5,6,7-hexahydro-1H-inden-1-one |
| 3b | 4-Hydroxy-3-methyl-2,3,4,5,6,7-hexahydro-1H-inden-1-one |
| 3c | 5-Hydroxy-3-methyl-2,3,4,5,6,7-hexahydro-1H-inden-1-one |
| 4 | Diethylaminosulfur trifluoride |
| 5 | 4-Fluoro-2,3-dimethyl-cyclopent-2-enone |
| 6 | 3-Fluoromethyl-2-methyl-cyclopent-2-enone |
| 7 | 4-Fluoro-3-methyl-2-pentyl-cyclopent-2-enone |
| 8 | 3-Fluoromethyl-2-pentyl-cyclopent-2-enone |
| 9 | 7-Fluoro-3-methyl-2,3,4,5,6,7-hexahydro-1H-inden-1-one |
| 10 | 4-Fluoro-3-methyl-2,3,4,5,6,7-hexahydro-1H-inden-1-one |
| 11 | 5-Fluoro-3-methyl-2,3,4,5,6,7-hexahydro-1H-inden-1-one |
| 12 | 2-(4-Isobutyl-phenyl)-propionic acid methyl ester |
| 13 | 2-[4-(1-Hydroxy-2-methyl-propyl)-phenyl]-propionic acid methyl ester |
| 14 | 2-[4-(2-Hydroxy-2-methyl-propyl)-phenyl]-propionic acid methyl ester |
| 15 | 2-[4-(1-Fluoro-2-methyl-propyl)-phenyl]-propionic acid methyl ester |
| 16 | 2-[4-(2-Fluoro-2-methyl-propyl)-phenyl]-propionic acid methyl ester |
| 17 | 2-[4-(2-Fluoro-1-hydroxy-2-methyl-propyl)-phenyl]-propionic acid methyl ester |
| 18 | 2-[4-(1,2-Difluoro-2-methyl-propyl)-phenyl]-propionic acid methyl ester |
| 19a | Phenyl-acetic acid methyl ester |
| 19b | (S)-Hydroxy-phenyl-acetic acid methyl ester |
| 19c | (R)-Fluoro-phenyl-acetic acid methyl ester |
| 20a | Phenyl-acetic acid ethyl ester |
| 20b | (S)-Hydroxy-phenyl-acetic acid ethyl ester |
| 20c | (R)-Fluoro-phenyl-acetic acid ethyl ester |
| 21a | (3-Chloro-phenyl)-acetic acid propyl ester |
| 21b | (S)-(3-Chloro-phenyl)-hydroxy-acetic acid propyl ester |
| 21c | (R)-(3-Chloro-phenyl)-fluoro-acetic acid propyl ester |
| 22a | o-Tolyl-acetic acid propyl ester |
| 22b | (S)-Hydroxy-o-tolyl-acetic acid propyl ester |
| 22c | (R)-Fluoro-o-tolyl-acetic acid propyl ester |
| 23a | p-Tolyl-acetic acid propyl ester |
| 23b | (S)-Hydroxy-p-tolyl-acetic acid propyl ester |
| 23c | (R)-Fluoro-p-tolyl-acetic acid propyl ester |
| 24 | (4S,5S)-4,5-Dihydro-4-(methoxymethyl)-2-methyl-5-phenyl-1,3-oxazole |
| 25 | (4S,5S)-4,5-Dihydro-2-methyl-5-phenyl-4-oxazolemethanol |
| 26 | (4R,5S)-4-Fluoromethyl-4,5-dihydro-2-methyl-5-phenyl-1,3-oxazole |
| 27a | (3aR,4S,5R,6aS)-Hexahydro-5-methoxy-4-(methoxymethyl)-2H-cyclopentafuran-2-one |
| 27b | (3aR,4S,5R,6aS)-Hexahydro-4-(hydroxymethyl)-5-methoxy-2H-cyclopentafuran-2-one |
| 27c | (3aR,4R,5R,6aS)-4-Fluoromethyl-hexahydro-5-methoxy-2H-cyclopentafuran-2-one |
| 28a | (3aR,4S,5R,6aS)-5-(Benzoyloxy)hexahydro-4-(methoxymethyl)-2H-cyclopentafuran-2-one |
| 28b | (3aR,4S,5R,6aS)-5-(Benzoyloxy)hexahydro-4-(hydroxymethyl)-2H-cyclopentafuran-2-one |
| 28c | (3aR,4R,5R,6aS)-5-(Benzoyloxy)4-(fluoromethyl)-hexahydro-2H-cyclopentafuran-2-one |
| 29a | (3aR,4S,5R,6aS)-[1,1'-Biphenyl]-4-carboxylic acid, hexahydro-4-(hydroxymethyl)-2-oxo-2H-cyclopentafuran-5-yl ester |
| 29b | (3aR,4S,5R,6aS)-[1,1'-Biphenyl]-4-carboxylic acid, hexahydro-4-(methoxymethyl)-2-oxo-2H-cyclopentafuran-5-yl ester |
| 29c | (3aR,4R,5R,6aS)-[1,1'-Biphenyl]-4-carboxylic acid,4-(fluoromethyl)-hexahydro-2-oxo-2H-cyclopentafuran-5-yl ester |
| 30 | Nabumetone |
| 31 | Phenylbutazone |
| 32 | Glipizide |

The disclosure thus provides a method and system, and in particular a chemo-enzymatic method and system for selectively fluorinating organic molecules on a target site wherein the target site is activated and then fluorinated are present together with a method and system for identifying a molecule having a biological activity. In particular, A chemo-enzymatic method for preparation of selectively fluorinated derivatives of organic compounds with diverse molecular structures is presented together with a system for fluorination of an organic molecule and a method for identification of a molecule having a biological activity.

A number of embodiments of the disclosure have been described. Nevertheless, it will be understood that various modifications may be made without departing from the spirit and scope of the disclosure. Accordingly, other embodiments are within the scope of the following claims.

REFERENCES

Bass, S., V. Sorrells, et al. (1988). "Mutant Trp repressors with new DNA-binding specificities." *Science* 242(4876): 240-5.

Beeson, T. D. and D. W. C. MacMillan (2005). "Enantioselective organocatalytic alpha-fluorination of aldehydes." *Journal of the American Chemical Society* 127(24): 8826-8828.

Blee, E., A. L. Wilcox, et al. (1993). "Mechanism of Reaction of Fatty-Acid Hydroperoxides with Soybean Peroxygenase." *Journal of Biological Chemistry* 268(3): 1708-1715.

Bobbio, C. and V. Gouverneur (2006). "Catalytic asymmetric fluorinations." *Org Biomol Chem* 4(11): 2065-75.

Bohm, H. J., D. Banner, et al. (2004). "Fluorine in medicinal chemistry." *Chembiochem* 5(5): 637-43.

Bornscheuer, U. T. (2003). "Immobilizing enzymes: how to create more suitable biocatalysts." *Angew. Chem. Int. Ed. Engl.* 42: 3336-3337.

Botstein, D. and D. Shortle (1985). "Strategies and applications of in vitro mutagenesis." *Science* 229(4719): 1193-201.

Braxton, S, and J. A. Wells (1991). "The importance of a distal hydrogen bonding group in stabilizing the transition state in subtilisin BPN'." *J Biol Chem* 266(18): 11797-800.

Burke, T. R., B. Ye, et al. (1996). "Small molecule interactions with protein-tyrosine phosphatase PTP1B and their use in inhibitor design." *Biochemistry* 35(50): 15989-15996.

Cahard, D., C. Audouard, et al. (2000). "Design, synthesis, and evaluation of a novel class of enantioselective electrophilic fluorinating agents: N-fluoro ammonium salts of cinchona alkaloids (F-CA-BF4)." *Organic Letters* 2(23): 3699-3701.

Camarero, J. A. and A. R. Mitchell (2005). "Synthesis of proteins by native chemical ligation using Fmoc-based chemistry." *Protein Pept. Lett.* 12(8): 723-8.

Cao, L. (2005). "Immobilised enzymes: science or art?" *Curr Opin Chem Biol* 9(2): 217-26.

Carter, P. (1986). "Site-directed mutagenesis." *Biochem J* 237(1): 1-7.

Casper, D., U. Yaparpalvi, et al. (2000). "Ibuprofen protects dopaminergic neurons against glutamate toxicity in vitro." *Neurosci Lett* 289(3): 201-4.

Chambers, R. D., J. Hutchinson, et al. (2000). *J. Fluorine Chem.* 102: 169.

Chambers, R. D., C. J. Skinner, et al. (1996). J. Chem. Soc., Perkin Trans. J: 605.

Cirino, P. C. and F. H. Arnold (2003). "A self-sufficient peroxide-driven hydroxylation biocatalyst." *Angewandte Chemie-International Edition* 42(28): 3299-3301.

Clader, J. W. (2004). "The discovery of ezetimibe: a view from outside the receptor." *J. Med. Chem.* 47(1): 1-9.

Dale, S. J. and I. R. Felix (1996). "Oligonucleotide-directed mutagenesis using an improved phosphorothioate approach." *Methods Mol Biol* 57: 55-64.

Davis, F. A. and W. Han (1992). "Diastereoselective Fluorination of Chiral Imide Enolates Using N-Fluoro-O-Benzenedisulfonimide (Nfobs)." *Tetrahedron Letters* 33(9): 1153-1156.

Davis, F. A., P. Zhou, et al. (1998). "Asymmetric fluorination of enolates with nonracemic N-fluoro-2,10-camphorsultams." *Journal of Organic Chemistry* 63(7): 2273-2280.

De-Moura, N. F., E. Simionatto, et al. (2002). "Quinoline Alkaloids, Coumarins and Volatile Constituents of Helietta longifoliata." *Planta Med.* 68: 631-634.

De Souza, M. V. N. (2005). "The furan-2(5H)-ones: Recent synthetic methodologies and its application in total synthesis of natural products" *Mini-rev. Org. Chem.* 2(2): 139-145.

Denisov, I. G., T. M. Makris, et al. (2005). "Structure and chemistry of cytochrome P450." *Chem. Rev.* 105(6): 2253-77.

Eghtedarzadeh, M. K. and S. Henikoff (1986). "Use of oligonucleotides to generate large deletions." *Nucleic Acids Res* 14(12): 5115.

Enders, D., M. Potthoff, et al. (1997). "Regio- and enantioselective synthesis of alpha-fluoroketones by electrophilic fluorination of alpha-silylketone enolates with N-fluorobenzosulfonimide." *Angewandte Chemie-International Edition in English* 36(21): 2362-2364.

Green, T. W. and P. G. M. Wuts (1999). *Protective Groups in Organic Synthesis*. New York, Wiley-Interscience.

Grundstrom, T., W. M. Zenke, et al. (1985). "Oligonucleotide-directed mutagenesis by microscale 'shot-gun' gene synthesis." *Nucleic Acids Res* 13(9): 3305-16.

Hamashima, Y. and M. Sodeoka (2006). "Enantioselective fluorination reactions catalyzed by chiral palladium complexes." *Synlett*(10): 1467-1478.

Hanano, A., M. Burcklen, et al. (2006). "Plant seed peroxygenase is an original heme-oxygenase with an EF-hand calcium binding motif." *Journal of Biological Chemistry* 281(44): 33140-33151.

Harper, D. B. and D. O'Hagan (1994). "The fluorinated natural products." *Nat Prod Rep* 11(2): 123-33.

Hayashi, H., H. Sonoda, et al. (2002). "2,2-difluoro-1,3-dimethylimidazolidine (DFI). A new fluorinating agent." *Chemical Communications* (15): 1618-1619.

Hintermann, L. and A. Togni (2000). "Catalytic enantioselective fluorination of beta-ketoesters." *Angewandte Chemie-International Edition* 39(23): 4359-+.

Joo, H., Z. L. Lin, et al. (1999). "Laboratory evolution of peroxide-mediated cytochrome P450 hydroxylation." *Nature* 399(6737): 670-673.

Kim, D. Y. and E. J. Park (2002). "Catalytic enantioselective fluorination of beta-keto esters by phase-transfer catalysis using chiral quaternary ammonium salts." *Organic Letters* 4(4): 545-547.

Knight, D. W. (1994). *Contemporary Organic Synthesis* 1: 287.

Kramer, W., V. Drutsa, et al. (1984). "The gapped duplex DNA approach to oligonucleotide-directed mutation construction." *Nucleic Acids Res* 12(24): 9441-56.

Kramer, W. and H. J. Fritz (1987). "Oligonucleotide-directed construction of mutations via gapped duplex DNA." *Methods Enzymol* 154: 350-67.

Kunkel, T. A., J. D. Roberts, et al. (1987). "Rapid and efficient site-specific mutagenesis without phenotypic selection." *Methods Enzymol* 154: 367-82.

Lal, G. S., G. P. Pez, et al. (1999). "Bis(2-methoxyethyl) aminosulfur trichloride: a new broad-spectrum deoxofluorinating agent with enhanced thermal stability." *J. Org. Chem.* 64: 7048-54.

Landwehr, M., M. Carbone, et al. (2007). "Diversification of catalytic function in a synthetic family of chimeric cytochrome p450s." *Chem Biol* 14(3): 269-78.

Leuchtenberger, S., D. Beher, et al. (2006). "Selective modulation of Abeta42 production in Alzheimer's disease: nonsteroidal anti-inflammatory drugs and beyond." *Curr Pharm Des* 12(33): 4337-55.

Ling, M. M. and B. H. Robinson (1997). "Approaches to DNA mutagenesis: an overview." *Anal Biochem* 254(2): 157-78.

Ma, J. A. and D. Cahard (2004). "Asymmetric fluorination, trifluoromethylation, and perfluoroalkylation reactions." *Chem Rev* 104(12): 6119-46.

Ma, J. A. and D. Cahard (2004). "Copper(II) triflate-bis(oxazoline)-catalysed enantioselective electrophilic fluorination of beta-ketoesters." *Tetrahedron-Asymmetry* 15(6): 1007-1011.

Mandecki, W. (1986). "Oligonucleotide-directed double-strand break repair in plasmids of *Escherichia coli*: a method for site-specific mutagenesis." *Proc Natl Acad Sci USA* 83(19): 7177-81.

Marigo, M., D. I. Fielenbach, et al. (2005). "Enantioselective formation of stereogenic carbon-fluorine centers by a simple catalytic method." *Angewandte Chemie-International Edition* 44(24): 3703-3706.

Matsunaga, I., T. Sumimoto, et al. (2002). "Functional modulation of a peroxygenase cytochrome P450: novel insight into the mechanisms of peroxygenase and peroxidase enzymes." *Febs Letters* 528(1-3): 90-94.

Matsunaga, I., A. Yamada, et al. (2002). "Enzymatic reaction of hydrogen peroxide-dependent peroxygenase cytochrome P450s: kinetic deuterium isotope effects and analyses by resonance Raman spectroscopy." *Biochemistry* 41(6): 1886-92.

Middleton, W. J. (1975). "New Fluorinating Reagents—Dialkylaminosulfur Fluorides." *Journal of Organic Chemistry* 40(5): 574-578.

Mikolajczyk, M., M. Mikina, et al. (1999). "New phosphonate-mediated synteses of cyclopentanoids and prostaglandins." *Pure Appl. Chem.* 71(3): 473-480.

Nakamaye, K. L. and F. Eckstein (1986). "Inhibition of restriction endonuclease Nci I cleavage by phosphorothioate groups and its application to oligonucleotide-directed mutagenesis." *Nucleic Acids Res* 14(24): 9679-98.

Nambiar, K. P., J. Stackhouse, et al. (1984). "Total synthesis and cloning of a gene coding for the ribonuclease S protein." *Science* 223(4642): 1299-301.

Nyffeler, P. T., S. G Duron, et al. (2005). "Selectfluor: Mechanistic insight and applications." *Angewandte Chemie-International Edition* 44(2): 192-212.

Ojima, I. (2004). "Use of fluorine in the medicinal chemistry and chemical biology of bioactive compounds—a case study on fluorinated taxane anticancer agents." *Chembiochem* 5(5): 628-35.

Otey, C. R., M. Landwehr, et al. (2006). "Structure-Guided Recombination Creates an Artificial Family of Cytochromes P450." *PLoS Biol* 4(5): e112.

Park, B. K., N. R. Kitteringham, et al. (2001). "Metabolism of fluorine-containing drugs." *Annu. Rev. Pharmacol. Toxicol.* 41: 443-70.

Presnell, S. R. and F. E. Cohen (1989). *Proc. Natl. Acad. Sci. U.S.A.* 86: 6592.

Pylypenko, O. and I. Schlichting (2004). "Structural aspects of ligand binding to and electron transfer in bacterial and fungal P450s." *Annu. Rev. Biochem.* 73: 991-1018.

Sakamoto, T., J. M. Joern, et al. (2001). "Laboratory evolution of toluene dioxygenase to accept 4-picoline as a substrate." *Applied and Environmental Microbiology* 67(9): 3882-+.

Sayers, J. R., W. Schmidt, et al. (1988). "5'-3' exonucleases in phosphorothioate-based oligonucleotide-directed mutagenesis." *Nucleic Acids Res* 16(3): 791-802.

Schwarzer, D. and P. A. Cole (2005). "Protein semisynthesis and expressed protein ligation: chasing a protein's tail." *Curr. Opin. Chem. Biol.* 9(6): 561-9.

Shibata, N., T. Ishimaru, et al. (2004). "First enantio-flexible fluorination reaction using metal-bis(oxazoline) complexes." *Synlett*(10): 1703-1706.

Shibata, N., E. Suzuki, et al. (2000). "A fundamentally new approach to enantioselective fluorination based on cinchona alkaloid derivatives/selectfluor combination." *Journal of the American Chemical Society* 122(43): 10728-10729.

Shimizu, Y., Y. Kuruma, et al. (2006). "Cell-free translation systems for protein engineering." *FEBS J.* 273(18): 4133-40.

Smith, M. (1985). "In vitro mutagenesis." *Annu Rev Genet.* 19: 423-62.

Swain, C. and N. M. J. Rupniak (1999). "Progress in the development of neurokinin antagonists." *Annual Reports in Medicinal Chemistry, Vol 34* 34: 51-60.

Taylor, J. W., W. Schmidt, et al. (1985). "The use of phosphorothioate-modified DNA in restriction enzyme reactions to prepare nicked DNA." *Nucleic Acids Res* 13(24): 8749-64.

Taylor, S. D., C. C. Kotoris, et al. (1999). "Recent advances in electrophilic fluorination." *Tetrahedron* 55(43): 12431-12477.

Togni, A., A. Mezzetti, et al. (2001). "Developing catalytic enantioselective fluorination." *Chimia* 55(10): 801-805.

Townsend, K. P. and D. Pratico (2005). "Novel therapeutic opportunities for Alzheimer's disease: focus on nonsteroidal anti-inflammatory drugs." *Faseb J* 19(12): 1592-601.

van Beilen, J. B. and E. G Funhoff (2007). "Alkane hydroxylases involved in microbial alkane degradation." *Appl Microbiol Biotechnol* 74(1): 13-21.

van Niel, M. B., I. Collins, et al. (1999). "Fluorination of 3-(3-(piperidin-1-yl)propyl)indoles and 3-(3-(piperazin-1-yl)propyl)indoles gives selective human 5-HT1D receptor ligands with improved pharmacokinetic profiles." *Journal of Medicinal Chemistry* 42(12): 2087-2104.

Wang, L., J. Xie, et al. (2006). "Expanding the genetic code." *Annu. Rev. Biophys. Biomol. Struct.* 35: 225-249.

Wells, J. A., M. Vasser, et al. (1985). "Cassette mutagenesis: an efficient method for generation of multiple mutations at defined sites." *Gene* 34(2-3): 315-23.

Yamazaki, Y., S. Yusa, et al. (1996). "Effect of fluorine substitution of alpha- and beta-hydrogen atoms in ethyl phenylacetate and phenylpropionate on their stereoselective hydrolysis by cultured cancer cells" *J. Fluorine Chem.* 79(2): 167-171.

Zoller, M. J. (1992). "New recombinant DNA methodology for protein engineering." *Curr Opin Biotechnol* 3(4): 348-54.

Zoller, M. J. and M. Smith (1983). "Oligonucleotide-directed mutagenesis of DNA fragments cloned into M13 vectors." *Methods Enzymol* 100: 468-500.

Zoller, M. J. and M. Smith (1987). "Oligonucleotide-directed mutagenesis: a simple method using two oligonucleotide primers and a single-stranded DNA template." *Methods Enzymol* 154: 329-50.

What is claimed is:

1. A method for fluorinating an organic molecule, the method comprising contacting an organic molecule comprising a structure of formula I:

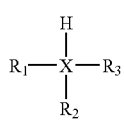

(I)

wherein,

X is the target site carbon;

$R_1$ is selected from the group consisting of hydrogen, aliphatic, aryl, substituted aliphatic, substituted aryl, heteroatom-containing aryl, substituted heteroatom-containing aliphatic, substituted heteroatom-containing aryl, and functional group;

$R_2$ is selected from the group consisting of a hydroxyl, alkoxy, or aryloxy; and $R_3$ is a Corey lactone or Corey lactone derivative;

with an oxygenase comprising a polypeptide having oxygenase activity, wherein the polypeptide has at least 95% identity to a polypeptide selected from the group consisting of SEQ ID NO: 21, SEQ ID NO: 22, SEQ ID NO: 23, SEQ ID NO:24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO:47, SEQ ID NO: 48, SEQ ID NO: 49, SEQ ID NO:50, SEQ ID NO: 51, SEQ ID NO: 52; SEQ ID NO: 63, SEQ ID NO:64, SEQ ID NO:65, SEQ ID NO:66, SEQ ID NO: 67, SEQ ID NO:68, and SEQ ID NO: 69; and contacting a fluorinating agent with the oxidized organic molecule, for a time and under condition to allow replacement of the oxygen-containing functional group with fluorine.

2. The method of claim 1, wherein the oxygenase is a variant P450$_{BM3}$ oxygenase enzyme.

3. The method of claim 1, wherein $R_1$ is a hydrogen.

4. The method of claim 1, wherein the organic molecule of formula I is a Corey lactone selected from the group consisting of:

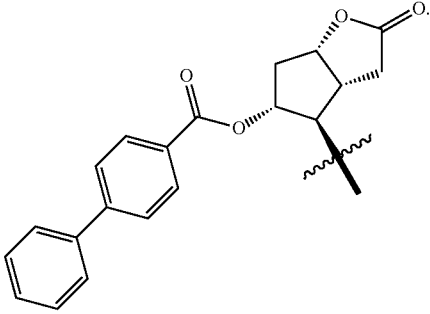

5. The method of claim 1, wherein the Corey lactone or Corey lactone derivative is a prostaglandin precursor.

6. The method of claim 1, wherein the oxygenase is selected from the group consisting of CYP102A1, CYP102A2, CYP102A3, CYP102A5, CYP102E1, CYP102A6, CYP101A1, CYP106A2, CYP153A6, CYP153A7, CYP153A8, CYP153A11, CYP153D2, CYP153D3, P450cin, P450terp, P450eryF, CYP1A2, CYP2C8, CYP2C9, CYP2C19, CYP2D6, CYP2E1, CYP2F1, CYP3A4, CYP153-AlkBurk, CYP153-EB104, CYP153-OC4, P450$_{BS\beta}$ (CYP152A1), P450$_{SP\alpha}$ (CYP152B1) and variants of any of the foregoing having oxygenase activity.

7. The method of claim 1, wherein the oxygenase is a monooxygenase or a peroxygenase.

8. The method of claim 1, wherein the organic molecule has the structure of formula (V)

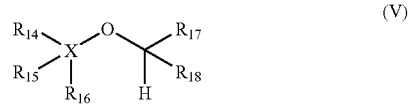

in which X is the target site C atom, $R_{14}$, is selected from the group consisting of hydrogen, aliphatic, aryl, substituted aliphatic, substituted aryl, heteroatom-containing aliphatic, heteroatom-containing aryl, substituted heteroatom-containing aliphatic, substituted heteroatom-containing aryl, and functional group, $R_{15}$ is hydrogen, $R_{16}$ is a Corey lactone or Corey lactone derivative, $R_{17}$ is selected from the group consisting of hydrogen, alkyl, and aryl, and $R_{18}$ is hydrogen.

9. The method of claim 8, wherein the oxygenase is a monooxygenase or a peroxygenase.

10. The method of claim 9, wherein the oxygenase or variant thereof is selected from the group consisting of CYP3A4 and an oxygenase having a sequence selected from the group consisting of SEQ ID NO:50, SEQ ID NO:24, SEQ ID NO:25, SEQ ID NO:27, SEQ ID NO:28, SEQ ID NO:31, SEQ ID NO:33, SEQ ID NO:38, SEQ ID NO:41, SEQ ID NO:40, SEQ ID NO:24, SEQ ID NO:25, SEQ ID NO:36, SEQ ID NO:37, SEQ ID NO:39, SEQ ID NO:31 and SEQ ID NO:69.

11. The method of claim 1, wherein the fluorinating agent is a nucleophilic fluorination reagent.

12. The method of claim 11, wherein the fluorinating agent is selected from the group consisting of diethylaminosulfur trifluoride, bis-(2-methoxyethyl)-aminosulfur trifluoride, and 2,2-difluoro-1,3-dimethylimidazolidine (DFI).

* * * * *

UNITED STATES PATENT AND TRADEMARK OFFICE
CERTIFICATE OF CORRECTION

PATENT NO. : 8,252,559 B2
APPLICATION NO. : 12/365884
DATED : August 28, 2012
INVENTOR(S) : Rudi Fasan and Frances H. Arnold Page 1 of 1

It is certified that error appears in the above-identified patent and that said Letters Patent is hereby corrected as shown below:

In Column 1, after line 16, please add

-- STATEMENT REGARDING FEDERALLY SPONSORED RESEARCH OR DEVELOPMENT

This invention was made with government support under Grant No. GM068664 awarded by the National Institutes of Health. The government has certain rights in the invention. --

Signed and Sealed this
Sixth Day of November, 2012

David J. Kappos
*Director of the United States Patent and Trademark Office*

SEQUENCE LISTING

<160> NUMBER OF SEQ ID NOS: 70

<210> SEQ ID NO 1
<211> LENGTH: 10
<212> TYPE: PRT
<213> ORGANISM: Artificial sequence
<220> FEATURE:
<223> OTHER INFORMATION: Cytochrome P450 signature sequence
<220> FEATURE:
<221> NAME/KEY: MISC_FEATURE
<222> LOCATION: (2)..(2)
<223> OTHER INFORMATION: Xaa can be any amino acid
<220> FEATURE:
<221> NAME/KEY: MISC_FEATURE
<222> LOCATION: (3)..(3)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be any amino acid
<220> FEATURE:
<221> NAME/KEY: MISC_FEATURE
<222> LOCATION: (6)..(6)
<223> OTHER INFORMATION: Xaa can be Histidine or Arginine
<220> FEATURE:
<221> NAME/KEY: MISC_FEATURE
<222> LOCATION: (7)..(7)
<223> OTHER INFORMATION: Xaa can be any amino acid
<220> FEATURE:
<221> NAME/KEY: MISC_FEATURE
<222> LOCATION: (9)..(9)
<223> OTHER INFORMATION: Xaa can be any amino acid

<400> SEQUENCE: 1

Phe Xaa Xaa Gly Xaa Xaa Xaa Cys Xaa Gly
1               5                   10

<210> SEQ ID NO 2
<211> LENGTH: 1048
<212> TYPE: PRT
<213> ORGANISM: Bacillus megaterium
<220> FEATURE:
<221> NAME/KEY: MISC_FEATURE
<222> LOCATION: (1)..(1048)
<223> OTHER INFORMATION: Cytochrome P450 enzyme CYP102A1

<400> SEQUENCE: 2

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Val Arg Asp
65                  70                  75                  80

Phe Ala Gly Asp Gly Leu Phe Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Pro Glu Asp
    130                 135                 140

-continued

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
            165                 170                 175

Met Val Arg Ala Leu Asp Glu Ala Met Asn Lys Leu Gln Arg Ala Asn
        180                 185                 190

Pro Asp Asp Pro Ala Tyr Asp Glu Asn Lys Arg Gln Phe Gln Glu Asp
    195                 200                 205

Ile Lys Val Met Asn Asp Leu Val Asp Lys Ile Ile Ala Asp Arg Lys
210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
            245                 250                 255

Gln Ile Ile Thr Phe Leu Ile Ala Gly His Glu Thr Thr Ser Gly Leu
        260                 265                 270

Leu Ser Phe Ala Leu Tyr Phe Leu Val Lys Asn Pro His Val Leu Gln
    275                 280                 285

Lys Ala Ala Glu Glu Ala Ala Arg Val Leu Val Asp Pro Val Pro Ser
290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
            325                 330                 335

Glu Asp Thr Val Leu Gly Gly Glu Tyr Pro Leu Glu Lys Gly Asp Glu
        340                 345                 350

Leu Met Val Leu Ile Pro Gln Leu His Arg Asp Lys Thr Ile Trp Gly
    355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
            405                 410                 415

Met Leu Lys His Phe Asp Phe Glu Asp His Thr Asn Tyr Glu Leu Asp
        420                 425                 430

Ile Lys Glu Thr Leu Thr Leu Lys Pro Glu Gly Phe Val Val Lys Ala
    435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
            485                 490                 495

Ala Arg Asp Leu Ala Asp Ile Ala Met Ser Lys Gly Phe Ala Pro Gln
        500                 505                 510

Val Ala Thr Leu Asp Ser His Ala Gly Asn Leu Pro Arg Glu Gly Ala
    515                 520                 525

Val Leu Ile Val Thr Ala Ser Tyr Asn Gly His Pro Pro Asp Asn Ala
530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
            565                 570                 575

```
Thr Tyr Gln Lys Val Pro Ala Phe Ile Asp Glu Thr Leu Ala Ala Lys
            580                 585                 590
Gly Ala Glu Asn Ile Ala Asp Arg Gly Glu Ala Asp Ala Ser Asp Asp
            595                 600                 605
Phe Glu Gly Thr Tyr Glu Glu Trp Arg Glu His Met Trp Ser Asp Val
610                 615                 620
Ala Ala Tyr Phe Asn Leu Asp Ile Glu Asn Ser Glu Asp Asn Lys Ser
625                 630                 635                 640
Thr Leu Ser Leu Gln Phe Val Asp Ser Ala Ala Asp Met Pro Leu Ala
                645                 650                 655
Lys Met His Gly Ala Phe Ser Thr Asn Val Val Ala Ser Lys Glu Leu
                660                 665                 670
Gln Gln Pro Gly Ser Ala Arg Ser Thr Arg His Leu Glu Ile Glu Leu
                675                 680                 685
Pro Lys Glu Ala Ser Tyr Gln Glu Gly Asp His Leu Gly Val Ile Pro
            690                 695                 700
Arg Asn Tyr Glu Gly Ile Val Asn Arg Val Thr Ala Arg Phe Gly Leu
705                 710                 715                 720
Asp Ala Ser Gln Gln Ile Arg Leu Glu Ala Glu Glu Lys Leu Ala
                725                 730                 735
His Leu Pro Leu Ala Lys Thr Val Ser Val Glu Glu Leu Leu Gln Tyr
                740                 745                 750
Val Glu Leu Gln Asp Pro Val Thr Arg Thr Gln Leu Arg Ala Met Ala
                755                 760                 765
Ala Lys Thr Val Cys Pro Pro His Lys Val Glu Leu Glu Ala Leu Leu
            770                 775                 780
Glu Lys Gln Ala Tyr Lys Glu Gln Val Leu Ala Lys Arg Leu Thr Met
785                 790                 795                 800
Leu Glu Leu Leu Glu Lys Tyr Pro Ala Cys Glu Met Lys Phe Ser Glu
                805                 810                 815
Phe Ile Ala Leu Leu Pro Ser Ile Arg Pro Arg Tyr Tyr Ser Ile Ser
                820                 825                 830
Ser Ser Pro Arg Val Asp Glu Lys Gln Ala Ser Ile Thr Val Ser Val
            835                 840                 845
Val Ser Gly Glu Ala Trp Ser Gly Tyr Gly Glu Tyr Lys Gly Ile Ala
            850                 855                 860
Ser Asn Tyr Leu Ala Glu Leu Gln Glu Gly Asp Thr Ile Thr Cys Phe
865                 870                 875                 880
Ile Ser Thr Pro Gln Ser Glu Phe Thr Leu Pro Lys Asp Pro Glu Thr
                885                 890                 895
Pro Leu Ile Met Val Gly Pro Gly Thr Gly Val Ala Pro Phe Arg Gly
                900                 905                 910
Phe Val Gln Ala Arg Lys Gln Leu Lys Glu Gln Gly Gln Ser Leu Gly
            915                 920                 925
Glu Ala His Leu Tyr Phe Gly Cys Arg Ser Pro His Glu Asp Tyr Leu
            930                 935                 940
Tyr Gln Glu Glu Leu Glu Asn Ala Gln Ser Glu Gly Ile Ile Thr Leu
945                 950                 955                 960
His Thr Ala Phe Ser Arg Met Pro Asn Gln Pro Lys Thr Tyr Val Gln
                965                 970                 975
His Val Met Glu Gln Asp Gly Lys Lys Leu Ile Glu Leu Leu Asp Gln
                980                 985                 990
Gly Ala His Phe Tyr Ile Cys Gly  Asp Gly Ser Gln Met  Ala Pro Ala
```

```
                           995                1000                1005
        Val Glu  Ala Thr Leu Met Lys  Ser Tyr Ala Asp Val  His Gln Val
                1010                1015                1020

Ser Glu  Ala Asp Ala Arg Leu  Trp Leu Gln Gln Leu  Glu Glu Lys
                1025                1030                1035

Gly Arg  Tyr Ala Lys Asp Val  Trp Ala Gly
                1040                1045

<210> SEQ ID NO 3
<211> LENGTH: 1059
<212> TYPE: PRT
<213> ORGANISM: Bacillus subtilis
<220> FEATURE:
<221> NAME/KEY: MISC_FEATURE
<222> LOCATION: (1)..(1059)
<223> OTHER INFORMATION: Cytochrome P450 enzyme CYP102A2

<400> SEQUENCE: 3

Lys Glu Thr Ser Pro Ile Pro Gln Pro Lys Thr Phe Gly Pro Leu Gly
 1               5                   10                  15

Asn Leu Pro Leu Ile Asp Lys Asp Lys Pro Thr Leu Ser Leu Ile Lys
            20                  25                  30

Leu Ala Glu Glu Gln Gly Pro Ile Phe Gln Ile His Thr Pro Ala Gly
        35                  40                  45

Thr Thr Ile Val Val Ser Gly His Glu Leu Val Lys Glu Val Cys Asp
 50                  55                  60

Glu Glu Arg Phe Asp Lys Ser Ile Glu Gly Ala Leu Gly Lys Val Arg
 65                  70                  75                  80

Ala Phe Ser Gly Asp Gly Leu Phe Thr Ser Trp Thr His Glu Pro Asn
                85                  90                  95

Trp Arg Lys Ala His Asn Ile Leu Met Pro Thr Phe Ser Gln Arg Ala
            100                 105                 110

Met Lys Asp Tyr His Glu Lys Met Val Asp Ile Ala Val Gln Leu Ile
        115                 120                 125

Gln Lys Trp Ala Arg Leu Asn Pro Asn Glu Ala Val Asp Val Pro Gly
    130                 135                 140

Asp Met Thr Arg Leu Thr Leu Asp Thr Ile Gly Leu Cys Gly Phe Asn
145                 150                 155                 160

Tyr Arg Phe Asn Ser Tyr Tyr Arg Glu Thr Pro His Pro Phe Ile Asn
                165                 170                 175

Ser Met Val Arg Ala Leu Asp Glu Ala Met His Gln Met Gln Arg Leu
            180                 185                 190

Asp Val Gln Asp Lys Leu Met Val Arg Thr Lys Arg Gln Phe Arg Tyr
        195                 200                 205

Asp Ile Gln Thr Met Phe Ser Leu Val Asp Ser Ile Ile Ala Glu Arg
    210                 215                 220

Arg Ala Asn Gly Asp Gln Asp Glu Lys Asp Leu Leu Ala Arg Met Leu
225                 230                 235                 240

Asn Val Glu Asp Pro Glu Thr Gly Glu Lys Leu Asp Asp Glu Asn Ile
                245                 250                 255

Arg Phe Gln Ile Ile Thr Phe Leu Ile Ala Gly His Glu Thr Thr Ser
            260                 265                 270

Gly Leu Leu Ser Phe Ala Thr Tyr Phe Leu Leu Lys His Pro Asp Lys
        275                 280                 285

Leu Lys Lys Ala Tyr Glu Glu Val Asp Arg Val Leu Thr Asp Ala Ala
    290                 295                 300
```

```
Pro Thr Tyr Lys Gln Val Leu Glu Leu Thr Tyr Ile Arg Met Ile Leu
305                 310                 315                 320

Asn Glu Ser Leu Arg Leu Trp Pro Thr Ala Pro Ala Phe Ser Leu Tyr
            325                 330                 335

Pro Lys Glu Asp Thr Val Ile Gly Gly Lys Phe Pro Ile Thr Thr Asn
        340                 345                 350

Asp Arg Ile Ser Val Leu Ile Pro Gln Leu His Arg Asp Arg Asp Ala
            355                 360                 365

Trp Gly Lys Asp Ala Glu Glu Phe Arg Pro Glu Arg Phe Glu His Gln
370                 375                 380

Asp Gln Val Pro His His Ala Tyr Lys Pro Phe Gly Asn Gly Gln Arg
385                 390                 395                 400

Ala Cys Ile Gly Met Gln Phe Ala Leu His Glu Ala Thr Leu Val Leu
        405                 410                 415

Gly Met Ile Leu Lys Tyr Phe Thr Leu Ile Asp His Glu Asn Tyr Glu
            420                 425                 430

Leu Asp Ile Lys Gln Thr Leu Thr Leu Lys Pro Gly Asp Phe His Ile
        435                 440                 445

Ser Val Gln Ser Arg His Gln Glu Ala Ile His Ala Asp Val Gln Ala
450                 455                 460

Ala Glu Lys Ala Ala Pro Asp Glu Gln Lys Glu Lys Thr Glu Ala Lys
465                 470                 475                 480

Gly Ala Ser Val Ile Gly Leu Asn Asn Arg Pro Leu Leu Val Leu Tyr
            485                 490                 495

Gly Ser Asp Thr Gly Thr Ala Glu Gly Val Ala Arg Glu Leu Ala Asp
            500                 505                 510

Thr Ala Ser Leu His Gly Val Arg Thr Lys Thr Ala Pro Leu Asn Asp
        515                 520                 525

Arg Ile Gly Lys Leu Pro Lys Glu Gly Ala Val Val Ile Val Thr Ser
        530                 535                 540

Ser Tyr Asn Gly Lys Pro Pro Ser Asn Ala Gly Gln Phe Val Gln Trp
545                 550                 555                 560

Leu Gln Glu Ile Lys Pro Gly Glu Leu Glu Gly Val His Tyr Ala Val
            565                 570                 575

Phe Gly Cys Gly Asp His Asn Trp Ala Ser Thr Tyr Gln Tyr Val Pro
            580                 585                 590

Arg Phe Ile Asp Glu Gln Leu Ala Glu Lys Gly Ala Thr Arg Phe Ser
        595                 600                 605

Ala Arg Gly Glu Gly Asp Val Ser Gly Asp Phe Glu Gly Gln Leu Asp
        610                 615                 620

Glu Trp Lys Lys Ser Met Trp Ala Asp Ala Ile Lys Ala Phe Gly Leu
625                 630                 635                 640

Glu Leu Asn Glu Asn Ala Asp Lys Glu Arg Ser Thr Leu Ser Leu Gln
            645                 650                 655

Phe Val Arg Gly Leu Gly Glu Ser Pro Leu Ala Arg Ser Tyr Glu Ala
            660                 665                 670

Ser His Ala Ser Ile Ala Glu Asn Arg Glu Leu Gln Ser Ala Asp Ser
        675                 680                 685

Asp Arg Ser Thr Arg His Ile Glu Ile Ala Leu Pro Pro Asp Val Glu
        690                 695                 700

Tyr Gln Glu Gly Asp His Leu Gly Val Leu Pro Lys Asn Ser Gln Thr
705                 710                 715                 720

Asn Val Ser Arg Ile Leu His Arg Phe Gly Leu Lys Gly Thr Asp Gln
            725                 730                 735
```

Val Thr Leu Ser Ala Ser Gly Arg Ser Ala Gly His Leu Pro Leu Gly
          740                 745                 750

Arg Pro Val Ser Leu His Asp Leu Leu Ser Tyr Ser Val Glu Val Gln
          755                 760                 765

Glu Ala Ala Thr Arg Ala Gln Ile Arg Glu Leu Ala Ser Phe Thr Val
770                 775                 780

Cys Pro Pro His Arg Arg Glu Leu Glu Glu Leu Ser Ala Glu Gly Val
785                 790                 795                 800

Tyr Gln Glu Gln Ile Leu Lys Lys Arg Ile Ser Met Leu Asp Leu Leu
              805                 810                 815

Glu Lys Tyr Glu Ala Cys Asp Met Pro Phe Glu Arg Phe Leu Glu Leu
              820                 825                 830

Leu Arg Pro Leu Lys Pro Arg Tyr Tyr Ser Ile Ser Ser Ser Pro Arg
              835                 840                 845

Val Asn Pro Arg Gln Ala Ser Ile Thr Val Gly Val Val Arg Gly Pro
          850                 855                 860

Ala Trp Ser Gly Arg Gly Glu Tyr Arg Gly Val Ala Ser Asn Asp Leu
865                 870                 875                 880

Ala Glu Arg Gln Ala Gly Asp Asp Val Val Met Phe Ile Arg Thr Pro
              885                 890                 895

Glu Ser Arg Phe Gln Leu Pro Lys Asp Pro Glu Thr Pro Ile Ile Met
              900                 905                 910

Val Gly Pro Gly Thr Gly Val Ala Pro Phe Arg Gly Phe Leu Gln Ala
              915                 920                 925

Arg Asp Val Leu Lys Arg Glu Gly Lys Thr Leu Gly Glu Ala His Leu
          930                 935                 940

Tyr Phe Gly Cys Arg Asn Asp Arg Asp Phe Ile Tyr Arg Asp Glu Leu
945                 950                 955                 960

Glu Arg Phe Glu Lys Asp Gly Ile Val Thr Val His Thr Ala Phe Ser
              965                 970                 975

Arg Lys Glu Gly Met Pro Lys Thr Tyr Val Gln His Leu Met Ala Asp
              980                 985                 990

Gln Ala Asp Thr Leu Ile Ser Ile Leu Asp Arg Gly Gly Arg Leu Tyr
          995                 1000                1005

Val Cys Gly Asp Gly Ser Lys Met Ala Pro Asp Val Glu Ala Ala
    1010                1015                1020

Leu Gln Lys Ala Tyr Gln Ala Val His Gly Thr Gly Glu Gln Glu
    1025                1030                1035

Ala Gln Asn Trp Leu Arg His Leu Gln Asp Thr Gly Met Tyr Ala
    1040                1045                1050

Lys Asp Val Trp Ala Gly
    1055

<210> SEQ ID NO 4
<211> LENGTH: 1052
<212> TYPE: PRT
<213> ORGANISM: Bacillus subtilis
<220> FEATURE:
<221> NAME/KEY: MISC_FEATURE
<222> LOCATION: (1)..(1052)
<223> OTHER INFORMATION: Cytochrome P450 enzyme CYP102A3

<400> SEQUENCE: 4

Lys Gln Ala Ser Ala Ile Pro Gln Pro Lys Thr Tyr Gly Pro Leu Lys
1               5                   10                  15

Asn Leu Pro His Leu Glu Lys Glu Gln Leu Ser Gln Ser Leu Trp Arg

```
            20                  25                  30
Ile Ala Asp Glu Leu Gly Pro Ile Phe Arg Phe Asp Phe Pro Gly Val
        35                  40                  45
Ser Ser Val Phe Val Ser Gly His Asn Leu Val Ala Glu Val Cys Asp
50                  55                  60
Glu Lys Arg Phe Asp Lys Asn Leu Gly Lys Gly Leu Gln Lys Val Arg
65                  70                  75                  80
Glu Phe Gly Gly Asp Gly Leu Phe Thr Ser Trp Thr His Glu Pro Asn
                85                  90                  95
Trp Gln Lys Ala His Arg Ile Leu Leu Pro Ser Phe Ser Gln Lys Ala
            100                 105                 110
Met Lys Gly Tyr His Ser Met Met Leu Asp Ile Ala Thr Gln Leu Ile
            115                 120                 125
Gln Lys Trp Ser Arg Leu Asn Pro Asn Glu Glu Ile Asp Val Ala Asp
        130                 135                 140
Asp Met Thr Arg Leu Thr Leu Asp Thr Ile Gly Leu Cys Gly Phe Asn
145                 150                 155                 160
Tyr Arg Phe Asn Ser Phe Tyr Arg Asp Ser Gln His Pro Phe Ile Thr
                165                 170                 175
Ser Met Leu Arg Ala Leu Lys Glu Ala Met Asn Gln Ser Lys Arg Leu
            180                 185                 190
Gly Leu Gln Asp Lys Met Met Val Lys Thr Lys Leu Gln Phe Gln Lys
            195                 200                 205
Asp Ile Glu Val Met Asn Ser Leu Val Asp Arg Met Ile Ala Glu Arg
        210                 215                 220
Lys Ala Asn Pro Asp Glu Asn Ile Lys Asp Leu Leu Ser Leu Met Leu
225                 230                 235                 240
Tyr Ala Lys Asp Pro Val Thr Gly Glu Thr Leu Asp Asp Glu Asn Ile
                245                 250                 255
Arg Tyr Gln Ile Ile Thr Phe Leu Ile Ala Gly His Glu Thr Thr Ser
            260                 265                 270
Gly Leu Leu Ser Phe Ala Ile Tyr Cys Leu Leu Thr His Pro Glu Lys
            275                 280                 285
Leu Lys Lys Ala Gln Glu Glu Ala Asp Arg Val Leu Thr Asp Asp Thr
290                 295                 300
Pro Glu Tyr Lys Gln Ile Gln Gln Leu Lys Tyr Ile Arg Met Val Leu
305                 310                 315                 320
Asn Glu Thr Leu Arg Leu Tyr Pro Thr Ala Pro Ala Phe Ser Leu Tyr
                325                 330                 335
Ala Lys Glu Asp Thr Val Leu Gly Gly Glu Tyr Pro Ile Ser Lys Gly
            340                 345                 350
Gln Pro Val Thr Val Leu Ile Pro Lys Leu His Arg Asp Gln Asn Ala
            355                 360                 365
Trp Gly Pro Asp Ala Glu Asp Phe Arg Pro Glu Arg Phe Glu Asp Pro
        370                 375                 380
Ser Ser Ile Pro His His Ala Tyr Lys Pro Phe Gly Asn Gly Gln Arg
385                 390                 395                 400
Ala Cys Ile Gly Met Gln Phe Ala Leu Gln Glu Ala Thr Met Val Leu
                405                 410                 415
Gly Leu Val Leu Lys His Phe Glu Leu Ile Asn His Thr Gly Tyr Glu
            420                 425                 430
Leu Lys Ile Lys Glu Ala Leu Thr Ile Lys Pro Asp Asp Phe Lys Ile
            435                 440                 445
```

-continued

```
Thr Val Lys Pro Arg Lys Thr Ala Ile Asn Val Gln Arg Lys Glu
    450                 455                 460

Gln Ala Asp Ile Lys Ala Glu Thr Lys Pro Lys Glu Thr Lys Pro Lys
465                 470                 475                 480

His Gly Thr Pro Leu Leu Val Leu Phe Gly Ser Asn Leu Gly Thr Ala
                485                 490                 495

Glu Gly Ile Ala Gly Glu Leu Ala Ala Gln Gly Arg Gln Met Gly Phe
            500                 505                 510

Thr Ala Glu Thr Ala Pro Leu Asp Asp Tyr Ile Gly Lys Leu Pro Glu
        515                 520                 525

Glu Gly Ala Val Val Ile Val Thr Ala Ser Tyr Asn Gly Ala Pro Pro
    530                 535                 540

Asp Asn Ala Ala Gly Phe Val Glu Trp Leu Lys Glu Leu Glu Glu Gly
545                 550                 555                 560

Gln Leu Lys Gly Val Ser Tyr Ala Val Phe Gly Cys Gly Asn Arg Ser
                565                 570                 575

Trp Ala Ser Thr Tyr Gln Arg Ile Pro Arg Leu Ile Asp Asp Met Met
            580                 585                 590

Lys Ala Lys Gly Ala Ser Arg Leu Thr Ala Ile Gly Glu Gly Asp Ala
        595                 600                 605

Ala Asp Asp Phe Glu Ser His Arg Glu Ser Trp Glu Asn Arg Phe Trp
    610                 615                 620

Lys Glu Thr Met Asp Ala Phe Asp Ile Asn Glu Ile Ala Gln Lys Glu
625                 630                 635                 640

Asp Arg Pro Ser Leu Ser Ile Thr Phe Leu Ser Glu Ala Thr Glu Thr
                645                 650                 655

Pro Val Ala Lys Ala Tyr Gly Ala Phe Glu Gly Ile Val Leu Glu Asn
            660                 665                 670

Arg Glu Leu Gln Thr Ala Ala Ser Thr Arg Ser Thr Arg His Ile Glu
        675                 680                 685

Leu Glu Ile Pro Ala Gly Lys Thr Tyr Lys Glu Gly Asp His Ile Gly
    690                 695                 700

Ile Leu Pro Lys Asn Ser Arg Glu Leu Val Gln Arg Val Leu Ser Arg
705                 710                 715                 720

Phe Gly Leu Gln Ser Asn His Val Ile Lys Val Ser Gly Ser Ala His
                725                 730                 735

Met Ala His Leu Pro Met Asp Arg Pro Ile Lys Val Val Asp Leu Leu
            740                 745                 750

Ser Ser Tyr Val Glu Leu Gln Glu Pro Ala Ser Arg Leu Gln Leu Arg
        755                 760                 765

Glu Leu Ala Ser Tyr Thr Val Cys Pro Pro His Gln Lys Glu Leu Glu
    770                 775                 780

Gln Leu Val Ser Asp Asp Gly Ile Tyr Lys Glu Gln Val Leu Ala Lys
785                 790                 795                 800

Arg Leu Thr Met Leu Asp Phe Leu Glu Asp Tyr Pro Ala Cys Glu Met
                805                 810                 815

Pro Phe Glu Arg Phe Leu Ala Leu Leu Pro Ser Leu Lys Pro Arg Tyr
            820                 825                 830

Tyr Ser Ile Ser Ser Ser Pro Lys Val His Ala Asn Ile Val Ser Met
        835                 840                 845

Thr Val Gly Val Val Lys Ala Ser Ala Trp Ser Gly Arg Gly Glu Tyr
    850                 855                 860

Arg Gly Val Ala Ser Asn Tyr Leu Ala Glu Leu Asn Thr Gly Asp Ala
865                 870                 875                 880
```

```
Ala Ala Cys Phe Ile Arg Thr Pro Gln Ser Gly Phe Gln Met Pro Asn
                885                 890                 895

Asp Pro Glu Thr Pro Met Ile Met Val Gly Pro Gly Thr Gly Ile Ala
            900                 905                 910

Pro Phe Arg Gly Phe Ile Gln Ala Arg Ser Val Leu Lys Lys Glu Gly
        915                 920                 925

Ser Thr Leu Gly Glu Ala Leu Leu Tyr Phe Gly Cys Arg Arg Pro Asp
    930                 935                 940

His Asp Asp Leu Tyr Arg Glu Glu Leu Asp Gln Ala Glu Gln Asp Gly
945                 950                 955                 960

Leu Val Thr Ile Arg Arg Cys Tyr Ser Arg Val Glu Asn Glu Pro Lys
                965                 970                 975

Gly Tyr Val Gln His Leu Leu Lys Gln Asp Thr Gln Lys Leu Met Thr
            980                 985                 990

Leu Ile Glu Lys Gly Ala His Ile  Tyr Val Cys Gly Asp  Gly Ser Gln
        995                 1000                1005

Met Ala  Pro Asp Val Glu Arg  Thr Leu Arg Leu Ala  Tyr Glu Ala
    1010                1015                1020

Glu Lys  Ala Ala Ser Gln Glu  Glu Ser Ala Val Trp  Leu Gln Lys
    1025                1030                1035

Leu Gln  Asp Gln Arg Arg Tyr  Val Lys Asp Val Trp  Thr Gly
    1040                1045                1050

<210> SEQ ID NO 5
<211> LENGTH: 1065
<212> TYPE: PRT
<213> ORGANISM: Bacillus cereus
<220> FEATURE:
<221> NAME/KEY: MISC_FEATURE
<222> LOCATION: (1)..(1065)
<223> OTHER INFORMATION: Cytochrome P450 enzyme CYP102A5

<400> SEQUENCE: 5

Met Asp Lys Lys Val Ser Ala Ile Pro Gln Pro Lys Thr Tyr Gly Pro
1               5                   10                  15

Leu Gly Asn Leu Pro Leu Ile Asp Lys Asp Lys Pro Thr Leu Ser Phe
            20                  25                  30

Ile Lys Ile Ala Glu Glu Tyr Gly Pro Ile Phe Gln Ile Gln Thr Leu
        35                  40                  45

Ser Asp Thr Ile Ile Val Ile Ser Gly His Glu Leu Val Ala Glu Val
    50                  55                  60

Cys Asp Glu Thr Arg Phe Asp Lys Ser Ile Glu Gly Ala Leu Ala Lys
65                  70                  75                  80

Val Arg Ala Phe Ala Gly Asp Gly Leu Phe Thr Ser Glu Thr Gln Glu
                85                  90                  95

Pro Asn Trp Lys Lys Ala His Asn Ile Leu Met Pro Thr Phe Ser Gln
            100                 105                 110

Arg Ala Met Lys Asp Tyr His Ala Met Met Val Asp Ile Ala Val Gln
        115                 120                 125

Leu Val Gln Lys Trp Ala Arg Leu Asn Pro Asn Glu Asn Val Asp Val
    130                 135                 140

Pro Glu Asp Met Thr Arg Leu Thr Leu Asp Thr Ile Gly Leu Cys Gly
145                 150                 155                 160

Phe Asn Tyr Arg Phe Asn Ser Phe Tyr Arg Glu Thr Pro His Pro Phe
                165                 170                 175

Ile Thr Ser Met Thr Arg Ala Leu Asp Glu Ala Met His Gln Leu Gln
```

-continued

```
                180                 185                 190
Arg Leu Asp Ile Glu Asp Lys Leu Met Trp Arg Thr Lys Arg Gln Phe
            195                 200                 205
Gln His Asp Ile Gln Ser Met Phe Ser Leu Val Asp Asn Ile Ile Ala
        210                 215                 220
Glu Arg Lys Ser Ser Gly Asn Gln Glu Glu Asn Asp Leu Leu Ser Arg
225                 230                 235                 240
Met Leu His Val Gln Asp Pro Glu Thr Gly Glu Lys Leu Asp Asp Glu
                245                 250                 255
Asn Ile Arg Phe Gln Ile Ile Thr Phe Leu Ile Ala Gly His Glu Thr
            260                 265                 270
Thr Ser Gly Leu Leu Ser Phe Ala Ile Tyr Phe Leu Leu Lys Asn Pro
        275                 280                 285
Asp Lys Leu Lys Lys Ala Tyr Glu Glu Val Asp Arg Val Leu Thr Asp
    290                 295                 300
Pro Thr Pro Thr Tyr Gln Gln Val Met Lys Leu Lys Tyr Ile Arg Met
305                 310                 315                 320
Ile Leu Asn Glu Ser Leu Arg Leu Trp Pro Thr Ala Pro Ala Phe Ser
                325                 330                 335
Leu Tyr Ala Lys Glu Asp Thr Val Ile Gly Gly Lys Tyr Pro Ile Lys
            340                 345                 350
Lys Gly Glu Asp Arg Ile Ser Val Leu Ile Pro Gln Leu His Arg Asp
        355                 360                 365
Lys Asp Ala Trp Gly Asp Asn Val Glu Glu Phe Gln Pro Glu Arg Phe
    370                 375                 380
Glu Asp Leu Asp Lys Val Pro His His Ala Tyr Lys Pro Phe Gly Asn
385                 390                 395                 400
Gly Gln Arg Ala Cys Ile Gly Met Gln Phe Ala Leu His Glu Ala Thr
                405                 410                 415
Leu Val Met Gly Met Leu Leu Gln His Phe Glu Phe Ile Asp Tyr Glu
            420                 425                 430
Asp Tyr Gln Leu Asp Val Lys Gln Thr Leu Thr Leu Lys Pro Gly Asp
        435                 440                 445
Phe Lys Ile Arg Ile Val Pro Arg Asn Gln Asn Ile Ser His Thr Thr
    450                 455                 460
Val Leu Ala Pro Thr Glu Glu Lys Leu Lys Asn His Glu Ile Lys Gln
465                 470                 475                 480
Gln Val Gln Lys Thr Pro Ser Ile Ile Gly Ala Asp Asn Leu Ser Leu
                485                 490                 495
Leu Val Leu Tyr Gly Ser Asp Thr Gly Val Ala Glu Gly Ile Ala Arg
            500                 505                 510
Glu Leu Ala Asp Thr Ala Ser Leu Glu Gly Val Gln Thr Glu Val Ala
        515                 520                 525
Ala Leu Asn Asp Arg Ile Gly Ser Leu Pro Lys Glu Gly Ala Val Leu
    530                 535                 540
Ile Val Thr Ser Ser Tyr Asn Gly Lys Pro Pro Ser Asn Ala Gly Gln
545                 550                 555                 560
Phe Val Gln Trp Leu Glu Glu Leu Lys Pro Asp Glu Leu Lys Gly Val
                565                 570                 575
Gln Tyr Ala Val Phe Gly Cys Gly Asp His Asn Trp Ala Ser Thr Tyr
            580                 585                 590
Gln Arg Ile Pro Arg Tyr Ile Asp Glu Gln Met Ala Gln Lys Gly Ala
        595                 600                 605
```

```
Thr Arg Phe Ser Thr Arg Gly Glu Ala Asp Ala Ser Gly Asp Phe Glu
610                 615                 620

Glu Gln Leu Glu Gln Trp Lys Glu Ser Met Trp Ser Asp Ala Met Lys
625                 630                 635                 640

Ala Phe Gly Leu Glu Leu Asn Lys Asn Met Glu Lys Glu Arg Ser Thr
            645                 650                 655

Leu Ser Leu Gln Phe Val Ser Arg Leu Gly Ser Pro Leu Ala Arg
            660                 665                 670

Thr Tyr Glu Ala Val Tyr Ala Ser Ile Leu Glu Asn Arg Glu Leu Gln
            675                 680                 685

Ser Ser Ser Ser Glu Arg Ser Thr Arg His Ile Glu Ile Ser Leu Pro
690                 695                 700

Glu Gly Ala Thr Tyr Lys Glu Gly Asp His Leu Gly Val Leu Pro Ile
705                 710                 715                 720

Asn Ser Glu Lys Asn Val Asn Arg Ile Leu Lys Arg Phe Gly Leu Asn
                425                 730                 735

Gly Lys Asp Gln Val Ile Leu Ser Ala Ser Gly Arg Ser Val Asn His
            740                 745                 750

Ile Pro Leu Asp Ser Pro Val Arg Leu Tyr Asp Leu Leu Ser Tyr Ser
            755                 760                 765

Val Glu Val Gln Glu Ala Ala Thr Arg Ala Gln Ile Arg Glu Met Val
770                 775                 780

Thr Phe Thr Ala Cys Pro Pro His Lys Lys Glu Leu Glu Ser Leu Leu
785                 790                 795                 800

Glu Asp Gly Val Tyr His Glu Gln Ile Leu Lys Lys Arg Ile Ser Met
                805                 810                 815

Leu Asp Leu Leu Glu Lys Tyr Glu Ala Cys Glu Ile Arg Phe Glu Arg
            820                 825                 830

Phe Leu Glu Leu Leu Pro Ala Leu Lys Pro Arg Tyr Tyr Ser Ile Ser
            835                 840                 845

Ser Ser Pro Leu Ile Ala Gln Asp Arg Leu Ser Ile Thr Val Gly Val
            850                 855                 860

Val Asn Ala Pro Ala Trp Ser Gly Glu Gly Thr Tyr Glu Gly Val Ala
865                 870                 875                 880

Ser Asn Tyr Leu Ala Gln Arg His Asn Lys Asp Glu Ile Ile Cys Phe
            885                 890                 895

Ile Arg Thr Pro Gln Ser Asn Phe Gln Leu Pro Glu Asn Pro Glu Thr
            900                 905                 910

Pro Ile Ile Met Val Gly Pro Gly Thr Gly Ile Ala Pro Phe Arg Gly
            915                 920                 925

Phe Leu Gln Ala Arg Arg Val Gln Lys Gln Lys Gly Met Asn Leu Gly
930                 935                 940

Glu Ala His Leu Tyr Phe Gly Cys Arg His Pro Glu Lys Asp Tyr Leu
945                 950                 955                 960

Tyr Arg Thr Glu Leu Glu Asn Asp Glu Arg Asp Gly Leu Ile Ser Leu
                965                 970                 975

His Thr Ala Phe Ser Arg Leu Glu Gly His Pro Lys Thr Tyr Val Gln
            980                 985                 990

His Val Ile Lys Glu Asp Arg Met Asn Leu Ile Ser Leu Leu Asp Asn
            995                 1000                1005

Gly Ala His Leu Tyr Ile Cys Gly Asp Gly Ser Lys Met Ala Pro
        1010            1015               1020

Asp Val Glu Asp Thr Leu Cys Gln Ala Tyr Gln Glu Ile His Glu
        1025            1030               1035
```

-continued

Val Ser Glu Gln Glu Ala Arg Asn Trp Leu Asp Arg Leu Gln Asp
    1040            1045                1050

Glu Gly Arg Tyr Gly Lys Asp Val Trp Ala Gly Ile
    1055            1060            1065

<210> SEQ ID NO 6
<211> LENGTH: 1063
<212> TYPE: PRT
<213> ORGANISM: Ralstonia metallidurans
<220> FEATURE:
<221> NAME/KEY: MISC_FEATURE
<222> LOCATION: (1)..(1063)
<223> OTHER INFORMATION: Cytochrome P450 enzyme CYP102E1

<400> SEQUENCE: 6

Ser Thr Ala Thr Pro Ala Ala Leu Glu Pro Ile Pro Arg Asp Pro
1               5                   10                  15

Gly Trp Pro Ile Phe Gly Asn Leu Phe Gln Ile Thr Pro Gly Glu Val
                20                  25                  30

Gly Gln His Leu Leu Ala Arg Ser Arg His His Asp Gly Ile Phe Glu
            35                  40                  45

Leu Asp Phe Ala Gly Lys Arg Val Pro Phe Val Ser Ser Val Ala Leu
50                  55                  60

Ala Ser Glu Leu Cys Asp Ala Thr Arg Phe Arg Lys Ile Ile Gly Pro
65                  70                  75                  80

Pro Leu Ser Tyr Leu Arg Asp Met Ala Gly Asp Gly Leu Phe Thr Ala
                85                  90                  95

His Ser Asp Glu Pro Asn Trp Gly Cys Ala His Arg Ile Leu Met Pro
            100                 105                 110

Ala Phe Ser Gln Arg Ala Met Lys Ala Tyr Phe Asp Val Met Leu Arg
        115                 120                 125

Val Ala Asn Arg Leu Val Asp Lys Trp Asp Arg Gln Gly Pro Asp Ala
    130                 135                 140

Asp Ile Ala Val Ala Asp Asp Met Thr Arg Leu Thr Leu Asp Thr Ile
145                 150                 155                 160

Ala Leu Ala Gly Phe Gly Tyr Asp Phe Ala Ser Phe Ala Ser Asp Glu
                165                 170                 175

Leu Asp Pro Phe Val Met Ala Met Val Gly Ala Leu Gly Glu Ala Met
            180                 185                 190

Gln Lys Leu Thr Arg Leu Pro Ile Gln Asp Arg Phe Met Gly Arg Ala
        195                 200                 205

His Arg Gln Ala Ala Glu Asp Ile Ala Tyr Met Arg Asn Leu Val Asp
    210                 215                 220

Asp Val Ile Arg Gln Arg Val Ser Pro Thr Ser Gly Met Asp Leu
225                 230                 235                 240

Leu Asn Leu Met Leu Glu Ala Arg Asp Pro Glu Thr Asp Arg Arg Leu
                245                 250                 255

Asp Asp Ala Asn Ile Arg Asn Gln Val Ile Thr Phe Leu Ile Ala Gly
            260                 265                 270

His Glu Thr Thr Ser Gly Leu Leu Thr Phe Ala Leu Tyr Glu Leu Leu
        275                 280                 285

Arg Asn Pro Gly Val Leu Ala Gln Ala Tyr Ala Glu Val Asp Thr Val
    290                 295                 300

Leu Pro Gly Asp Ala Leu Pro Val Tyr Ala Asp Leu Ala Arg Met Pro
305                 310                 315                 320

Val Leu Asp Arg Val Leu Lys Glu Thr Leu Arg Leu Trp Pro Thr Ala

-continued

```
               325                 330                 335
Pro Ala Phe Ala Val Ala Pro Phe Asp Asp Val Val Leu Gly Gly Arg
            340                 345                 350

Tyr Arg Leu Arg Lys Asp Arg Arg Ile Ser Val Val Leu Thr Ala Leu
            355                 360                 365

His Arg Asp Pro Lys Val Trp Ala Asn Pro Glu Arg Phe Asp Ile Asp
        370                 375                 380

Arg Phe Leu Pro Glu Asn Glu Ala Lys Leu Pro Ala His Ala Tyr Met
385                 390                 395                 400

Pro Phe Gly Gln Gly Glu Arg Ala Cys Ile Gly Arg Gln Phe Ala Leu
                405                 410                 415

Thr Glu Ala Lys Leu Ala Leu Ala Leu Met Leu Arg Asn Phe Ala Phe
            420                 425                 430

Gln Asp Pro His Asp Tyr Gln Phe Arg Leu Lys Glu Thr Leu Thr Ile
        435                 440                 445

Lys Pro Asp Gln Phe Val Leu Arg Val Arg Arg Arg Pro His Glu
    450                 455                 460

Arg Phe Val Thr Arg Gln Ala Ser Gln Ala Val Ala Asp Ala Ala Gln
465                 470                 475                 480

Thr Asp Val Arg Gly His Gly Gln Ala Met Thr Val Leu Cys Ala Ser
                485                 490                 495

Ser Leu Gly Thr Ala Arg Glu Leu Ala Glu Gln Ile His Ala Gly Ala
            500                 505                 510

Ile Ala Ala Gly Phe Asp Ala Lys Leu Ala Asp Leu Asp Asp Ala Val
        515                 520                 525

Gly Val Leu Pro Thr Ser Gly Leu Val Val Val Ala Ala Thr Tyr
    530                 535                 540

Asn Gly Arg Ala Pro Asp Ser Ala Arg Lys Phe Glu Ala Met Leu Asp
545                 550                 555                 560

Ala Asp Asp Ala Ser Gly Tyr Arg Ala Asn Gly Met Arg Leu Ala Leu
                565                 570                 575

Leu Gly Cys Gly Asn Ser Gln Trp Ala Thr Tyr Gln Ala Phe Pro Arg
            580                 585                 590

Arg Val Phe Asp Phe Phe Ile Thr Ala Gly Ala Val Pro Leu Leu Pro
        595                 600                 605

Arg Gly Glu Ala Asp Gly Asn Gly Asp Phe Asp Gln Ala Ala Glu Arg
    610                 615                 620

Trp Leu Ala Gln Leu Trp Gln Ala Leu Gln Ala Asp Gly Ala Gly Thr
625                 630                 635                 640

Gly Gly Leu Gly Val Asp Val Gln Val Arg Ser Met Ala Ala Ile Arg
                645                 650                 655

Ala Glu Thr Leu Pro Ala Gly Thr Gln Ala Phe Thr Val Leu Ser Asn
            660                 665                 670

Asp Glu Leu Val Gly Asp Pro Ser Gly Leu Trp Asp Phe Ser Ile Glu
        675                 680                 685

Ala Pro Arg Thr Ser Thr Arg Asp Ile Arg Leu Gln Leu Pro Pro Gly
    690                 695                 700

Ile Thr Tyr Arg Thr Gly Asp His Ile Ala Val Trp Pro Gln Asn Asp
705                 710                 715                 720

Ala Gln Leu Val Ser Glu Leu Cys Glu Arg Leu Asp Leu Asp Pro Asp
                725                 730                 735

Ala Gln Ala Thr Ile Ser Ala Pro His Gly Met Gly Arg Gly Leu Pro
            740                 745                 750
```

-continued

Ile Asp Gln Ala Leu Pro Val Arg Gln Leu Leu Thr His Phe Ile Glu
        755                 760                 765

Leu Gln Asp Val Val Ser Arg Gln Thr Leu Arg Ala Leu Ala Gln Ala
    770                 775                 780

Thr Arg Cys Pro Phe Thr Lys Gln Ser Ile Glu Gln Leu Ala Ser Asp
785                 790                 795                 800

Asp Ala Glu His Gly Tyr Ala Thr Lys Val Val Ala Arg Arg Leu Gly
                805                 810                 815

Ile Leu Asp Val Leu Val Glu His Pro Ala Ile Ala Leu Thr Leu Gln
            820                 825                 830

Glu Leu Leu Ala Cys Thr Val Pro Met Arg Pro Arg Leu Tyr Ser Ile
        835                 840                 845

Ala Ser Ser Pro Leu Val Ser Pro Asp Val Ala Thr Leu Leu Val Gly
    850                 855                 860

Thr Val Cys Ala Pro Ala Leu Ser Gly Arg Gly Gln Phe Arg Gly Val
865                 870                 875                 880

Ala Ser Thr Trp Leu Gln His Leu Pro Pro Gly Ala Arg Val Ser Ala
                885                 890                 895

Ser Ile Arg Thr Pro Asn Pro Pro Phe Ala Pro Asp Pro Asp Pro Ala
            900                 905                 910

Ala Pro Met Leu Leu Ile Gly Pro Gly Thr Gly Ile Ala Pro Phe Arg
        915                 920                 925

Gly Phe Leu Glu Glu Arg Ala Leu Arg Lys Met Ala Gly Asn Ala Val
    930                 935                 940

Thr Pro Ala Gln Leu Tyr Phe Gly Cys Arg His Pro Gln His Asp Trp
945                 950                 955                 960

Leu Tyr Arg Glu Asp Ile Glu Arg Trp Ala Gly Gln Gly Val Val Glu
                965                 970                 975

Val His Pro Ala Tyr Ser Val Val Pro Asp Ala Pro Arg Tyr Val Gln
            980                 985                 990

Asp Leu Leu Trp Gln Arg Arg Glu Gln Val Trp Ala Gln Val Arg Asp
        995                 1000                1005

Gly Ala Thr Ile Tyr Val Cys Gly Asp Gly Arg Arg Met Ala Pro
    1010                1015                1020

Ala Val Arg Gln Thr Leu Ile Glu Ile Gly Met Ala Gln Gly Gly
    1025                1030                1035

Met Thr Asp Lys Ala Ala Ser Asp Trp Phe Gly Leu Val Ala
    1040                1045                1050

Gln Gly Arg Tyr Arg Gln Asp Val Phe Asn
    1055                1060

<210> SEQ ID NO 7
<211> LENGTH: 1077
<212> TYPE: PRT
<213> ORGANISM: Bradyrhizobium japonicum
<220> FEATURE:
<221> NAME/KEY: MISC_FEATURE
<222> LOCATION: (1)..(1077)
<223> OTHER INFORMATION: Cytochrome P450 enzyme CYP102A6

<400> SEQUENCE: 7

Ser Ser Lys Asn Arg Leu Asp Pro Ile Pro Gln Pro Pro Thr Lys Pro
1               5                   10                  15

Val Val Gly Asn Met Leu Ser Leu Asp Ser Ala Ala Pro Val Gln His
            20                  25                  30

Leu Thr Arg Leu Ala Lys Glu Leu Gly Pro Ile Phe Trp Leu Asp Met
        35                  40                  45

```
Met Gly Ser Pro Ile Val Val Ser Gly His Asp Leu Val Asp Glu
     50                  55                  60

Leu Ser Asp Glu Lys Arg Phe Asp Lys Thr Val Arg Gly Ala Leu Arg
65                  70                  75                  80

Arg Val Arg Ala Val Gly Gly Asp Gly Leu Phe Thr Ala Asp Thr Arg
                     85                  90                  95

Glu Pro Asn Trp Ser Lys Ala His Asn Ile Leu Leu Gln Pro Phe Gly
               100                 105                 110

Asn Arg Ala Met Gln Ser Tyr His Pro Ser Met Val Asp Ile Ala Glu
             115                 120                 125

Gln Leu Val Gln Lys Trp Glu Arg Leu Asn Ala Asp Asp Glu Ile Asp
         130                 135                 140

Val Val His Asp Met Thr Ala Leu Thr Leu Asp Thr Ile Gly Leu Cys
145                 150                 155                 160

Gly Phe Asp Tyr Arg Phe Asn Ser Phe Tyr Arg Arg Asp Tyr His Pro
                 165                 170                 175

Phe Val Glu Ser Leu Val Arg Ser Leu Glu Thr Ile Met Met Thr Arg
             180                 185                 190

Gly Leu Pro Phe Glu Gln Ile Trp Met Gln Lys Arg Arg Lys Thr Leu
         195                 200                 205

Ala Glu Asp Val Ala Phe Met Asn Lys Met Val Asp Glu Ile Ile Ala
210                 215                 220

Glu Arg Arg Lys Ser Ala Glu Gly Ile Asp Asp Lys Lys Asp Met Leu
225                 230                 235                 240

Ala Ala Met Met Thr Gly Val Asp Arg Ser Thr Gly Glu Gln Leu Asp
                 245                 250                 255

Asp Val Asn Ile Arg Tyr Gln Ile Asn Thr Phe Leu Ile Ala Gly His
             260                 265                 270

Glu Thr Thr Ser Gly Leu Leu Ser Tyr Thr Leu Tyr Ala Leu Leu Lys
         275                 280                 285

His Pro Asp Ile Leu Lys Lys Ala Tyr Asp Glu Val Asp Arg Val Phe
290                 295                 300

Gly Pro Asp Val Asn Ala Lys Pro Thr Tyr Gln Gln Val Thr Gln Leu
305                 310                 315                 320

Thr Tyr Ile Thr Gln Ile Leu Lys Glu Ala Leu Arg Leu Trp Pro Pro
                 325                 330                 335

Ala Pro Ala Tyr Gly Ile Ser Pro Leu Ala Asp Glu Thr Ile Gly Gly
             340                 345                 350

Gly Lys Tyr Lys Leu Arg Lys Gly Thr Phe Ile Thr Ile Leu Val Thr
         355                 360                 365

Ala Leu His Arg Asp Pro Ser Val Trp Gly Pro Asn Pro Asp Ala Phe
370                 375                 380

Asp Pro Glu Asn Phe Ser Arg Glu Ala Glu Ala Lys Arg Pro Ile Asn
385                 390                 395                 400

Ala Trp Lys Pro Phe Gly Asn Gly Gln Arg Ala Cys Ile Gly Arg Gly
                 405                 410                 415

Phe Ala Met His Glu Ala Ala Leu Ala Leu Gly Met Ile Leu Gln Arg
             420                 425                 430

Phe Lys Leu Ile Asp His Gln Arg Tyr Gln Met His Leu Lys Glu Thr
         435                 440                 445

Leu Thr Met Lys Pro Glu Gly Phe Lys Ile Lys Val Arg Pro Arg Ala
450                 455                 460

Asp Arg Glu Arg Gly Ala Tyr Gly Gly Pro Val Ala Ala Val Ser Ser
```

```
                465                 470                 475                 480
Ala Pro Arg Ala Pro Arg Gln Pro Thr Ala Arg Pro Gly His Asn Thr
                485                 490                 495

Pro Met Leu Val Leu Tyr Gly Ser Asn Leu Gly Thr Ala Glu Glu Leu
            500                 505                 510

Ala Thr Arg Met Ala Asp Leu Ala Glu Ile Asn Gly Phe Ala Val His
            515                 520                 525

Leu Gly Ala Leu Asp Glu Tyr Val Gly Lys Leu Pro Gln Glu Gly Gly
            530                 535                 540

Val Leu Ile Ile Cys Ala Ser Tyr Asn Gly Ala Pro Pro Asp Asn Ala
545                 550                 555                 560

Thr Gln Phe Val Lys Trp Leu Gly Ser Asp Leu Pro Lys Asp Ala Phe
                565                 570                 575

Ala Asn Val Arg Tyr Ala Val Phe Gly Cys Gly Asn Ser Asp Trp Ala
                580                 585                 590

Ala Thr Tyr Gln Ser Val Pro Arg Phe Ile Asp Glu Gln Leu Ser Gly
            595                 600                 605

His Gly Ala Arg Ala Val Tyr Pro Arg Gly Glu Gly Asp Ala Arg Ser
            610                 615                 620

Asp Leu Asp Gly Gln Phe Gln Lys Trp Phe Pro Ala Ala Gln Val
625                 630                 635                 640

Ala Thr Lys Glu Phe Gly Ile Asp Trp Asn Phe Thr Arg Thr Ala Glu
                645                 650                 655

Asp Asp Pro Leu Tyr Ala Ile Glu Pro Val Ala Val Thr Ala Val Asn
            660                 665                 670

Thr Ile Val Ala Gln Gly Gly Ala Val Ala Met Lys Val Leu Val Asn
            675                 680                 685

Asp Glu Leu Gln Asn Lys Ser Gly Ser Asn Pro Ser Glu Arg Ser Thr
            690                 695                 700

Arg His Ile Glu Val Gln Leu Pro Ser Asn Ile Thr Tyr Arg Val Gly
705                 710                 715                 720

Asp His Leu Ser Val Val Pro Arg Asn Asp Pro Thr Leu Val Asp Ser
                725                 730                 735

Val Ala Arg Arg Phe Gly Phe Leu Pro Ala Asp Gln Ile Arg Leu Gln
            740                 745                 750

Val Ala Glu Gly Arg Arg Ala Gln Leu Pro Val Gly Glu Ala Val Ser
            755                 760                 765

Val Gly Arg Leu Leu Ser Glu Phe Val Glu Leu Gln Gln Val Ala Thr
            770                 775                 780

Arg Lys Gln Ile Gln Ile Met Ala Glu His Thr Arg Cys Pro Val Thr
785                 790                 795                 800

Lys Pro Lys Leu Leu Ala Phe Val Gly Glu Glu Ala Glu Pro Ala Glu
                805                 810                 815

Arg Tyr Arg Thr Glu Ile Leu Ala Met Arg Lys Ser Val Tyr Asp Leu
            820                 825                 830

Leu Leu Glu Tyr Pro Ala Cys Glu Leu Pro Phe His Val Tyr Leu Glu
            835                 840                 845

Met Leu Ser Leu Leu Ala Pro Arg Tyr Tyr Ser Ile Ser Ser Ser Pro
            850                 855                 860

Ser Val Asp Pro Ala Arg Cys Ser Ile Thr Val Gly Val Val Glu Gly
865                 870                 875                 880

Pro Ala Ala Ser Gly Arg Gly Val Tyr Lys Gly Ile Cys Ser Asn Tyr
                885                 890                 895
```

```
Leu Ala Asn Arg Arg Ala Ser Asp Ala Ile Tyr Ala Thr Val Arg Glu
                900                 905                 910

Thr Lys Ala Gly Phe Arg Leu Pro Asp Asp Ser Ser Val Pro Ile Ile
                915                 920                 925

Met Ile Gly Pro Gly Thr Gly Leu Ala Pro Phe Arg Gly Phe Leu Gln
            930                 935                 940

Glu Arg Ala Ala Arg Lys Ala Lys Gly Ala Ser Leu Gly Pro Ala Met
945                 950                 955                 960

Leu Phe Phe Gly Cys Arg His Pro Asp Gln Asp Phe Leu Tyr Ala Asp
                965                 970                 975

Glu Leu Lys Ala Leu Ala Ala Ser Gly Val Thr Glu Leu Phe Thr Ala
            980                 985                 990

Phe Ser Arg Ala Asp Gly Pro Lys Thr Tyr Val Gln His Val Leu Ala
        995                 1000                1005

Ala Gln Lys Asp Lys Val Trp Pro Leu Ile Glu Gln Gly Ala Ile
    1010                1015                1020

Ile Tyr Val Cys Gly Asp Gly Gly Gln Met Glu Pro Asp Val Lys
    1025                1030                1035

Ala Ala Leu Val Ala Ile Arg His Glu Lys Ser Gly Ser Asp Thr
    1040                1045                1050

Ala Thr Ala Ala Arg Trp Ile Glu Glu Met Gly Ala Thr Asn Arg
    1055                1060                1065

Tyr Val Leu Asp Val Trp Ala Gly Gly
    1070                1075
```

<210> SEQ ID NO 8
<211> LENGTH: 415
<212> TYPE: PRT
<213> ORGANISM: Pseudomonas putida
<220> FEATURE:
<221> NAME/KEY: MISC_FEATURE
<222> LOCATION: (1)..(415)
<223> OTHER INFORMATION: Cytochrome P450 enzyme CYP101A1

<400> SEQUENCE: 8

```
Met Thr Thr Glu Thr Ile Gln Ser Asn Ala Asn Leu Ala Pro Leu Pro
1               5                   10                  15

Pro His Val Pro Glu His Leu Val Phe Asp Phe Asp Met Tyr Asn Pro
                20                  25                  30

Ser Asn Leu Ser Ala Gly Val Gln Glu Ala Trp Ala Val Leu Gln Glu
            35                  40                  45

Ser Asn Val Pro Asp Leu Val Trp Thr Arg Cys Asn Gly Gly His Trp
        50                  55                  60

Ile Ala Thr Arg Gly Gln Leu Ile Arg Glu Ala Tyr Glu Asp Tyr Arg
65                  70                  75                  80

His Phe Ser Ser Glu Cys Pro Phe Ile Pro Arg Glu Ala Gly Glu Ala
                85                  90                  95

Tyr Asp Phe Ile Pro Thr Ser Met Asp Pro Pro Glu Gln Arg Gln Phe
            100                 105                 110

Arg Ala Leu Ala Asn Gln Val Val Gly Met Pro Val Val Asp Lys Leu
        115                 120                 125

Glu Asn Arg Ile Gln Glu Leu Ala Cys Ser Leu Ile Glu Ser Leu Arg
130                 135                 140

Pro Gln Gly Gln Cys Asn Phe Thr Glu Asp Tyr Ala Glu Pro Phe Pro
145                 150                 155                 160

Ile Arg Ile Phe Met Leu Leu Ala Gly Leu Pro Glu Glu Asp Ile Pro
                165                 170                 175
```

```
His Leu Lys Tyr Leu Thr Asp Gln Met Thr Arg Pro Asp Gly Ser Met
                180                 185                 190

Thr Phe Ala Glu Ala Lys Glu Ala Leu Tyr Asp Tyr Leu Ile Pro Ile
            195                 200                 205

Ile Glu Gln Arg Arg Gln Lys Pro Gly Thr Asp Ala Ile Ser Ile Val
        210                 215                 220

Ala Asn Gly Gln Val Asn Gly Arg Pro Ile Thr Ser Asp Glu Ala Lys
225                 230                 235                 240

Arg Met Cys Gly Leu Leu Val Gly Gly Leu Asp Thr Val Val Asn
                245                 250                 255

Phe Leu Ser Phe Ser Met Glu Phe Leu Ala Lys Ser Pro Glu His Arg
                260                 265                 270

Gln Glu Leu Ile Glu Arg Pro Glu Arg Ile Pro Ala Ala Cys Glu Glu
                275                 280                 285

Leu Leu Arg Arg Phe Ser Leu Val Ala Asp Gly Arg Ile Leu Thr Ser
            290                 295                 300

Asp Tyr Glu Phe His Gly Val Gln Leu Lys Lys Gly Asp Gln Ile Leu
305                 310                 315                 320

Leu Pro Gln Met Leu Ser Gly Leu Asp Glu Arg Glu Asn Ala Cys Pro
                325                 330                 335

Met His Val Asp Phe Ser Arg Gly Lys Val Ser His Thr Thr Phe Gly
                340                 345                 350

His Gly Ser His Leu Cys Leu Gly Gln His Leu Ala Arg Arg Glu Ile
            355                 360                 365

Ile Val Thr Leu Lys Glu Trp Leu Thr Arg Ile Pro Asp Phe Ser Ile
        370                 375                 380

Ala Pro Gly Ala Gln Ile Gln His Lys Ser Gly Ile Val Ser Gly Val
385                 390                 395                 400

Gln Ala Leu Pro Leu Val Trp Asp Pro Ala Thr Thr Lys Ala Val
                405                 410                 415

<210> SEQ ID NO 9
<211> LENGTH: 410
<212> TYPE: PRT
<213> ORGANISM: Bacillus megaterium
<220> FEATURE:
<221> NAME/KEY: MISC_FEATURE
<222> LOCATION: (1)..(410)
<223> OTHER INFORMATION: Cytochrome P450 enzyme CYP106A2

<400> SEQUENCE: 9

Met Lys Glu Val Ile Ala Val Lys Glu Ile Thr Arg Phe Lys Thr Arg
1               5                   10                  15

Thr Glu Glu Phe Ser Pro Tyr Ala Trp Cys Lys Arg Met Leu Glu Asn
                20                  25                  30

Asp Pro Val Ser Tyr His Glu Gly Thr Asp Thr Trp Asn Val Phe Lys
            35                  40                  45

Tyr Glu Asp Val Lys Arg Val Leu Ser Asp Tyr Lys His Phe Ser Ser
        50                  55                  60

Val Arg Lys Arg Thr Thr Ile Ser Val Gly Thr Asp Ser Glu Glu Gly
65                  70                  75                  80

Ser Val Pro Glu Lys Ile Gln Ile Thr Glu Ser Asp Pro Pro Asp His
                85                  90                  95

Arg Lys Arg Arg Ser Leu Leu Ala Ala Ala Phe Thr Pro Arg Ser Leu
                100                 105                 110

Gln Asn Trp Glu Pro Arg Ile Gln Glu Ile Ala Asp Glu Leu Ile Gly
```

115                 120                 125
Gln Met Asp Gly Gly Thr Glu Ile Asp Ile Val Ala Ser Leu Ala Ser
            130                 135                 140

Pro Leu Pro Ile Ile Val Met Ala Asp Leu Met Gly Val Pro Ser Lys
145                 150                 155                 160

Asp Arg Leu Leu Phe Lys Lys Trp Val Asp Thr Leu Phe Leu Pro Phe
                165                 170                 175

Asp Arg Glu Lys Gln Glu Glu Val Asp Lys Leu Lys Gln Val Ala Ala
            180                 185                 190

Lys Glu Tyr Tyr Gln Tyr Leu Tyr Pro Ile Val Val Gln Lys Arg Leu
            195                 200                 205

Asn Pro Ala Asp Asp Ile Ile Ser Asp Leu Leu Lys Ser Glu Val Asp
210                 215                 220

Gly Glu Met Phe Thr Asp Asp Glu Val Val Arg Thr Thr Met Leu Ile
225                 230                 235                 240

Leu Gly Ala Gly Val Glu Thr Thr Ser His Leu Leu Ala Asn Ser Phe
                245                 250                 255

Tyr Ser Leu Leu Tyr Asp Asp Lys Glu Val Tyr Gln Glu Leu His Glu
            260                 265                 270

Asn Leu Asp Leu Val Pro Gln Ala Val Glu Glu Met Leu Arg Phe Arg
            275                 280                 285

Phe Asn Leu Ile Lys Leu Asp Arg Thr Val Lys Glu Asp Asn Asp Leu
290                 295                 300

Leu Gly Val Glu Leu Lys Glu Gly Asp Ser Val Val Trp Met Ser
305                 310                 315                 320

Ala Ala Asn Met Asp Glu Glu Met Phe Glu Asp Pro Phe Thr Leu Asn
                325                 330                 335

Ile His Arg Pro Asn Asn Lys Lys His Leu Thr Phe Gly Asn Gly Pro
            340                 345                 350

His Phe Cys Leu Gly Ala Pro Leu Ala Arg Leu Glu Ala Lys Ile Ala
            355                 360                 365

Leu Thr Ala Phe Leu Lys Lys Phe Lys His Ile Glu Ala Val Pro Ser
370                 375                 380

Phe Gln Leu Glu Glu Asn Leu Thr Asp Ser Ala Thr Gly Gln Thr Leu
385                 390                 395                 400

Thr Ser Leu Pro Leu Lys Ala Ser Arg Met
                405                 410

<210> SEQ ID NO 10
<211> LENGTH: 404
<212> TYPE: PRT
<213> ORGANISM: Citrobacter brakii
<220> FEATURE:
<221> NAME/KEY: MISC_FEATURE
<222> LOCATION: (1)..(404)
<223> OTHER INFORMATION: Cytochrome P450 enzyme P450cin

<400> SEQUENCE: 10

Met Thr Ala Thr Val Ala Ser Thr Ser Leu Phe Thr Thr Ala Asp His
1               5                   10                  15

Tyr His Thr Pro Leu Gly Pro Asp Gly Thr Pro His Ala Phe Phe Glu
                20                  25                  30

Ala Leu Arg Asp Glu Ala Glu Thr Thr Pro Ile Gly Trp Ser Glu Ala
            35                  40                  45

Tyr Gly Gly His Trp Val Val Ala Gly Tyr Lys Glu Ile Gln Ala Val
        50                  55                  60

Ile Gln Asn Thr Lys Ala Phe Ser Asn Lys Gly Val Thr Phe Pro Arg
65                  70                  75                  80

Tyr Glu Thr Gly Glu Phe Glu Leu Met Met Ala Gly Gln Asp Asp Pro
            85                  90                  95

Val His Lys Lys Tyr Arg Gln Leu Val Ala Lys Pro Phe Ser Pro Glu
            100                 105                 110

Ala Thr Asp Leu Phe Thr Glu Gln Leu Arg Gln Ser Thr Asn Asp Leu
        115                 120                 125

Ile Asp Ala Arg Ile Glu Leu Gly Glu Gly Asp Ala Ala Thr Trp Leu
130                 135                 140

Ala Asn Glu Ile Pro Ala Arg Leu Thr Ala Ile Leu Leu Gly Leu Pro
145                 150                 155                 160

Pro Glu Asp Gly Asp Thr Tyr Arg Arg Trp Val Trp Ala Ile Thr His
            165                 170                 175

Val Glu Asn Pro Glu Glu Gly Ala Glu Ile Phe Ala Glu Leu Val Ala
            180                 185                 190

His Ala Arg Thr Leu Ile Ala Glu Arg Thr Asn Pro Gly Asn Asp
        195                 200                 205

Ile Met Ser Arg Val Ile Met Ser Lys Ile Asp Gly Glu Ser Leu Ser
210                 215                 220

Glu Asp Asp Leu Ile Gly Phe Phe Thr Ile Leu Leu Leu Gly Gly Ile
225                 230                 235                 240

Asp Asn Thr Ala Arg Phe Leu Ser Ser Val Phe Trp Arg Leu Ala Trp
            245                 250                 255

Asp Ile Glu Leu Arg Arg Arg Leu Ile Ala His Pro Glu Leu Ile Pro
            260                 265                 270

Asn Ala Val Asp Glu Leu Leu Arg Phe Tyr Gly Pro Ala Met Val Gly
        275                 280                 285

Arg Leu Val Thr Gln Glu Val Thr Val Gly Asp Ile Thr Met Lys Pro
290                 295                 300

Gly Gln Thr Ala Met Leu Trp Phe Pro Ile Ala Ser Arg Asp Arg Ser
305                 310                 315                 320

Ala Phe Asp Ser Pro Asp Asn Ile Val Ile Glu Arg Thr Pro Asn Arg
            325                 330                 335

His Leu Ser Leu Gly His Gly Ile His Arg Cys Leu Gly Ala His Leu
            340                 345                 350

Ile Arg Val Glu Ala Arg Val Ala Ile Thr Glu Phe Leu Lys Arg Ile
        355                 360                 365

Pro Glu Phe Ser Leu Asp Pro Asn Lys Glu Cys Glu Trp Leu Met Gly
370                 375                 380

Gln Val Ala Gly Met Leu His Val Pro Ile Ile Phe Pro Lys Gly Lys
385                 390                 395                 400

Arg Leu Ser Glu

<210> SEQ ID NO 11
<211> LENGTH: 428
<212> TYPE: PRT
<213> ORGANISM: Pseudomonas sp
<220> FEATURE:
<221> NAME/KEY: MISC_FEATURE
<222> LOCATION: (1)..(428)
<223> OTHER INFORMATION: Cytochrome P450 enzyme P450terp

<400> SEQUENCE: 11

Met Asp Ala Arg Ala Thr Ile Pro Glu His Ile Ala Arg Thr Val Ile
1               5                   10                  15

```
Leu Pro Gln Gly Tyr Ala Asp Asp Glu Val Ile Tyr Pro Ala Phe Lys
         20                  25                  30

Trp Leu Arg Asp Glu Gln Pro Leu Ala Met Ala His Ile Glu Gly Tyr
         35                  40                  45

Asp Pro Met Trp Ile Ala Thr Lys His Ala Asp Val Met Gln Ile Gly
 50                  55                  60

Lys Gln Pro Gly Leu Phe Ser Asn Ala Glu Gly Ser Glu Ile Leu Tyr
 65                  70                  75                  80

Asp Gln Asn Asn Glu Ala Phe Met Arg Ser Ile Ser Gly Gly Cys Pro
                 85                  90                  95

His Val Ile Asp Ser Leu Thr Ser Met Asp Pro Pro Thr His Thr Ala
            100                 105                 110

Tyr Arg Gly Leu Thr Leu Asn Trp Phe Gln Pro Ala Ser Ile Arg Lys
            115                 120                 125

Leu Glu Glu Asn Ile Arg Arg Ile Ala Gln Ala Ser Val Gln Arg Leu
        130                 135                 140

Leu Asp Phe Asp Gly Glu Cys Asp Phe Met Thr Asp Cys Ala Leu Tyr
145                 150                 155                 160

Tyr Pro Leu His Val Val Met Thr Ala Leu Gly Val Pro Glu Asp Asp
                    165                 170                 175

Glu Pro Leu Met Leu Lys Leu Thr Gln Asp Phe Phe Gly Val His Glu
                180                 185                 190

Pro Asp Glu Gln Ala Val Ala Ala Pro Arg Gln Ser Ala Asp Glu Ala
            195                 200                 205

Ala Arg Arg Phe His Glu Thr Ile Ala Thr Phe Tyr Asp Tyr Phe Asn
        210                 215                 220

Gly Phe Thr Val Asp Arg Arg Ser Cys Pro Lys Asp Asp Val Met Ser
225                 230                 235                 240

Leu Leu Ala Asn Ser Lys Leu Asp Gly Asn Tyr Ile Asp Asp Lys Tyr
                245                 250                 255

Ile Asn Ala Tyr Tyr Val Ala Ile Ala Thr Ala Gly His Asp Thr Thr
            260                 265                 270

Ser Ser Ser Gly Gly Ala Ile Ile Gly Leu Ser Arg Asn Pro Glu
        275                 280                 285

Gln Leu Ala Leu Ala Lys Ser Asp Pro Ala Leu Ile Pro Arg Leu Val
    290                 295                 300

Asp Glu Ala Val Arg Trp Thr Ala Pro Val Lys Ser Phe Met Arg Thr
305                 310                 315                 320

Ala Leu Ala Asp Thr Glu Val Arg Gly Gln Asn Ile Lys Arg Gly Asp
                325                 330                 335

Arg Ile Met Leu Ser Tyr Pro Ser Ala Asn Arg Asp Glu Glu Val Phe
            340                 345                 350

Ser Asn Pro Asp Glu Phe Asp Ile Thr Arg Phe Pro Asn Arg His Leu
        355                 360                 365

Gly Phe Gly Trp Gly Ala His Met Cys Leu Gly Gln His Leu Ala Lys
370                 375                 380

Leu Glu Met Lys Ile Phe Phe Glu Glu Leu Leu Pro Lys Leu Lys Ser
385                 390                 395                 400

Val Glu Leu Ser Gly Pro Pro Arg Leu Val Ala Thr Asn Phe Val Gly
                405                 410                 415

Gly Pro Lys Asn Val Pro Ile Arg Phe Thr Lys Ala
            420                 425

<210> SEQ ID NO 12
```

```
<211> LENGTH: 404
<212> TYPE: PRT
<213> ORGANISM: Saccharopolyspora erythreae
<220> FEATURE:
<221> NAME/KEY: MISC_FEATURE
<222> LOCATION: (1)..(404)
<223> OTHER INFORMATION: Cytochrome P450 enzyme P450eryF

<400> SEQUENCE: 12
```

| Met | Thr | Thr | Val | Pro | Asp | Leu | Glu | Ser | Asp | Ser | Phe | His | Val | Asp | Trp |
|---|---|---|---|---|---|---|---|---|---|---|---|---|---|---|---|
| 1 | | | | 5 | | | | | 10 | | | | | 15 | |

Tyr Arg Thr Tyr Ala Glu Leu Arg Glu Thr Ala Pro Val Thr Pro Val
                20                  25                  30

Arg Phe Leu Gly Gln Asp Ala Trp Leu Val Thr Gly Tyr Asp Glu Ala
            35                  40                  45

Lys Ala Ala Leu Ser Asp Leu Arg Leu Ser Ser Asp Pro Lys Lys Lys
50                  55                  60

Tyr Pro Gly Val Glu Val Glu Phe Pro Ala Tyr Leu Gly Phe Pro Glu
65                  70                  75                  80

Asp Val Arg Asn Tyr Phe Ala Thr Asn Met Gly Thr Ser Asp Pro Pro
                85                  90                  95

Thr His Thr Arg Leu Arg Lys Leu Val Ser Gln Glu Phe Thr Val Arg
            100                 105                 110

Arg Val Glu Ala Met Arg Pro Arg Val Glu Gln Ile Thr Ala Glu Leu
        115                 120                 125

Leu Asp Glu Val Gly Asp Ser Gly Val Val Asp Ile Val Asp Arg Phe
130                 135                 140

Ala His Pro Leu Pro Ile Lys Val Ile Cys Glu Leu Leu Gly Val Asp
145                 150                 155                 160

Glu Lys Tyr Arg Gly Glu Phe Gly Arg Trp Ser Ser Glu Ile Leu Val
                165                 170                 175

Met Asp Pro Glu Arg Ala Glu Gln Arg Gly Gln Ala Ala Arg Glu Val
            180                 185                 190

Val Asn Phe Ile Leu Asp Leu Val Glu Arg Arg Thr Glu Pro Gly
        195                 200                 205

Asp Asp Leu Leu Ser Ala Leu Ile Arg Val Gln Asp Asp Asp Gly
210                 215                 220

Arg Leu Ser Ala Asp Glu Leu Thr Ser Ile Ala Leu Val Leu Leu Leu
225                 230                 235                 240

Ala Gly Phe Glu Ala Ser Val Ser Leu Ile Gly Ile Gly Thr Tyr Leu
                245                 250                 255

Leu Leu Thr His Pro Asp Gln Leu Ala Leu Val Arg Arg Asp Pro Ser
            260                 265                 270

Ala Leu Pro Asn Ala Val Glu Glu Ile Leu Arg Tyr Ile Ala Pro Pro
        275                 280                 285

Glu Thr Thr Thr Arg Phe Ala Ala Glu Glu Val Glu Ile Gly Gly Val
290                 295                 300

Ala Ile Pro Gln Tyr Ser Thr Val Leu Val Ala Asn Gly Ala Ala Asn
305                 310                 315                 320

Arg Asp Pro Lys Gln Phe Pro Asp Pro His Arg Phe Asp Val Thr Arg
                325                 330                 335

Asp Thr Arg Gly His Leu Ser Phe Gly Gln Gly Ile His Phe Cys Met
            340                 345                 350

Gly Arg Pro Leu Ala Lys Leu Glu Gly Glu Val Ala Leu Arg Ala Leu
        355                 360                 365

Phe Gly Arg Phe Pro Ala Leu Ser Leu Gly Ile Asp Ala Asp Asp Val

```
            370                 375                 380
Val Trp Arg Arg Ser Leu Leu Leu Arg Gly Ile Asp His Leu Pro Val
385                 390                 395                 400

Arg Leu Asp Gly

<210> SEQ ID NO 13
<211> LENGTH: 516
<212> TYPE: PRT
<213> ORGANISM: homo sapiens
<220> FEATURE:
<221> NAME/KEY: MISC_FEATURE
<222> LOCATION: (1)..(516)
<223> OTHER INFORMATION: Cytochrome P450 enzyme CYP1A2

<400> SEQUENCE: 13

Met Ala Leu Ser Gln Ser Val Pro Phe Ser Ala Thr Glu Leu Leu Leu
1               5                   10                  15

Ala Ser Ala Ile Phe Cys Leu Val Phe Trp Val Leu Lys Gly Leu Arg
            20                  25                  30

Pro Arg Val Pro Lys Gly Leu Lys Ser Pro Pro Glu Pro Trp Gly Trp
        35                  40                  45

Pro Leu Leu Gly His Val Leu Thr Leu Gly Lys Asn Pro His Leu Ala
    50                  55                  60

Leu Ser Arg Met Ser Gln Arg Tyr Gly Asp Val Leu Gln Ile Arg Ile
65                  70                  75                  80

Gly Ser Thr Pro Val Leu Val Leu Ser Arg Leu Asp Thr Ile Arg Gln
                85                  90                  95

Ala Leu Val Arg Gln Gly Asp Asp Phe Lys Gly Arg Pro Asp Leu Tyr
            100                 105                 110

Thr Ser Thr Leu Ile Thr Asp Gly Gln Ser Leu Thr Phe Ser Thr Asp
        115                 120                 125

Ser Gly Pro Val Trp Ala Ala Arg Arg Arg Leu Ala Gln Asn Ala Leu
    130                 135                 140

Asn Thr Phe Ser Ile Ala Ser Asp Pro Ala Ser Ser Ser Ser Cys Tyr
145                 150                 155                 160

Leu Glu Glu His Val Ser Lys Glu Ala Lys Ala Leu Ile Ser Arg Leu
                165                 170                 175

Gln Glu Leu Met Ala Gly Pro Gly His Phe Asp Pro Tyr Asn Gln Val
            180                 185                 190

Val Val Ser Val Ala Asn Val Ile Gly Ala Met Cys Phe Gly Gln His
        195                 200                 205

Phe Pro Glu Ser Ser Asp Glu Met Leu Ser Leu Val Lys Asn Thr His
    210                 215                 220

Glu Phe Val Glu Thr Ala Ser Ser Gly Asn Pro Leu Asp Phe Phe Pro
225                 230                 235                 240

Ile Leu Arg Tyr Leu Pro Asn Pro Ala Leu Gln Arg Phe Lys Ala Phe
                245                 250                 255

Asn Gln Arg Phe Leu Trp Phe Leu Gln Lys Thr Val Gln Glu His Tyr
            260                 265                 270

Gln Asp Phe Asp Lys Asn Ser Val Arg Asp Ile Thr Gly Ala Leu Phe
        275                 280                 285

Lys His Ser Lys Lys Gly Pro Arg Ala Ser Gly Asn Leu Ile Pro Gln
    290                 295                 300

Glu Lys Ile Val Asn Leu Val Asn Asp Ile Phe Gly Ala Gly Phe Asp
305                 310                 315                 320

Thr Val Thr Thr Ala Ile Ser Trp Ser Leu Met Tyr Leu Val Thr Lys
```

```
                        325                 330                 335
Pro Glu Ile Gln Arg Lys Ile Gln Lys Glu Leu Asp Thr Val Ile Gly
                340                 345                 350

Arg Glu Arg Arg Pro Arg Leu Ser Asp Arg Pro Gln Leu Pro Tyr Leu
            355                 360                 365

Glu Ala Phe Ile Leu Glu Thr Phe Arg His Ser Ser Phe Leu Pro Phe
        370                 375                 380

Thr Ile Pro His Ser Thr Thr Arg Asp Thr Thr Leu Asn Gly Phe Tyr
385                 390                 395                 400

Ile Pro Lys Lys Cys Cys Val Phe Val Asn Gln Trp Gln Val Asn His
                405                 410                 415

Asp Pro Glu Leu Trp Glu Asp Pro Ser Glu Phe Arg Pro Glu Arg Phe
            420                 425                 430

Leu Thr Ala Asp Gly Thr Ala Ile Asn Lys Pro Leu Ser Glu Lys Met
        435                 440                 445

Met Leu Phe Gly Met Gly Lys Arg Arg Cys Ile Gly Glu Val Leu Ala
    450                 455                 460

Lys Trp Glu Ile Phe Leu Phe Leu Ala Ile Leu Leu Gln Gln Leu Glu
465                 470                 475                 480

Phe Ser Val Pro Pro Gly Val Lys Val Asp Leu Thr Pro Ile Tyr Gly
                485                 490                 495

Leu Thr Met Lys His Ala Arg Cys Glu His Val Gln Ala Arg Leu Arg
            500                 505                 510

Phe Ser Ile Asn
        515

<210> SEQ ID NO 14
<211> LENGTH: 489
<212> TYPE: PRT
<213> ORGANISM: homo sapiens
<220> FEATURE:
<221> NAME/KEY: MISC_FEATURE
<222> LOCATION: (1)..(489)
<223> OTHER INFORMATION: Cytochrome P450 enzyme CYP2C8

<400> SEQUENCE: 14

Met Glu Pro Phe Val Val Leu Val Leu Cys Leu Ser Phe Met Leu Leu
1               5                   10                  15

Phe Ser Leu Trp Arg Gln Ser Cys Arg Arg Lys Leu Pro Pro Gly
            20                  25                  30

Pro Thr Pro Leu Pro Ile Ile Gly Asn Met Leu Gln Ile Asp Val Lys
        35                  40                  45

Asp Ile Cys Lys Ser Phe Thr Asn Phe Ser Lys Val Tyr Gly Pro Val
    50                  55                  60

Phe Thr Val Tyr Phe Gly Asn Pro Ile Val Val Phe His Gly Tyr Glu
65                  70                  75                  80

Ala Val Lys Glu Ala Leu Ile Asp Asn Gly Glu Glu Phe Ser Gly Arg
                85                  90                  95

Gly Asn Ser Pro Ile Ser Gln Arg Ile Thr Lys Gly Leu Gly Ile Ile
            100                 105                 110

Ser Ser Asn Gly Lys Arg Trp Lys Glu Ile Arg Arg Phe Ser Leu Thr
        115                 120                 125

Thr Leu Arg Asn Phe Gly Met Gly Lys Arg Ser Ile Glu Asp Arg Val
    130                 135                 140

Gln Glu Glu Ala His Cys Leu Val Glu Glu Leu Arg Lys Thr Lys Ala
145                 150                 155                 160
```

```
Ser Pro Cys Asp Pro Thr Phe Ile Leu Gly Cys Ala Pro Cys Asn Val
            165                 170                 175

Ile Cys Ser Val Val Phe Gln Lys Arg Phe Asp Tyr Lys Asp Gln Asn
        180                 185                 190

Phe Leu Thr Leu Met Lys Arg Phe Asn Glu Asn Phe Arg Ile Leu Asn
        195                 200                 205

Ser Pro Trp Ile Gln Val Cys Asn Asn Phe Pro Leu Leu Ile Asp Cys
    210                 215                 220

Phe Pro Gly Thr His Asn Lys Val Leu Lys Asn Val Ala Leu Thr Arg
225                 230                 235                 240

Ser Tyr Ile Arg Glu Lys Val Lys Glu His Gln Ala Ser Leu Asp Val
                245                 250                 255

Asn Asn Pro Arg Asp Phe Ile Asp Cys Phe Leu Ile Lys Met Glu Gln
            260                 265                 270

Glu Lys Asp Asn Gln Lys Ser Glu Phe Asn Ile Glu Asn Leu Val Gly
        275                 280                 285

Thr Val Ala Asp Leu Phe Val Ala Gly Thr Glu Thr Thr Ser Thr Thr
    290                 295                 300

Leu Arg Tyr Gly Leu Leu Leu Leu Lys His Pro Glu Val Thr Ala
305                 310                 315                 320

Lys Val Gln Glu Glu Ile Asp His Val Ile Gly Arg His Arg Ser Pro
                325                 330                 335

Cys Met Gln Asp Arg Ser His Met Pro Tyr Thr Asp Ala Val Val His
            340                 345                 350

Glu Ile Gln Arg Tyr Ser Asp Leu Val Pro Thr Gly Val Pro His Ala
        355                 360                 365

Val Thr Thr Asp Thr Lys Phe Arg Asn Tyr Leu Ile Pro Lys Gly Thr
370                 375                 380

Thr Ile Met Ala Leu Leu Thr Ser Val Leu His Asp Asp Lys Glu Phe
385                 390                 395                 400

Pro Asn Pro Asn Ile Phe Asp Pro Gly His Phe Leu Asp Lys Asn Gly
            405                 410                 415

Asn Phe Lys Lys Ser Asp Tyr Phe Met Pro Phe Ser Ala Gly Lys Arg
        420                 425                 430

Ile Cys Ala Gly Glu Gly Leu Ala Arg Met Glu Leu Phe Leu Phe Leu
    435                 440                 445

Thr Thr Ile Leu Gln Asn Phe Asn Leu Lys Ser Val Asp Asp Leu Lys
    450                 455                 460

Asn Leu Asn Thr Thr Ala Val Thr Lys Gly Ile Val Ser Leu Pro Pro
465                 470                 475                 480

Ser Tyr Gln Ile Cys Phe Ile Pro Val
                485

<210> SEQ ID NO 15
<211> LENGTH: 490
<212> TYPE: PRT
<213> ORGANISM: homo sapiens
<220> FEATURE:
<221> NAME/KEY: MISC_FEATURE
<222> LOCATION: (1)..(490)
<223> OTHER INFORMATION: Cytochrome P450 enzyme CYP2C9

<400> SEQUENCE: 15

Met Asp Ser Leu Val Val Leu Val Leu Cys Leu Ser Cys Leu Leu Leu
1               5                   10                  15

Leu Ser Leu Trp Arg Gln Ser Ser Gly Arg Gly Lys Leu Pro Pro Gly
            20                  25                  30
```

```
Pro Thr Pro Leu Pro Val Ile Gly Asn Ile Leu Gln Ile Gly Ile Lys
         35                  40                  45

Asp Ile Ser Lys Ser Leu Thr Asn Leu Ser Lys Val Tyr Gly Pro Val
 50                  55                  60

Phe Thr Leu Tyr Phe Gly Leu Lys Pro Ile Val Val Leu His Gly Tyr
 65                  70                  75                  80

Glu Ala Val Lys Glu Ala Leu Ile Asp Leu Gly Glu Glu Phe Ser Gly
                 85                  90                  95

Arg Gly Ile Phe Pro Leu Ala Glu Arg Ala Asn Arg Gly Phe Gly Ile
                100                 105                 110

Val Phe Ser Asn Gly Lys Lys Trp Lys Glu Ile Arg Arg Phe Ser Leu
             115                 120                 125

Met Thr Leu Arg Asn Phe Gly Met Gly Lys Arg Ser Ile Glu Asp Arg
         130                 135                 140

Val Gln Glu Glu Ala Arg Cys Leu Val Glu Glu Leu Arg Lys Thr Lys
145                 150                 155                 160

Ala Ser Pro Cys Asp Pro Thr Phe Ile Leu Gly Cys Ala Pro Cys Asn
                165                 170                 175

Val Ile Cys Ser Ile Ile Phe His Lys Arg Phe Asp Tyr Lys Asp Gln
             180                 185                 190

Gln Phe Leu Asn Leu Met Glu Lys Leu Asn Glu Asn Ile Lys Ile Leu
         195                 200                 205

Ser Ser Pro Trp Ile Gln Ile Cys Asn Asn Phe Ser Pro Ile Ile Asp
     210                 215                 220

Tyr Phe Pro Gly Thr His Asn Lys Leu Leu Lys Asn Val Ala Phe Met
225                 230                 235                 240

Lys Ser Tyr Ile Leu Glu Lys Val Lys Glu His Gln Glu Ser Met Asp
                245                 250                 255

Met Asn Asn Pro Gln Asp Phe Ile Asp Cys Phe Leu Met Lys Met Glu
            260                 265                 270

Lys Glu Lys His Asn Gln Pro Ser Glu Phe Thr Ile Glu Ser Leu Glu
         275                 280                 285

Asn Thr Ala Val Asp Leu Phe Gly Ala Gly Thr Glu Thr Thr Ser Thr
     290                 295                 300

Thr Leu Arg Tyr Ala Leu Leu Leu Leu Leu Lys His Pro Glu Val Thr
305                 310                 315                 320

Ala Lys Val Gln Glu Glu Ile Glu Arg Val Ile Gly Arg Asn Arg Ser
                325                 330                 335

Pro Cys Met Gln Asp Arg Ser His Met Pro Tyr Thr Asp Ala Val Val
            340                 345                 350

His Glu Val Gln Arg Tyr Ile Asp Leu Leu Pro Thr Ser Leu Pro His
         355                 360                 365

Ala Val Thr Cys Asp Ile Lys Phe Arg Asn Tyr Leu Ile Pro Lys Gly
     370                 375                 380

Thr Thr Ile Leu Ile Ser Leu Thr Ser Val Leu His Asp Asn Lys Glu
385                 390                 395                 400

Phe Pro Asn Pro Glu Met Phe Asp Pro His His Phe Leu Asp Glu Gly
                405                 410                 415

Gly Asn Phe Lys Lys Ser Lys Tyr Phe Met Pro Phe Ser Ala Gly Lys
            420                 425                 430

Arg Ile Cys Val Gly Glu Ala Leu Ala Gly Met Glu Leu Phe Leu Phe
         435                 440                 445

Leu Thr Ser Ile Leu Gln Asn Phe Asn Leu Lys Ser Leu Val Asp Pro
```

```
                450             455             460
Lys Asn Leu Asp Thr Thr Pro Val Val Asn Gly Phe Ala Ser Val Pro
465                 470                 475                 480

Pro Phe Tyr Gln Leu Cys Phe Ile Pro Val
                485                 490

<210> SEQ ID NO 16
<211> LENGTH: 490
<212> TYPE: PRT
<213> ORGANISM: homo sapiens
<220> FEATURE:
<221> NAME/KEY: MISC_FEATURE
<222> LOCATION: (1)..(490)
<223> OTHER INFORMATION: Cytochrome P450 enzyme CYP2C19

<400> SEQUENCE: 16

Met Asp Pro Phe Val Val Leu Val Leu Cys Leu Ser Cys Leu Leu Leu
1               5                   10                  15

Leu Ser Ile Trp Arg Gln Ser Ser Gly Arg Gly Lys Leu Pro Pro Gly
            20                  25                  30

Pro Thr Pro Leu Pro Val Ile Gly Asn Ile Leu Gln Ile Asp Ile Lys
        35                  40                  45

Asp Val Ser Lys Ser Leu Thr Asn Leu Ser Lys Ile Tyr Gly Pro Val
50                  55                  60

Phe Thr Leu Tyr Phe Gly Leu Glu Arg Met Val Val Leu His Gly Tyr
65                  70                  75                  80

Glu Val Val Lys Glu Ala Leu Ile Asp Leu Gly Glu Glu Phe Ser Gly
                85                  90                  95

Arg Gly His Phe Pro Leu Ala Glu Arg Ala Asn Arg Gly Phe Gly Ile
            100                 105                 110

Val Phe Ser Asn Gly Lys Arg Trp Lys Glu Ile Arg Arg Phe Ser Leu
        115                 120                 125

Met Thr Leu Arg Asn Phe Gly Met Gly Lys Arg Ser Ile Glu Asp Arg
130                 135                 140

Val Gln Glu Glu Ala Arg Cys Leu Val Glu Glu Leu Arg Lys Thr Lys
145                 150                 155                 160

Ala Ser Pro Cys Asp Pro Thr Phe Ile Leu Gly Cys Ala Pro Cys Asn
                165                 170                 175

Val Ile Cys Ser Ile Ile Phe Gln Lys Arg Phe Asp Tyr Lys Asp Gln
            180                 185                 190

Gln Phe Leu Asn Leu Met Glu Lys Leu Asn Glu Asn Ile Arg Ile Val
        195                 200                 205

Ser Thr Pro Trp Ile Gln Ile Cys Asn Asn Phe Pro Thr Ile Ile Asp
210                 215                 220

Tyr Phe Pro Gly Thr His Asn Lys Leu Leu Lys Asn Leu Ala Phe Met
225                 230                 235                 240

Glu Ser Asp Ile Leu Glu Lys Val Lys Glu His Gln Glu Ser Met Asp
                245                 250                 255

Ile Asn Asn Pro Arg Asp Phe Ile Asp Cys Phe Leu Ile Lys Met Glu
            260                 265                 270

Lys Glu Lys Gln Asn Gln Gln Ser Glu Phe Thr Ile Glu Asn Leu Val
        275                 280                 285

Ile Thr Ala Ala Asp Leu Leu Gly Ala Gly Thr Glu Thr Thr Ser Thr
290                 295                 300

Thr Leu Arg Tyr Ala Leu Leu Leu Leu Leu Lys His Pro Glu Val Thr
305                 310                 315                 320
```

-continued

```
Ala Lys Val Gln Glu Ile Glu Arg Val Ile Gly Arg Asn Arg Ser
            325                 330                 335

Pro Cys Met Gln Asp Arg Gly His Met Pro Tyr Thr Asp Ala Val Val
            340                 345                 350

His Glu Val Gln Arg Tyr Ile Asp Leu Ile Pro Thr Ser Leu Pro His
            355                 360                 365

Ala Val Thr Cys Asp Val Lys Phe Arg Asn Tyr Leu Ile Pro Lys Gly
            370                 375                 380

Thr Thr Ile Leu Thr Ser Leu Thr Ser Val Leu His Asp Asn Lys Glu
385                 390                 395                 400

Phe Pro Asn Pro Glu Met Phe Asp Pro Arg His Phe Leu Asp Glu Gly
                405                 410                 415

Gly Asn Phe Lys Lys Ser Asn Tyr Phe Met Pro Phe Ser Ala Gly Lys
                420                 425                 430

Arg Ile Cys Val Gly Glu Gly Leu Ala Arg Met Glu Leu Phe Leu Phe
            435                 440                 445

Leu Thr Phe Ile Leu Gln Asn Phe Asn Leu Lys Ser Leu Ile Asp Pro
            450                 455                 460

Lys Asp Leu Asp Thr Thr Pro Val Val Asn Gly Phe Ala Ser Val Pro
465                 470                 475                 480

Pro Phe Tyr Gln Leu Cys Phe Ile Pro Val
                485                 490

<210> SEQ ID NO 17
<211> LENGTH: 446
<212> TYPE: PRT
<213> ORGANISM: homo sapiens
<220> FEATURE:
<221> NAME/KEY: MISC_FEATURE
<222> LOCATION: (1)..(446)
<223> OTHER INFORMATION: Cytochrome P450 enzyme CYP2D6

<400> SEQUENCE: 17

Met Gly Leu Glu Ala Leu Val Pro Leu Ala Val Ile Val Ala Ile Phe
1               5                   10                  15

Leu Leu Leu Val Asp Leu Met His Arg Arg Gln Arg Trp Ala Ala Arg
            20                  25                  30

Tyr Pro Pro Gly Pro Leu Pro Leu Pro Gly Leu Gly Asn Leu Leu His
            35                  40                  45

Val Asp Phe Gln Asn Thr Pro Tyr Cys Phe Asp Gln Leu Arg Arg Arg
        50                  55                  60

Phe Gly Asp Val Phe Ser Leu Gln Leu Ala Trp Thr Pro Val Val Val
65                  70                  75                  80

Leu Asn Gly Leu Ala Ala Val Arg Glu Ala Leu Val Thr His Gly Glu
                85                  90                  95

Asp Thr Ala Asp Arg Pro Pro Val Pro Ile Thr Gln Ile Leu Gly Phe
            100                 105                 110

Gly Pro Arg Ser Gln Gly Arg Pro Phe Arg Pro Asn Gly Leu Leu Asp
        115                 120                 125

Lys Ala Val Ser Asn Val Ile Ala Ser Leu Thr Cys Gly Arg Arg Phe
    130                 135                 140

Glu Tyr Asp Asp Pro Arg Phe Leu Arg Leu Leu Asp Leu Ala Gln Glu
145                 150                 155                 160

Gly Leu Lys Glu Glu Ser Gly Phe Leu Arg Glu Val Leu Asn Ala Val
                165                 170                 175

Pro Val Leu Leu His Ile Pro Ala Leu Ala Gly Lys Val Leu Arg Phe
            180                 185                 190
```

```
Gln Lys Ala Phe Leu Thr Gln Leu Asp Glu Leu Leu Thr Glu His Arg
            195                 200                 205
Met Thr Trp Asp Pro Ala Gln Pro Pro Arg Asp Leu Thr Glu Ala Phe
            210                 215                 220
Leu Ala Glu Met Glu Lys Ala Lys Gly Asn Pro Glu Ser Ser Phe Asn
225                 230                 235                 240
Asp Glu Asn Leu Cys Ile Val Val Ala Asp Leu Phe Ser Ala Gly Met
            245                 250                 255
Val Thr Thr Ser Thr Thr Leu Ala Trp Gly Leu Leu Leu Met Ile Leu
            260                 265                 270
His Pro Asp Val Gln Arg Arg Val Gln Gln Glu Ile Asp Asp Val Ile
            275                 280                 285
Gly Gln Val Arg Arg Pro Glu Met Gly Asp Gln Ala His Met Pro Tyr
            290                 295                 300
Thr Thr Ala Val Ile His Glu Val Gln Arg Phe Gly Asp Ile Val Pro
305                 310                 315                 320
Leu Gly Val Thr His Met Thr Ser Arg Asp Ile Glu Val Gln Gly Phe
            325                 330                 335
Arg Ile Pro Lys Gly Thr Thr Leu Ile Thr Asn Leu Ser Ser Val Leu
            340                 345                 350
Lys Asp Glu Ala Val Trp Glu Lys Pro Phe Arg Phe His Pro Glu His
            355                 360                 365
Phe Leu Asp Ala Gln Gly His Phe Val Lys Pro Glu Ala Phe Leu Pro
370                 375                 380
Phe Ser Ala Gly Arg Arg Ala Cys Leu Gly Glu Pro Leu Ala Arg Met
385                 390                 395                 400
Glu Leu Phe Leu Phe Phe Thr Ser Leu Leu Gln His Phe Ser Phe Ser
            405                 410                 415
Val Pro Thr Gly Gln Pro Arg Pro Ser His His Gly Val Phe Ala Phe
            420                 425                 430
Leu Val Thr Pro Ser Pro Tyr Glu Leu Cys Ala Val Pro Arg
            435                 440                 445

<210> SEQ ID NO 18
<211> LENGTH: 493
<212> TYPE: PRT
<213> ORGANISM: homo sapiens
<220> FEATURE:
<221> NAME/KEY: MISC_FEATURE
<222> LOCATION: (1)..(493)
<223> OTHER INFORMATION: Cytochrome P450 enzyme CYP2E1

<400> SEQUENCE: 18

Met Ser Ala Leu Gly Val Thr Val Ala Leu Leu Val Trp Ala Ala Phe
1               5                   10                  15
Leu Leu Leu Val Ser Met Trp Arg Gln Val His Ser Ser Trp Asn Leu
            20                  25                  30
Pro Pro Gly Pro Phe Pro Leu Pro Ile Ile Gly Asn Leu Phe Gln Leu
            35                  40                  45
Glu Leu Lys Asn Ile Pro Lys Ser Phe Thr Arg Leu Ala Gln Arg Phe
        50                  55                  60
Gly Pro Val Phe Thr Leu Tyr Val Gly Ser Gln Arg Met Val Val Met
65                  70                  75                  80
His Gly Tyr Lys Ala Val Lys Glu Ala Leu Leu Asp Tyr Lys Asp Glu
            85                  90                  95
Phe Ser Gly Arg Gly Asp Leu Pro Ala Phe His Ala His Arg Asp Arg
```

```
                100             105             110
Gly Ile Ile Phe Asn Asn Gly Pro Thr Trp Lys Asp Ile Arg Arg Phe
            115                 120                 125
Ser Leu Thr Thr Leu Arg Asn Tyr Gly Met Gly Lys Gln Gly Asn Glu
        130                 135                 140
Ser Arg Ile Gln Arg Glu Ala His Phe Leu Glu Ala Leu Arg Lys
145                 150                 155                 160
Thr Gln Gly Gln Pro Phe Asp Pro Thr Phe Leu Ile Gly Cys Ala Pro
                165                 170                 175
Cys Asn Val Ile Ala Asp Ile Leu Phe Arg Lys His Phe Asp Tyr Asn
            180                 185                 190
Asp Glu Lys Phe Leu Arg Leu Met Tyr Leu Phe Asn Glu Asn Phe His
        195                 200                 205
Leu Leu Ser Thr Pro Trp Leu Gln Leu Tyr Asn Asn Phe Pro Ser Phe
    210                 215                 220
Leu His Tyr Leu Pro Gly Ser His Arg Lys Val Ile Lys Asn Val Ala
225                 230                 235                 240
Glu Val Lys Glu Tyr Val Ser Glu Arg Val Lys Glu His His Gln Ser
                245                 250                 255
Leu Asp Pro Asn Cys Pro Arg Asp Leu Thr Asp Cys Leu Leu Val Glu
            260                 265                 270
Met Glu Lys Glu Lys His Ser Ala Glu Arg Leu Tyr Thr Met Asp Gly
        275                 280                 285
Ile Thr Val Thr Val Ala Asp Leu Phe Phe Ala Gly Thr Glu Thr Thr
    290                 295                 300
Ser Thr Thr Leu Arg Tyr Gly Leu Leu Ile Leu Met Lys Tyr Pro Glu
305                 310                 315                 320
Ile Glu Glu Lys Leu His Glu Glu Ile Asp Arg Val Ile Gly Pro Ser
                325                 330                 335
Arg Ile Pro Ala Ile Lys Asp Arg Gln Glu Met Pro Tyr Met Asp Ala
            340                 345                 350
Val Val His Glu Ile Gln Arg Phe Ile Thr Leu Val Pro Ser Asn Leu
        355                 360                 365
Pro His Glu Ala Thr Arg Asp Thr Ile Phe Arg Gly Tyr Leu Ile Pro
    370                 375                 380
Lys Gly Thr Val Val Val Pro Thr Leu Asp Ser Val Leu Tyr Asp Asn
385                 390                 395                 400
Gln Glu Phe Pro Asp Pro Glu Lys Phe Lys Pro Glu His Phe Leu Asn
                405                 410                 415
Glu Asn Gly Lys Phe Lys Tyr Ser Asp Tyr Phe Lys Pro Phe Ser Thr
            420                 425                 430
Gly Lys Arg Val Cys Ala Gly Glu Gly Leu Ala Arg Met Glu Leu Phe
        435                 440                 445
Leu Leu Leu Cys Ala Ile Leu Gln His Phe Asn Leu Lys Pro Leu Val
    450                 455                 460
Asp Pro Lys Asp Ile Asp Leu Ser Pro Ile His Ile Gly Phe Gly Cys
465                 470                 475                 480
Ile Pro Pro Arg Tyr Lys Leu Cys Val Ile Pro Arg Ser
                485                 490

<210> SEQ ID NO 19
<211> LENGTH: 491
<212> TYPE: PRT
<213> ORGANISM: homo sapiens
<220> FEATURE:
```

-continued

```
<221> NAME/KEY: MISC_FEATURE
<222> LOCATION: (1)..(491)
<223> OTHER INFORMATION: Cytochrome P450 enzyme CYP2F1

<400> SEQUENCE: 19
```

| Met<br>1 | Asp | Ser | Ile | Ser<br>5 | Thr | Ala | Ile | Leu | Leu<br>10 | Leu | Leu | Ala | Leu | Val<br>15 |
|---|---|---|---|---|---|---|---|---|---|---|---|---|---|---|
| Cys | Leu | Leu | Leu<br>20 | Thr | Leu | Ser | Ser | Arg<br>25 | Asp | Lys | Gly | Lys | Leu<br>30 | Pro | Pro |
| Gly | Pro | Arg<br>35 | Pro | Leu | Ser | Ile | Leu<br>40 | Gly | Asn | Leu | Leu | Leu<br>45 | Leu | Cys | Ser |
| Gln | Asp<br>50 | Met | Leu | Thr | Ser | Leu<br>55 | Thr | Lys | Leu | Ser | Lys<br>60 | Glu | Tyr | Gly | Ser |
| Met<br>65 | Tyr | Thr | Val | His | Leu<br>70 | Gly | Pro | Arg | Val | Val<br>75 | Val | Leu | Ser | Gly<br>80 |
| Tyr | Gln | Ala | Val | Lys<br>85 | Glu | Ala | Leu | Val | Asp<br>90 | Gln | Gly | Glu | Glu | Phe<br>95 | Ser |
| Gly | Arg | Gly | Asp<br>100 | Tyr | Pro | Ala | Phe | Phe<br>105 | Asn | Phe | Thr | Lys | Gly<br>110 | Asn | Gly |
| Ile | Ala | Phe<br>115 | Ser | Ser | Gly | Asp | Arg<br>120 | Trp | Lys | Val | Leu | Arg<br>125 | Gln | Phe | Ser |
| Ile | Gln<br>130 | Ile | Leu | Arg | Asn | Phe<br>135 | Gly | Met | Gly | Lys | Arg<br>140 | Ser | Ile | Glu | Glu |
| Arg<br>145 | Ile | Leu | Glu | Glu | Gly<br>150 | Ser | Phe | Leu | Leu | Ala<br>155 | Glu | Leu | Arg | Lys | Thr<br>160 |
| Glu | Gly | Glu | Pro | Phe<br>165 | Asp | Pro | Thr | Phe | Val<br>170 | Leu | Ser | Arg | Ser | Val<br>175 | Ser |
| Asn | Ile | Ile | Cys<br>180 | Ser | Val | Leu | Phe | Gly<br>185 | Ser | Arg | Phe | Asp | Tyr<br>190 | Asp | Asp |
| Glu | Arg | Leu<br>195 | Leu | Thr | Ile | Ile | Arg<br>200 | Leu | Ile | Asn | Asp | Asn<br>205 | Phe | Gln | Ile |
| Met | Ser<br>210 | Ser | Pro | Trp | Gly | Glu<br>215 | Leu | Tyr | Asp | Ile | Phe<br>220 | Pro | Ser | Leu | Leu |
| Asp<br>225 | Trp | Val | Pro | Gly | Pro<br>230 | His | Gln | Arg | Ile | Phe<br>235 | Gln | Asn | Phe | Lys | Cys<br>240 |
| Leu | Arg | Asp | Leu | Ile<br>245 | Ala | His | Ser | Val | His<br>250 | Asp | His | Gln | Ala | Ser<br>255 | Leu |
| Asp | Pro | Arg | Ser<br>260 | Pro | Arg | Asp | Phe | Ile<br>265 | Gln | Cys | Phe | Leu | Thr<br>270 | Lys | Met |
| Ala | Glu | Glu<br>275 | Lys | Glu | Asp | Pro | Leu<br>280 | Ser | His | Phe | His | Met<br>285 | Asp | Thr | Leu |
| Leu | Met<br>290 | Thr | Thr | His | Asn | Leu<br>295 | Leu | Phe | Gly | Gly | Thr<br>300 | Lys | Thr | Val | Ser |
| Thr<br>305 | Thr | Leu | His | His | Ala<br>310 | Phe | Leu | Ala | Leu | Met<br>315 | Lys | Tyr | Pro | Lys | Val<br>320 |
| Gln | Ala | Arg | Val | Gln<br>325 | Glu | Glu | Ile | Asp | Leu<br>330 | Val | Val | Gly | Arg | Ala<br>335 | Arg |
| Leu | Pro | Ala | Leu<br>340 | Lys | Asp | Arg | Ala | Ala<br>345 | Met | Pro | Tyr | Thr | Asp<br>350 | Ala | Val |
| Ile | His | Glu<br>355 | Val | Gln | Arg | Phe | Ala<br>360 | Asp | Ile | Ile | Pro | Met<br>365 | Asn | Leu | Pro |
| His | Arg | Val<br>370 | Thr | Arg | Asp | Thr | Ala<br>375 | Phe | Arg | Gly | Phe | Leu<br>380 | Ile | Pro | Lys |
| Gly<br>385 | Thr | Asp | Val | Ile | Thr<br>390 | Leu | Leu | Asn | Thr | Val<br>395 | His | Tyr | Asp | Pro<br>400 | Ser |

```
Gln Phe Leu Thr Pro Gln Glu Phe Asn Pro Glu His Phe Leu Asp Ala
                405                 410                 415

Asn Gln Ser Phe Lys Lys Ser Pro Ala Phe Met Pro Phe Ser Ala Gly
            420                 425                 430

Arg Arg Leu Cys Leu Gly Glu Ser Leu Ala Arg Met Glu Leu Phe Leu
                435                 440                 445

Tyr Leu Thr Ala Ile Leu Gln Ser Phe Ser Leu Gln Pro Leu Gly Ala
        450                 455                 460

Pro Glu Asp Ile Asp Leu Thr Pro Leu Ser Ser Gly Leu Gly Asn Leu
465                 470                 475                 480

Pro Arg Pro Phe Gln Leu Cys Leu Arg Pro Arg
                485                 490

<210> SEQ ID NO 20
<211> LENGTH: 503
<212> TYPE: PRT
<213> ORGANISM: homo sapiens
<220> FEATURE:
<221> NAME/KEY: MISC_FEATURE
<222> LOCATION: (1)..(503)
<223> OTHER INFORMATION: Cytochrome P450 enzyme CYP3A4

<400> SEQUENCE: 20

Met Ala Leu Ile Pro Asp Leu Ala Met Glu Thr Trp Leu Leu Leu Ala
1               5                   10                  15

Val Ser Leu Val Leu Leu Tyr Leu Tyr Gly Thr His Ser His Gly Leu
                20                  25                  30

Phe Lys Lys Leu Gly Ile Pro Gly Pro Thr Pro Leu Pro Phe Leu Gly
            35                  40                  45

Asn Ile Leu Ser Tyr His Lys Gly Phe Cys Met Phe Asp Met Glu Cys
        50                  55                  60

His Lys Lys Tyr Gly Lys Val Trp Gly Phe Tyr Asp Gly Gln Gln Pro
65                  70                  75                  80

Val Leu Ala Ile Thr Asp Pro Asp Met Ile Lys Thr Val Leu Val Lys
                85                  90                  95

Glu Cys Tyr Ser Val Phe Thr Asn Arg Arg Pro Phe Gly Pro Val Gly
            100                 105                 110

Phe Met Lys Ser Ala Ile Ser Ile Ala Glu Asp Glu Glu Trp Lys Arg
        115                 120                 125

Leu Arg Ser Leu Leu Ser Pro Thr Phe Thr Ser Gly Lys Leu Lys Glu
130                 135                 140

Met Val Pro Ile Ile Ala Gln Tyr Gly Asp Val Leu Val Arg Asn Leu
145                 150                 155                 160

Arg Arg Glu Ala Glu Thr Gly Lys Pro Val Thr Leu Lys Asp Val Phe
                165                 170                 175

Gly Ala Tyr Ser Met Asp Val Ile Thr Ser Thr Ser Phe Gly Val Asn
            180                 185                 190

Ile Asp Ser Leu Asn Asn Pro Gln Asp Pro Phe Val Glu Asn Thr Lys
        195                 200                 205

Lys Leu Leu Arg Phe Asp Phe Leu Asp Pro Phe Phe Leu Ser Ile Thr
210                 215                 220

Val Phe Pro Phe Leu Ile Pro Ile Leu Glu Val Leu Asn Ile Cys Val
225                 230                 235                 240

Phe Pro Arg Glu Val Thr Asn Phe Leu Arg Lys Ser Val Lys Arg Met
                245                 250                 255

Lys Glu Ser Arg Leu Glu Asp Thr Gln Lys His Arg Val Asp Phe Leu
```

```
                    260                 265                 270
Gln Leu Met Ile Asp Ser Gln Asn Ser Lys Glu Thr Glu Ser His Lys
            275                 280                 285
Ala Leu Ser Asp Leu Glu Leu Val Ala Gln Ser Ile Ile Phe Ile Phe
        290                 295                 300
Ala Gly Tyr Glu Thr Thr Ser Ser Val Leu Ser Phe Ile Met Tyr Glu
305                 310                 315                 320
Leu Ala Thr His Pro Asp Val Gln Gln Lys Leu Gln Glu Glu Ile Asp
                325                 330                 335
Ala Val Leu Pro Asn Lys Ala Pro Pro Thr Tyr Asp Thr Val Leu Gln
            340                 345                 350
Met Glu Tyr Leu Asp Met Val Val Asn Glu Thr Leu Arg Leu Phe Pro
        355                 360                 365
Ile Ala Met Arg Leu Glu Arg Val Cys Lys Lys Asp Val Glu Ile Asn
370                 375                 380
Gly Met Phe Ile Pro Lys Gly Val Val Met Ile Pro Ser Tyr Ala
385                 390                 395                 400
Leu His Arg Asp Pro Lys Tyr Trp Thr Glu Pro Glu Lys Phe Leu Pro
                405                 410                 415
Glu Arg Phe Ser Lys Lys Asn Lys Asp Asn Ile Asp Pro Tyr Ile Tyr
            420                 425                 430
Thr Pro Phe Gly Ser Gly Pro Arg Asn Cys Ile Gly Met Arg Phe Ala
        435                 440                 445
Leu Met Asn Met Lys Leu Ala Leu Ile Arg Val Leu Gln Asn Phe Ser
450                 455                 460
Phe Lys Pro Cys Lys Glu Thr Gln Ile Pro Leu Lys Leu Ser Leu Gly
465                 470                 475                 480
Gly Leu Leu Gln Pro Glu Lys Pro Val Val Leu Lys Val Glu Ser Arg
                485                 490                 495
Asp Gly Thr Val Ser Gly Ala
            500

<210> SEQ ID NO 21
<211> LENGTH: 1048
<212> TYPE: PRT
<213> ORGANISM: Artificial sequence
<220> FEATURE:
<223> OTHER INFORMATION: Cytochrome P450 variant CYP102A1var1

<400> SEQUENCE: 21

Thr Ile Lys Glu Met Pro Gln Pro Lys Thr Phe Gly Glu Leu Lys Asn
1               5                   10                  15
Leu Pro Leu Leu Asn Thr Asp Lys Pro Val Gln Ala Leu Met Lys Ile
            20                  25                  30
Ala Asp Glu Leu Gly Glu Ile Phe Lys Phe Glu Ala Pro Gly Arg Val
        35                  40                  45
Thr Arg Tyr Leu Ser Ser Gln Arg Leu Ile Lys Glu Ala Cys Asp Glu
    50                  55                  60
Ser Arg Phe Asp Lys Asn Leu Ser Gln Ala Leu Lys Phe Ala Arg Asp
65                  70                  75                  80
Phe Ala Gly Asp Gly Leu Phe Thr Ser Trp Thr His Glu Lys Asn Trp
                85                  90                  95
Lys Lys Ala His Asn Ile Leu Leu Pro Ser Phe Ser Gln Gln Ala Met
            100                 105                 110
Lys Gly Tyr His Ala Met Met Val Asp Ile Ala Val Gln Leu Val Gln
        115                 120                 125
```

```
Lys Trp Glu Arg Leu Asn Ala Asp Glu Tyr Ile Glu Val Pro Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Ile Arg Ala Leu Asp Glu Val Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ile Ala Asp Arg Lys
    210                 215                 220

Ala Ser Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Val Ala Glu Ala Thr Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
    370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr Glu
    450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
    530                 535                 540

Lys Gln Phe Val Asp Trp Leu Asp Gln Ala Ser Ala Asp Glu Val Lys
```

```
             545                 550                 555                 560
Gly Val Arg Tyr Ser Val Phe Gly Cys Gly Asp Lys Asn Trp Ala Thr
                    565                 570                 575

Thr Tyr Gln Lys Val Pro Ala Phe Ile Asp Glu Thr Leu Ala Ala Lys
                580                 585                 590

Gly Ala Glu Asn Ile Ala Asp Arg Gly Glu Ala Asp Ala Ser Asp Asp
                595                 600                 605

Phe Glu Gly Thr Tyr Glu Glu Trp Arg Glu His Met Trp Ser Asp Val
            610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                    645                 650                 655

Lys Met His Gly Ala Phe Ser Thr Asn Val Val Ala Ser Lys Glu Leu
                660                 665                 670

Gln Gln Pro Gly Ser Ala Arg Ser Thr Arg His Leu Glu Ile Glu Leu
                675                 680                 685

Pro Lys Glu Ala Ser Tyr Gln Glu Gly Asp His Leu Gly Val Ile Pro
            690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                    725                 730                 735

His Leu Pro Leu Ala Lys Thr Val Ser Val Glu Glu Leu Leu Gln Tyr
                    740                 745                 750

Val Glu Leu Gln Asp Pro Val Thr Arg Thr Gln Leu Arg Ala Met Ala
                755                 760                 765

Ala Lys Thr Val Cys Pro Pro His Lys Val Glu Leu Glu Ala Leu Leu
                770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                    805                 810                 815

Phe Ile Ala Leu Leu Pro Ser Ile Arg Pro Arg Tyr Tyr Ser Ile Ser
                820                 825                 830

Ser Ser Pro Arg Val Asp Glu Lys Gln Ala Ser Ile Thr Val Ser Val
                835                 840                 845

Val Ser Gly Glu Ala Trp Ser Gly Tyr Gly Glu Tyr Lys Gly Ile Ala
                850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                    885                 890                 895

Pro Leu Ile Met Val Gly Pro Gly Thr Gly Val Ala Pro Phe Arg Gly
                900                 905                 910

Phe Val Gln Ala Arg Lys Gln Leu Lys Glu Gln Gly Gln Ser Leu Gly
                915                 920                 925

Glu Ala His Leu Tyr Phe Gly Cys Arg Ser Pro His Glu Asp Tyr Leu
            930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                    965                 970                 975
```

-continued

```
His Val Met Glu Gln Asp Gly Lys Lys Leu Ile Glu Leu Leu Asp Gln
                980                 985                 990

Gly Ala His Phe Tyr Ile Cys Gly Asp Gly Ser Gln Met Ala Pro Ala
            995                1000                1005

Val Glu Ala Thr Leu Met Lys Ser Tyr Ala Asp Val His Gln Val
       1010                1015                1020

Ser Glu Ala Asp Ala Arg Leu Trp Leu Gln Gln Leu Glu Glu Lys
       1025                1030                1035

Gly Arg Tyr Ala Lys Asp Val Trp Ala Gly
       1040                1045

<210> SEQ ID NO 22
<211> LENGTH: 1048
<212> TYPE: PRT
<213> ORGANISM: Artificial sequence
<220> FEATURE:
<223> OTHER INFORMATION: Cytochrome P450 variant CYP102A1var2

<400> SEQUENCE: 22

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
                20                  25                  30

Ala Asp Glu Leu Gly Glu Ile Phe Lys Phe Glu Ala Pro Gly Arg Val
            35                  40                  45

Thr Arg Tyr Leu Ser Ser Gln Arg Leu Ile Lys Glu Ala Cys Asp Glu
        50                  55                  60

Ser Arg Phe Asp Lys Asn Leu Ser Gln Ala Leu Lys Ala Val Arg Asp
65                  70                  75                  80

Phe Ala Gly Asp Gly Leu Phe Thr Ser Trp Thr His Glu Lys Asn Trp
                85                  90                  95

Lys Lys Ala His Asn Ile Leu Leu Pro Ser Phe Ser Gln Gln Ala Met
                100                 105                 110

Lys Gly Tyr His Ala Met Met Val Asp Ile Ala Val Gln Leu Val Gln
            115                 120                 125

Lys Trp Glu Arg Leu Asn Ala Asp Glu His Ile Glu Val Pro Glu Asp
        130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
                180                 185                 190

Pro Asp Asp Pro Ala Tyr Asp Glu Asn Lys Arg Gln Cys Gln Glu Asp
            195                 200                 205

Ile Lys Val Met Asn Asp Leu Val Asp Lys Ile Ala Asp Arg Lys
        210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
```

```
                290                 295                 300
Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
            325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Ile Trp Gly
            355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
            405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
            435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
            485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
            515                 520                 525

Val Leu Ile Val Thr Ala Ser Tyr Asn Gly His Pro Pro Asp Asn Ala
            530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
            565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
            595                 600                 605

Phe Glu Gly Thr Tyr Glu Glu Trp Arg Glu His Met Trp Ser Asp Val
            610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
            645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
            675                 680                 685

Pro Lys Glu Ala Ser Tyr Gln Glu Gly Asp His Leu Gly Val Ile Pro
            690                 695                 700

Arg Asn Tyr Glu Gly Ile Val Asn Arg Val Thr Ala Arg Phe Gly Leu
705                 710                 715                 720
```

-continued

```
Asp Ala Ser Gln Gln Ile Arg Leu Glu Ala Glu Glu Lys Leu Ala
                725                 730                 735

His Leu Pro Leu Ala Lys Thr Val Ser Val Glu Leu Leu Gln Tyr
            740                 745                 750

Val Glu Leu Gln Asp Pro Val Thr Arg Thr Gln Leu Arg Ala Met Ala
        755                 760                 765

Ala Lys Thr Val Cys Pro Pro His Lys Val Glu Leu Glu Ala Leu Leu
    770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
        835                 840                 845

Val Ser Gly Glu Ala Trp Ser Gly Tyr Gly Glu Tyr Lys Gly Ile Ala
    850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
        915                 920                 925

Glu Ala His Leu Tyr Phe Gly Cys Arg Ser Pro His Glu Asp Tyr Leu
    930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
        995                 1000                1005

Val Glu Ala Thr Leu Met Lys Ser Tyr Ala Asp Val His Gln Val
    1010                1015                1020

Ser Glu Ala Asp Ala Arg Leu Trp Leu Gln Gln Leu Glu Glu Lys
    1025                1030                1035

Gly Arg Tyr Ala Lys Asp Val Trp Ala Gly
    1040                1045

<210> SEQ ID NO 23
<211> LENGTH: 1048
<212> TYPE: PRT
<213> ORGANISM: Artificial sequence
<220> FEATURE:
<223> OTHER INFORMATION: Cytochrome P450 variant CYP102A1var3

<400> SEQUENCE: 23

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Cys Val
```

```
                35                  40                  45
Thr Arg Tyr Leu Ser Ser Gln Arg Leu Ile Lys Glu Ala Cys Asp Glu
 50                  55                  60

Ser Arg Phe Asp Lys Asn Leu Ser Gln Ala Leu Lys Ala Val Arg Asp
 65                  70                  75                  80

Phe Ala Gly Asp Gly Leu Phe Thr Ser Trp Thr His Glu Ile Asn Trp
                 85                  90                  95

Lys Lys Ala His Asn Ile Leu Leu Pro Ser Phe Ser Gln Gln Ala Met
                100                 105                 110

Lys Gly Tyr His Ala Met Met Val Asp Ile Ala Val Gln Leu Val Gln
                115                 120                 125

Lys Trp Glu Arg Leu Asn Ala Asp Glu His Ile Glu Val Ser Glu Asp
                130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
                180                 185                 190

Pro Asp Asp Pro Ala Tyr Asp Glu Asn Lys Arg Gln Cys Gln Glu Asp
                195                 200                 205

Ile Lys Val Met Asn Asp Leu Val Asp Lys Ile Ile Ala Asp Arg Lys
                210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
                260                 265                 270

Leu Ser Phe Ala Leu Tyr Phe Leu Val Lys Asn Pro His Val Leu Gln
                275                 280                 285

Lys Val Ala Glu Glu Ala Ala Arg Val Leu Val Asp Pro Val Pro Ser
                290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
                340                 345                 350

Val Met Val Leu Ile Pro Gln Leu His Arg Asp Lys Thr Ile Trp Gly
                355                 360                 365

Asp Asp Val Glu Glu Phe Arg Pro Glu Arg Phe Glu Asn Pro Ser Ala
                370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
                420                 425                 430

Ile Lys Glu Thr Leu Thr Leu Lys Pro Glu Gly Phe Val Val Lys Ala
                435                 440                 445

Lys Ser Lys Lys Ile Pro Leu Gly Gly Ile Pro Ser Pro Ser Thr Glu
450                 455                 460
```

-continued

```
Gln Ser Ala Lys Lys Val Arg Lys Ala Glu Asn Ala His Asn Thr
465                 470                 475                 480

Pro Leu Leu Val Leu Tyr Gly Ser Asn Met Gly Thr Ala Glu Gly Thr
            485                 490                 495

Ala Arg Asp Leu Ala Asp Ile Ala Met Ser Lys Gly Phe Ala Pro Gln
        500                 505                 510

Val Ala Thr Leu Asp Ser His Ala Gly Asn Leu Pro Arg Glu Gly Ala
    515                 520                 525

Val Leu Ile Val Thr Ala Ser Tyr Asn Gly His Pro Pro Asp Asn Ala
530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
    610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
        675                 680                 685

Pro Lys Glu Ala Ser Tyr Gln Glu Gly Asp His Leu Gly Val Ile Pro
    690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
            740                 745                 750

Val Glu Leu Gln Asp Pro Val Thr Arg Thr Gln Leu Arg Ala Met Ala
        755                 760                 765

Ala Lys Thr Val Cys Pro Pro His Lys Val Glu Leu Glu Ala Leu Leu
    770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
        835                 840                 845

Val Ser Gly Glu Ala Trp Ser Gly Tyr Gly Glu Tyr Lys Gly Ile Ala
    850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895
```

Pro Leu Ile Met Val Gly Pro Gly Thr Gly Val Ala Pro Phe Arg Gly
                900                 905                 910

Phe Val Gln Ala Arg Lys Gln Leu Lys Glu Gln Gly Gln Ser Leu Gly
                915                 920                 925

Glu Ala His Leu Tyr Phe Gly Cys Arg Ser Pro His Glu Asp Tyr Leu
930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
                980                 985                 990

Gly Ala His Phe Tyr Ile Cys Gly Asp Gly Ser Gln Met Ala Pro Ala
                995                 1000                1005

Val Glu Ala Thr Leu Met Lys Ser Tyr Ala Asp Val His Gln Val
        1010                1015                1020

Ser Glu Ala Asp Ala Arg Leu Trp Leu Gln Gln Leu Glu Glu Lys
        1025                1030                1035

Gly Arg Tyr Ala Lys Asp Val Trp Ala Gly
        1040                1045

<210> SEQ ID NO 24
<211> LENGTH: 1048
<212> TYPE: PRT
<213> ORGANISM: Artificial sequence
<220> FEATURE:
<223> OTHER INFORMATION: Cytochrome P450 variant CYP102A1var3-2

<400> SEQUENCE: 24

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
                20                  25                  30

Ala Asp Glu Leu Gly Glu Ile Phe Lys Phe Glu Ala Pro Gly Arg Val
            35                  40                  45

Thr Arg Tyr Leu Ser Ser Gln Arg Leu Ile Lys Glu Ala Cys Asp Glu
        50                  55                  60

Ser Arg Phe Asp Lys Asn Leu Ser Gln Ala Leu Lys Ala Val Arg Asp
65                  70                  75                  80

Pro Leu Gly Asp Gly Leu Phe Ala Ser Trp Thr His Glu Lys Asn Trp
                85                  90                  95

Lys Lys Ala His Asn Ile Leu Leu Pro Ser Phe Ser Gln Gln Ala Met
                100                 105                 110

Lys Gly Tyr His Ala Met Met Val Asp Ile Ala Val Gln Leu Val Gln
            115                 120                 125

Lys Trp Glu Arg Leu Asn Ala Asp Glu His Ile Glu Val Ser Glu Asp
        130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Thr Leu Asp Glu Val Met Asn Lys Leu Gln Arg Ala Asn
                180                 185                 190

Pro Asp Asp Pro Val Tyr Asp Glu Asn Lys Arg Gln Cys Gln Glu Asp
            195                 200                 205

-continued

```
Ile Lys Val Met Asn Asp Leu Val Asp Lys Ile Ile Ala Asp Arg Lys
    210                 215                 220
Ala Arg Gly Glu Gln Ser Asp Asp Leu Leu Thr Gln Met Leu Asn Gly
225                 230                 235                 240
Lys Asp Pro Glu Thr Gly Glu Pro Leu Asp Asp Gly Asn Ile Ser Tyr
                245                 250                 255
Gln Ile Ile Thr Phe Leu Ile Ala Gly His Glu Thr Thr Ser Gly Leu
            260                 265                 270
Leu Ser Phe Ala Leu Tyr Phe Leu Val Lys Asn Pro His Val Leu Gln
        275                 280                 285
Lys Val Ala Glu Glu Ala Ala Arg Val Leu Val Asp Pro Val Pro Ser
290                 295                 300
Tyr Lys Gln Val Lys Gln Leu Lys Tyr Val Gly Met Val Leu Asn Glu
305                 310                 315                 320
Ala Leu Arg Leu Trp Pro Thr Ala Pro Ala Phe Ser Leu Tyr Ala Lys
                325                 330                 335
Glu Asp Thr Val Leu Gly Gly Glu Tyr Pro Leu Glu Lys Gly Asp Glu
            340                 345                 350
Val Met Val Leu Ile Pro Gln Leu His Arg Asp Lys Thr Ile Trp Gly
        355                 360                 365
Asp Asp Val Glu Glu Phe Arg Pro Glu Arg Phe Glu Asn Pro Ser Ala
370                 375                 380
Ile Pro Gln His Ala Phe Lys Pro Phe Gly Asn Gly Gln Arg Ala Cys
385                 390                 395                 400
Ile Gly Gln Gln Phe Ala Leu His Glu Ala Thr Leu Val Leu Gly Met
                405                 410                 415
Met Leu Lys His Phe Asp Phe Glu Asp His Thr Asn Tyr Glu Leu Asp
            420                 425                 430
Ile Lys Glu Thr Leu Thr Leu Lys Pro Glu Gly Phe Val Val Lys Ala
        435                 440                 445
Lys Ser Lys Lys Ile Pro Leu Gly Gly Ile Pro Ser Pro Ser Thr Glu
450                 455                 460
Gln Ser Ala Lys Lys Val Arg Lys Lys Ala Glu Asn Ala His Asn Thr
465                 470                 475                 480
Pro Leu Leu Val Leu Tyr Gly Ser Asn Met Gly Thr Ala Glu Gly Thr
                485                 490                 495
Ala Arg Asp Leu Ala Asp Ile Ala Met Ser Lys Gly Phe Ala Pro Gln
            500                 505                 510
Val Ala Thr Leu Asp Ser His Ala Gly Asn Leu Pro Arg Glu Gly Ala
        515                 520                 525
Val Leu Ile Val Thr Ala Ser Tyr Asn Gly His Pro Pro Asp Asn Ala
530                 535                 540
Lys Gln Phe Val Asp Trp Leu Asp Gln Ala Ser Ala Asp Glu Val Lys
545                 550                 555                 560
Gly Val Arg Tyr Ser Val Phe Gly Cys Gly Asp Lys Asn Trp Ala Thr
                565                 570                 575
Thr Tyr Gln Lys Val Pro Ala Phe Ile Asp Glu Thr Leu Ala Ala Lys
            580                 585                 590
Gly Ala Glu Asn Ile Ala Asp Arg Gly Glu Ala Asp Ala Ser Asp Asp
        595                 600                 605
Phe Glu Gly Thr Tyr Glu Glu Trp Arg Glu His Met Trp Ser Asp Val
610                 615                 620
Ala Ala Tyr Phe Asn Leu Asp Ile Glu Asn Ser Glu Asp Asn Lys Ser
625                 630                 635                 640
```

-continued

```
Thr Leu Ser Leu Gln Phe Val Asp Ser Ala Asp Met Pro Leu Ala
            645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
            675                 680                 685

Pro Lys Glu Ala Ser Tyr Gln Glu Gly Asp His Leu Gly Val Ile Pro
            690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
            725                 730                 735

His Leu Pro Leu Ala Lys Thr Val Ser Val Glu Leu Leu Gln Tyr
            740                 745                 750

Val Glu Leu Gln Asp Pro Val Thr Arg Thr Gln Leu Arg Ala Met Ala
            755                 760                 765

Ala Lys Thr Val Cys Pro Pro His Lys Val Glu Leu Glu Ala Leu Leu
            770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                    805                 810                 815

Phe Ile Ala Leu Leu Pro Ser Ile Arg Pro Arg Tyr Tyr Ser Ile Ser
                    820                 825                 830

Ser Ser Pro Arg Val Asp Glu Lys Gln Ala Ser Ile Thr Val Ser Val
            835                 840                 845

Val Ser Gly Glu Ala Trp Ser Gly Tyr Gly Glu Tyr Lys Gly Ile Ala
            850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                    885                 890                 895

Pro Leu Ile Met Val Gly Pro Gly Thr Gly Val Ala Pro Phe Arg Gly
                    900                 905                 910

Phe Val Gln Ala Arg Lys Gln Leu Lys Glu Gln Gly Gln Ser Leu Gly
            915                 920                 925

Glu Ala His Leu Tyr Phe Gly Cys Arg Ser Pro His Glu Asp Tyr Leu
930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                    965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
            995                 1000                1005

Val Glu Ala Thr Leu Met Lys Ser Tyr Ala Asp Val His Gln Val
            1010                1015                1020

Ser Glu Ala Asp Ala Arg Leu Trp Leu Gln Gln Leu Glu Glu Lys
            1025                1030                1035

Gly Arg Tyr Ala Lys Asp Val Trp Ala Gly
            1040                1045
```

```
<210> SEQ ID NO 25
<211> LENGTH: 1048
<212> TYPE: PRT
<213> ORGANISM: Artificial sequence
<220> FEATURE:
<223> OTHER INFORMATION: Cytochrome P450 variant CYP102A1var3-3

<400> SEQUENCE: 25

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Ala Val Arg Asp
65                  70                  75                  80

Cys Pro Gly Asp Gly Leu Ala Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Thr Leu Asp Glu Val Met Asn Lys Leu Gln Arg Ala Asn
            180                 185                 190

Pro Asp Asp Pro Val Tyr Asp Glu Asn Lys Arg Gln Cys Gln Glu Asp
        195                 200                 205

Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
    370                 375                 380
```

```
Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
            405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
            435                 440                 445

Lys Ser Lys Lys Ile Pro Leu Gly Gly Ile Pro Ser Pro Ser Thr Glu
        450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
                500                 505                 510

Val Ala Thr Leu Asp Ser His Ala Gly Asn Leu Pro Arg Glu Gly Ala
                515                 520                 525

Val Leu Ile Val Thr Ala Ser Tyr Asn Gly His Pro Pro Asp Asn Ala
530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
                580                 585                 590

Gly Ala Glu Asn Ile Ala Asp Arg Gly Glu Ala Asp Ala Ser Asp Asp
                595                 600                 605

Phe Glu Gly Thr Tyr Glu Glu Trp Arg Glu His Met Trp Ser Asp Val
610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
                660                 665                 670

Gln Gln Pro Gly Ser Ala Arg Ser Thr Arg His Leu Glu Ile Glu Leu
            675                 680                 685

Pro Lys Glu Ala Ser Tyr Gln Glu Gly Asp His Leu Gly Val Ile Pro
690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
            740                 745                 750

Val Glu Leu Gln Asp Pro Val Thr Arg Thr Gln Leu Arg Ala Met Ala
            755                 760                 765

Ala Lys Thr Val Cys Pro Pro His Lys Val Glu Leu Glu Ala Leu Leu
            770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
```

```
                    805                 810                 815
Phe Ile Ala Leu Leu Pro Ser Ile Arg Pro Arg Tyr Tyr Ser Ile Ser
                820                 825                 830

Ser Ser Pro Arg Val Asp Glu Lys Gln Ala Ser Ile Thr Val Ser Val
            835                 840                 845

Val Ser Gly Glu Ala Trp Ser Gly Tyr Gly Glu Tyr Lys Gly Ile Ala
        850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
        915                 920                 925

Glu Ala His Leu Tyr Phe Gly Cys Arg Ser Pro His Glu Asp Tyr Leu
    930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
        995                1000                1005

Val Glu Ala Thr Leu Met Lys Ser Tyr Ala Asp Val His Gln Val
       1010                1015                1020

Ser Glu Ala Asp Ala Arg Leu Trp Leu Gln Gln Leu Glu Glu Lys
       1025                1030                1035

Gly Arg Tyr Ala Lys Asp Val Trp Ala Gly
       1040                1045

<210> SEQ ID NO 26
<211> LENGTH: 1048
<212> TYPE: PRT
<213> ORGANISM: Artificial sequence
<220> FEATURE:
<223> OTHER INFORMATION: Cytochrome P450 variant CYP102A1var3-4

<400> SEQUENCE: 26

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Ala Val Arg Asp
65                  70                  75                  80

Trp Ile Gly Asp Gly Leu Ala Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125
```

```
Lys Trp Glu Arg Leu Asn Ala Asp Glu His Ile Glu Val Ser Glu Asp
            130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Thr Leu Asp Glu Val Met Asn Lys Leu Gln Arg Ala Asn
            180                 185                 190

Pro Asp Asp Pro Val Tyr Asp Glu Asn Lys Arg Gln Cys Gln Glu Asp
        195                 200                 205

Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
    370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr Glu
    450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
    530                 535                 540

Lys Gln Phe Val Asp Trp Leu Asp Gln Ala Ser Ala Asp Glu Val Lys
```

```
              545                 550                 555                 560
Gly Val Arg Tyr Ser Val Phe Gly Cys Gly Asp Lys Asn Trp Ala Thr
                    565                 570                 575

Thr Tyr Gln Lys Val Pro Ala Phe Ile Asp Glu Thr Leu Ala Ala Lys
                580                 585                 590

Gly Ala Glu Asn Ile Ala Asp Arg Gly Glu Ala Asp Ala Ser Asp Asp
            595                 600                 605

Phe Glu Gly Thr Tyr Glu Glu Trp Arg Glu His Met Trp Ser Asp Val
        610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                    645                 650                 655

Lys Met His Gly Ala Phe Ser Thr Asn Val Val Ala Ser Lys Glu Leu
                660                 665                 670

Gln Gln Pro Gly Ser Ala Arg Ser Thr Arg His Leu Glu Ile Glu Leu
            675                 680                 685

Pro Lys Glu Ala Ser Tyr Gln Glu Gly Asp His Leu Gly Val Ile Pro
        690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                    725                 730                 735

His Leu Pro Leu Ala Lys Thr Val Ser Val Glu Glu Leu Leu Gln Tyr
                740                 745                 750

Val Glu Leu Gln Asp Pro Val Thr Arg Thr Gln Leu Arg Ala Met Ala
            755                 760                 765

Ala Lys Thr Val Cys Pro Pro His Lys Val Glu Leu Glu Ala Leu Leu
        770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                    805                 810                 815

Phe Ile Ala Leu Leu Pro Ser Ile Arg Pro Arg Tyr Tyr Ser Ile Ser
                820                 825                 830

Ser Ser Pro Arg Val Asp Glu Lys Gln Ala Ser Ile Thr Val Ser Val
            835                 840                 845

Val Ser Gly Glu Ala Trp Ser Gly Tyr Gly Glu Tyr Lys Gly Ile Ala
        850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                    885                 890                 895

Pro Leu Ile Met Val Gly Pro Gly Thr Gly Val Ala Pro Phe Arg Gly
                900                 905                 910

Phe Val Gln Ala Arg Lys Gln Leu Lys Glu Gln Gly Gln Ser Leu Gly
            915                 920                 925

Glu Ala His Leu Tyr Phe Gly Cys Arg Ser Pro His Glu Asp Tyr Leu
        930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                    965                 970                 975
```

-continued

```
His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
            995                 1000                1005

Val Glu Ala Thr Leu Met Lys Ser Tyr Ala Asp Val His Gln Val
        1010                1015                1020

Ser Glu Ala Asp Ala Arg Leu Trp Leu Gln Gln Leu Glu Glu Lys
        1025                1030                1035

Gly Arg Tyr Ala Lys Asp Val Trp Ala Gly
        1040                1045

<210> SEQ ID NO 27
<211> LENGTH: 1048
<212> TYPE: PRT
<213> ORGANISM: Artificial sequence
<220> FEATURE:
<223> OTHER INFORMATION: Cytochrome P450 variant CYP102A1var3-5

<400> SEQUENCE: 27

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Ala Val Arg Asp
65                  70                  75                  80

Phe Gly Gly Asp Gly Leu Val Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Cys Gln Glu Asp
        195                 200                 205

Ile Lys Val Met Asn Asp Leu Val Asp Lys Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
```

```
                  290             295             300
Tyr Lys Gln Val Lys Gln Leu Lys Tyr Val Gly Met Val Leu Asn Glu
305             310             315             320

Ala Leu Arg Leu Trp Pro Thr Val Pro Ala Phe Ser Leu Tyr Ala Lys
                325             330             335

Glu Asp Thr Val Leu Gly Gly Glu Tyr Pro Leu Glu Lys Gly Asp Glu
            340             345             350

Val Met Val Leu Ile Pro Gln Leu His Arg Asp Lys Thr Ile Trp Gly
        355             360             365

Asp Asp Val Glu Glu Phe Arg Pro Glu Arg Phe Glu Asn Pro Ser Ala
370             375             380

Ile Pro Gln His Ala Phe Lys Pro Phe Gly Asn Gly Gln Arg Ala Cys
385             390             395             400

Ile Gly Gln Gln Phe Ala Leu His Glu Ala Thr Leu Val Leu Gly Met
                405             410             415

Met Leu Lys His Phe Asp Phe Glu Asp His Thr Asn Tyr Glu Leu Asp
            420             425             430

Ile Lys Glu Thr Leu Thr Leu Lys Pro Glu Gly Phe Val Val Lys Ala
        435             440             445

Lys Ser Lys Lys Ile Pro Leu Gly Gly Ile Pro Ser Pro Ser Thr Glu
450             455             460

Gln Ser Ala Lys Lys Val Arg Lys Lys Ala Glu Asn Ala His Asn Thr
465             470             475             480

Pro Leu Leu Val Leu Tyr Gly Ser Asn Met Gly Thr Ala Glu Gly Thr
                485             490             495

Ala Arg Asp Leu Ala Asp Ile Ala Met Ser Lys Gly Phe Ala Pro Gln
            500             505             510

Val Ala Thr Leu Asp Ser His Ala Gly Asn Leu Pro Arg Glu Gly Ala
        515             520             525

Val Leu Ile Val Thr Ala Ser Tyr Asn Gly His Pro Pro Asp Asn Ala
530             535             540

Lys Gln Phe Val Asp Trp Leu Asp Gln Ala Ser Ala Asp Glu Val Lys
545             550             555             560

Gly Val Arg Tyr Ser Val Phe Gly Cys Gly Asp Lys Asn Trp Ala Thr
                565             570             575

Thr Tyr Gln Lys Val Pro Ala Phe Ile Asp Glu Thr Leu Ala Ala Lys
            580             585             590

Gly Ala Glu Asn Ile Ala Asp Arg Gly Glu Ala Asp Ala Ser Asp Asp
        595             600             605

Phe Glu Gly Thr Tyr Glu Glu Trp Arg Glu His Met Trp Ser Asp Val
610             615             620

Ala Ala Tyr Phe Asn Leu Asp Ile Glu Asn Ser Glu Asp Asn Lys Ser
625             630             635             640

Thr Leu Ser Leu Gln Phe Val Asp Ser Ala Ala Asp Met Pro Leu Ala
                645             650             655

Lys Met His Gly Ala Phe Ser Thr Asn Val Val Ala Ser Lys Glu Leu
            660             665             670

Gln Gln Pro Gly Ser Ala Arg Ser Thr Arg His Leu Glu Ile Glu Leu
        675             680             685

Pro Lys Glu Ala Ser Tyr Gln Glu Gly Asp His Leu Gly Val Ile Pro
690             695             700

Arg Asn Tyr Glu Gly Ile Val Asn Arg Val Thr Ala Arg Phe Gly Leu
705             710             715             720
```

```
Asp Ala Ser Gln Gln Ile Arg Leu Glu Ala Glu Glu Lys Leu Ala
                725                 730                 735

His Leu Pro Leu Ala Lys Thr Val Ser Val Glu Leu Leu Gln Tyr
            740                 745                 750

Val Glu Leu Gln Asp Pro Val Thr Arg Thr Gln Leu Arg Ala Met Ala
        755                 760                 765

Ala Lys Thr Val Cys Pro Pro His Lys Val Glu Leu Glu Ala Leu Leu
    770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
            805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
            835                 840                 845

Val Ser Gly Glu Ala Trp Ser Gly Tyr Gly Glu Tyr Lys Gly Ile Ala
        850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
            885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
            915                 920                 925

Glu Ala His Leu Tyr Phe Gly Cys Arg Ser Pro His Glu Asp Tyr Leu
        930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
            965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
        995                 1000                1005

Val Glu Ala Thr Leu Met Lys Ser Tyr Ala Asp Val His Gln Val
    1010                1015                1020

Ser Glu Ala Asp Ala Arg Leu Trp Leu Gln Gln Leu Glu Glu Lys
    1025                1030                1035

Gly Arg Tyr Ala Lys Asp Val Trp Ala Gly
    1040                1045

<210> SEQ ID NO 28
<211> LENGTH: 1048
<212> TYPE: PRT
<213> ORGANISM: Artificial sequence
<220> FEATURE:
<223> OTHER INFORMATION: Cytochrome P450 variant CYP102A1var3-8

<400> SEQUENCE: 28

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Cys Val
```

-continued

```
            35                  40                  45
Thr Arg Tyr Leu Ser Ser Gln Arg Leu Ile Lys Glu Ala Cys Asp Glu
 50                  55                  60

Ser Arg Phe Asp Lys Asn Leu Ser Gln Ala Leu Lys Ala Val Arg Asp
 65                  70                  75                  80

Phe Ala Gly Asp Gly Leu Ile Thr Ser Trp Thr His Glu Ile Asn Trp
                     85                  90                  95

Lys Lys Ala His Asn Ile Leu Leu Pro Ser Phe Ser Gln Gln Ala Met
                100                 105                 110

Lys Gly Tyr His Ala Met Met Val Asp Ile Ala Val Gln Leu Val Gln
                115                 120                 125

Lys Trp Glu Arg Leu Asn Ala Asp Glu His Ile Glu Val Ser Glu Asp
                130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
                180                 185                 190

Pro Asp Asp Pro Ala Tyr Asp Glu Asn Lys Arg Gln Cys Gln Glu Asp
                195                 200                 205

Ile Lys Val Met Asn Asp Leu Val Asp Lys Ile Ile Ala Asp Arg Lys
                210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
                260                 265                 270

Leu Ser Phe Ala Leu Tyr Phe Leu Val Lys Asn Pro His Val Leu Gln
                275                 280                 285

Lys Val Ala Glu Glu Ala Ala Arg Val Leu Val Asp Pro Val Pro Ser
                290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
                340                 345                 350

Val Met Val Leu Ile Pro Gln Leu His Arg Asp Lys Thr Ile Trp Gly
                355                 360                 365

Asp Asp Val Glu Glu Phe Arg Pro Glu Arg Phe Glu Asn Pro Ser Ala
                370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
                420                 425                 430

Ile Lys Glu Thr Leu Thr Leu Lys Pro Glu Gly Phe Val Val Lys Ala
                435                 440                 445

Lys Ser Lys Lys Ile Pro Leu Gly Gly Ile Pro Ser Pro Ser Thr Glu
450                 455                 460
```

```
Gln Ser Ala Lys Lys Val Arg Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
            515                 520                 525

Val Leu Ile Val Thr Ala Ser Tyr Asn Gly His Pro Pro Asp Asn Ala
530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
            595                 600                 605

Phe Glu Gly Thr Tyr Glu Glu Trp Arg Glu His Met Trp Ser Asp Val
610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
            675                 680                 685

Pro Lys Glu Ala Ser Tyr Gln Glu Gly Asp His Leu Gly Val Ile Pro
690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
            740                 745                 750

Val Glu Leu Gln Asp Pro Val Thr Arg Thr Gln Leu Arg Ala Met Ala
            755                 760                 765

Ala Lys Thr Val Cys Pro Pro His Lys Val Glu Leu Glu Ala Leu Leu
770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
            835                 840                 845

Val Ser Gly Glu Ala Trp Ser Gly Tyr Gly Tyr Lys Gly Ile Ala
850                 855                 860

Ser Asn Tyr Leu Ala Glu Leu Gln Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895
```

```
Pro Leu Ile Met Val Gly Pro Gly Thr Gly Val Ala Pro Phe Arg Gly
                900                 905                 910

Phe Val Gln Ala Arg Lys Gln Leu Lys Glu Gln Gly Gln Ser Leu Gly
                915                 920                 925

Glu Ala His Leu Tyr Phe Gly Cys Arg Ser Pro His Glu Asp Tyr Leu
                930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
                980                 985                 990

Gly Ala His Phe Tyr Ile Cys Gly Asp Gly Ser Gln Met Ala Pro Ala
                995                 1000                1005

Val Glu Ala Thr Leu Met Lys Ser Tyr Ala Asp Val His Gln Val
         1010                1015                1020

Ser Glu Ala Asp Ala Arg Leu Trp Leu Gln Gln Leu Glu Glu Lys
         1025                1030                1035

Gly Arg Tyr Ala Lys Asp Val Trp Ala Gly
         1040                1045
```

<210> SEQ ID NO 29
<211> LENGTH: 1048
<212> TYPE: PRT
<213> ORGANISM: Artificial sequence
<220> FEATURE:
<223> OTHER INFORMATION: Cytochrome P450 variant CYP102A1var3-7

<400> SEQUENCE: 29

```
Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
                20                  25                  30

Ala Asp Glu Leu Gly Glu Ile Phe Lys Phe Glu Ala Pro Gly Cys Val
                35                  40                  45

Thr Arg Tyr Leu Ser Ser Gln Arg Leu Ile Lys Glu Ala Cys Asp Glu
            50                  55                  60

Ser Arg Phe Asp Lys Asn Leu Ser Gln Ala Leu Lys Ala Val Arg Asp
65                  70                  75                  80

Phe Ala Gly Asp Gly Leu Ala Thr Ser Trp Thr His Glu Ile Asn Trp
                85                  90                  95

Lys Lys Ala His Asn Ile Leu Leu Pro Ser Phe Ser Gln Gln Ala Met
                100                 105                 110

Lys Gly Tyr His Ala Met Met Val Asp Ile Ala Val Gln Leu Val Gln
            115                 120                 125

Lys Trp Glu Arg Leu Asn Ala Asp Glu His Ile Glu Val Ser Glu Asp
                130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
                180                 185                 190

Pro Asp Asp Pro Ala Tyr Asp Glu Asn Lys Arg Gln Cys Gln Glu Asp
            195                 200                 205
```

```
Ile Lys Val Met Asn Asp Leu Val Asp Lys Ile Ile Ala Asp Arg Lys
210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
            245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
            325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
            405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
            485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
            565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
    610                 615                 620

Ala Ala Tyr Phe Asn Leu Asp Ile Glu Asn Ser Glu Asp Asn Lys Ser
625                 630                 635                 640
```

```
Thr Leu Ser Leu Gln Phe Val Asp Ser Ala Asp Met Pro Leu Ala
                645                 650                 655

Lys Met His Gly Ala Phe Ser Thr Asn Val Val Ala Ser Lys Glu Leu
                660                 665                 670

Gln Gln Pro Gly Ser Ala Arg Ser Thr Arg His Leu Glu Ile Glu Leu
                675                 680                 685

Pro Lys Glu Ala Ser Tyr Gln Glu Gly Asp His Leu Gly Val Ile Pro
                690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Leu Leu Gln Tyr
                740                 745                 750

Val Glu Leu Gln Asp Pro Val Thr Arg Thr Gln Leu Arg Ala Met Ala
                755                 760                 765

Ala Lys Thr Val Cys Pro Pro His Lys Val Glu Leu Glu Ala Leu Leu
770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
                820                 825                 830

Ser Ser Pro Arg Val Asp Glu Lys Gln Ala Ser Ile Thr Val Ser Val
                835                 840                 845

Val Ser Gly Glu Ala Trp Ser Gly Tyr Gly Glu Tyr Lys Gly Ile Ala
                850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
                900                 905                 910

Phe Val Gln Ala Arg Lys Gln Leu Lys Glu Gln Gly Gln Ser Leu Gly
                915                 920                 925

Glu Ala His Leu Tyr Phe Gly Cys Arg Ser Pro His Glu Asp Tyr Leu
                930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
                980                 985                 990

Gly Ala His Phe Tyr Ile Cys Gly Asp Gly Ser Gln Met Ala Pro Ala
                995                1000                1005

Val Glu Ala Thr Leu Met Lys Ser Tyr Ala Asp Val His Gln Val
               1010                1015                1020

Ser Glu Ala Asp Ala Arg Leu Trp Leu Gln Gln Leu Glu Glu Lys
               1025                1030                1035

Gly Arg Tyr Ala Lys Asp Val Trp Ala Gly
               1040                1045
```

```
<210> SEQ ID NO 30
<211> LENGTH: 1048
<212> TYPE: PRT
<213> ORGANISM: Artificial sequence
<220> FEATURE:
<223> OTHER INFORMATION: Cytochrome P450 variant CYP102A1var3-8

<400> SEQUENCE: 30

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Cys Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Ala Val Arg Asp
65                  70                  75                  80

Phe Leu Gly Asp Gly Leu Phe Thr Ser Trp Thr His Glu Ile Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Cys Gln Glu Asp
        195                 200                 205

Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
    370                 375                 380
```

```
Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
            405                 410                 415

Met Leu Lys His Phe Asp Phe Glu Asp His Thr Asn Tyr Glu Leu Asp
        420                 425                 430

Ile Lys Glu Thr Leu Thr Leu Lys Pro Glu Gly Phe Val Val Lys Ala
    435                 440                 445

Lys Ser Lys Lys Ile Pro Leu Gly Gly Ile Pro Ser Pro Ser Thr Glu
    450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
                500                 505                 510

Val Ala Thr Leu Asp Ser His Ala Gly Asn Leu Pro Arg Glu Gly Ala
            515                 520                 525

Val Leu Ile Val Thr Ala Ser Tyr Asn Gly His Pro Pro Asp Asn Ala
        530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
    610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
                660                 665                 670

Gln Gln Pro Gly Ser Ala Arg Ser Thr Arg His Leu Glu Ile Glu Leu
            675                 680                 685

Pro Lys Glu Ala Ser Tyr Gln Glu Gly Asp His Leu Gly Val Ile Pro
        690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
                740                 745                 750

Val Glu Leu Gln Asp Pro Val Thr Arg Thr Gln Leu Arg Ala Met Ala
            755                 760                 765

Ala Lys Thr Val Cys Pro Pro His Lys Val Glu Leu Glu Ala Leu Leu
        770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
```

```
                    805                 810                 815
Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
            835                 840                 845

Val Ser Gly Glu Ala Trp Ser Gly Tyr Gly Glu Tyr Lys Gly Ile Ala
            850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
            915                 920                 925

Glu Ala His Leu Tyr Phe Gly Cys Arg Ser Pro His Glu Asp Tyr Leu
            930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
            995                 1000                1005

Val Glu Ala Thr Leu Met Lys Ser Tyr Ala Asp Val His Gln Val
            1010                1015                1020

Ser Glu Ala Asp Ala Arg Leu Trp Leu Gln Gln Leu Glu Glu Lys
            1025                1030                1035

Gly Arg Tyr Ala Lys Asp Val Trp Ala Gly
            1040                1045

<210> SEQ ID NO 31
<211> LENGTH: 1048
<212> TYPE: PRT
<213> ORGANISM: Artificial sequence
<220> FEATURE:
<223> OTHER INFORMATION: Cytochrome P450 variant CYP102A1var3-9

<400> SEQUENCE: 31

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Cys Val
            35                  40                  45

Thr Arg Tyr Leu Ser Ser Gln Arg Leu Ile Lys Glu Ala Cys Asp Glu
        50                  55                  60

Ser Arg Phe Asp Lys Asn Leu Ser Gln Ala Leu Lys Thr Val Arg Asp
65                  70                  75                  80

Phe Gly Gly Asp Gly Leu Val Thr Ser Trp Thr His Glu Ile Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
            115                 120                 125
```

```
Lys Trp Glu Arg Leu Asn Ala Asp Glu His Ile Glu Val Ser Glu Asp
        130                 135                 140
Met Thr Arg Leu Thr Leu Asp Thr Ile Gly Leu Cys Gly Phe Asn Tyr
145                 150                 155                 160
Arg Phe Asn Ser Phe Tyr Arg Asp Gln Pro His Pro Phe Ile Ile Ser
                165                 170                 175
Met Val Arg Ala Leu Asp Glu Val Met Asn Lys Leu Gln Arg Ala Asn
                180                 185                 190
Pro Asp Asp Pro Ala Tyr Asp Glu Asn Lys Arg Gln Cys Gln Glu Asp
                195                 200                 205
Ile Lys Val Met Asn Asp Leu Val Asp Lys Ile Ile Ala Asp Arg Lys
                210                 215                 220
Ala Arg Gly Glu Gln Ser Asp Asp Leu Leu Thr Gln Met Leu Asn Gly
225                 230                 235                 240
Lys Asp Pro Glu Thr Gly Glu Pro Leu Asp Asp Gly Asn Ile Ser Tyr
                245                 250                 255
Gln Ile Ile Thr Phe Leu Ile Ala Gly His Glu Thr Thr Ser Gly Leu
                260                 265                 270
Leu Ser Phe Ala Leu Tyr Phe Leu Val Lys Asn Pro His Val Leu Gln
                275                 280                 285
Lys Val Ala Glu Glu Ala Ala Arg Val Leu Val Asp Pro Val Pro Ser
290                 295                 300
Tyr Lys Gln Val Lys Gln Leu Lys Tyr Val Gly Met Val Leu Asn Glu
305                 310                 315                 320
Ala Leu Arg Leu Trp Pro Thr Leu Pro Ala Phe Ser Leu Tyr Ala Lys
                325                 330                 335
Glu Asp Thr Val Leu Gly Gly Glu Tyr Pro Leu Glu Lys Gly Asp Glu
                340                 345                 350
Val Met Val Leu Ile Pro Gln Leu His Arg Asp Lys Thr Ile Trp Gly
                355                 360                 365
Asp Asp Val Glu Glu Phe Arg Pro Glu Arg Phe Glu Asn Pro Ser Ala
370                 375                 380
Ile Pro Gln His Ala Phe Lys Pro Phe Gly Asn Gly Gln Arg Ala Cys
385                 390                 395                 400
Ile Gly Gln Gln Phe Ala Leu His Glu Ala Thr Leu Val Leu Gly Met
                405                 410                 415
Met Leu Lys His Phe Asp Phe Glu Asp His Thr Asn Tyr Glu Leu Asp
                420                 425                 430
Ile Lys Glu Thr Leu Thr Leu Lys Pro Glu Gly Phe Val Val Lys Ala
                435                 440                 445
Lys Ser Lys Lys Ile Pro Leu Gly Gly Ile Pro Ser Pro Ser Thr Glu
                450                 455                 460
Gln Ser Ala Lys Lys Val Arg Lys Lys Ala Glu Asn Ala His Asn Thr
465                 470                 475                 480
Pro Leu Leu Val Leu Tyr Gly Ser Asn Met Gly Thr Ala Glu Gly Thr
                485                 490                 495
Ala Arg Asp Leu Ala Asp Ile Ala Met Ser Lys Gly Phe Ala Pro Gln
                500                 505                 510
Val Ala Thr Leu Asp Ser His Ala Gly Asn Leu Pro Arg Glu Gly Ala
                515                 520                 525
Val Leu Ile Val Thr Ala Ser Tyr Asn Gly His Pro Pro Asp Asn Ala
                530                 535                 540
Lys Gln Phe Val Asp Trp Leu Asp Gln Ala Ser Ala Asp Glu Val Lys
```

-continued

```
            545                 550                 555                 560
Gly Val Arg Tyr Ser Val Phe Gly Cys Gly Asp Lys Asn Trp Ala Thr
                    565                 570                 575

Thr Tyr Gln Lys Val Pro Ala Phe Ile Asp Glu Thr Leu Ala Ala Lys
                580                 585                 590

Gly Ala Glu Asn Ile Ala Asp Arg Gly Glu Ala Asp Ala Ser Asp Asp
                595                 600                 605

Phe Glu Gly Thr Tyr Glu Glu Trp Arg Glu His Met Trp Ser Asp Val
            610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
                660                 665                 670

Gln Gln Pro Gly Ser Ala Arg Ser Thr Arg His Leu Glu Ile Glu Leu
                675                 680                 685

Pro Lys Glu Ala Ser Tyr Gln Glu Gly Asp His Leu Gly Val Ile Pro
            690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
                740                 745                 750

Val Glu Leu Gln Asp Pro Val Thr Arg Thr Gln Leu Arg Ala Met Ala
            755                 760                 765

Ala Lys Thr Val Cys Pro Pro His Lys Val Glu Leu Glu Ala Leu Leu
770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
                835                 840                 845

Val Ser Gly Glu Ala Trp Ser Gly Tyr Gly Tyr Lys Gly Ile Ala
850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
                900                 905                 910

Phe Val Gln Ala Arg Lys Gln Leu Lys Glu Gln Gly Gln Ser Leu Gly
            915                 920                 925

Glu Ala His Leu Tyr Phe Gly Cys Arg Ser Pro His Glu Asp Tyr Leu
            930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975
```

```
His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
            995                 1000                1005

Val Glu Ala Thr Leu Met Lys Ser Tyr Ala Asp Val His Gln Val
        1010                1015                1020

Ser Glu Ala Asp Ala Arg Leu Trp Leu Gln Gln Leu Glu Glu Lys
        1025                1030                1035

Gly Arg Tyr Ala Lys Asp Val Trp Ala Gly
        1040                1045

<210> SEQ ID NO 32
<211> LENGTH: 1048
<212> TYPE: PRT
<213> ORGANISM: Artificial sequence
<220> FEATURE:
<223> OTHER INFORMATION: Cytochrome P450 variant CYP102A1var3-10

<400> SEQUENCE: 32

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Cys Val
        35                  40                  45

Thr Arg Tyr Ile Ser Ser Gln Arg Leu Ile Lys Glu Ala Cys Asp Glu
    50                  55                  60

Ser Arg Phe Asp Lys Asn Leu Ser Gln Ala Leu Lys Ala Phe Arg Asp
65                  70                  75                  80

Phe Ser Gly Asp Gly Leu Phe Thr Ser Trp Thr His Glu Ile Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Cys Gln Glu Asp
        195                 200                 205

Ile Lys Val Met Asn Asp Leu Val Asp Lys Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
```

```
              290                 295                 300
Tyr Lys Gln Val Lys Gln Leu Lys Tyr Val Gly Met Val Leu Asn Glu
305                 310                 315                 320

Ala Leu Arg Leu Trp Pro Thr Phe Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Val Trp Gly
            355                 360                 365

Asp Asp Val Glu Glu Phe Arg Pro Glu Arg Phe Glu Asn Pro Ser Ala
    370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr Gly
    450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
    530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
    610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
        675                 680                 685

Pro Lys Glu Ala Ser Tyr Gln Glu Gly Asp His Leu Gly Val Ile Pro
    690                 695                 700

Arg Asn Tyr Glu Gly Thr Val Asn Arg Val Thr Ala Arg Phe Gly Leu
705                 710                 715                 720
```

Asp Ala Ser Gln Gln Ile Arg Leu Glu Ala Glu Glu Lys Leu Ala
              725                 730                 735

His Leu Pro Leu Ala Lys Thr Val Ser Val Glu Leu Leu Gln Tyr
            740                 745                 750

Val Glu Leu Gln Asp Pro Val Thr Arg Thr Gln Leu Arg Ala Met Ala
        755                 760                 765

Ala Lys Thr Val Cys Pro Pro His Lys Val Glu Leu Glu Ala Leu Leu
770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
        835                 840                 845

Val Ser Gly Glu Ala Trp Ser Gly Tyr Gly Glu Tyr Lys Gly Ile Ala
850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
        915                 920                 925

Glu Ala His Leu Tyr Phe Gly Cys Arg Ser Pro His Glu Asp Tyr Leu
930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
        995                 1000                1005

Val Glu Ala Thr Leu Met Lys Ser Tyr Ala Asp Val His Gln Val
    1010                1015                1020

Ser Glu Ala Asp Ala Arg Leu Trp Leu Gln Gln Leu Glu Glu Lys
    1025                1030                1035

Gly Arg Tyr Ala Lys Asp Val Trp Ala Gly
    1040                1045

<210> SEQ ID NO 33
<211> LENGTH: 1048
<212> TYPE: PRT
<213> ORGANISM: Artificial sequence
<220> FEATURE:
<223> OTHER INFORMATION: Cytochrome P450 variant CYP102A1var3-11

<400> SEQUENCE: 33

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Cys Val

-continued

```
                35                  40                  45
Thr Arg Tyr Ile Ser Ser Gln Arg Leu Ile Lys Glu Ala Cys Asp Glu
 50                  55                  60
Ser Arg Phe Asp Lys Asn Leu Ser Gln Ala Leu Lys Ala Phe Arg Asp
 65                  70                  75                  80
Phe Ser Gly Asp Gly Leu Phe Thr Ser Trp Thr His Glu Ile Asn Trp
                 85                  90                  95
Lys Lys Ala His Asn Ile Leu Pro Ser Phe Ser Gln Gln Ala Met
                100                 105                 110
Lys Gly Tyr His Ala Met Met Val Asp Ile Ala Val Gln Leu Val Gln
                115                 120                 125
Lys Trp Glu Arg Leu Asn Ala Asp Glu His Ile Glu Val Ser Glu Asp
                130                 135                 140
Met Thr Arg Leu Thr Leu Asp Thr Ile Gly Leu Cys Gly Phe Asn Tyr
145                 150                 155                 160
Arg Phe Asn Ser Phe Tyr Arg Asp Gln Pro His Pro Phe Ile Ile Ser
                165                 170                 175
Met Val Arg Ala Leu Asp Glu Val Met Asn Lys Leu Gln Arg Ala Asn
                180                 185                 190
Pro Asp Asp Pro Ala Tyr Asp Glu Asn Lys Arg Gln Cys Gln Glu Asp
                195                 200                 205
Ile Lys Val Met Asn Asp Leu Val Asp Lys Ile Ile Ala Asp Arg Lys
                210                 215                 220
Ala Arg Gly Glu Gln Ser Asp Asp Leu Leu Thr Gln Met Leu Asn Gly
225                 230                 235                 240
Lys Asp Pro Glu Thr Gly Glu Pro Leu Asp Asp Gly Asn Ile Ser Tyr
                245                 250                 255
Gln Ile Ile Thr Phe Leu Ile Ala Gly His Glu Thr Thr Ser Gly Leu
                260                 265                 270
Leu Ser Phe Ala Leu Tyr Phe Leu Val Lys Asn Pro His Val Leu Gln
                275                 280                 285
Lys Val Ala Glu Glu Ala Ala Arg Val Leu Val Asp Pro Val Pro Ser
                290                 295                 300
Tyr Lys Gln Val Lys Gln Leu Lys Tyr Val Gly Met Val Leu Asn Glu
305                 310                 315                 320
Ala Leu Arg Leu Trp Pro Thr Leu Pro Ala Phe Ser Leu Tyr Ala Lys
                325                 330                 335
Glu Asp Thr Val Leu Gly Gly Glu Tyr Pro Leu Glu Asn Gly Asp Glu
                340                 345                 350
Val Met Val Leu Ile Pro Gln Leu His Arg Asp Lys Thr Val Trp Gly
                355                 360                 365
Asp Asp Val Glu Glu Phe Arg Pro Glu Arg Phe Glu Asn Pro Ser Ala
                370                 375                 380
Ile Pro Gln His Ala Phe Lys Pro Phe Gly Asn Gly Gln Arg Ala Cys
385                 390                 395                 400
Ile Gly Gln Gln Phe Ala Leu His Glu Ala Thr Leu Val Leu Gly Met
                405                 410                 415
Met Leu Lys His Phe Asp Phe Glu Asp His Thr Asn Tyr Glu Leu Asp
                420                 425                 430
Ile Lys Glu Thr Leu Thr Leu Lys Pro Glu Gly Phe Val Val Lys Ala
                435                 440                 445
Lys Ser Lys Lys Ile Pro Leu Gly Gly Ile Pro Ser Pro Ser Thr Gly
                450                 455                 460
```

```
Gln Ser Ala Lys Lys Val Arg Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
    530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
    610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
        675                 680                 685

Pro Lys Glu Ala Ser Tyr Gln Glu Gly Asp His Leu Gly Val Ile Pro
    690                 695                 700

Arg Asn Tyr Glu Gly Thr Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
            740                 745                 750

Val Glu Leu Gln Asp Pro Val Thr Arg Thr Gln Leu Arg Ala Met Ala
        755                 760                 765

Ala Lys Thr Val Cys Pro Pro His Lys Val Glu Leu Glu Ala Leu Leu
    770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
        835                 840                 845

Val Ser Gly Glu Ala Trp Ser Gly Tyr Gly Tyr Lys Gly Ile Ala
    850                 855                 860

Ser Asn Tyr Leu Ala Glu Leu Gln Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895
```

Pro Leu Ile Met Val Gly Pro Gly Thr Gly Val Ala Pro Phe Arg Gly
                900                 905                 910

Phe Val Gln Ala Arg Lys Gln Leu Lys Glu Gln Gly Gln Ser Leu Gly
            915                 920                 925

Glu Ala His Leu Tyr Phe Gly Cys Arg Ser Pro His Glu Asp Tyr Leu
    930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
        995                 1000                1005

Val Glu Ala Thr Leu Met Lys Ser Tyr Ala Asp Val His Gln Val
    1010                1015                1020

Ser Glu Ala Asp Ala Arg Leu Trp Leu Gln Gln Leu Glu Glu Lys
    1025                1030                1035

Gly Arg Tyr Ala Lys Asp Val Trp Ala Gly
    1040                1045

<210> SEQ ID NO 34
<211> LENGTH: 1048
<212> TYPE: PRT
<213> ORGANISM: Artificial sequence
<220> FEATURE:
<223> OTHER INFORMATION: Cytochrome P450 variant CYP102A1var3-12

<400> SEQUENCE: 34

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Cys Val
        35                  40                  45

Thr Arg Tyr Ile Ser Ser Gln Arg Leu Ile Lys Glu Ala Cys Asp Glu
    50                  55                  60

Ser Arg Phe Asp Lys Asn Leu Ser Gln Ala Leu Lys Ala Phe Arg Asp
65                  70                  75                  80

Phe Ser Gly Asp Gly Leu Phe Thr Ser Trp Thr His Glu Ile Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Pro Gln Arg Ala Asn
            180                 185                 190

Pro Asp Asp Pro Ala Tyr Asp Glu Asn Lys Arg Gln Cys Gln Glu Asp
        195                 200                 205

-continued

```
Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
290                 295                 300

Tyr Lys Gln Val Lys Gln Leu Lys Tyr Val Gly Met Val Leu Asn Glu
305                 310                 315                 320

Ala Leu Arg Leu Trp Pro Thr Phe Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Val Trp Gly
        355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr Gly
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
610                 615                 620

Ala Ala Tyr Phe Asn Leu Asp Ile Glu Asn Ser Glu Asp Asn Lys Ser
625                 630                 635                 640
```

```
Thr Leu Ser Leu Gln Phe Val Asp Ser Ala Asp Met Pro Leu Ala
            645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
            675                 680                 685

Pro Lys Glu Ala Ser Tyr Gln Glu Gly Asp His Leu Gly Val Ile Pro
            690                 695                 700

Arg Asn Tyr Glu Gly Thr Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Leu Leu Gln Tyr
            740                 745                 750

Val Glu Leu Gln Asp Pro Val Thr Arg Thr Gln Leu Arg Ala Met Ala
            755                 760                 765

Ala Lys Thr Val Cys Pro Pro His Lys Val Glu Leu Glu Ala Leu Leu
            770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
                820                 825                 830

Ser Ser Pro Arg Val Asp Glu Lys Gln Ala Ser Ile Thr Val Ser Val
            835                 840                 845

Val Ser Gly Glu Ala Trp Ser Gly Tyr Gly Glu Tyr Lys Gly Ile Ala
            850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
            915                 920                 925

Glu Ala His Leu Tyr Phe Gly Cys Arg Ser Pro His Glu Asp Tyr Leu
            930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
            995                 1000                1005

Val Glu Ala Thr Leu Met Lys Ser Tyr Ala Asp Val His Gln Val
            1010                1015                1020

Ser Glu Ala Asp Ala Arg Leu Trp Leu Gln Gln Leu Glu Glu Lys
            1025                1030                1035

Gly Arg Tyr Ala Lys Asp Val Trp Ala Gly
            1040                1045
```

<210> SEQ ID NO 35
<211> LENGTH: 1048
<212> TYPE: PRT
<213> ORGANISM: Artificial sequence
<220> FEATURE:
<223> OTHER INFORMATION: Cytochrome P450 variant CYP102A1var3-13

<400> SEQUENCE: 35

```
Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Cys Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Thr Val Arg Asp
65                  70                  75                  80

Phe Gly Gly Asp Gly Leu Phe Thr Ser Trp Thr His Glu Ile Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Cys Gln Glu Asp
        195                 200                 205

Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Leu Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
    370                 375                 380
```

```
Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
            405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
            435                 440                 445

Lys Ser Lys Lys Ile Pro Leu Gly Gly Ile Pro Ser Pro Ser Thr Glu
            450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
                500                 505                 510

Val Ala Thr Leu Asp Ser His Ala Gly Asn Leu Pro Arg Glu Gly Ala
                515                 520                 525

Val Leu Ile Val Thr Ala Ser Tyr Asn Gly His Pro Pro Asp Asn Ala
530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
                580                 585                 590

Gly Ala Glu Asn Ile Ala Asp Arg Gly Glu Ala Asp Ala Ser Asp Asp
            595                 600                 605

Phe Glu Gly Thr Tyr Glu Glu Trp Arg Glu His Met Trp Ser Asp Val
610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
                660                 665                 670

Gln Gln Pro Gly Ser Ala Arg Ser Thr Arg His Leu Glu Ile Glu Leu
            675                 680                 685

Pro Lys Glu Ala Ser Tyr Gln Glu Gly Asp His Leu Gly Val Ile Pro
690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
            740                 745                 750

Val Glu Leu Gln Asp Pro Val Thr Arg Thr Gln Leu Arg Ala Met Ala
            755                 760                 765

Ala Lys Thr Val Cys Pro Pro His Lys Val Glu Leu Glu Ala Leu Leu
            770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
```

-continued

```
                805                 810                 815
Phe Ile Ala Leu Leu Pro Ser Ile Arg Pro Arg Tyr Tyr Ser Ile Ser
        820                 825                 830

Ser Ser Pro Arg Val Asp Glu Lys Gln Ala Ser Ile Thr Val Ser Val
        835                 840                 845

Val Ser Gly Glu Ala Trp Ser Gly Tyr Gly Glu Tyr Lys Gly Ile Ala
        850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
        900                 905                 910

Phe Val Gln Ala Arg Lys Gln Leu Lys Glu Gln Gly Gln Ser Leu Gly
        915                 920                 925

Glu Ala His Leu Tyr Phe Gly Cys Arg Ser Pro His Glu Asp Tyr Leu
        930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Leu Leu Ile Glu Leu Leu Asp Gln
        980                 985                 990

Gly Ala His Phe Tyr Ile Cys Gly Asp Gly Ser Gln Met Ala Pro Ala
        995                1000                1005

Val Glu Ala Thr Leu Met Lys Ser Tyr Ala Asp Val His Gln Val
        1010                1015                1020

Ser Glu Ala Asp Ala Arg Leu Trp Leu Gln Gln Leu Glu Glu Lys
        1025                1030                1035

Gly Arg Tyr Ala Lys Asp Val Trp Ala Gly
        1040                1045
```

<210> SEQ ID NO 36
<211> LENGTH: 1048
<212> TYPE: PRT
<213> ORGANISM: Artificial sequence
<220> FEATURE:
<223> OTHER INFORMATION: Cytochrome P450 variant CYP102A1var3-14

<400> SEQUENCE: 36

```
Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
        20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
        50                  55                  60

Ser Arg Phe Asp Lys Asn Leu Ser Gln Ala Leu Lys Ala Val Arg Asp
65                  70                  75                  80

Arg Val Gly Asp Gly Leu Ala Thr Ser Trp Thr His Glu Lys Asn Trp
                85                  90                  95

Lys Lys Ala His Asn Ile Leu Leu Pro Ser Phe Ser Gln Gln Ala Met
        100                 105                 110

Lys Gly Tyr His Ala Met Met Val Asp Ile Ala Val Gln Leu Val Gln
        115                 120                 125
```

Lys Trp Glu Arg Leu Asn Ala Asp Glu His Ile Glu Val Ser Glu Asp
            130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Thr Leu Asp Glu Val Met Asn Lys Leu Gln Arg Ala Asn
            180                 185                 190

Pro Asp Asp Pro Val Tyr Asp Glu Asn Lys Arg Gln Cys Gln Glu Asp
            195                 200                 205

Ile Lys Val Met Asn Asp Leu Val Asp Lys Ile Ile Ala Asp Arg Lys
            210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
            275                 280                 285

Lys Val Ala Glu Ala Ala Arg Val Leu Val Asp Pro Val Pro Ser
290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Ile Trp Gly
            355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
            435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
            515                 520                 525

Val Leu Ile Val Thr Ala Ser Tyr Asn Gly His Pro Pro Asp Asn Ala
530                 535                 540

Lys Gln Phe Val Asp Trp Leu Asp Gln Ala Ser Ala Asp Glu Val Lys

-continued

```
          545                 550                 555                 560
        Gly Val Arg Tyr Ser Val Phe Gly Cys Gly Asp Lys Asn Trp Ala Thr
                            565                 570                 575
        Thr Tyr Gln Lys Val Pro Ala Phe Ile Asp Glu Thr Leu Ala Ala Lys
                        580                 585                 590
        Gly Ala Glu Asn Ile Ala Asp Arg Gly Glu Ala Asp Ala Ser Asp Asp
                        595                 600                 605
        Phe Glu Gly Thr Tyr Glu Glu Trp Arg Glu His Met Trp Ser Asp Val
                    610                 615                 620
        Ala Ala Tyr Phe Asn Leu Asp Ile Glu Asn Ser Glu Asp Asn Lys Ser
        625                 630                 635                 640
        Thr Leu Ser Leu Gln Phe Val Asp Ser Ala Ala Asp Met Pro Leu Ala
                            645                 650                 655
        Lys Met His Gly Ala Phe Ser Thr Asn Val Val Ala Ser Lys Glu Leu
                            660                 665                 670
        Gln Gln Pro Gly Ser Ala Arg Ser Thr Arg His Leu Glu Ile Glu Leu
                        675                 680                 685
        Pro Lys Glu Ala Ser Tyr Gln Glu Gly Asp His Leu Gly Val Ile Pro
                    690                 695                 700
        Arg Asn Tyr Glu Gly Ile Val Asn Arg Val Thr Ala Arg Phe Gly Leu
        705                 710                 715                 720
        Asp Ala Ser Gln Gln Ile Arg Leu Glu Ala Glu Glu Lys Leu Ala
                            725                 730                 735
        His Leu Pro Leu Ala Lys Thr Val Ser Val Glu Glu Leu Leu Gln Tyr
                            740                 745                 750
        Val Glu Leu Gln Asp Pro Val Thr Arg Thr Gln Leu Arg Ala Met Ala
                        755                 760                 765
        Ala Lys Thr Val Cys Pro Pro His Lys Val Glu Leu Glu Ala Leu Leu
                        770                 775                 780
        Glu Lys Gln Ala Tyr Lys Glu Gln Val Leu Ala Lys Arg Leu Thr Met
        785                 790                 795                 800
        Leu Glu Leu Leu Glu Lys Tyr Pro Ala Cys Glu Met Lys Phe Ser Glu
                            805                 810                 815
        Phe Ile Ala Leu Leu Pro Ser Ile Arg Pro Arg Tyr Tyr Ser Ile Ser
                        820                 825                 830
        Ser Ser Pro Arg Val Asp Glu Lys Gln Ala Ser Ile Thr Val Ser Val
                        835                 840                 845
        Val Ser Gly Glu Ala Trp Ser Gly Tyr Gly Tyr Lys Gly Ile Ala
        850                 855                 860
        Ser Asn Tyr Leu Ala Glu Leu Gln Glu Gly Asp Thr Ile Thr Cys Phe
        865                 870                 875                 880
        Ile Ser Thr Pro Gln Ser Glu Phe Thr Leu Pro Lys Asp Pro Glu Thr
                        885                 890                 895
        Pro Leu Ile Met Val Gly Pro Gly Thr Gly Val Ala Pro Phe Arg Gly
                    900                 905                 910
        Phe Val Gln Ala Arg Lys Gln Leu Lys Glu Gln Gly Gln Ser Leu Gly
                    915                 920                 925
        Glu Ala His Leu Tyr Phe Gly Cys Arg Ser Pro His Glu Asp Tyr Leu
                    930                 935                 940
        Tyr Gln Glu Glu Leu Glu Asn Ala Gln Ser Glu Gly Ile Ile Thr Leu
        945                 950                 955                 960
        His Thr Ala Phe Ser Arg Met Pro Asn Gln Pro Lys Thr Tyr Val Gln
                            965                 970                 975
```

```
His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
            995                 1000                1005

Val Glu Ala Thr Leu Met Lys Ser Tyr Ala Asp Val His Gln Val
        1010                1015                1020

Ser Glu Ala Asp Ala Arg Leu Trp Leu Gln Gln Leu Glu Glu Lys
        1025                1030                1035

Gly Arg Tyr Ala Lys Asp Val Trp Ala Gly
        1040                1045

<210> SEQ ID NO 37
<211> LENGTH: 1048
<212> TYPE: PRT
<213> ORGANISM: Artificial sequence
<220> FEATURE:
<223> OTHER INFORMATION: Cytochrome P450 variant CYP102A1var3-15

<400> SEQUENCE: 37

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Ala Val Arg Asp
65                  70                  75                  80

Trp Ser Gly Asp Gly Leu Ala Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Val Tyr Asp Glu Asn Lys Arg Gln Cys Gln Glu Asp
        195                 200                 205

Ile Lys Val Met Asn Asp Leu Val Asp Lys Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
```

```
                290                 295                 300
Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
                340                 345                 350

Val Met Val Leu Ile Pro Gln Leu His Arg Asp Lys Thr Ile Trp Gly
                355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
                420                 425                 430

Ile Lys Glu Thr Leu Thr Leu Lys Pro Glu Gly Phe Val Val Lys Ala
                435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
                500                 505                 510

Val Ala Thr Leu Asp Ser His Ala Gly Asn Leu Pro Arg Glu Gly Ala
                515                 520                 525

Val Leu Ile Val Thr Ala Ser Tyr Asn Gly His Pro Pro Asp Asn Ala
                530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
                580                 585                 590

Gly Ala Glu Asn Ile Ala Asp Arg Gly Glu Ala Asp Ala Ser Asp Asp
                595                 600                 605

Phe Glu Gly Thr Tyr Glu Glu Trp Arg Glu His Met Trp Ser Asp Val
                610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
                660                 665                 670

Gln Gln Pro Gly Ser Ala Arg Ser Thr Arg His Leu Glu Ile Glu Leu
                675                 680                 685

Pro Lys Glu Ala Ser Tyr Gln Glu Gly Asp His Leu Gly Val Ile Pro
                690                 695                 700

Arg Asn Tyr Glu Gly Ile Val Asn Arg Val Thr Ala Arg Phe Gly Leu
705                 710                 715                 720
```

```
Asp Ala Ser Gln Gln Ile Arg Leu Glu Ala Glu Glu Lys Leu Ala
            725                 730                 735

His Leu Pro Leu Ala Lys Thr Val Ser Val Glu Leu Leu Gln Tyr
            740                 745                 750

Val Glu Leu Gln Asp Pro Val Thr Arg Thr Gln Leu Arg Ala Met Ala
        755                 760                 765

Ala Lys Thr Val Cys Pro Pro His Lys Val Glu Leu Glu Ala Leu Leu
770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
            805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
            835                 840                 845

Val Ser Gly Glu Ala Trp Ser Gly Tyr Gly Glu Tyr Lys Gly Ile Ala
            850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
            915                 920                 925

Glu Ala His Leu Tyr Phe Gly Cys Arg Ser Pro His Glu Asp Tyr Leu
930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
            995                 1000                1005

Val Glu Ala Thr Leu Met Lys Ser Tyr Ala Asp Val His Gln Val
    1010                1015                1020

Ser Glu Ala Asp Ala Arg Leu Trp Leu Gln Gln Leu Glu Glu Lys
    1025                1030                1035

Gly Arg Tyr Ala Lys Asp Val Trp Ala Gly
    1040                1045

<210> SEQ ID NO 38
<211> LENGTH: 1048
<212> TYPE: PRT
<213> ORGANISM: Artificial sequence
<220> FEATURE:
<223> OTHER INFORMATION: Cytochrome P450 variant CYP102A1var3-16

<400> SEQUENCE: 38

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Cys Val
```

```
                35                  40                  45
Thr Arg Tyr Leu Ser Ser Gln Arg Leu Ile Lys Glu Ala Cys Asp Glu
 50                  55                  60

Ser Arg Phe Asp Lys Asn Leu Ser Gln Ala Leu Lys Ala Phe Arg Asp
 65                  70                  75                  80

Phe Ser Gly Asp Gly Leu Phe Thr Ser Trp Thr His Glu Ile Asn Trp
                 85                  90                  95

Lys Lys Ala His Asn Ile Leu Leu Pro Ser Phe Ser Gln Gln Ala Met
                100                 105                 110

Lys Gly Tyr His Ala Met Met Val Asp Ile Ala Val Gln Leu Val Gln
                115                 120                 125

Lys Trp Glu Arg Leu Asn Ala Asp Glu His Ile Glu Val Ser Glu Asp
130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
                180                 185                 190

Pro Asp Asp Pro Ala Tyr Asp Glu Asn Lys Arg Gln Cys Gln Glu Asp
                195                 200                 205

Ile Lys Val Met Asn Asp Leu Val Asp Lys Ile Ile Ala Asp Arg Lys
                210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
                260                 265                 270

Leu Ser Phe Ala Leu Tyr Phe Leu Val Lys Asn Pro His Val Leu Gln
                275                 280                 285

Lys Val Ala Glu Glu Ala Ala Arg Val Leu Val Asp Pro Val Pro Ser
                290                 295                 300

Tyr Lys Gln Val Lys Gln Leu Lys Tyr Val Gly Met Val Leu Asn Glu
305                 310                 315                 320

Ala Leu Arg Leu Trp Pro Thr Phe Pro Ala Phe Ser Leu Tyr Ala Lys
                325                 330                 335

Glu Asp Thr Val Leu Gly Gly Glu Tyr Pro Leu Glu Lys Gly Asp Glu
                340                 345                 350

Val Met Val Leu Ile Pro Gln Leu His Arg Asp Lys Thr Ile Trp Gly
                355                 360                 365

Asp Asp Val Glu Glu Phe Arg Pro Glu Arg Phe Glu Asn Pro Ser Ala
                370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
                420                 425                 430

Ile Lys Glu Thr Leu Thr Leu Lys Pro Glu Gly Phe Val Val Lys Ala
                435                 440                 445

Lys Ser Lys Lys Ile Pro Leu Gly Gly Ile Pro Ser Pro Ser Thr Gly
                450                 455                 460
```

-continued

```
Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
    530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
        675                 680                 685

Pro Lys Glu Ala Ser Tyr Gln Glu Gly Asp His Leu Gly Val Ile Pro
    690                 695                 700

Arg Asn Tyr Glu Gly Thr Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
            740                 745                 750

Val Glu Leu Gln Asp Pro Val Thr Arg Thr Gln Leu Arg Ala Met Ala
        755                 760                 765

Ala Lys Thr Val Cys Pro Pro His Lys Val Glu Leu Glu Ala Leu Leu
    770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
        835                 840                 845

Val Ser Gly Glu Ala Trp Ser Gly Tyr Gly Tyr Lys Gly Ile Ala
    850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895
```

```
Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
            915                 920                 925

Glu Ala His Leu Tyr Phe Gly Cys Arg Ser Pro His Glu Asp Tyr Leu
            930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
            965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
            995                 1000                1005

Val Glu Ala Thr Leu Met Lys Ser Tyr Ala Asp Val His Gln Val
        1010                1015                1020

Ser Glu Ala Asp Ala Arg Leu Trp Leu Gln Gln Leu Glu Glu Lys
        1025                1030                1035

Gly Arg Tyr Ala Lys Asp Val Trp Ala Gly
        1040                1045

<210> SEQ ID NO 39
<211> LENGTH: 1048
<212> TYPE: PRT
<213> ORGANISM: Artificial sequence
<220> FEATURE:
<223> OTHER INFORMATION: Cytochrome P450 variant CYP102A1var3-17

<400> SEQUENCE: 39

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Ala Val Arg Asp
65                  70                  75                  80

Val Thr Gly Asp Gly Leu Ala Thr Ser Trp Thr His Glu Lys Asn Trp
            85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
            165                 170                 175

Met Val Arg Thr Leu Asp Glu Val Met Asn Lys Leu Gln Arg Ala Asn
            180                 185                 190

Pro Asp Asp Pro Val Tyr Asp Glu Asn Lys Arg Gln Cys Gln Glu Asp
        195                 200                 205
```

```
Ile Lys Val Met Asn Asp Leu Val Asp Lys Ile Ile Ala Asp Arg Lys
210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
610                 615                 620

Ala Ala Tyr Phe Asn Leu Asp Ile Glu Asn Ser Glu Asp Asn Lys Ser
625                 630                 635                 640
```

```
Thr Leu Ser Leu Gln Phe Val Asp Ser Ala Asp Met Pro Leu Ala
            645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
            675                 680                 685

Pro Lys Glu Ala Ser Tyr Gln Glu Gly Asp His Leu Gly Val Ile Pro
            690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
            725                 730                 735

His Leu Pro Leu Ala Lys Thr Val Ser Val Glu Leu Leu Gln Tyr
            740                 745                 750

Val Glu Leu Gln Asp Pro Val Thr Arg Thr Gln Leu Arg Ala Met Ala
            755                 760                 765

Ala Lys Thr Val Cys Pro Pro His Lys Val Glu Leu Glu Ala Leu Leu
770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
            805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
            835                 840                 845

Val Ser Gly Glu Ala Trp Ser Gly Tyr Gly Glu Tyr Lys Gly Ile Ala
            850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
            885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
            915                 920                 925

Glu Ala His Leu Tyr Phe Gly Cys Arg Ser Pro His Glu Asp Tyr Leu
            930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
            965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
            995                 1000                1005

Val Glu Ala Thr Leu Met Lys Ser Tyr Ala Asp Val His Gln Val
            1010                1015                1020

Ser Glu Ala Asp Ala Arg Leu Trp Leu Gln Gln Leu Glu Glu Lys
            1025                1030                1035

Gly Arg Tyr Ala Lys Asp Val Trp Ala Gly
            1040                1045
```

<210> SEQ ID NO 40
<211> LENGTH: 1048
<212> TYPE: PRT
<213> ORGANISM: Artificial sequence
<220> FEATURE:
<223> OTHER INFORMATION: Cytochrome P450 variant CYP102A1var3-18

<400> SEQUENCE: 40

```
Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Cys Val
        35                  40                  45

Thr Arg Tyr Ile Ser Ser Gln Arg Leu Ile Lys Glu Ala Cys Asp Glu
    50                  55                  60

Ser Arg Phe Asp Lys Asn Leu Ser Gln Ala Leu Lys Ala Phe Arg Asp
65                  70                  75                  80

Phe Ser Gly Asp Gly Leu Phe Thr Ser Trp Thr His Glu Ile Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Pro Gln Arg Ala Asn
            180                 185                 190

Pro Asp Asp Pro Ala Tyr Asp Glu Asn Lys Arg Gln Cys Gln Glu Asp
        195                 200                 205

Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Phe Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Val Trp Gly
        355                 360                 365

Asp Asp Val Glu Glu Phe Arg Pro Glu Arg Phe Glu Asn Pro Ser Ala
    370                 375                 380
```

```
Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
            405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
            435                 440                 445

Lys Ser Lys Lys Ile Pro Leu Gly Gly Ile Pro Ser Pro Ser Thr Gly
        450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
                500                 505                 510

Val Ala Thr Leu Asp Ser His Ala Gly Asn Leu Pro Arg Glu Gly Ala
                515                 520                 525

Val Leu Ile Val Thr Ala Ser Tyr Asn Gly His Pro Pro Asp Asn Ala
        530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
                580                 585                 590

Gly Ala Glu Asn Ile Ala Asp Arg Gly Glu Ala Asp Ala Ser Asp Asp
            595                 600                 605

Phe Glu Gly Thr Tyr Glu Glu Trp Arg Glu His Met Trp Ser Asp Val
            610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
                660                 665                 670

Gln Gln Pro Gly Ser Ala Arg Ser Thr Arg His Leu Glu Ile Glu Leu
            675                 680                 685

Pro Lys Glu Ala Ser Tyr Gln Glu Gly Asp His Leu Gly Val Ile Pro
690                 695                 700

Arg Asn Tyr Glu Gly Thr Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
                740                 745                 750

Val Glu Leu Gln Asp Pro Val Thr Arg Thr Gln Leu Arg Ala Met Ala
            755                 760                 765

Ala Lys Thr Val Cys Pro Pro His Lys Val Glu Leu Glu Ala Leu Leu
        770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
```

```
                805                 810                 815
Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
            835                 840                 845

Val Ser Gly Glu Ala Trp Ser Gly Tyr Gly Glu Tyr Lys Gly Ile Ala
            850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
            915                 920                 925

Glu Ala His Leu Tyr Phe Gly Cys Arg Ser Pro His Glu Asp Tyr Leu
            930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
            995                1000                1005

Val Glu Ala Thr Leu Met Lys Ser Tyr Ala Asp Val His Gln Val
        1010                1015                1020

Ser Glu Ala Asp Ala Arg Leu Trp Leu Gln Gln Leu Glu Glu Lys
        1025                1030                1035

Gly Arg Tyr Ala Lys Asp Val Trp Ala Gly
        1040                1045

<210> SEQ ID NO 41
<211> LENGTH: 1048
<212> TYPE: PRT
<213> ORGANISM: Artificial sequence
<220> FEATURE:
<223> OTHER INFORMATION: Cytochrome P450 variant CYP102A1var3-19

<400> SEQUENCE: 41

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Cys Val
        35                  40                  45

Thr Arg Tyr Ile Ser Ser Gln Arg Leu Ile Lys Glu Ala Cys Asp Glu
    50                  55                  60

Ser Arg Phe Asp Lys Asn Leu Ser Gln Ser Leu Lys Ala Phe Arg Asp
65                  70                  75                  80

Phe Ser Gly Asp Gly Leu Phe Thr Ser Trp Thr His Glu Ile Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125
```

```
Lys Trp Glu Arg Leu Asn Ala Asp Glu His Ile Glu Val Ser Glu Asp
        130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Ala Met Asn Lys Pro Gln Arg Ala Asn
                180                 185                 190

Pro Asp Asp Pro Ala Tyr Asp Glu Asn Lys Arg Gln Cys Gln Glu Asp
                195                 200                 205

Ile Lys Val Met Asn Asp Leu Val Asp Lys Ile Ile Ala Asp Arg Lys
                210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
                260                 265                 270

Leu Ser Phe Ala Leu Tyr Phe Leu Val Lys Asn Pro His Val Leu Gln
                275                 280                 285

Lys Val Ala Glu Glu Ala Ala Arg Val Leu Val Asp Pro Val Pro Ser
290                 295                 300

Tyr Lys Gln Val Lys Gln Leu Lys Tyr Val Gly Met Val Leu Asn Glu
305                 310                 315                 320

Ala Leu Arg Leu Trp Pro Thr Phe Pro Ala Phe Ser Leu Tyr Ala Lys
                325                 330                 335

Glu Asp Thr Val Leu Gly Gly Glu Tyr Pro Leu Glu Lys Gly Asp Glu
                340                 345                 350

Val Met Val Leu Ile Pro Gln Leu His Arg Asp Lys Thr Val Trp Gly
                355                 360                 365

Asp Asp Val Glu Glu Phe Arg Pro Glu Arg Phe Glu Asn Pro Ser Ala
                370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
                420                 425                 430

Ile Lys Glu Thr Leu Thr Leu Lys Pro Glu Gly Phe Val Val Lys Ala
                435                 440                 445

Lys Ser Lys Lys Ile Pro Leu Gly Gly Ile Pro Ser Pro Ser Thr Gly
                450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
                500                 505                 510

Val Ala Thr Leu Asp Ser His Ala Gly Asn Leu Pro Arg Glu Gly Ala
                515                 520                 525

Val Leu Ile Val Thr Ala Ser Tyr Asn Gly His Pro Pro Asp Asn Ala
530                 535                 540

Lys Gln Phe Val Asp Trp Leu Asp Gln Ala Ser Ala Asp Glu Val Lys
```

```
            545                 550                 555                 560
Gly Val Arg Tyr Ser Val Phe Gly Cys Gly Asp Lys Asn Trp Ala Thr
                565                 570                 575
Thr Tyr Gln Lys Val Pro Ala Phe Ile Asp Glu Thr Leu Ala Ala Lys
                580                 585                 590
Gly Ala Glu Asn Ile Ala Asp Arg Gly Glu Ala Asp Ala Ser Asp Asp
                595                 600                 605
Phe Glu Gly Thr Tyr Glu Glu Trp Arg Glu His Met Trp Ser Asp Val
610                 615                 620
Ala Ala Tyr Phe Asn Leu Asp Ile Glu Asn Ser Glu Asp Asn Lys Ser
625                 630                 635                 640
Thr Leu Ser Leu Gln Phe Val Asp Ser Ala Ala Asp Met Pro Leu Ala
                645                 650                 655
Lys Met His Gly Ala Phe Ser Thr Asn Val Val Ala Ser Lys Glu Leu
                660                 665                 670
Gln Gln Pro Gly Ser Ala Arg Ser Thr Arg His Leu Glu Ile Glu Leu
                675                 680                 685
Pro Lys Glu Ala Ser Tyr Gln Glu Gly Asp His Leu Gly Val Ile Pro
                690                 695                 700
Arg Asn Tyr Glu Gly Thr Val Asn Arg Val Thr Ala Arg Phe Gly Leu
705                 710                 715                 720
Asp Ala Ser Gln Gln Ile Arg Leu Glu Ala Glu Glu Lys Leu Ala
                725                 730                 735
His Leu Pro Leu Ala Lys Thr Val Ser Val Glu Glu Leu Leu Gln Tyr
                740                 745                 750
Val Glu Leu Gln Asp Pro Val Thr Arg Thr Gln Leu Arg Ala Met Ala
                755                 760                 765
Ala Lys Thr Val Cys Pro Pro His Lys Val Glu Leu Glu Ala Leu Leu
                770                 775                 780
Glu Lys Gln Ala Tyr Lys Glu Gln Val Leu Ala Lys Arg Leu Thr Met
785                 790                 795                 800
Leu Glu Leu Leu Glu Lys Tyr Pro Ala Cys Glu Met Lys Phe Ser Glu
                805                 810                 815
Phe Ile Ala Leu Leu Pro Ser Ile Arg Pro Arg Tyr Tyr Ser Ile Ser
                820                 825                 830
Ser Ser Pro Arg Val Asp Glu Lys Gln Ala Ser Ile Thr Val Ser Val
                835                 840                 845
Val Ser Gly Glu Ala Trp Ser Gly Tyr Gly Glu Tyr Lys Gly Ile Ala
850                 855                 860
Ser Asn Tyr Leu Ala Glu Leu Gln Glu Gly Asp Thr Ile Thr Cys Phe
865                 870                 875                 880
Ile Ser Thr Pro Gln Ser Glu Phe Thr Leu Pro Lys Asp Pro Glu Thr
                885                 890                 895
Pro Leu Ile Met Val Gly Pro Gly Thr Gly Val Ala Pro Phe Arg Gly
                900                 905                 910
Phe Val Gln Ala Arg Lys Gln Leu Lys Glu Gln Gly Gln Ser Leu Gly
                915                 920                 925
Glu Ala His Leu Tyr Phe Gly Cys Arg Ser Pro His Glu Asp Tyr Leu
                930                 935                 940
Tyr Gln Glu Glu Leu Glu Asn Ala Gln Ser Glu Gly Ile Ile Thr Leu
945                 950                 955                 960
His Thr Ala Phe Ser Arg Met Pro Asn Gln Pro Lys Thr Tyr Val Gln
                965                 970                 975
```

-continued

```
His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
            995                 1000                1005

Val Glu Ala Thr Leu Met Lys Ser Tyr Ala Asp Val His Gln Val
        1010                1015                1020

Ser Glu Ala Asp Ala Arg Leu Trp Leu Gln Gln Leu Glu Glu Lys
        1025                1030                1035

Gly Arg Tyr Ala Lys Asp Val Trp Ala Gly
        1040                1045

<210> SEQ ID NO 42
<211> LENGTH: 1048
<212> TYPE: PRT
<213> ORGANISM: Artificial sequence
<220> FEATURE:
<223> OTHER INFORMATION: Cytochrome P450 variant CYP102A1var3-20

<400> SEQUENCE: 42

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Cys Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Ala Val Arg Asp
65                  70                  75                  80

Phe Val Gly Asp Gly Leu Phe Thr Ser Trp Thr His Glu Ile Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Cys Gln Glu Asp
        195                 200                 205

Ile Lys Val Met Asn Asp Leu Val Asp Lys Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
```

-continued

```
            290                 295                 300
Tyr Lys Gln Val Lys Gln Leu Lys Tyr Val Gly Met Val Leu Asn Glu
305                 310                 315                 320

Ala Leu Arg Leu Trp Pro Thr Val Pro Ala Phe Ser Leu Tyr Ala Lys
                325                 330                 335

Glu Asp Thr Val Leu Gly Gly Glu Tyr Pro Leu Glu Lys Gly Asp Glu
                340                 345                 350

Val Met Val Leu Ile Pro Gln Leu His Arg Asp Lys Thr Ile Trp Gly
                355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
                420                 425                 430

Ile Lys Glu Thr Leu Thr Leu Lys Pro Glu Gly Phe Val Val Lys Ala
                435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
                500                 505                 510

Val Ala Thr Leu Asp Ser His Ala Gly Asn Leu Pro Arg Glu Gly Ala
                515                 520                 525

Val Leu Ile Val Thr Ala Ser Tyr Asn Gly His Pro Pro Asp Asn Ala
                530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
                580                 585                 590

Gly Ala Glu Asn Ile Ala Asp Arg Gly Glu Ala Asp Ala Ser Asp Asp
                595                 600                 605

Phe Glu Gly Thr Tyr Glu Glu Trp Arg Glu His Met Trp Ser Asp Val
610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
                660                 665                 670

Gln Gln Pro Gly Ser Ala Arg Ser Thr Arg His Leu Glu Ile Glu Leu
                675                 680                 685

Pro Lys Glu Ala Ser Tyr Gln Glu Gly Asp His Leu Gly Val Ile Pro
                690                 695                 700

Arg Asn Tyr Glu Gly Ile Val Asn Arg Val Thr Ala Arg Phe Gly Leu
705                 710                 715                 720
```

-continued

Asp Ala Ser Gln Gln Ile Arg Leu Glu Ala Glu Glu Lys Leu Ala
                725                 730                 735

His Leu Pro Leu Ala Lys Thr Val Ser Val Glu Leu Leu Gln Tyr
            740                 745                 750

Val Glu Leu Gln Asp Pro Val Thr Arg Thr Gln Leu Arg Ala Met Ala
        755                 760                 765

Ala Lys Thr Val Cys Pro Pro His Lys Val Glu Leu Glu Ala Leu Leu
    770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
        835                 840                 845

Val Ser Gly Glu Ala Trp Ser Gly Tyr Gly Glu Tyr Lys Gly Ile Ala
    850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
        915                 920                 925

Glu Ala His Leu Tyr Phe Gly Cys Arg Ser Pro His Glu Asp Tyr Leu
    930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
        995                 1000                1005

Val Glu Ala Thr Leu Met Lys Ser Tyr Ala Asp Val His Gln Val
    1010                1015                1020

Ser Glu Ala Asp Ala Arg Leu Trp Leu Gln Gln Leu Glu Glu Lys
    1025                1030                1035

Gly Arg Tyr Ala Lys Asp Val Trp Ala Gly
    1040                1045

<210> SEQ ID NO 43
<211> LENGTH: 1048
<212> TYPE: PRT
<213> ORGANISM: Artificial sequence
<220> FEATURE:
<223> OTHER INFORMATION: Cytochrome P450 variant CYP102A1var3-21

<400> SEQUENCE: 43

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Cys Val

```
                  35                  40                  45
Thr Arg Tyr Leu Ser Ser Gln Arg Leu Ile Lys Glu Ala Cys Asp Glu
 50                  55                  60

Ser Arg Phe Asp Lys Asn Leu Ser Gln Ala Leu Lys Ala Val Arg Asp
 65                  70                  75                  80

Phe Ala Gly Asp Gly Leu Val Thr Ser Trp Thr His Glu Ile Asn Trp
                 85                  90                  95

Lys Lys Ala His Asn Ile Leu Leu Pro Ser Phe Ser Gln Gln Ala Met
                100                 105                 110

Lys Gly Tyr His Ala Met Met Val Asp Ile Ala Val Gln Leu Val Gln
                115                 120                 125

Lys Trp Glu Arg Leu Asn Ala Asp Glu His Ile Glu Val Ser Glu Asp
                130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
                180                 185                 190

Pro Asp Asp Pro Ala Tyr Asp Glu Asn Lys Arg Gln Cys Gln Glu Asp
                195                 200                 205

Ile Lys Val Met Asn Asp Leu Val Asp Lys Ile Ile Ala Asp Arg Lys
                210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ala Ala Gly His Glu Thr Thr Ser Gly Leu
                260                 265                 270

Leu Ser Phe Ala Leu Tyr Phe Leu Val Lys Asn Pro His Val Leu Gln
                275                 280                 285

Lys Val Ala Glu Glu Ala Ala Arg Val Leu Val Asp Pro Val Pro Ser
                290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
                340                 345                 350

Val Met Val Leu Ile Pro Gln Leu His Arg Asp Lys Thr Ile Trp Gly
                355                 360                 365

Asp Asp Val Glu Glu Phe Arg Pro Glu Arg Phe Glu Asn Pro Ser Ala
                370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
                420                 425                 430

Ile Lys Glu Thr Leu Thr Leu Lys Pro Glu Gly Phe Val Val Lys Ala
                435                 440                 445

Lys Ser Lys Lys Ile Pro Leu Gly Gly Ile Pro Ser Pro Ser Thr Glu
450                 455                 460
```

```
Gln Ser Ala Lys Lys Val Arg Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
            515                 520                 525

Val Leu Ile Val Thr Ala Ser Tyr Asn Gly His Pro Pro Asp Asn Ala
530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
            595                 600                 605

Phe Glu Gly Thr Tyr Glu Glu Trp Arg Glu His Met Trp Ser Asp Val
610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
            675                 680                 685

Pro Lys Glu Ala Ser Tyr Gln Glu Gly Asp His Leu Gly Val Ile Pro
690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
            740                 745                 750

Val Glu Leu Gln Asp Pro Val Thr Arg Thr Gln Leu Arg Ala Met Ala
            755                 760                 765

Ala Lys Thr Val Cys Pro Pro His Lys Val Glu Leu Glu Ala Leu Leu
770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
            835                 840                 845

Val Ser Gly Glu Ala Trp Ser Gly Tyr Gly Tyr Lys Gly Ile Ala
850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895
```

```
Pro Leu Ile Met Val Gly Pro Gly Thr Gly Val Ala Pro Phe Arg Gly
                900                 905                 910

Phe Val Gln Ala Arg Lys Gln Leu Lys Glu Gln Gly Gln Ser Leu Gly
                915                 920                 925

Glu Ala His Leu Tyr Phe Gly Cys Arg Ser Pro His Glu Asp Tyr Leu
                930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
                980                 985                 990

Gly Ala His Phe Tyr Ile Cys Gly Asp Gly Ser Gln Met Ala Pro Ala
                995                 1000                1005

Val Glu Ala Thr Leu Met Lys Ser Tyr Ala Asp Val His Gln Val
    1010                1015                1020

Ser Glu Ala Asp Ala Arg Leu Trp Leu Gln Gln Leu Glu Glu Lys
    1025                1030                1035

Gly Arg Tyr Ala Lys Asp Val Trp Ala Gly
    1040                1045

<210> SEQ ID NO 44
<211> LENGTH: 1048
<212> TYPE: PRT
<213> ORGANISM: Artificial sequence
<220> FEATURE:
<223> OTHER INFORMATION: Cytochrome P450 variant CYP102A1var3-22

<400> SEQUENCE: 44

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
                20                  25                  30

Ala Asp Glu Leu Gly Glu Ile Phe Lys Phe Glu Ala Pro Gly Cys Val
            35                  40                  45

Thr Arg Tyr Leu Ser Ser Gln Arg Leu Ile Lys Glu Ala Cys Asp Glu
        50                  55                  60

Ser Arg Phe Asp Lys Asn Leu Ser Gln Ala Leu Lys Ala Val Arg Asp
65                  70                  75                  80

Phe Phe Gly Asp Gly Leu Phe Thr Ser Trp Thr His Glu Ile Asn Trp
                85                  90                  95

Lys Lys Ala His Asn Ile Leu Leu Pro Ser Phe Ser Gln Gln Ala Met
                100                 105                 110

Lys Gly Tyr His Ala Met Met Val Asp Ile Ala Val Gln Leu Val Gln
            115                 120                 125

Lys Trp Glu Arg Leu Asn Ala Asp Glu His Ile Glu Val Ser Glu Asp
        130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Cys Gln Glu Asp
        195                 200                 205
```

-continued

```
Ile Lys Val Met Asn Asp Leu Val Asp Lys Ile Ile Ala Asp Arg Lys
210                 215                 220
Ala Arg Gly Glu Gln Ser Asp Asp Leu Leu Thr Gln Met Leu Asn Gly
225                 230                 235                 240
Lys Asp Pro Glu Thr Gly Glu Pro Leu Asp Asp Gly Asn Ile Ser Tyr
                245                 250                 255
Gln Ile Ile Thr Phe Leu Ala Ala Gly His Glu Thr Thr Ser Gly Leu
            260                 265                 270
Leu Ser Phe Ala Leu Tyr Phe Leu Val Lys Asn Pro His Val Leu Gln
        275                 280                 285
Lys Val Ala Glu Glu Ala Ala Arg Val Leu Val Asp Pro Val Pro Ser
290                 295                 300
Tyr Lys Gln Val Lys Gln Leu Lys Tyr Val Gly Met Val Leu Asn Glu
305                 310                 315                 320
Ala Leu Arg Leu Trp Pro Thr Val Pro Ala Phe Ser Leu Tyr Ala Lys
                325                 330                 335
Glu Asp Thr Val Leu Gly Gly Glu Tyr Pro Leu Glu Lys Gly Asp Glu
            340                 345                 350
Val Met Val Leu Ile Pro Gln Leu His Arg Asp Lys Thr Ile Trp Gly
        355                 360                 365
Asp Asp Val Glu Glu Phe Arg Pro Glu Arg Phe Glu Asn Pro Ser Ala
370                 375                 380
Ile Pro Gln His Ala Phe Lys Pro Phe Gly Asn Gly Gln Arg Ala Cys
385                 390                 395                 400
Ile Gly Gln Gln Phe Ala Leu His Glu Ala Thr Leu Val Leu Gly Met
                405                 410                 415
Met Leu Lys His Phe Asp Phe Glu Asp His Thr Asn Tyr Glu Leu Asp
            420                 425                 430
Ile Lys Glu Thr Leu Thr Leu Lys Pro Glu Gly Phe Val Val Lys Ala
        435                 440                 445
Lys Ser Lys Lys Ile Pro Leu Gly Gly Ile Pro Ser Pro Ser Thr Glu
450                 455                 460
Gln Ser Ala Lys Lys Val Arg Lys Lys Ala Glu Asn Ala His Asn Thr
465                 470                 475                 480
Pro Leu Leu Val Leu Tyr Gly Ser Asn Met Gly Thr Ala Glu Gly Thr
                485                 490                 495
Ala Arg Asp Leu Ala Asp Ile Ala Met Ser Lys Gly Phe Ala Pro Gln
            500                 505                 510
Val Ala Thr Leu Asp Ser His Ala Gly Asn Leu Pro Arg Glu Gly Ala
        515                 520                 525
Val Leu Ile Val Thr Ala Ser Tyr Asn Gly His Pro Pro Asp Asn Ala
530                 535                 540
Lys Gln Phe Val Asp Trp Leu Asp Gln Ala Ser Ala Asp Glu Val Lys
545                 550                 555                 560
Gly Val Arg Tyr Ser Val Phe Gly Cys Gly Asp Lys Asn Trp Ala Thr
                565                 570                 575
Thr Tyr Gln Lys Val Pro Ala Phe Ile Asp Glu Thr Leu Ala Ala Lys
            580                 585                 590
Gly Ala Glu Asn Ile Ala Asp Arg Gly Glu Ala Asp Ala Ser Asp Asp
        595                 600                 605
Phe Glu Gly Thr Tyr Glu Glu Trp Arg Glu His Met Trp Ser Asp Val
610                 615                 620
Ala Ala Tyr Phe Asn Leu Asp Ile Glu Asn Ser Glu Asp Asn Lys Ser
625                 630                 635                 640
```

```
Thr Leu Ser Leu Gln Phe Val Asp Ser Ala Asp Met Pro Leu Ala
                645                 650                 655

Lys Met His Gly Ala Phe Ser Thr Asn Val Val Ala Ser Lys Glu Leu
                660                 665                 670

Gln Gln Pro Gly Ser Ala Arg Ser Thr Arg His Leu Glu Ile Glu Leu
                675                 680                 685

Pro Lys Glu Ala Ser Tyr Gln Glu Gly Asp His Leu Gly Val Ile Pro
                690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Leu Leu Gln Tyr
                740                 745                 750

Val Glu Leu Gln Asp Pro Val Thr Arg Thr Gln Leu Arg Ala Met Ala
                755                 760                 765

Ala Lys Thr Val Cys Pro Pro His Lys Val Glu Leu Glu Ala Leu Leu
                770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
                820                 825                 830

Ser Ser Pro Arg Val Asp Glu Lys Gln Ala Ser Ile Thr Val Ser Val
                835                 840                 845

Val Ser Gly Glu Ala Trp Ser Gly Tyr Gly Glu Tyr Lys Gly Ile Ala
                850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
                900                 905                 910

Phe Val Gln Ala Arg Lys Gln Leu Lys Glu Gln Gly Gln Ser Leu Gly
                915                 920                 925

Glu Ala His Leu Tyr Phe Gly Cys Arg Ser Pro His Glu Asp Tyr Leu
                930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
                980                 985                 990

Gly Ala His Phe Tyr Ile Cys Gly Asp Gly Ser Gln Met Ala Pro Ala
                995                 1000                1005

Val Glu Ala Thr Leu Met Lys Ser Tyr Ala Asp Val His Gln Val
                1010                1015                1020

Ser Glu Ala Asp Ala Arg Leu Trp Leu Gln Gln Leu Glu Glu Lys
                1025                1030                1035

Gly Arg Tyr Ala Lys Asp Val Trp Ala Gly
                1040                1045
```

```
<210> SEQ ID NO 45
<211> LENGTH: 1048
<212> TYPE: PRT
<213> ORGANISM: Artificial sequence
<220> FEATURE:
<223> OTHER INFORMATION: Cytochrome P450 variant CYP102A1var3-23

<400> SEQUENCE: 45

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Cys Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Ala Val Arg Asp
65                  70                  75                  80

Phe Ala Gly Asp Gly Leu Phe Thr Ser Trp Thr His Glu Ile Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Cys Gln Glu Asp
        195                 200                 205

Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Val Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
    370                 375                 380
```

```
Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
            405                 410                 415

Met Leu Lys His Phe Asp Phe Glu Asp His Thr Asn Tyr Glu Leu Asp
        420                 425                 430

Ile Lys Glu Thr Leu Thr Leu Lys Pro Glu Gly Phe Val Val Lys Ala
            435                 440                 445

Lys Ser Lys Lys Ile Pro Leu Gly Gly Ile Pro Ser Pro Ser Thr Glu
    450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
                500                 505                 510

Val Ala Thr Leu Asp Ser His Ala Gly Asn Leu Pro Arg Glu Gly Ala
                515                 520                 525

Val Leu Ile Val Thr Ala Ser Tyr Asn Gly His Pro Pro Asp Asn Ala
    530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
            595                 600                 605

Phe Glu Gly Thr Tyr Glu Glu Trp Arg Glu His Met Trp Ser Asp Val
            610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
                660                 665                 670

Gln Gln Pro Gly Ser Ala Arg Ser Thr Arg His Leu Glu Ile Glu Leu
        675                 680                 685

Pro Lys Glu Ala Ser Tyr Gln Glu Gly Asp His Leu Gly Val Ile Pro
    690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
            740                 745                 750

Val Glu Leu Gln Asp Pro Val Thr Arg Thr Gln Leu Arg Ala Met Ala
        755                 760                 765

Ala Lys Thr Val Cys Pro Pro His Lys Val Glu Leu Glu Ala Leu Leu
        770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
```

```
                    805                 810                 815
Phe Ile Ala Leu Leu Pro Ser Ile Arg Pro Arg Tyr Tyr Ser Ile Ser
                820                 825                 830

Ser Ser Pro Arg Val Asp Glu Lys Gln Ala Ser Ile Thr Val Ser Val
                835                 840                 845

Val Ser Gly Glu Ala Trp Ser Gly Tyr Gly Glu Tyr Lys Gly Ile Ala
            850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
                900                 905                 910

Phe Val Gln Ala Arg Lys Gln Leu Lys Glu Gln Gly Gln Ser Leu Gly
                915                 920                 925

Glu Ala His Leu Tyr Phe Gly Cys Arg Ser Pro His Glu Asp Tyr Leu
            930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
                980                 985                 990

Gly Ala His Phe Tyr Ile Cys Gly Asp Gly Ser Gln Met Ala Pro Ala
                995                1000                1005

Val Glu Ala Thr Leu Met Lys Ser Tyr Ala Asp Val His Gln Val
        1010                1015                1020

Ser Glu Ala Asp Ala Arg Leu Trp Leu Gln Gln Leu Glu Glu Lys
        1025                1030                1035

Gly Arg Tyr Ala Lys Asp Val Trp Ala Gly
        1040                1045

<210> SEQ ID NO 46
<211> LENGTH: 1048
<212> TYPE: PRT
<213> ORGANISM: Artificial sequence
<220> FEATURE:
<223> OTHER INFORMATION: Cytochrome P450 variant CYP102A1var4

<400> SEQUENCE: 46

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
                20                  25                  30

Ala Asp Glu Leu Gly Glu Ile Phe Lys Phe Glu Ala Pro Gly Arg Val
            35                  40                  45

Thr Arg Tyr Leu Ser Ser Gln Arg Leu Ile Lys Glu Ala Cys Asp Glu
        50                  55                  60

Ser Arg Phe Asp Lys Asn Leu Ser Gln Ala Leu Lys Phe Val Arg Asp
65                  70                  75                  80

Phe Ala Gly Asp Gly Leu Ala Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125
```

```
Lys Trp Glu Arg Leu Asn Ala Asp Glu His Ile Glu Val Pro Glu Asp
130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                165                 170                 175

Met Val Arg Ala Leu Asp Glu Ala Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ile Ala Asp Arg Lys
210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Ala Glu Glu Ala Ala Arg Val Leu Val Asp Pro Val Pro Ser
290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Leu Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
530                 535                 540

Lys Gln Phe Val Asp Trp Leu Asp Gln Ala Ser Ala Asp Glu Val Lys
```

```
                545                 550                 555                 560
            Gly Val Arg Tyr Ser Val Phe Gly Cys Gly Asp Lys Asn Trp Ala Thr
                            565                 570                 575

Thr Tyr Gln Lys Val Pro Ala Phe Ile Asp Glu Thr Leu Ala Ala Lys
                        580                 585                 590

Gly Ala Glu Asn Ile Ala Asp Arg Gly Glu Ala Asp Ala Ser Asp Asp
                        595                 600                 605

Phe Glu Gly Thr Tyr Glu Glu Trp Arg Glu His Met Trp Ser Asp Val
                    610                 615                 620

Ala Ala Tyr Phe Asn Leu Asp Ile Glu Asn Ser Glu Asp Asn Lys Ser
            625                 630                 635                 640

Thr Leu Ser Leu Gln Phe Val Asp Ser Ala Ala Asp Met Pro Leu Ala
                            645                 650                 655

Lys Met His Gly Ala Phe Ser Thr Asn Val Val Ala Ser Lys Glu Leu
                        660                 665                 670

Gln Gln Pro Gly Ser Ala Arg Ser Thr Arg His Leu Glu Ile Glu Leu
                        675                 680                 685

Pro Lys Glu Ala Ser Tyr Gln Glu Gly Asp His Leu Gly Val Ile Pro
                    690                 695                 700

Arg Asn Tyr Glu Gly Ile Val Asn Arg Val Thr Ala Arg Phe Gly Leu
            705                 710                 715                 720

Asp Ala Ser Gln Gln Ile Arg Leu Glu Ala Glu Glu Lys Leu Ala
                            725                 730                 735

His Leu Pro Leu Ala Lys Thr Val Ser Val Glu Glu Leu Leu Gln Tyr
                            740                 745                 750

Val Glu Leu Gln Asp Pro Val Thr Arg Thr Gln Leu Arg Ala Met Ala
                        755                 760                 765

Ala Lys Thr Val Cys Pro Pro His Lys Val Glu Leu Glu Ala Leu Leu
                        770                 775                 780

Glu Lys Gln Ala Tyr Lys Glu Gln Val Leu Ala Lys Arg Leu Thr Met
            785                 790                 795                 800

Leu Glu Leu Leu Glu Lys Tyr Pro Ala Cys Glu Met Lys Phe Ser Glu
                            805                 810                 815

Phe Ile Ala Leu Leu Pro Ser Ile Arg Pro Arg Tyr Tyr Ser Ile Ser
                        820                 825                 830

Ser Ser Pro Arg Val Asp Glu Lys Gln Ala Ser Ile Thr Val Ser Val
                        835                 840                 845

Val Ser Gly Glu Ala Trp Ser Gly Tyr Gly Tyr Lys Gly Ile Ala
            850                 855                 860

Ser Asn Tyr Leu Ala Glu Leu Gln Glu Gly Asp Thr Ile Thr Cys Phe
            865                 870                 875                 880

Ile Ser Thr Pro Gln Ser Glu Phe Thr Leu Pro Lys Asp Pro Glu Thr
                            885                 890                 895

Pro Leu Ile Met Val Gly Pro Gly Thr Gly Val Ala Pro Phe Arg Gly
                        900                 905                 910

Phe Val Gln Ala Arg Lys Gln Leu Lys Glu Gln Gly Gln Ser Leu Gly
                        915                 920                 925

Glu Ala His Leu Tyr Phe Gly Cys Arg Ser Pro His Glu Asp Tyr Leu
                    930                 935                 940

Tyr Gln Glu Glu Leu Glu Asn Ala Gln Ser Glu Gly Ile Ile Thr Leu
            945                 950                 955                 960

His Thr Ala Phe Ser Arg Met Pro Asn Gln Pro Lys Thr Tyr Val Gln
                            965                 970                 975
```

-continued

His Val Met Glu Gln Asp Gly Lys Lys Leu Ile Glu Leu Leu Asp Gln
                980                 985                 990

Gly Ala His Phe Tyr Ile Cys Gly Asp Gly Ser Gln Met Ala Pro Ala
            995                 1000                1005

Val Glu Ala Thr Leu Met Lys Ser Tyr Ala Asp Val His Gln Val
        1010                1015                1020

Ser Glu Ala Asp Ala Arg Leu Trp Leu Gln Gln Leu Glu Glu Lys
        1025                1030                1035

Gly Arg Tyr Ala Lys Asp Val Trp Ala Gly
        1040                1045

<210> SEQ ID NO 47
<211> LENGTH: 1048
<212> TYPE: PRT
<213> ORGANISM: Artificial sequence
<220> FEATURE:
<223> OTHER INFORMATION: Cytochrome P450 variant CYP102A1var5

<400> SEQUENCE: 47

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Val Arg Asp
65              70                  75                  80

Phe Ala Gly Asp Gly Leu Val Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Pro Glu Asp
    130                 135                 140

Met Thr Arg Leu Thr Leu Asp Thr Ile Gly Leu Cys Gly Phe Asn Tyr
145             150                 155                 160

Arg Phe Asn Ser Phe Tyr Arg Asp Gln Pro His Pro Phe Ile Thr Ser
                165                 170                 175

Met Val Arg Ala Leu Asp Glu Ala Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ala Asp Arg Lys
    210                 215                 220

Ala Ser Gly Glu Gln Ser Asp Asp Leu Leu Thr His Met Leu Asn Gly
225             230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Ala Ala Glu Glu Ala Ala Arg Val Leu Val Asp Pro Val Pro Ser

```
              290                 295                 300
Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Lys Gly Asp Glu
            340                 345                 350

Leu Met Val Leu Ile Pro Gln Leu His Arg Asp Lys Thr Ile Trp Gly
                355                 360                 365

Asp Asp Val Glu Glu Phe Arg Pro Glu Arg Phe Glu Asn Pro Ser Ala
        370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
        530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
    610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
        675                 680                 685

Pro Lys Glu Ala Ser Tyr Gln Glu Gly Asp His Leu Gly Val Ile Pro
        690                 695                 700

Arg Asn Tyr Glu Gly Ile Val Asn Arg Val Thr Ala Arg Phe Gly Leu
705                 710                 715                 720
```

```
Asp Ala Ser Gln Gln Ile Arg Leu Glu Ala Glu Glu Lys Leu Ala
                725                 730                 735

His Leu Pro Leu Ala Lys Thr Val Ser Val Glu Leu Leu Gln Tyr
            740                 745                 750

Val Glu Leu Gln Asp Pro Val Thr Arg Thr Gln Leu Arg Ala Met Ala
        755                 760                 765

Ala Lys Thr Val Cys Pro Pro His Lys Val Glu Leu Glu Ala Leu Leu
770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
            805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
            835                 840                 845

Val Ser Gly Glu Ala Trp Ser Gly Tyr Gly Glu Tyr Lys Gly Ile Ala
        850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
            885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
            915                 920                 925

Glu Ala His Leu Tyr Phe Gly Cys Arg Ser Pro His Glu Asp Tyr Leu
930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
        995                 1000                1005

Val Glu Ala Thr Leu Met Lys Ser Tyr Ala Asp Val His Gln Val
    1010                1015                1020

Ser Glu Ala Asp Ala Arg Leu Trp Leu Gln Gln Leu Glu Glu Lys
    1025                1030                1035

Gly Arg Tyr Ala Lys Asp Val Trp Ala Gly
    1040                1045

<210> SEQ ID NO 48
<211> LENGTH: 1048
<212> TYPE: PRT
<213> ORGANISM: Artificial sequence
<220> FEATURE:
<223> OTHER INFORMATION: Cytochrome P450 variant CYP102A1var6

<400> SEQUENCE: 48

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
```

```
                35                  40                  45
Thr Arg Tyr Leu Ser Ser Gln Arg Leu Ile Lys Glu Ala Cys Asp Glu
 50                  55                  60

Ser Arg Phe Asp Lys Asn Leu Ser Gln Ala Leu Lys Phe Val Arg Asp
 65                  70                  75                  80

Phe Ala Gly Asp Gly Leu Val Thr Ser Trp Thr His Glu Lys Asn Trp
                 85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
            115                 120                 125

Lys Trp Glu Arg Leu Asn Ala Asp Glu His Ile Glu Val Pro Glu Asp
130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                165                 170                 175

Met Val Arg Ala Leu Asp Glu Ala Met Asn Lys Gln Gln Arg Ala Asn
            180                 185                 190

Pro Asp Asp Pro Ala Tyr Asp Glu Asn Lys Arg Gln Phe Gln Glu Asp
            195                 200                 205

Ile Lys Val Met Asn Asp Leu Val Asp Lys Ile Ile Ala Asp Arg Lys
            210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
            275                 280                 285

Lys Ala Ala Glu Glu Ala Ala Arg Val Leu Val Asp Pro Val Pro Ser
290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Leu Met Val Leu Ile Pro Gln Leu His Arg Asp Lys Thr Ile Trp Gly
            355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
            435                 440                 445

Lys Ser Lys Lys Ile Pro Leu Gly Gly Ile Pro Ser Pro Ser Thr Glu
450                 455                 460
```

```
Gln Ser Ala Lys Lys Val Arg Lys Ala Glu Asn Ala His Asn Thr
465                 470                 475                 480

Pro Leu Leu Val Leu Tyr Gly Ser Asn Met Gly Thr Ala Glu Gly Thr
            485                 490                 495

Ala Arg Asp Leu Ala Asp Ile Ala Met Ser Lys Gly Phe Ala Pro Gln
                500                 505                 510

Val Ala Thr Leu Asp Ser His Ala Gly Asn Leu Pro Arg Glu Gly Ala
            515                 520                 525

Val Leu Ile Val Thr Ala Ser Tyr Asn Gly His Pro Pro Asp Asn Ala
530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
            595                 600                 605

Phe Glu Gly Thr Tyr Glu Glu Trp Arg Glu His Met Trp Ser Asp Val
    610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
            675                 680                 685

Pro Lys Glu Ala Ser Tyr Gln Glu Gly Asp His Leu Gly Val Ile Pro
    690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
            740                 745                 750

Val Glu Leu Gln Asp Pro Val Thr Arg Thr Gln Leu Arg Ala Met Ala
    755                 760                 765

Ala Lys Thr Val Cys Pro Pro His Lys Val Glu Leu Glu Ala Leu Leu
770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
            835                 840                 845

Val Ser Gly Glu Ala Trp Ser Gly Tyr Gly Tyr Lys Gly Ile Ala
850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895
```

```
Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
            915                 920                 925

Glu Ala His Leu Tyr Phe Gly Cys Arg Ser Pro His Glu Asp Tyr Leu
            930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
            965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
            995                 1000                1005

Val Glu Ala Thr Leu Met Lys Ser Tyr Ala Asp Val His Gln Val
        1010                1015                1020

Ser Glu Ala Asp Ala Arg Leu Trp Leu Gln Gln Leu Glu Glu Lys
        1025                1030                1035

Gly Arg Tyr Ala Lys Asp Val Trp Ala Gly
        1040                1045

<210> SEQ ID NO 49
<211> LENGTH: 1048
<212> TYPE: PRT
<213> ORGANISM: Artificial sequence
<220> FEATURE:
<223> OTHER INFORMATION: Cytochrome P450 variant CYP102A1var7

<400> SEQUENCE: 49

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Gly Leu Lys Phe Val Arg Asp
65                  70                  75                  80

Phe Ala Gly Asp Gly Leu Val Thr Ser Trp Thr His Glu Lys Asn Trp
            85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Pro Glu Asp
        130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
            165                 170                 175

Met Val Arg Ala Leu Asp Glu Ala Met Asn Lys Gln Gln Arg Ala Asn
            180                 185                 190

Pro Asp Asp Pro Ala Tyr Asp Glu Asn Lys Arg Gln Phe Gln Glu Asp
        195                 200                 205
```

-continued

```
Ile Lys Val Met Asn Asp Leu Val Asp Lys Ile Ile Ala Asp Arg Lys
210                 215                 220
Ala Ser Gly Glu Gln Ser Asp Leu Leu Thr His Met Leu Asn Gly
225                 230                 235                 240
Lys Asp Pro Glu Thr Gly Glu Pro Leu Asp Asp Glu Asn Ile Arg Tyr
                245                 250                 255
Gln Ile Ile Thr Phe Leu Ile Ala Gly His Glu Thr Thr Ser Gly Leu
                260                 265                 270
Leu Ser Phe Ala Leu Tyr Phe Leu Val Lys Asn Pro His Val Leu Gln
            275                 280                 285
Lys Ala Ala Glu Glu Ala Ala Arg Val Leu Val Asp Pro Val Pro Ser
290                 295                 300
Tyr Lys Gln Val Lys Gln Leu Lys Tyr Val Gly Met Val Leu Asn Glu
305                 310                 315                 320
Ala Leu Arg Leu Trp Pro Thr Ala Pro Ala Phe Ser Leu Tyr Ala Lys
                325                 330                 335
Glu Asp Thr Val Leu Gly Gly Glu Tyr Pro Leu Glu Lys Gly Asp Glu
                340                 345                 350
Leu Met Val Leu Ile Pro Gln Leu His Arg Asp Lys Thr Ile Trp Gly
            355                 360                 365
Asp Asp Val Glu Glu Phe Arg Pro Glu Arg Phe Glu Asn Pro Ser Ala
370                 375                 380
Ile Pro Gln His Ala Phe Lys Pro Phe Gly Asn Gly Gln Arg Ala Cys
385                 390                 395                 400
Ile Gly Gln Gln Phe Ala Leu His Glu Ala Thr Leu Val Leu Gly Met
                405                 410                 415
Met Leu Lys His Phe Asp Phe Glu Asp His Thr Asn Tyr Glu Leu Asp
                420                 425                 430
Ile Lys Glu Thr Leu Thr Leu Lys Pro Glu Gly Phe Val Val Lys Ala
            435                 440                 445
Lys Ser Lys Lys Ile Pro Leu Gly Gly Ile Pro Ser Pro Ser Thr Glu
450                 455                 460
Gln Ser Ala Lys Lys Val Arg Lys Lys Ala Glu Asn Ala His Asn Thr
465                 470                 475                 480
Pro Leu Leu Val Leu Tyr Gly Ser Asn Met Gly Thr Ala Glu Gly Thr
                485                 490                 495
Ala Arg Asp Leu Ala Asp Ile Ala Met Ser Lys Gly Phe Ala Pro Gln
                500                 505                 510
Val Ala Thr Leu Asp Ser His Ala Gly Asn Leu Pro Arg Glu Gly Ala
            515                 520                 525
Val Leu Ile Val Thr Ala Ser Tyr Asn Gly His Pro Pro Asp Asn Ala
530                 535                 540
Lys Gln Phe Val Asp Trp Leu Asp Gln Ala Ser Ala Asp Glu Val Lys
545                 550                 555                 560
Gly Val Arg Tyr Ser Val Phe Gly Cys Gly Asp Lys Asn Trp Ala Thr
                565                 570                 575
Thr Tyr Gln Lys Val Pro Ala Phe Ile Asp Glu Thr Leu Ala Ala Lys
                580                 585                 590
Gly Ala Glu Asn Ile Ala Asp Arg Gly Glu Ala Asp Ala Ser Asp Asp
            595                 600                 605
Phe Glu Gly Thr Tyr Glu Glu Trp Arg Glu His Met Trp Ser Asp Val
610                 615                 620
Ala Ala Tyr Phe Asn Leu Asp Ile Glu Asn Ser Glu Asp Asn Lys Ser
625                 630                 635                 640
```

```
Thr Leu Ser Leu Gln Phe Val Asp Ser Ala Asp Met Pro Leu Ala
            645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
            675                 680                 685

Pro Lys Glu Ala Ser Tyr Gln Glu Gly Asp His Leu Gly Val Ile Pro
            690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
            725                 730                 735

His Leu Pro Leu Ala Lys Thr Val Ser Val Glu Leu Leu Gln Tyr
            740                 745                 750

Val Glu Leu Gln Asp Pro Val Thr Arg Thr Gln Leu Arg Ala Met Ala
            755                 760                 765

Ala Lys Thr Val Cys Pro Pro His Lys Val Glu Leu Glu Ala Leu Leu
            770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                    805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
            835                 840                 845

Val Ser Gly Glu Ala Trp Ser Gly Tyr Gly Glu Tyr Lys Gly Ile Ala
            850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
            885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
            915                 920                 925

Glu Ala His Leu Tyr Phe Gly Cys Arg Ser Pro His Glu Asp Tyr Leu
930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
            965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
            995                 1000                1005

Val Glu Ala Thr Leu Met Lys Ser Tyr Ala Asp Val His Gln Val
            1010                1015                1020

Ser Glu Ala Asp Ala Arg Leu Trp Leu Gln Gln Leu Glu Glu Lys
            1025                1030                1035

Gly Arg Tyr Ala Lys Asp Val Trp Ala Gly
            1040                1045
```

```
<210> SEQ ID NO 50
<211> LENGTH: 1048
<212> TYPE: PRT
<213> ORGANISM: Artificial sequence
<220> FEATURE:
<223> OTHER INFORMATION: Cytochrome P450 variant CYP102A1var8

<400> SEQUENCE: 50
```

| | | | | | | | | | | | | | | | |
|---|---|---|---|---|---|---|---|---|---|---|---|---|---|---|---|
| Thr | Ile | Lys | Glu | Met | Pro | Gln | Pro | Lys | Thr | Phe | Gly | Glu | Leu | Lys | Asn |
| 1 | | | | 5 | | | | | 10 | | | | | 15 | |
| Leu | Pro | Leu | Leu | Asn | Thr | Asp | Lys | Pro | Val | Gln | Ala | Leu | Met | Lys | Ile |
| | | | 20 | | | | | 25 | | | | | 30 | | |
| Ala | Asp | Glu | Leu | Gly | Glu | Ile | Phe | Lys | Phe | Glu | Ala | Pro | Gly | Leu | Val |
| | | | 35 | | | | | 40 | | | | | 45 | | |
| Thr | Arg | Tyr | Leu | Ser | Ser | Gln | Arg | Leu | Ile | Lys | Glu | Ala | Cys | Asp | Glu |
| | | 50 | | | | | 55 | | | | | 60 | | | |
| Ser | Arg | Phe | Asp | Lys | Asn | Leu | Ser | Gln | Ala | Leu | Lys | Phe | Val | Arg | Asp |
| 65 | | | | | 70 | | | | | 75 | | | | | 80 |
| Phe | Ala | Gly | Asp | Gly | Leu | Val | Thr | Ser | Trp | Thr | His | Glu | Lys | Asn | Trp |
| | | | | 85 | | | | | 90 | | | | | 95 | |
| Lys | Lys | Ala | His | Asn | Ile | Leu | Leu | Pro | Ser | Phe | Ser | Gln | Gln | Ala | Met |
| | | | 100 | | | | | 105 | | | | | 110 | | |
| Lys | Gly | Tyr | His | Ala | Met | Met | Val | Asp | Ile | Ala | Val | Gln | Leu | Val | Gln |
| | | | 115 | | | | | 120 | | | | | 125 | | |
| Lys | Trp | Glu | Arg | Leu | Asn | Ala | Asp | Glu | His | Ile | Glu | Val | Pro | Glu | Asp |
| | | 130 | | | | | 135 | | | | | 140 | | | |
| Met | Thr | Arg | Leu | Thr | Leu | Asp | Thr | Ile | Gly | Leu | Cys | Gly | Phe | Asn | Tyr |
| 145 | | | | | 150 | | | | | 155 | | | | | 160 |
| Arg | Phe | Asn | Ser | Phe | Tyr | Arg | Asp | Gln | Pro | His | Pro | Phe | Ile | Thr | Ser |
| | | | | 165 | | | | | 170 | | | | | 175 | |
| Met | Val | Arg | Ala | Leu | Asp | Glu | Ala | Met | Asn | Lys | Gln | Gln | Arg | Ala | Asn |
| | | | 180 | | | | | 185 | | | | | 190 | | |
| Pro | Asp | Asp | Pro | Ala | Tyr | Asp | Glu | Asn | Lys | Arg | Gln | Phe | Gln | Glu | Asp |
| | | 195 | | | | | 200 | | | | | 205 | | | |
| Ile | Lys | Val | Met | Asn | Asp | Leu | Val | Asp | Lys | Ile | Ile | Ala | Asp | Arg | Lys |
| | 210 | | | | | 215 | | | | | 220 | | | | |
| Ala | Ser | Gly | Glu | Gln | Ser | Asp | Asp | Leu | Leu | Thr | His | Met | Leu | Asn | Gly |
| 225 | | | | | 230 | | | | | 235 | | | | | 240 |
| Lys | Asp | Pro | Glu | Thr | Gly | Glu | Pro | Leu | Asp | Asp | Glu | Asn | Ile | Arg | Tyr |
| | | | | 245 | | | | | 250 | | | | | 255 | |
| Gln | Ile | Ile | Thr | Phe | Leu | Ile | Ala | Gly | His | Glu | Thr | Thr | Ser | Gly | Leu |
| | | | 260 | | | | | 265 | | | | | 270 | | |
| Leu | Ser | Phe | Ala | Leu | Tyr | Phe | Leu | Val | Lys | Asn | Pro | His | Val | Leu | Gln |
| | | 275 | | | | | 280 | | | | | 285 | | | |
| Lys | Ala | Ala | Glu | Glu | Ala | Ala | Arg | Val | Leu | Val | Asp | Pro | Val | Pro | Ser |
| | 290 | | | | | 295 | | | | | 300 | | | | |
| Tyr | Lys | Gln | Val | Lys | Gln | Leu | Lys | Tyr | Val | Gly | Met | Val | Leu | Asn | Glu |
| 305 | | | | | 310 | | | | | 315 | | | | | 320 |
| Ala | Leu | Arg | Leu | Trp | Pro | Thr | Ala | Pro | Ala | Phe | Ser | Leu | Tyr | Ala | Lys |
| | | | | 325 | | | | | 330 | | | | | 335 | |
| Glu | Asp | Thr | Val | Leu | Gly | Gly | Glu | Tyr | Pro | Leu | Glu | Lys | Gly | Asp | Glu |
| | | | 340 | | | | | 345 | | | | | 350 | | |
| Leu | Met | Val | Leu | Ile | Pro | Gln | Leu | His | Arg | Asp | Lys | Thr | Ile | Trp | Gly |
| | | 355 | | | | | 360 | | | | | 365 | | | |
| Asp | Asp | Val | Glu | Glu | Phe | Arg | Pro | Glu | Arg | Phe | Glu | Asn | Pro | Ser | Ala |
| | 370 | | | | | 375 | | | | | 380 | | | | |

-continued

```
Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
            405                 410                 415

Met Leu Lys His Phe Asp Phe Glu Asp His Thr Asn Tyr Glu Leu Asp
        420                 425                 430

Ile Lys Glu Thr Leu Thr Leu Lys Pro Glu Gly Phe Val Val Lys Ala
    435                 440                 445

Lys Ser Lys Lys Ile Pro Leu Gly Gly Ile Pro Ser Pro Ser Thr Glu
    450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
    530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
    610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
        675                 680                 685

Pro Lys Glu Ala Ser Tyr Gln Glu Gly Asp His Leu Gly Val Ile Pro
    690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
            740                 745                 750

Val Glu Leu Gln Asp Pro Val Thr Arg Thr Gln Leu Arg Ala Met Ala
        755                 760                 765

Ala Lys Thr Val Cys Pro Pro His Lys Val Glu Leu Glu Ala Leu Leu
    770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
```

-continued

```
                805                 810                 815
Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
            835                 840                 845

Val Ser Gly Glu Ala Trp Ser Gly Tyr Gly Glu Tyr Lys Gly Ile Ala
            850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
                900                 905                 910

Phe Val Gln Ala Arg Lys Gln Leu Lys Glu Gln Gly Gln Ser Leu Gly
                915                 920                 925

Glu Ala His Leu Tyr Phe Gly Cys Arg Ser Pro His Glu Asp Tyr Leu
            930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
                980                 985                 990

Gly Ala His Phe Tyr Ile Cys Gly Asp Gly Ser Gln Met Ala Pro Ala
            995                1000                1005

Val Glu Ala Thr Leu Met Lys Ser Tyr Ala Asp Val His Gln Val
        1010                1015                1020

Ser Glu Ala Asp Ala Arg Leu Trp Leu Gln Gln Leu Glu Glu Lys
        1025                1030                1035

Gly Arg Tyr Ala Lys Asp Val Trp Ala Gly
        1040                1045
```

<210> SEQ ID NO 51
<211> LENGTH: 1048
<212> TYPE: PRT
<213> ORGANISM: Artificial sequence
<220> FEATURE:
<223> OTHER INFORMATION: Cytochrome P450 variant CYP102A1var9

<400> SEQUENCE: 51

```
Thr Ile Lys Glu Met Pro Gln Pro Lys Thr Phe Gly Glu Leu Lys Asn
1               5                  10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Val Arg Asp
65                  70                  75                  80

Phe Ala Gly Asp Gly Leu Ala Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125
```

```
Lys Trp Glu Arg Leu Asn Ala Asp Glu His Ile Glu Val Pro Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                165                 170                 175

Met Val Arg Ala Leu Asp Glu Ala Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ile Ala Asp Arg Lys
    210                 215                 220

Ala Ser Gly Glu Gln Ser Asp Asp Leu Leu Ala His Met Leu Asn Gly
225                 230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Ala Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Leu Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
    370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr Glu
    450                 455                 460

Gln Ser Ala Lys Lys Val Ala Lys Lys Ala Glu Asn Ala His Asn Thr
465                 470                 475                 480

Pro Leu Leu Val Leu Tyr Gly Ser Asn Met Gly Thr Ala Lys Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
    530                 535                 540

Lys Gln Phe Val Asp Trp Leu Asp Gln Ala Ser Ala Asp Glu Val Lys
```

```
            545                 550                 555                 560
       Gly Val Arg Tyr Ser Val Phe Gly Cys Gly Asp Lys Asn Trp Ala Thr
                           565                 570                 575

Thr Tyr Gln Lys Val Pro Ala Phe Ile Asp Glu Thr Leu Ala Ala Lys
                       580                 585                 590

Gly Ala Glu Asn Ile Ala Asp Arg Gly Glu Ala Asp Ala Ser Asp Asp
                       595                 600                 605

Phe Glu Gly Thr Tyr Glu Glu Trp Arg Glu His Met Trp Ser Asp Val
                   610                 615                 620

Ala Ala Tyr Phe Asn Leu Asp Ile Glu Asn Ser Glu Asp Asn Lys Ser
       625                 630                 635                 640

Thr Leu Ser Leu Gln Phe Val Asp Ser Ala Ala Asp Met Pro Leu Ala
                           645                 650                 655

Lys Met His Gly Ala Phe Ser Thr Asn Val Val Ala Ser Lys Glu Leu
                       660                 665                 670

Gln Gln Pro Gly Ser Ala Arg Ser Thr Arg His Leu Glu Ile Glu Leu
                       675                 680                 685

Pro Lys Glu Ala Ser Tyr Gln Glu Gly Asp His Leu Gly Val Ile Pro
                   690                 695                 700

Arg Asn Tyr Glu Gly Ile Val Asn Arg Val Thr Ala Arg Phe Gly Leu
       705                 710                 715                 720

Asp Ala Ser Gln Gln Ile Arg Leu Glu Ala Glu Glu Lys Leu Ala
                           725                 730                 735

His Leu Pro Leu Ala Lys Thr Val Ser Val Glu Glu Leu Leu Gln Tyr
                           740                 745                 750

Val Glu Leu Gln Asp Pro Val Thr Arg Thr Gln Leu Arg Ala Met Ala
                           755                 760                 765

Ala Lys Thr Val Cys Pro Pro His Lys Val Glu Leu Glu Ala Leu Leu
                           770                 775                 780

Glu Lys Gln Ala Tyr Lys Glu Gln Val Leu Ala Lys Arg Leu Thr Met
       785                 790                 795                 800

Leu Glu Leu Leu Glu Lys Tyr Pro Ala Cys Glu Met Lys Phe Ser Glu
                           805                 810                 815

Phe Ile Ala Leu Leu Pro Ser Ile Arg Pro Arg Tyr Tyr Ser Ile Ser
                       820                 825                 830

Ser Ser Pro Arg Val Asp Glu Lys Gln Ala Ser Ile Thr Val Ser Val
                       835                 840                 845

Val Ser Gly Glu Ala Trp Ser Gly Tyr Gly Glu Tyr Lys Gly Ile Ala
                       850                 855                 860

Ser Asn Tyr Leu Ala Glu Leu Gln Glu Gly Asp Thr Ile Thr Cys Phe
       865                 870                 875                 880

Ile Ser Thr Pro Gln Ser Glu Phe Thr Leu Pro Lys Asp Pro Glu Thr
                           885                 890                 895

Pro Leu Ile Met Val Gly Pro Gly Thr Gly Val Ala Pro Phe Arg Gly
                       900                 905                 910

Phe Val Gln Ala Arg Lys Gln Leu Lys Glu Gln Gly Gln Ser Leu Gly
                       915                 920                 925

Glu Ala His Leu Tyr Phe Gly Cys Arg Ser Pro His Glu Asp Tyr Leu
                       930                 935                 940

Tyr Gln Glu Glu Leu Glu Asn Ala Gln Ser Glu Gly Ile Ile Thr Leu
       945                 950                 955                 960

His Thr Ala Phe Ser Arg Met Pro Asn Gln Pro Lys Thr Tyr Val Gln
                           965                 970                 975
```

```
His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
            995                 1000                1005

Val Glu Ala Thr Leu Met Lys Ser Tyr Ala Asp Val His Gln Val
        1010                1015                1020

Glu Glu Ala Asp Ala Arg Leu Trp Leu Gln Gln Leu Glu Glu Lys
        1025                1030                1035

Gly Arg Tyr Ala Lys Asp Val Trp Ala Gly
        1040                1045

<210> SEQ ID NO 52
<211> LENGTH: 1048
<212> TYPE: PRT
<213> ORGANISM: Artificial sequence
<220> FEATURE:
<223> OTHER INFORMATION: Cytochrome P450 variant CYP102A1var9-1

<400> SEQUENCE: 52

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Val Arg Asp
65                  70                  75                  80

Phe Ala Gly Asp Gly Leu Ala Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Pro Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                165                 170                 175

Met Val Arg Ala Leu Asp Glu Lys Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ala Asp Arg Lys
    210                 215                 220

Ala Ser Gly Glu Gln Ser Asp Asp Leu Leu Ala His Met Leu Asn Gly
225                 230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Ala Ala Glu Glu Ala Ala Arg Val Leu Val Asp Pro Val Pro Ser
```

```
                290             295             300
Tyr Lys Gln Val Lys Gln Leu Lys Tyr Val Gly Met Val Leu Asn Glu
305                 310             315                 320

Ala Leu Arg Leu Trp Pro Thr Ala Pro Ala Phe Ser Leu Tyr Ala Lys
                325             330                 335

Glu Asp Thr Val Leu Gly Gly Glu Tyr Pro Leu Glu Lys Gly Asp Glu
            340             345             350

Leu Met Val Leu Ile Pro Gln Leu His Arg Asp Lys Thr Ile Trp Gly
                355             360             365

Asp Asp Val Glu Glu Phe Arg Pro Glu Arg Phe Glu Asn Pro Ser Ala
        370             375             380

Ile Pro Gln His Ala Phe Lys Pro Phe Gly Asn Gly Gln Arg Ala Cys
385             390             395                 400

Ile Gly Gln Gln Phe Ala Leu His Glu Ala Thr Leu Val Leu Gly Met
                405             410             415

Met Leu Lys His Phe Asp Phe Glu Asp His Thr Asn Tyr Glu Leu Asp
            420             425             430

Ile Lys Glu Thr Leu Thr Leu Lys Pro Glu Gly Phe Val Val Lys Ala
        435             440             445

Lys Ser Lys Lys Ile Pro Leu Gly Gly Ile Pro Ser Pro Ser Thr Glu
450             455             460

Gln Ser Ala Lys Lys Val Ala Lys Lys Ala Glu Asn Ala His Asn Thr
465             470             475                 480

Pro Leu Leu Val Leu Tyr Gly Ser Asn Met Gly Thr Ala Lys Gly Thr
                485             490             495

Ala Arg Asp Leu Ala Asp Ile Ala Met Ser Lys Gly Phe Ala Pro Gln
            500             505             510

Val Ala Thr Leu Asp Ser His Ala Gly Asn Leu Pro Arg Glu Gly Ala
        515             520             525

Val Leu Ile Val Thr Ala Ser Tyr Asn Gly His Pro Pro Asp Asn Ala
        530             535             540

Lys Gln Phe Val Asp Trp Leu Asp Gln Ala Ser Ala Asp Glu Val Lys
545             550             555                 560

Gly Val Arg Tyr Ser Val Phe Gly Cys Gly Asp Lys Asn Trp Ala Thr
                565             570             575

Thr Tyr Gln Lys Val Pro Ala Phe Ile Asp Glu Thr Leu Ala Ala Lys
            580             585             590

Gly Ala Glu Asn Ile Ala Asp Arg Gly Glu Ala Asp Ala Ser Asp Asp
        595             600             605

Phe Glu Gly Thr Tyr Glu Glu Trp Arg Glu His Met Trp Ser Asp Val
        610             615             620

Ala Ala Tyr Phe Asn Leu Asp Ile Glu Asn Ser Glu Asp Asn Lys Ser
625             630             635                 640

Thr Leu Ser Leu Gln Phe Val Asp Ser Ala Ala Asp Met Pro Leu Ala
                645             650             655

Lys Met His Gly Ala Phe Ser Thr Asn Val Val Ala Ser Lys Glu Leu
            660             665             670

Gln Gln Pro Gly Ser Ala Arg Ser Thr Arg His Leu Glu Ile Glu Leu
        675             680             685

Pro Lys Glu Ala Ser Tyr Gln Glu Gly Asp His Leu Gly Val Ile Pro
        690             695             700

Arg Asn Tyr Glu Gly Ile Val Asn Arg Val Thr Ala Arg Phe Gly Leu
705             710             715                 720
```

```
Asp Ala Ser Gln Gln Ile Arg Leu Glu Ala Glu Glu Lys Leu Ala
            725                 730                 735

His Leu Pro Leu Ala Lys Thr Val Ser Val Glu Leu Leu Gln Tyr
            740                 745                 750

Val Glu Leu Gln Asp Pro Val Thr Arg Thr Gln Leu Arg Ala Met Ala
        755                 760                 765

Ala Lys Thr Val Cys Pro Pro His Lys Val Glu Leu Glu Ala Leu Leu
770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
            805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
            835                 840                 845

Val Ser Gly Glu Ala Trp Ser Gly Tyr Gly Glu Tyr Lys Gly Ile Ala
        850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
            885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
            915                 920                 925

Glu Ala His Leu Tyr Phe Gly Cys Arg Ser Pro His Glu Asp Tyr Leu
930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
            965                 970                 975

His Val Met Glu Gln Asp Gly Lys Lys Leu Ile Glu Leu Leu Asp Gln
            980                 985                 990

Gly Ala His Phe Tyr Ile Cys Gly  Asp Gly Ser Gln Met Ala Pro Ala
            995                 1000                1005

Val Glu  Ala Thr Leu Met Lys  Ser Tyr Ala Asp Val  His Gln Val
    1010                1015                1020

Glu Glu  Ala Asp Ala Arg Leu  Trp Leu Gln Gln Leu  Glu Glu Lys
    1025                1030                1035

Gly Arg  Tyr Ala Lys Asp Val  Trp Ala Gly
    1040                1045

<210> SEQ ID NO 53
<211> LENGTH: 417
<212> TYPE: PRT
<213> ORGANISM: Bacillus Subtilis

<400> SEQUENCE: 53

Met Asn Glu Gln Ile Pro His Asp Lys Ser Leu Asp Asn Ser Leu Thr
1               5                   10                  15

Leu Leu Lys Glu Gly Tyr Leu Phe Ile Lys Asn Arg Thr Glu Arg Tyr
            20                  25                  30

Asn Ser Asp Leu Phe Gln Ala Arg Leu Leu Gly Lys Asn Phe Ile Cys
        35                  40                  45
```

Met Thr Gly Ala Glu Ala Ala Lys Val Phe Tyr Asp Thr Asp Arg Phe
50                  55                  60

Gln Arg Gln Asn Ala Leu Pro Lys Arg Val Gln Lys Ser Leu Phe Gly
65                  70                  75                  80

Val Asn Ala Ile Gln Gly Met Asp Gly Ser Ala His Ile His Arg Lys
                85                  90                  95

Met Leu Phe Leu Ser Leu Met Thr Pro Pro His Gln Lys Arg Leu Ala
                100                 105                 110

Glu Leu Met Thr Glu Glu Trp Lys Ala Ala Val Thr Arg Trp Glu Lys
                115                 120                 125

Ala Asp Glu Val Val Leu Phe Glu Glu Ala Lys Glu Ile Leu Cys Arg
130                 135                 140

Val Ala Cys Tyr Trp Ala Gly Val Pro Leu Lys Glu Thr Glu Val Lys
145                 150                 155                 160

Glu Arg Ala Asp Asp Phe Ile Asp Met Val Asp Ala Phe Gly Ala Val
                165                 170                 175

Gly Pro Arg His Trp Lys Gly Arg Arg Ala Arg Pro Arg Ala Glu Glu
                180                 185                 190

Trp Ile Glu Val Met Ile Glu Asp Ala Arg Ala Gly Leu Leu Lys Thr
                195                 200                 205

Thr Ser Gly Thr Ala Leu His Glu Met Ala Phe His Thr Gln Glu Asp
210                 215                 220

Gly Ser Gln Leu Asp Ser Arg Met Ala Ala Ile Glu Leu Ile Asn Val
225                 230                 235                 240

Leu Arg Pro Ile Val Ala Ile Ser Tyr Phe Leu Val Phe Ser Ala Leu
                245                 250                 255

Ala Leu His Glu His Pro Lys Tyr Lys Glu Trp Leu Arg Ser Gly Asn
                260                 265                 270

Ser Arg Glu Arg Glu Met Phe Val Gln Glu Val Arg Arg Tyr Tyr Pro
                275                 280                 285

Phe Gly Pro Phe Leu Gly Ala Leu Val Lys Lys Asp Phe Val Trp Asn
290                 295                 300

Asn Cys Glu Phe Lys Lys Gly Thr Ser Val Leu Leu Asp Leu Tyr Gly
305                 310                 315                 320

Thr Asn His Asp Pro Arg Leu Trp Asp His Pro Asp Glu Phe Arg Pro
                325                 330                 335

Glu Arg Phe Ala Glu Arg Glu Asn Leu Phe Asp Met Ile Pro Gln
                340                 345                 350

Gly Gly Gly His Ala Glu Lys Gly His Arg Cys Pro Gly Glu Gly Ile
                355                 360                 365

Thr Ile Glu Val Met Lys Ala Ser Leu Asp Phe Leu Val His Gln Ile
370                 375                 380

Glu Tyr Asp Val Pro Glu Gln Ser Leu His Tyr Ser Leu Ala Arg Met
385                 390                 395                 400

Pro Ser Leu Pro Glu Ser Gly Phe Val Met Ser Gly Ile Arg Arg Lys
                405                 410                 415

Ser

<210> SEQ ID NO 54
<211> LENGTH: 420
<212> TYPE: PRT
<213> ORGANISM: Mycobacterium sp
<220> FEATURE:
<221> NAME/KEY: MISC_FEATURE
<222> LOCATION: (1)..(420)
<223> OTHER INFORMATION: Cytochrome P450 enzyme CYP153A6

<400> SEQUENCE: 54

```
Met Thr Glu Met Thr Val Ala Ala Ser Asp Ala Thr Asn Ala Ala Tyr
 1               5                  10                  15
Gly Met Ala Leu Glu Asp Ile Asp Val Ser Asn Pro Val Leu Phe Arg
            20                  25                  30
Asp Asn Thr Trp His Pro Tyr Phe Lys Arg Leu Arg Glu Glu Asp Pro
                35                  40                  45
Val His Tyr Cys Lys Ser Ser Met Phe Gly Pro Tyr Trp Ser Val Thr
 50                  55                  60
Lys Tyr Arg Asp Ile Met Ala Val Glu Thr Asn Pro Lys Val Phe Ser
 65                  70                  75                  80
Ser Glu Ala Lys Ser Gly Gly Ile Thr Ile Met Asp Asp Asn Ala Ala
                85                  90                  95
Ala Ser Leu Pro Met Phe Ile Ala Met Asp Pro Pro Lys His Asp Val
            100                 105                 110
Gln Arg Lys Thr Val Ser Pro Ile Val Ala Pro Glu Asn Leu Ala Thr
        115                 120                 125
Met Glu Ser Val Ile Arg Gln Arg Thr Ala Asp Leu Leu Asp Gly Leu
130                 135                 140
Pro Ile Asn Glu Glu Phe Asp Trp Val His Arg Val Ser Ile Glu Leu
145                 150                 155                 160
Thr Thr Lys Met Leu Ala Thr Leu Phe Asp Phe Pro Trp Asp Asp Arg
                165                 170                 175
Ala Lys Leu Thr Arg Trp Ser Asp Val Thr Thr Ala Leu Pro Gly Gly
            180                 185                 190
Gly Ile Ile Asp Ser Glu Glu Gln Arg Met Ala Glu Leu Met Glu Cys
        195                 200                 205
Ala Thr Tyr Phe Thr Glu Leu Trp Asn Gln Arg Val Asn Ala Glu Pro
210                 215                 220
Lys Asn Asp Leu Ile Ser Met Met Ala His Ser Glu Ser Thr Arg His
225                 230                 235                 240
Met Ala Pro Glu Glu Tyr Leu Gly Asn Ile Val Leu Leu Ile Val Gly
                245                 250                 255
Gly Asn Asp Thr Thr Arg Asn Ser Met Thr Gly Gly Val Leu Ala Leu
            260                 265                 270
Asn Glu Phe Pro Asp Glu Tyr Arg Lys Leu Ser Ala Asn Pro Ala Leu
        275                 280                 285
Ile Ser Ser Met Val Ser Glu Ile Ile Arg Trp Gln Thr Pro Leu Ser
290                 295                 300
His Met Arg Arg Thr Ala Leu Glu Asp Ile Glu Phe Gly Gly Lys His
305                 310                 315                 320
Ile Arg Gln Gly Asp Lys Val Val Met Trp Tyr Val Ser Gly Asn Arg
                325                 330                 335
Asp Pro Glu Ala Ile Asp Asn Pro Asp Thr Phe Ile Ile Asp Arg Ala
            340                 345                 350
Lys Pro Arg Gln His Leu Ser Phe Gly Phe Gly Ile His Arg Cys Val
        355                 360                 365
Gly Asn Arg Leu Ala Glu Leu Gln Leu Asn Ile Leu Trp Glu Glu Ile
370                 375                 380
Leu Lys Arg Trp Pro Asp Pro Leu Gln Ile Gln Val Leu Gln Glu Pro
385                 390                 395                 400
Thr Arg Val Leu Ser Pro Phe Val Lys Gly Tyr Glu Ser Leu Pro Val
                405                 410                 415
```

Arg Ile Asn Ala
           420

<210> SEQ ID NO 55
<211> LENGTH: 416
<212> TYPE: PRT
<213> ORGANISM: Sphingopyxis macrogoltabida
<220> FEATURE:
<221> NAME/KEY: MISC_FEATURE
<222> LOCATION: (1)..(416)
<223> OTHER INFORMATION: Cytochrome P450 enzyme CYP153A7

<400> SEQUENCE: 55

Met Glu His Thr Gly Gln Ser Ala Ala Thr Met Pro Leu Asp Ser
1               5                   10                  15

Ile Asp Val Ser Ile Pro Glu Leu Phe Tyr Asn Asp Ser Val Gly Glu
            20                  25                  30

Tyr Phe Lys Arg Leu Arg Lys Asp Pro Val His Tyr Cys Ala Asp
            35                  40                  45

Ser Ala Phe Gly Pro Tyr Trp Ser Ile Thr Lys Tyr Asn Asp Ile Met
    50                  55                  60

His Val Asp Thr Asn His Asp Ile Phe Ser Ser Asp Ala Gly Tyr Gly
65                  70                  75                  80

Gly Ile Ile Ile Asp Asp Gly Ile Gln Lys Gly Gly Asp Gly Leu
                85                  90                  95

Asp Leu Pro Asn Phe Ile Ala Met Asp Arg Pro Arg His Asp Glu Gln
                100                 105                 110

Arg Lys Ala Val Ser Pro Ile Val Ala Pro Ala Asn Leu Ala Ala Leu
                115                 120                 125

Glu Gly Thr Ile Arg Glu Arg Val Ser Lys Thr Leu Asp Gly Leu Pro
    130                 135                 140

Val Gly Glu Glu Phe Asp Trp Val Asp Arg Val Ser Ile Glu Ile Thr
145                 150                 155                 160

Thr Gln Met Leu Ala Thr Leu Phe Asp Phe Pro Phe Glu Glu Arg Arg
                165                 170                 175

Lys Leu Thr Arg Trp Ser Asp Val Thr Thr Ala Ala Pro Gly Gly Gly
                180                 185                 190

Val Val Glu Ser Trp Asp Gln Arg Lys Thr Glu Leu Leu Glu Cys Ala
                195                 200                 205

Ala Tyr Phe Gln Val Leu Trp Asn Glu Arg Val Asn Lys Asp Pro Gly
    210                 215                 220

Asn Asp Leu Ile Ser Met Leu Ala His Ser Pro Ala Thr Arg Asn Met
225                 230                 235                 240

Thr Pro Glu Glu Tyr Leu Gly Asn Val Leu Leu Leu Ile Val Gly Gly
                245                 250                 255

Asn Asp Thr Thr Arg Asn Ser Met Thr Gly Gly Val Leu Ala Leu His
                260                 265                 270

Lys Asn Pro Asp Gln Phe Ala Lys Leu Lys Ala Asn Pro Ala Leu Val
                275                 280                 285

Glu Thr Met Val Pro Glu Ile Ile Arg Trp Gln Thr Pro Leu Ala His
    290                 295                 300

Met Arg Arg Thr Ala Ile Ala Asp Ser Glu Leu Gly Gly Lys Thr Ile
305                 310                 315                 320

Arg Lys Gly Asp Lys Val Val Met Trp Tyr Tyr Ser Gly Asn Arg Asp
                325                 330                 335

Asp Glu Val Ile Asp Arg Pro Glu Glu Phe Ile Ile Asp Arg Pro Arg

```
                340                 345                 350
Pro Arg Gln His Leu Ser Phe Gly Phe Gly Ile His Arg Cys Val Gly
                355                 360                 365

Asn Arg Leu Ala Glu Met Gln Leu Arg Ile Leu Trp Glu Glu Ile Leu
            370                 375                 380

Thr Arg Phe Ser Arg Ile Glu Val Met Ala Glu Pro Glu Arg Val Arg
385                 390                 395                 400

Ser Asn Phe Val Arg Gly Tyr Ala Lys Met Met Val Arg Val His Ala
                405                 410                 415

<210> SEQ ID NO 56
<211> LENGTH: 419
<212> TYPE: PRT
<213> ORGANISM: Sphingopyxis macrogoltabida
<220> FEATURE:
<221> NAME/KEY: MISC_FEATURE
<222> LOCATION: (1)..(419)
<223> OTHER INFORMATION: Cytochrome P450 enzyme CYP153A8

<400> SEQUENCE: 56

Met Asp Thr Asp Met Val Glu Pro Asn Ile Arg Glu Lys Val Ala Phe
1               5                   10                  15

Ile Pro Ile Asp Glu Ile Asp Val Ala Arg Pro Ser Leu Phe Gln Lys
            20                  25                  30

Asp Thr Val Gly Leu Phe Phe Glu Arg Leu Arg Arg Glu Pro Val
        35                  40                  45

His Tyr Cys Arg Glu Ser Tyr Val Gly Pro Tyr Trp Ser Ile Thr Lys
    50                  55                  60

Phe Asp Asp Ile Met Ala Val Asp Thr Asn His Lys Val Phe Ser Ser
65                  70                  75                  80

Glu Ala Lys Leu Gly Gly Ile Ala Ile Glu Asp Met His Ser Ala Lys
                85                  90                  95

Ser Ala Leu Glu Leu Glu Met Phe Ile Ala Met Asp Pro Pro Lys His
            100                 105                 110

Asn Gln Gln Arg Lys Ala Val Thr Gly Ala Val Ala Pro Ser Asn Leu
        115                 120                 125

Leu Leu Leu Glu Pro Thr Ile Arg Glu Arg Ala Cys Gln Ile Leu Asp
130                 135                 140

Asp Leu Pro Val Gly Glu Asp Ile Asp Trp Val Asp Lys Val Ala Val
145                 150                 155                 160

Glu Leu Thr Thr Met Thr Leu Ala Thr Leu Phe Asp Phe Pro Trp Glu
                165                 170                 175

Glu Arg Arg Lys Thr Arg Trp Ser Asp Val Thr Thr Ala Ala Pro Glu
            180                 185                 190

Thr Gly Ile Val Ala Ser Tyr Glu Ala Arg Arg Ala Glu Leu Ile Glu
        195                 200                 205

Cys Ala Met Tyr Phe Lys Gly Leu Trp Glu Gln Arg Ile Asn Ala Glu
210                 215                 220

Pro Lys Asn Asp Leu Ile Ser Met Met Ala His Ser Pro Ala Thr Arg
225                 230                 235                 240

Asp Met Pro Phe Leu Glu Phe Leu Gly Asn Leu Leu Leu Ile Val
                245                 250                 255

Gly Gly Asn Asp Thr Thr Arg Asn Ser Ile Ser Gly Val Leu Ala
            260                 265                 270

Leu Asn Gln Asn Pro Asp Ala Tyr Leu Lys Leu Asn Asn Asp Pro Gly
        275                 280                 285
```

```
Leu Ile Thr Ser Met Val Pro Glu Ile Ile Arg Trp Gln Thr Pro Leu
290                 295                 300

Thr His Met Arg Arg Thr Ala Leu Gln Asp Trp Glu Ile Gly Gly Lys
305                 310                 315                 320

Lys Ile Arg Lys Gly Asp Lys Val Val Met Trp Tyr Leu Ser Gly Asn
                325                 330                 335

Arg Asp Glu Thr Val Ile Asp Arg Ala Asp Glu Phe Ile Ile Asp Arg
            340                 345                 350

Lys Asn Pro Arg His His Leu Ser Phe Gly Tyr Gly Ile His Arg Cys
        355                 360                 365

Met Gly Asn Arg Leu Ala Glu Leu Gln Leu Arg Ile Ile Trp Glu Glu
370                 375                 380

Ile His Lys Arg Phe Ala Lys Ile Glu Val Thr Gly Glu Pro Glu Arg
385                 390                 395                 400

Leu Phe Ser Asn Leu Val Arg Gly Ile Thr Lys Leu Pro Val Arg Leu
                405                 410                 415

His Ala Arg

<210> SEQ ID NO 57
<211> LENGTH: 425
<212> TYPE: PRT
<213> ORGANISM: Sphingopyxis macrogoltabida
<220> FEATURE:
<221> NAME/KEY: MISC_FEATURE
<222> LOCATION: (1)..(425)
<223> OTHER INFORMATION: Cytochrome P450 enzyme CYP153A11

<400> SEQUENCE: 57

Met Ala Thr Arg Ser Met Gln Ser Gly Pro Asp Arg Glu Glu Pro Asp
1               5                   10                  15

Arg Pro Ile Ala Glu Ile Pro Leu Ala Glu Ile Asp Val Ser Arg Pro
            20                  25                  30

Ser Leu Phe Gln Ser Asp Lys Val Gly Ala Phe Phe Gly Arg Leu Arg
        35                  40                  45

Arg Glu Asp Pro Val His Tyr Cys Ser Glu Ser Ala Phe Gly Pro Tyr
    50                  55                  60

Trp Ser Ile Thr Arg Tyr Asn Asp Ile Met Ala Val Asp Thr Asn His
65                  70                  75                  80

Lys Leu Phe Ser Ser Glu Ala Lys Leu Gly Ile Ala Ile Gln Asp
                85                  90                  95

Met His Asn Asp Ala Thr Asn Leu Glu Leu Glu Met Phe Ile Ala Met
                100                 105                 110

Asp Gln Pro Lys His Asp Ala Gln Arg Lys Ala Val Thr Pro Ala Val
            115                 120                 125

Ala Pro Ser Asn Leu Leu Leu Glu Pro Val Ile Arg Glu Arg Ala
        130                 135                 140

Gly Ala Ile Leu Asp Ser Leu Pro Val Gly Glu Ile Asp Trp Val
145                 150                 155                 160

Lys Ser Val Ser Val Glu Leu Thr Thr Met Thr Leu Ala Thr Leu Phe
                165                 170                 175

Asp Phe Pro Trp Asp Glu Arg Ala Lys Leu Thr Arg Trp Ser Asp Val
            180                 185                 190

Thr Thr Ala Ile Pro Gly Ser Gly Ile Val Glu Ser Asn Glu Gln Arg
        195                 200                 205

Arg Gln Glu Leu Ile Glu Cys Ala Met Tyr Phe Lys Gly Leu Trp Asp
    210                 215                 220
```

```
Gln Arg Ile Asp Arg Ser Glu Gly Ser Asp Leu Ile Thr Met Met Ala
225                 230                 235                 240

Asn Ser Pro Ala Thr Arg Glu Met Pro Phe Leu Glu Phe Leu Gly Asn
            245                 250                 255

Leu Leu Leu Leu Ile Val Gly Gly Asn Asp Thr Thr Arg Asn Ser Ile
        260                 265                 270

Ser Gly Gly Val Ile Ala Leu Asn Gln Asn Pro Asp Gln Tyr Glu Lys
    275                 280                 285

Leu Arg Gln His Pro Ser Leu Ile Gly Ser Met Val Pro Glu Ile Ile
290                 295                 300

Arg Trp Gln Thr Pro Leu Thr His Met Arg Arg Thr Ala Leu Ala Asp
305                 310                 315                 320

Ser Glu Ile Gly Gly Lys Arg Ile Ala Lys Gly Asp Lys Val Val Met
            325                 330                 335

Trp Tyr Leu Ser Gly Asn Arg Asp Glu Thr Val Ile Glu Arg Pro Glu
        340                 345                 350

Glu Phe Ile Ile Asp Arg Lys Asn Pro Arg Gln His Leu Ser Phe Gly
    355                 360                 365

Tyr Gly Ile His Arg Cys Met Gly Asn Arg Leu Ala Glu Leu Gln Leu
370                 375                 380

Arg Ile Ile Trp Glu Glu Ile His Lys Arg Phe Arg Leu Val Glu Met
385                 390                 395                 400

Val Gly Glu Pro Glu Arg Leu Leu Ser Asn Leu Val Arg Gly Ile Thr
            405                 410                 415

Arg Leu Pro Val Lys Leu His Ala His
            420                 425

<210> SEQ ID NO 58
<211> LENGTH: 429
<212> TYPE: PRT
<213> ORGANISM: Sphingopyxis macrogoltabida
<220> FEATURE:
<221> NAME/KEY: MISC_FEATURE
<222> LOCATION: (1)..(429)
<223> OTHER INFORMATION: Cytochrome P450 enzyme CYP153D2

<400> SEQUENCE: 58

Met Ala Thr Val Ile Arg Glu Thr Pro Ala Asp Leu His Pro Leu Asp
1               5                   10                  15

Leu Ser Arg Ala Asp Leu Trp Arg Glu Asp Gln Trp Gln Glu Pro Met
            20                  25                  30

Arg Gln Leu Arg Ala Glu Ser Pro Ile Tyr Tyr Cys Glu Asp Ser Lys
        35                  40                  45

Phe Gly Pro Tyr Trp Ser Val Thr Thr Tyr Lys Pro Ile Gln His Ile
    50                  55                  60

Glu Ala Leu Pro Lys Ile Phe Ser Ser Trp Glu Tyr Gly Gly Ile
65                  70                  75                  80

Thr Val Ala Gly Asp Gly Ile Glu His Leu Lys Glu Gly Glu Ile Pro
                85                  90                  95

Met Pro Met Phe Ile Ala Met Asp Pro Pro Gln His Thr Ala Gln Arg
            100                 105                 110

Arg Thr Val Ala Pro Ala Phe Gly Pro Ser Glu Ile Glu Arg Met Arg
        115                 120                 125

Ala Asp Thr Gln Ala Arg Thr Ala Ala Leu Ile Asp Thr Leu Pro Val
    130                 135                 140

Gly Glu Ala Phe Asp Trp Val Glu Arg Leu Ser Ile Glu Leu Thr Thr
145                 150                 155                 160
```

```
Asp Met Leu Ala Ile Leu Phe Asp Phe Pro Trp Glu Asn Arg His Asn
            165                 170                 175
Leu Thr Arg Trp Ser Asp Ala Leu Gly Asp Ile Glu Ser Phe Asn Thr
        180                 185                 190
Leu Glu Glu Arg Gln Gln Arg Leu Ala Thr Ala Phe Glu Met Gly Ala
    195                 200                 205
Ala Phe Lys Glu Leu Trp Asp His Lys Ala Lys Asn Pro Gly Lys His
210                 215                 220
Asp Leu Ile Ser Ile Met Leu Gln Ser Asp Ala Met Asn His Met Ser
225                 230                 235                 240
His Glu Glu Phe Met Gly Asn Leu Ile Leu Leu Ile Val Gly Gly Asn
            245                 250                 255
Asp Thr Thr Arg Asn Ser Met Ser Ala Tyr Ala Tyr Gly Leu His Cys
        260                 265                 270
Phe Pro Glu Glu Arg Ala Lys Leu Glu Ala Asn His Asp Pro Asp Leu
    275                 280                 285
Ala Val Asn Ala Met His Glu Ile Ile Arg Trp Gln Thr Pro Leu Ala
290                 295                 300
His Met Arg Arg Thr Ala Leu Glu Asp Thr Glu Leu Phe Gly His Gln
305                 310                 315                 320
Ile Arg Ala Arg Asp Lys Ile Ala Leu Trp Tyr Ala Ser Ala Asn Arg
            325                 330                 335
Asp Glu Ser Ile Phe Pro Asp Gly Asp Arg Ile Ile Val Asp Arg Glu
        340                 345                 350
Asn Ala Arg Arg His Leu Ala Phe Gly Tyr Gly Ile His Arg Cys Val
    355                 360                 365
Gly Ala Arg Val Ala Glu Leu Gln Leu Thr Thr Leu Ile Ser Glu Met
370                 375                 380
Gln Lys Arg Arg Leu Arg Val Asn Val Leu Ala Glu Pro Glu Arg Val
385                 390                 395                 400
Asn Ala Ser Phe Val His Val Ser Pro His Ala Gly Arg Thr Arg Ala
            405                 410                 415
Leu Leu Thr Ala Val Thr Ala Gly Pro Ile Ser Ala Arg
        420                 425
```

```
<210> SEQ ID NO 59
<211> LENGTH: 416
<212> TYPE: PRT
<213> ORGANISM: Sphingopyxis macrogoltabida
<220> FEATURE:
<221> NAME/KEY: MISC_FEATURE
<222> LOCATION: (1)..(416)
<223> OTHER INFORMATION: Cytochrome P450 enzyme CYP153D3

<400> SEQUENCE: 59
```

```
Met Ala Ser Thr Ala Thr Leu Val Arg Thr Ala Ser Pro Ile Ala Pro
1               5                   10                  15
Ile Asp Val Ser Leu Pro Glu Leu Tyr Ala Glu Asp Arg Trp Gln Glu
            20                  25                  30
Pro Phe Arg Thr Leu Arg Ala Gln Ala Pro Ile Gln Tyr Val Pro Asp
        35                  40                  45
Ser Lys Phe Gly Pro Tyr Trp Ser Val Thr Thr Tyr Lys Pro Ile Val
    50                  55                  60
Tyr Ile Glu Ala Leu Pro Lys Leu Phe Ser Ser Ser Trp Gln Tyr Gly
65                  70                  75                  80
Gly Ile Ser Ile Ala Phe Asp Ser Asp Lys Leu Leu Glu His Glu Val
```

```
                    85                  90                  95
Arg Gln Pro Met Phe Ile Ala Met Asp Pro Gln His Thr Ala Gln
                100                 105                 110

Arg Arg Thr Val Ala Xaa Ser Phe Gly Pro Ser Glu Val Ala Ala Met
                115                 120                 125

Lys Ala Glu Val Gln Leu Arg Thr Gly Ala Leu Leu Asp Ser Leu Pro
                130                 135                 140

Val Gly Asp Pro Phe Asp Trp Val Gln Lys Val Ser Ile Glu Leu Thr
145                 150                 155                 160

Thr Gly Met Leu Ala Arg Leu Phe Asp Phe Pro Trp Glu Glu Arg His
                165                 170                 175

Asn Leu Thr His Trp Ser Asp Ile Gly Asp Val Glu Leu Ile Arg
                180                 185                 190

Ser Pro Glu Gly Leu Val Glu Arg Asn Thr Lys Leu Leu Gln Met Gly
                195                 200                 205

Met Ala Phe Ala Ala Leu Trp Gln Glu Lys Ala Gln Asn Pro Gly Lys
                210                 215                 220

Asp Leu Ile Ser Val Met Leu Lys Ser Asp Ala Met Asn His Met Ser
225                 230                 235                 240

Asn Glu Glu Phe Ile Gly Asn Leu Val Leu Leu Ile Val Gly Gly Asn
                245                 250                 255

Asp Thr Thr Arg Asn Ser Met Ser Ser Tyr Ala Tyr Gly Leu Ala Gln
                260                 265                 270

Phe Pro Glu Glu Arg Ala Lys Leu Glu Ala Asn Pro Ala Leu Ile Pro
                275                 280                 285

Asn Ala Val Gln Glu Leu Ile Arg Trp Gln Thr Pro Leu Ala His Met
                290                 295                 300

Arg Arg Thr Val Glu Glu Asp Thr Glu Ile Xaa Gly Gln Xaa Xaa Lys
305                 310                 315                 320

Lys Gly Asp Lys Val Val Leu Trp Tyr Leu Ser Ala Asn Arg Asp Glu
                325                 330                 335

Thr Val Phe Lys Asp Ala Asp Arg Ile Ile Val Gly Arg Glu Asn Ala
                340                 345                 350

Arg Arg His Leu Ser Phe Gly Tyr Gly Ile His Arg Cys Val Gly Ala
                355                 360                 365

Arg Val Ala Glu Leu Gln Leu Val Thr Leu Leu Glu Glu Met Ala Lys
                370                 375                 380

Arg Arg Leu Arg Ala Asn Val Leu Ala Glu Pro Val Arg Val Pro Ala
385                 390                 395                 400

Cys Phe Val His Gly Tyr Lys Ser Leu Gln Val Glu Leu Ser His Tyr
                405                 410                 415

<210> SEQ ID NO 60
<211> LENGTH: 470
<212> TYPE: PRT
<213> ORGANISM: Alcanivorax borkumensis
<220> FEATURE:
<221> NAME/KEY: MISC_FEATURE
<222> LOCATION: (1)..(470)
<223> OTHER INFORMATION: Cytochrome P450 enzyme CYP153AlkBurk

<400> SEQUENCE: 60

Met Ser Thr Ser Ser Thr Ser Asn Asp Ile Gln Ala Lys Val Ile
1               5                   10                  15

Asn Ala Thr Ser Lys Val Val Pro Met His Leu Gln Ile Lys Ala Leu
                20                  25                  30
```

-continued

```
Lys Asn Leu Met Lys Val Lys Arg Lys Thr Ile Gly Thr Ser Arg Pro
             35                  40                  45

Gln Val His Phe Val Glu Thr Asp Leu Pro Asp Val Asn Asp Leu Ala
 50                      55                  60

Ile Glu Asp Ile Asp Thr Ser Asn Pro Phe Leu Tyr Arg Gln Gly Lys
 65                  70                  75                  80

Ala Asn Ala Tyr Phe Lys Arg Leu Arg Asp Glu Ala Pro Val His Tyr
                 85                  90                  95

Gln Lys Asn Ser Ala Phe Gly Pro Phe Trp Ser Val Thr Arg Tyr Glu
                100                 105                 110

Asp Ile Val Phe Val Asp Lys Ser His Asp Leu Phe Ser Ala Glu Pro
            115                 120                 125

Gln Ile Ile Leu Gly Asp Pro Pro Glu Gly Leu Ser Val Glu Met Phe
130                 135                 140

Ile Ala Met Asp Pro Pro Lys His Asp Val Gln Arg Arg Ala Val Gln
145                 150                 155                 160

Gly Val Val Ala Pro Lys Asn Leu Lys Glu Met Glu Gly Leu Ile Arg
                165                 170                 175

Lys Arg Thr Gly Asp Val Leu Asp Ser Leu Pro Leu Asp Thr Pro Phe
            180                 185                 190

Asn Trp Val Pro Val Val Ser Lys Glu Leu Thr Gly Arg Met Leu Ala
            195                 200                 205

Ser Leu Leu Asp Phe Pro Tyr Asp Glu Arg Glu Lys Leu Val Gly Trp
210                 215                 220

Ser Asp Arg Leu Ser Gly Ala Ser Ser Ala Thr Gly Gly Glu Phe Thr
225                 230                 235                 240

Asn Glu Asp Val Phe Phe Asp Asp Ala Ala Asp Met Ala Trp Ala Phe
                245                 250                 255

Ser Lys Leu Trp Arg Asp Lys Glu Ala Arg Gln Lys Ala Gly Glu Glu
            260                 265                 270

Pro Gly Phe Asp Leu Ile Ser Met Leu Gln Ser Asn Glu Asp Thr Lys
            275                 280                 285

Asp Leu Ile Asn Arg Pro Leu Glu Phe Ile Gly Asn Leu Ala Leu Leu
290                 295                 300

Ile Val Gly Gly Asn Asp Thr Thr Arg Asn Ser Met Ser Gly Gly Val
305                 310                 315                 320

Leu Ala Leu Asn Gln Phe Pro Glu Gln Phe Glu Lys Leu Lys Ala Asn
                325                 330                 335

Pro Lys Leu Ile Pro Asn Met Val Ser Glu Ile Ile Arg Trp Gln Thr
            340                 345                 350

Pro Leu Ala Tyr Met Arg Arg Val Ala Lys Gln Asp Val Glu Leu Asn
            355                 360                 365

Gly Glu Thr Ile Lys Lys Gly Asp Arg Val Leu Met Trp Tyr Ala Ser
370                 375                 380

Gly Asn Gln Asp Glu Arg Lys Phe Glu Asn Pro Glu Gln Phe Ile Ile
385                 390                 395                 400

Asp Arg Lys Asp Thr Arg Asn His Val Ser Phe Gly Tyr Gly Val His
                405                 410                 415

Arg Cys Met Gly Asn Arg Leu Ala Glu Leu Gln Leu Arg Ile Leu Trp
            420                 425                 430

Glu Glu Leu Leu Pro Arg Phe Glu Asn Ile Glu Val Ile Gly Glu Pro
            435                 440                 445

Glu Arg Val Gln Ser Asn Phe Val Arg Gly Tyr Ser Lys Met Met Val
450                 455                 460
```

```
Lys Leu Thr Ala Lys Lys
465                 470

<210> SEQ ID NO 61
<211> LENGTH: 497
<212> TYPE: PRT
<213> ORGANISM: Acinetobacter sp EB104
<220> FEATURE:
<221> NAME/KEY: MISC_FEATURE
<222> LOCATION: (1)..(497)
<223> OTHER INFORMATION: Cytochrome P450 enzyme CYP153EB104

<400> SEQUENCE: 61

Met Asn Ser Val Ala Glu Ile Phe Glu Lys Ile Thr Gln Thr Val Thr
1               5                   10                  15

Ser Thr Ala Ala Asp Val Ala Thr Thr Val Thr Asp Lys Val Lys Ser
            20                  25                  30

Asn Glu Gln Phe Gln Thr Gly Lys Gln Phe Leu His Gly Gln Val Thr
        35                  40                  45

Arg Phe Val Pro Leu His Thr Gln Val Arg Gly Ile Gln Trp Met Gln
    50                  55                  60

Lys Ala Lys Phe Arg Val Phe Asn Val Gln Glu Phe Pro Ala Phe Ile
65                  70                  75                  80

Glu Gln Pro Ile Pro Glu Val Ala Thr Leu Ala Leu Ala Glu Ile Asp
                85                  90                  95

Val Ser Asn Pro Phe Leu Tyr Lys Gln Lys Lys Trp Gln Ser Tyr Phe
            100                 105                 110

Lys Arg Leu Arg Asp Glu Ala Pro Val His Tyr Gln Ala Asn Ser Pro
        115                 120                 125

Phe Gly Ala Phe Trp Ser Val Thr Arg Tyr Asp Asp Ile Val Tyr Val
    130                 135                 140

Asp Lys Asn His Glu Ile Phe Ser Ala Glu Pro Val Ile Ala Ile Gly
145                 150                 155                 160

Asn Thr Pro Pro Gly Leu Asp Ala Glu Met Phe Ile Ala Met Asp Pro
                165                 170                 175

Pro Lys His Asp Val Gln Arg Gln Ala Val Gln Asp Val Val Ala Pro
            180                 185                 190

Lys Asn Leu Lys Glu Leu Glu Gly Leu Ile Arg Leu Arg Val Gln Gly
        195                 200                 205

Val Leu Asp Gln Leu Pro Thr Asp Gln Pro Phe Asp Trp Val Gln Asn
    210                 215                 220

Val Ser Ile Glu Leu Thr Ala Arg Met Leu Ala Thr Leu Phe Asp Phe
225                 230                 235                 240

Pro Tyr Glu Lys Arg His Lys Leu Val Glu Trp Ser Asp Leu Met Ala
                245                 250                 255

Gly Thr Ala Glu Ala Thr Gly Gly Thr Val Thr Asn Leu Asp Glu Ile
            260                 265                 270

Phe Asp Ala Ala Val Asp Ala Lys His Phe Ala Glu Leu Trp His
        275                 280                 285

Arg Lys Ala Ala Gln Lys Ser Ala Gly Ala Glu Met Gly Tyr Asp Leu
    290                 295                 300

Ile Ser Leu Met Gln Ser Asn Glu Ala Thr Lys Asp Leu Ile Tyr Arg
305                 310                 315                 320

Pro Met Glu Phe Met Gly Asn Leu Val Leu Leu Ile Val Gly Gly Asn
                325                 330                 335

Asp Thr Thr Arg Asn Ser Met Thr Gly Gly Val Tyr Ala Leu Asn Leu
```

```
                340                 345                 350
Phe Pro Asn Glu Phe Val Lys Leu Lys Asn Asn Pro Ser Leu Ile Pro
            355                 360                 365
Asn Met Val Ser Glu Ile Ile Arg Trp Gln Thr Pro Leu Ala Tyr Met
        370                 375                 380
Arg Arg Ile Ala Lys Gln Asp Val Glu Leu Asn Gly Gln Thr Ile Lys
385                 390                 395                 400
Lys Gly Asp Lys Val Val Met Trp Tyr Val Ser Gly Asn Arg Asp Glu
                405                 410                 415
Arg Val Ile Glu Arg Pro Asp Glu Leu Ile Ile Asp Arg Lys Gly Ala
            420                 425                 430
Arg Asn His Leu Ser Phe Gly Phe Gly Val His Arg Cys Met Gly Asn
        435                 440                 445
Arg Leu Ala Glu Met Gln Leu Arg Ile Leu Trp Glu Glu Leu Leu Gln
        450                 455                 460
Arg Phe Glu Asn Ile Glu Val Leu Gly Glu Pro Glu Ile Val Gln Ser
465                 470                 475                 480
Asn Phe Val Arg Gly Tyr Ala Lys Met Met Val Lys Leu Thr Ala Lys
                485                 490                 495
Ala

<210> SEQ ID NO 62
<211> LENGTH: 497
<212> TYPE: PRT
<213> ORGANISM: Acinetobacter sp OC4
<220> FEATURE:
<221> NAME/KEY: MISC_FEATURE
<222> LOCATION: (1)..(497)
<223> OTHER INFORMATION: Cytochrome P450 enzyme CYP153OC4

<400> SEQUENCE: 62

Met Asn Ser Val Ala Glu Ile Phe Glu Lys Ile Thr Gln Thr Val Thr
1               5                   10                  15
Ser Thr Ala Ala Asp Val Ala Thr Thr Val Thr Asp Lys Val Lys Ser
            20                  25                  30
Asn Glu Gln Phe Gln Thr Gly Lys Gln Phe Leu His Gly Gln Val Thr
        35                  40                  45
Arg Phe Val Pro Leu His Thr Gln Val Arg Gly Ile Gln Trp Met Gln
    50                  55                  60
Lys Ala Lys Phe Arg Val Phe Asn Val Gln Glu Phe Pro Ala Phe Ile
65                  70                  75                  80
Glu Gln Pro Ile Pro Glu Val Ala Thr Leu Ala Leu Ala Glu Ile Asp
                85                  90                  95
Val Ser Asn Pro Phe Leu Tyr Lys Gln Lys Lys Trp Gln Ser Tyr Phe
            100                 105                 110
Lys Arg Leu Arg Asp Glu Ala Pro Val His Tyr Gln Ala Asn Ser Pro
        115                 120                 125
Phe Gly Ala Phe Trp Ser Val Thr Arg Tyr Asp Asp Ile Val Tyr Val
    130                 135                 140
Asp Lys Asn His Glu Ile Phe Ser Ala Glu Pro Val Ile Ala Ile Gly
145                 150                 155                 160
Asn Thr Pro Pro Gly Leu Gly Ala Glu Met Phe Ile Ala Met Asp Pro
                165                 170                 175
Pro Lys His Asp Val Gln Arg Gln Ala Val Gln Asp Val Val Ala Pro
            180                 185                 190
Lys Asn Leu Lys Glu Leu Glu Gly Leu Ile Arg Leu Arg Val Gln Glu
```

-continued

```
                195                 200                 205
Val Leu Asp Gln Leu Pro Thr Asp Gln Pro Phe Asp Trp Val Gln Asn
210                 215                 220

Val Ser Ile Glu Leu Thr Ala Arg Met Leu Ala Thr Leu Phe Asp Phe
225                 230                 235                 240

Pro Tyr Glu Lys Arg His Lys Leu Val Glu Trp Ser Asp Leu Met Ala
                245                 250                 255

Gly Thr Ala Glu Ala Thr Gly Gly Thr Val Thr Asn Leu Asp Glu Ile
                260                 265                 270

Phe Asp Ala Ala Val Asp Ala Lys His Phe Ala Glu Leu Trp His
        275                 280                 285

Arg Lys Ala Ala Gln Lys Ser Ala Gly Ala Glu Met Gly Tyr Asp Leu
290                 295                 300

Ile Ser Leu Met Gln Ser Asn Glu Ala Thr Lys Asp Leu Ile Tyr Arg
305                 310                 315                 320

Pro Met Glu Phe Met Gly Asn Leu Val Leu Ile Val Gly Gly Asn
                325                 330                 335

Asp Thr Thr Arg Asn Ser Met Thr Gly Gly Val Tyr Ala Leu Asn Leu
                340                 345                 350

Phe Pro Asn Glu Phe Val Lys Leu Lys Asn Asn Pro Ser Leu Ile Pro
            355                 360                 365

Asn Met Val Ser Glu Ile Ile Arg Trp Gln Thr Pro Leu Ala Tyr Met
370                 375                 380

Arg Arg Ile Ala Lys Gln Asp Val Glu Leu Asn Gly Gln Thr Ile Lys
385                 390                 395                 400

Lys Gly Asp Lys Val Val Met Trp Tyr Val Ser Gly Asn Arg Asp Glu
                405                 410                 415

Arg Val Ile Glu Arg Pro Asp Glu Leu Ile Ile Asp Arg Lys Gly Ala
                420                 425                 430

Arg Asn His Leu Ser Phe Gly Phe Gly Val His Arg Cys Met Gly Asn
            435                 440                 445

Arg Leu Ala Glu Met Gln Leu Arg Ile Leu Trp Glu Glu Leu Leu Gln
450                 455                 460

Arg Phe Glu Asn Ile Glu Val Leu Gly Glu Pro Glu Ile Val Gln Ser
465                 470                 475                 480

Asn Phe Val Arg Gly Tyr Ala Lys Met Met Val Lys Leu Thr Ala Lys
                485                 490                 495

Ala
```

```
<210> SEQ ID NO 63
<211> LENGTH: 1059
<212> TYPE: PRT
<213> ORGANISM: Artificial Sequence
<220> FEATURE:
<223> OTHER INFORMATION: Cytochrome P450 variant CYP102A2var1

<400> SEQUENCE: 63

Lys Glu Thr Ser Pro Ile Pro Gln Pro Lys Thr Phe Gly Pro Leu Gly
1               5                   10                  15

Asn Leu Pro Leu Ile Asp Lys Asp Lys Pro Thr Leu Ser Leu Ile Lys
                20                  25                  30

Leu Ala Glu Glu Gln Gly Pro Ile Phe Gln Ile His Thr Pro Ala Gly
            35                  40                  45

Thr Thr Ile Val Val Ser Gly His Glu Leu Val Lys Glu Val Cys Asp
50                  55                  60
```

-continued

```
Glu Glu Arg Phe Asp Lys Ser Ile Glu Gly Ala Leu Glu Lys Val Arg
 65                  70                  75                  80

Ala Phe Ser Gly Asp Gly Leu Ala Thr Ser Trp Thr His Glu Pro Asn
                 85                  90                  95

Trp Arg Lys Ala His Asn Ile Leu Met Pro Thr Phe Ser Gln Arg Ala
            100                 105                 110

Met Lys Asp Tyr His Glu Lys Met Val Asp Ile Ala Val Gln Leu Ile
        115                 120                 125

Gln Lys Trp Ala Arg Leu Asn Pro Asn Glu Ala Val Asp Val Pro Gly
130                 135                 140

Asp Met Thr Arg Leu Thr Leu Asp Thr Ile Gly Leu Cys Gly Phe Asn
145                 150                 155                 160

Tyr Arg Phe Asn Ser Tyr Tyr Arg Glu Thr Pro His Pro Phe Ile Asn
                165                 170                 175

Ser Met Val Arg Ala Leu Asp Glu Ala Met His Gln Met Gln Arg Leu
            180                 185                 190

Asp Val Gln Asp Lys Leu Met Val Arg Thr Lys Arg Gln Phe Arg Tyr
        195                 200                 205

Asp Ile Gln Thr Met Phe Ser Leu Val Asp Ser Ile Ile Ala Glu Arg
210                 215                 220

Arg Ala Asn Gly Asp Gln Asp Glu Lys Asp Leu Leu Ala Arg Met Leu
225                 230                 235                 240

Asn Val Glu Asp Pro Glu Thr Gly Glu Lys Leu Asp Asp Glu Asn Ile
                245                 250                 255

Arg Phe Gln Ile Ile Thr Phe Leu Ile Ala Gly His Glu Thr Thr Ser
            260                 265                 270

Gly Leu Leu Ser Phe Ala Thr Tyr Phe Leu Leu Lys His Pro Asp Lys
        275                 280                 285

Leu Lys Lys Ala Tyr Glu Glu Val Asp Arg Val Leu Thr Asp Ala Ala
290                 295                 300

Pro Thr Tyr Lys Gln Val Leu Glu Leu Thr Tyr Ile Arg Met Ile Leu
305                 310                 315                 320

Asn Glu Ser Leu Arg Leu Trp Pro Thr Ala Pro Ala Phe Ser Leu Tyr
                325                 330                 335

Pro Lys Glu Asp Thr Val Ile Gly Gly Lys Phe Pro Ile Thr Thr Asn
            340                 345                 350

Asp Arg Ile Ser Val Leu Ile Pro Gln Leu His Arg Asp Arg Asp Ala
        355                 360                 365

Trp Gly Lys Asp Ala Glu Glu Phe Arg Pro Glu Arg Phe Glu His Gln
370                 375                 380

Asp Gln Val Pro His His Ala Tyr Lys Pro Phe Gly Asn Gly Gln Arg
385                 390                 395                 400

Ala Cys Ile Gly Met Gln Phe Ala Leu His Glu Ala Thr Leu Val Leu
                405                 410                 415

Gly Met Ile Leu Lys Tyr Phe Thr Leu Ile Asp His Glu Asn Tyr Glu
            420                 425                 430

Leu Asp Ile Lys Gln Thr Leu Thr Leu Lys Pro Gly Asp Phe His Ile
        435                 440                 445

Ser Val Gln Ser Arg His Gln Glu Ala Ile His Ala Asp Val Gln Ala
450                 455                 460

Ala Glu Lys Ala Ala Pro Asp Glu Gln Lys Glu Lys Thr Glu Ala Lys
465                 470                 475                 480

Gly Ala Ser Val Ile Gly Leu Asn Asn Arg Pro Leu Leu Val Leu Tyr
                485                 490                 495
```

```
Gly Ser Asp Thr Gly Thr Ala Glu Gly Val Ala Arg Glu Leu Ala Asp
            500                 505                 510
Thr Ala Ser Leu His Gly Val Arg Thr Lys Thr Ala Pro Leu Asn Asp
            515                 520                 525
Arg Ile Gly Lys Leu Pro Lys Glu Gly Ala Val Ile Val Thr Ser
530                 535                 540
Ser Tyr Asn Gly Lys Pro Pro Ser Asn Ala Gly Gln Phe Val Gln Trp
545                 550                 555                 560
Leu Gln Glu Ile Lys Pro Gly Glu Leu Glu Gly Val His Tyr Ala Val
            565                 570                 575
Phe Gly Cys Gly Asp His Asn Trp Ala Ser Thr Tyr Gln Tyr Val Pro
            580                 585                 590
Arg Phe Ile Asp Glu Gln Leu Ala Glu Lys Gly Ala Thr Arg Phe Ser
            595                 600                 605
Ala Arg Gly Glu Gly Asp Val Ser Gly Asp Phe Glu Gly Gln Leu Asp
            610                 615                 620
Glu Trp Lys Lys Ser Met Trp Ala Asp Ala Ile Lys Ala Phe Gly Leu
625                 630                 635                 640
Glu Leu Asn Glu Asn Ala Asp Lys Glu Arg Ser Thr Leu Ser Leu Gln
            645                 650                 655
Phe Val Arg Gly Leu Gly Glu Ser Pro Leu Ala Arg Ser Tyr Glu Ala
            660                 665                 670
Ser His Ala Ser Ile Ala Glu Asn Arg Glu Leu Gln Ser Ala Asp Ser
            675                 680                 685
Asp Arg Ser Thr Arg His Ile Glu Ile Ala Leu Pro Pro Asp Val Glu
            690                 695                 700
Tyr Gln Glu Gly Asp His Leu Gly Val Leu Pro Lys Asn Ser Gln Thr
705                 710                 715                 720
Asn Val Ser Arg Ile Leu His Arg Phe Gly Leu Lys Gly Thr Asp Gln
            725                 730                 735
Val Thr Leu Ser Ala Ser Gly Arg Ser Ala Gly His Leu Pro Leu Gly
            740                 745                 750
Arg Pro Val Ser Leu His Asp Leu Leu Ser Tyr Ser Val Glu Val Gln
            755                 760                 765
Glu Ala Ala Thr Arg Ala Gln Ile Arg Glu Leu Ala Ser Phe Thr Val
            770                 775                 780
Cys Pro Pro His Arg Arg Glu Leu Glu Leu Ser Ala Glu Gly Val
785                 790                 795                 800
Tyr Gln Glu Gln Ile Leu Lys Lys Arg Ile Ser Met Leu Asp Leu Leu
            805                 810                 815
Glu Lys Tyr Glu Ala Cys Asp Met Pro Phe Glu Arg Phe Leu Glu Leu
            820                 825                 830
Leu Arg Pro Leu Lys Pro Arg Tyr Tyr Ser Ile Ser Ser Ser Pro Arg
            835                 840                 845
Val Asn Pro Arg Gln Ala Ser Ile Thr Val Gly Val Val Arg Gly Pro
850                 855                 860
Ala Trp Ser Gly Arg Gly Glu Tyr Arg Gly Val Ala Ser Asn Asp Leu
865                 870                 875                 880
Ala Glu Arg Gln Ala Gly Asp Asp Val Val Met Phe Ile Arg Thr Pro
            885                 890                 895
Glu Ser Arg Phe Gln Leu Pro Lys Asp Pro Glu Thr Pro Ile Ile Met
            900                 905                 910
Val Gly Pro Gly Thr Gly Val Ala Pro Phe Arg Gly Phe Leu Gln Ala
```

```
                915                 920                 925
Arg Asp Val Leu Lys Arg Glu Gly Lys Thr Leu Gly Glu Ala His Leu
    930                 935                 940

Tyr Phe Gly Cys Arg Asn Asp Arg Asp Phe Ile Tyr Arg Asp Glu Leu
945                 950                 955                 960

Glu Arg Phe Glu Lys Asp Gly Ile Val Thr Val His Thr Ala Phe Ser
                965                 970                 975

Arg Lys Glu Gly Met Pro Lys Thr Tyr Val Gln His Leu Met Ala Asp
                980                 985                 990

Gln Ala Asp Thr Leu Ile Ser Ile Leu Asp Arg Gly Gly Arg Leu Tyr
                995                 1000                1005

Val Cys Gly Asp Gly Ser Lys Met Ala Pro Asp Val Glu Ala Ala
    1010                1015                1020

Leu Gln Lys Ala Tyr Gln Ala Val His Gly Thr Gly Glu Gln Glu
    1025                1030                1035

Ala Gln Asn Trp Leu Arg His Leu Gln Asp Thr Gly Met Tyr Ala
    1040                1045                1050

Lys Asp Val Trp Ala Gly
    1055

<210> SEQ ID NO 64
<211> LENGTH: 1052
<212> TYPE: PRT
<213> ORGANISM: Artificial Sequence
<220> FEATURE:
<223> OTHER INFORMATION: Cytochrome P450 variant CYP102A3var1

<400> SEQUENCE: 64

Lys Gln Ala Ser Ala Ile Pro Gln Pro Lys Thr Tyr Gly Pro Leu Lys
1               5                   10                  15

Asn Leu Pro His Leu Glu Lys Glu Gln Leu Ser Gln Ser Leu Trp Arg
                20                  25                  30

Ile Ala Asp Glu Leu Gly Pro Ile Phe Arg Phe Asp Phe Pro Gly Val
            35                  40                  45

Ser Ser Val Phe Val Ser Gly His Asn Leu Val Ala Glu Val Cys Asp
        50                  55                  60

Glu Lys Arg Phe Asp Lys Asn Leu Gly Lys Gly Leu Gln Lys Val Arg
65                  70                  75                  80

Glu Phe Gly Gly Asp Gly Leu Ala Thr Ser Trp Thr His Glu Pro Asn
                85                  90                  95

Trp Gln Lys Ala His Arg Ile Leu Leu Pro Ser Phe Ser Gln Lys Ala
                100                 105                 110

Met Lys Gly Tyr His Ser Met Met Leu Asp Ile Ala Thr Gln Leu Ile
            115                 120                 125

Gln Lys Trp Ser Arg Leu Asn Pro Asn Glu Glu Ile Asp Val Ala Asp
        130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Ser Gln His Pro Phe Ile Thr
                165                 170                 175

Ser Met Leu Arg Ala Leu Lys Glu Ala Met Asn Gln Ser Lys Arg Leu
                180                 185                 190

Gly Leu Gln Asp Lys Met Met Val Lys Thr Lys Leu Gln Phe Gln Lys
            195                 200                 205

Asp Ile Glu Val Met Asn Ser Leu Val Asp Arg Met Ile Ala Glu Arg
        210                 215                 220
```

-continued

```
Lys Ala Asn Pro Asp Glu Asn Ile Lys Asp Leu Leu Ser Leu Met Leu
225                 230                 235                 240

Tyr Ala Lys Asp Pro Val Thr Gly Glu Thr Leu Asp Asp Glu Asn Ile
            245                 250                 255

Arg Tyr Gln Ile Ile Thr Phe Leu Ile Ala Gly His Glu Thr Thr Ser
        260                 265                 270

Gly Leu Leu Ser Phe Ala Ile Tyr Cys Leu Leu Thr His Pro Glu Lys
    275                 280                 285

Leu Lys Lys Ala Gln Glu Glu Ala Asp Arg Val Leu Thr Asp Asp Thr
290                 295                 300

Pro Glu Tyr Lys Gln Ile Gln Gln Leu Lys Tyr Ile Arg Met Val Leu
305                 310                 315                 320

Asn Glu Thr Leu Arg Leu Tyr Pro Thr Ala Pro Ala Phe Ser Leu Tyr
                325                 330                 335

Ala Lys Glu Asp Thr Val Leu Gly Gly Glu Tyr Pro Ile Ser Lys Gly
            340                 345                 350

Gln Pro Val Thr Val Leu Ile Pro Lys Leu His Arg Asp Gln Asn Ala
        355                 360                 365

Trp Gly Pro Asp Ala Glu Asp Phe Arg Pro Glu Arg Phe Glu Asp Pro
    370                 375                 380

Ser Ser Ile Pro His His Ala Tyr Lys Pro Phe Gly Asn Gly Gln Arg
385                 390                 395                 400

Ala Cys Ile Gly Met Gln Phe Ala Leu Gln Glu Ala Thr Met Val Leu
                405                 410                 415

Gly Leu Val Leu Lys His Phe Glu Leu Ile Asn His Thr Gly Tyr Glu
            420                 425                 430

Leu Lys Ile Lys Glu Ala Leu Thr Ile Lys Pro Asp Asp Phe Lys Ile
        435                 440                 445

Thr Val Lys Pro Arg Lys Thr Ala Ala Ile Asn Val Gln Arg Lys Glu
    450                 455                 460

Gln Ala Asp Ile Lys Ala Glu Thr Lys Pro Lys Glu Thr Lys Pro Lys
465                 470                 475                 480

His Gly Thr Pro Leu Leu Val Leu Phe Gly Ser Asn Leu Gly Thr Ala
                485                 490                 495

Glu Gly Ile Ala Gly Glu Leu Ala Ala Gln Gly Arg Gln Met Gly Phe
            500                 505                 510

Thr Ala Glu Thr Ala Pro Leu Asp Asp Tyr Ile Gly Lys Leu Pro Glu
        515                 520                 525

Glu Gly Ala Val Val Ile Val Thr Ala Ser Tyr Asn Gly Ala Pro Pro
    530                 535                 540

Asp Asn Ala Ala Gly Phe Val Glu Trp Leu Lys Glu Leu Glu Glu Gly
545                 550                 555                 560

Gln Leu Lys Gly Val Ser Tyr Ala Val Phe Gly Cys Gly Asn Arg Ser
                565                 570                 575

Trp Ala Ser Thr Tyr Gln Arg Ile Pro Arg Leu Ile Asp Asp Met Met
            580                 585                 590

Lys Ala Lys Gly Ala Ser Arg Leu Thr Ala Ile Gly Glu Gly Asp Ala
        595                 600                 605

Ala Asp Asp Phe Glu Ser His Arg Glu Ser Trp Glu Asn Arg Phe Trp
    610                 615                 620

Lys Glu Thr Met Asp Ala Phe Asp Ile Asn Glu Ile Ala Gln Lys Glu
625                 630                 635                 640

Asp Arg Pro Ser Leu Ser Ile Thr Phe Leu Ser Glu Ala Thr Glu Thr
```

```
                645                 650                 655
Pro Val Ala Lys Ala Tyr Gly Ala Phe Glu Gly Ile Val Leu Glu Asn
            660                 665                 670

Arg Glu Leu Gln Thr Ala Ala Ser Thr Arg Ser Thr Arg His Ile Glu
            675                 680                 685

Leu Glu Ile Pro Ala Gly Lys Thr Tyr Lys Glu Gly Asp His Ile Gly
            690                 695                 700

Ile Leu Pro Lys Asn Ser Arg Glu Leu Val Gln Arg Val Leu Ser Arg
705                 710                 715                 720

Phe Gly Leu Gln Ser Asn His Val Ile Lys Val Ser Gly Ser Ala His
                725                 730                 735

Met Ala His Leu Pro Met Asp Arg Pro Ile Lys Val Val Asp Leu Leu
            740                 745                 750

Ser Ser Tyr Val Glu Leu Gln Glu Pro Ala Ser Arg Leu Gln Leu Arg
            755                 760                 765

Glu Leu Ala Ser Tyr Thr Val Cys Pro His Gln Lys Glu Leu Glu
            770                 775                 780

Gln Leu Val Ser Asp Asp Gly Ile Tyr Lys Glu Gln Val Leu Ala Lys
785                 790                 795                 800

Arg Leu Thr Met Leu Asp Phe Leu Glu Asp Tyr Pro Ala Cys Glu Met
                805                 810                 815

Pro Phe Glu Arg Phe Leu Ala Leu Pro Ser Leu Lys Pro Arg Tyr
            820                 825                 830

Tyr Ser Ile Ser Ser Ser Pro Lys Val His Ala Asn Ile Val Ser Met
                835                 840                 845

Thr Val Gly Val Val Lys Ala Ser Ala Trp Ser Gly Arg Gly Glu Tyr
            850                 855                 860

Arg Gly Val Ala Ser Asn Tyr Leu Ala Glu Leu Asn Thr Gly Asp Ala
865                 870                 875                 880

Ala Ala Cys Phe Ile Arg Thr Pro Gln Ser Gly Phe Gln Met Pro Asn
                885                 890                 895

Asp Pro Glu Thr Pro Met Ile Met Val Gly Pro Gly Thr Gly Ile Ala
            900                 905                 910

Pro Phe Arg Gly Phe Ile Gln Ala Arg Ser Val Leu Lys Lys Glu Gly
            915                 920                 925

Ser Thr Leu Gly Glu Ala Leu Leu Tyr Phe Gly Cys Arg Arg Pro Asp
            930                 935                 940

His Asp Asp Leu Tyr Arg Glu Glu Leu Asp Gln Ala Glu Gln Asp Gly
945                 950                 955                 960

Leu Val Thr Ile Arg Arg Cys Tyr Ser Arg Val Glu Asn Glu Pro Lys
                965                 970                 975

Gly Tyr Val Gln His Leu Leu Lys Gln Asp Thr Gln Lys Leu Met Thr
            980                 985                 990

Leu Ile Glu Lys Gly Ala His Ile Tyr Val Cys Gly Asp  Gly Ser Gln
            995                 1000                1005

Met Ala  Pro Asp Val Glu Arg  Thr Leu Arg Leu Ala  Tyr Glu Ala
            1010                1015                 1020

Glu Lys  Ala Ala Ser Gln Glu  Glu Ser Ala Val Trp  Leu Gln Lys
            1025                1030                 1035

Leu Gln  Asp Gln Arg Arg Tyr  Val Lys Asp Val Trp  Thr Gly
            1040                1045                 1050

<210> SEQ ID NO 65
<211> LENGTH: 414
```

<212> TYPE: PRT
<213> ORGANISM: Artificial Sequence
<220> FEATURE:
<223> OTHER INFORMATION: Cytochrome P450 variant CYP101A1var1

<400> SEQUENCE: 65

```
Thr Thr Glu Thr Ile Gln Ser Asn Ala Asn Leu Ala Pro Leu Pro Pro
1               5                   10                  15

His Val Pro Glu His Leu Val Phe Asp Phe Asp Met Tyr Asn Pro Ser
            20                  25                  30

Asn Leu Ser Ala Gly Val Gln Glu Ala Trp Ala Val Leu Gln Glu Ser
        35                  40                  45

Asn Val Pro Asp Leu Val Trp Thr Arg Cys Asn Gly Gly His Trp Ile
    50                  55                  60

Ala Thr Arg Gly Gln Leu Ile Arg Glu Ala Tyr Glu Asp Tyr Arg His
65                  70                  75                  80

Phe Ser Ser Glu Cys Pro Phe Ile Pro Arg Glu Ala Gly Glu Ala Ala
                85                  90                  95

Asp Phe Ile Pro Thr Ser Met Asp Pro Pro Glu Gln Arg Gln Phe Arg
            100                 105                 110

Ala Leu Ala Asn Gln Val Val Gly Met Pro Val Val Asp Lys Leu Glu
        115                 120                 125

Asn Arg Ile Gln Glu Leu Ala Cys Ser Leu Ile Glu Ser Leu Arg Pro
130                 135                 140

Gln Gly Gln Cys Asn Phe Thr Glu Asp Tyr Ala Glu Pro Phe Pro Ile
145                 150                 155                 160

Arg Ile Phe Met Leu Leu Ala Gly Leu Pro Glu Glu Asp Ile Pro His
                165                 170                 175

Leu Lys Tyr Leu Thr Asp Gln Met Thr Arg Pro Asp Gly Ser Met Thr
            180                 185                 190

Phe Ala Glu Ala Lys Glu Ala Leu Tyr Asp Tyr Leu Ile Pro Ile Ile
        195                 200                 205

Glu Gln Arg Arg Gln Lys Pro Gly Thr Asp Ala Ile Ser Ile Val Ala
210                 215                 220

Asn Gly Gln Val Asn Gly Arg Pro Ile Thr Ser Asp Glu Ala Lys Arg
225                 230                 235                 240

Met Cys Gly Leu Leu Leu Val Gly Gly Leu Asp Thr Val Val Asn Phe
                245                 250                 255

Leu Ser Phe Ser Met Glu Phe Leu Ala Lys Ser Pro Glu His Arg Gln
            260                 265                 270

Glu Leu Ile Glu Arg Pro Glu Arg Ile Pro Ala Ala Cys Glu Glu Leu
        275                 280                 285

Leu Arg Arg Phe Ser Leu Val Ala Asp Gly Arg Ile Leu Thr Ser Asp
290                 295                 300

Tyr Glu Phe His Gly Val Gln Leu Lys Lys Gly Asp Gln Ile Leu Leu
305                 310                 315                 320

Pro Gln Met Leu Ser Gly Leu Asp Glu Arg Glu Asn Ala Cys Pro Met
                325                 330                 335

His Val Asp Phe Ser Arg Gln Lys Val Ser His Thr Thr Phe Gly His
            340                 345                 350

Gly Ser His Leu Cys Leu Gly Gln His Leu Ala Arg Arg Glu Ile Ile
        355                 360                 365

Val Thr Leu Lys Glu Trp Leu Thr Arg Ile Pro Asp Phe Ser Ile Ala
370                 375                 380

Pro Gly Ala Gln Ile Gln His Lys Ser Gly Ile Val Ser Gly Val Gln
```

```
                385                 390                 395                 400
Ala Leu Pro Leu Val Trp Asp Pro Ala Thr Thr Lys Ala Val
                    405                 410
```

<210> SEQ ID NO 66
<211> LENGTH: 414
<212> TYPE: PRT
<213> ORGANISM: Artificial Sequence
<220> FEATURE:
<223> OTHER INFORMATION: Cytochrome P450 variant CYP101A1var2

<400> SEQUENCE: 66

```
Thr Thr Glu Thr Ile Gln Ser Asn Ala Asn Leu Ala Pro Leu Pro Pro
1               5                   10                  15

His Val Pro Glu His Leu Val Phe Asp Phe Asp Met Tyr Asn Pro Ser
            20                  25                  30

Asn Leu Ser Ala Gly Val Gln Glu Ala Trp Ala Val Leu Gln Glu Ser
        35                  40                  45

Asn Val Pro Asp Leu Val Trp Thr Arg Cys Asn Gly Gly His Trp Ile
    50                  55                  60

Ala Thr Arg Gly Gln Leu Ile Arg Glu Ala Tyr Glu Asp Tyr Arg His
65                  70                  75                  80

Phe Ser Ser Glu Cys Pro Phe Ile Pro Arg Glu Ala Gly Glu Ala Phe
                85                  90                  95

Asp Phe Ile Pro Thr Ser Met Asp Pro Pro Glu Gln Arg Gln Phe Arg
            100                 105                 110

Ala Leu Ala Asn Gln Val Val Gly Met Pro Val Val Asp Lys Leu Glu
        115                 120                 125

Asn Arg Ile Gln Glu Leu Ala Cys Ser Leu Ile Glu Ser Leu Arg Pro
    130                 135                 140

Gln Gly Gln Cys Asn Phe Thr Glu Asp Tyr Ala Glu Pro Phe Pro Ile
145                 150                 155                 160

Arg Ile Phe Met Leu Leu Ala Gly Leu Pro Glu Glu Asp Ile Pro His
                165                 170                 175

Leu Lys Tyr Leu Thr Asp Gln Met Thr Arg Pro Asp Gly Ser Met Thr
            180                 185                 190

Phe Ala Glu Ala Lys Glu Ala Leu Tyr Asp Tyr Leu Ile Pro Ile Ile
        195                 200                 205

Glu Gln Arg Arg Gln Lys Pro Gly Thr Asp Ala Ile Ser Ile Val Ala
    210                 215                 220

Asn Gly Gln Val Asn Gly Arg Pro Ile Thr Ser Asp Glu Ala Lys Arg
225                 230                 235                 240

Met Cys Gly Leu Leu Leu Val Gly Gly Leu Asp Thr Val Val Asn Phe
                245                 250                 255

Leu Ser Phe Ser Met Glu Phe Leu Ala Lys Ser Pro Glu His Arg Gln
            260                 265                 270

Glu Leu Ile Glu Arg Pro Glu Arg Ile Pro Ala Ala Cys Glu Glu Leu
        275                 280                 285

Leu Arg Arg Phe Ser Leu Val Ala Asp Gly Arg Ile Leu Thr Ser Asp
    290                 295                 300

Tyr Glu Phe His Gly Val Gln Leu Lys Lys Gly Asp Gln Ile Leu Leu
305                 310                 315                 320

Pro Gln Met Leu Ser Gly Leu Asp Glu Arg Glu Asn Ala Cys Pro Met
                325                 330                 335

His Val Asp Phe Ser Arg Gln Lys Val Ser His Thr Thr Phe Gly His
            340                 345                 350
```

```
Gly Ser His Leu Cys Leu Gly Gln His Leu Ala Arg Arg Glu Ile Ile
         355                 360                 365

Val Thr Leu Lys Glu Trp Leu Thr Arg Ile Pro Asp Phe Ser Ile Ala
    370                 375                 380

Pro Gly Ala Gln Ile Gln His Lys Ser Gly Ile Val Ser Gly Val Gln
385                 390                 395                 400

Ala Leu Pro Leu Val Trp Asp Pro Ala Thr Thr Lys Ala Val
                405                 410

<210> SEQ ID NO 67
<211> LENGTH: 414
<212> TYPE: PRT
<213> ORGANISM: Artificial Sequence
<220> FEATURE:
<223> OTHER INFORMATION: Cytochrome P450 variant CYP101A1var2-1

<400> SEQUENCE: 67

Thr Thr Glu Thr Ile Gln Ser Asn Ala Asn Leu Ala Pro Leu Pro Pro
1               5                   10                  15

His Val Pro Glu His Leu Val Phe Asp Phe Asp Met Tyr Asn Pro Ser
            20                  25                  30

Asn Leu Ser Ala Gly Val Gln Glu Ala Trp Ala Val Leu Gln Glu Ser
        35                  40                  45

Asn Val Pro Asp Leu Val Trp Thr Arg Cys Asn Gly Gly His Trp Ile
    50                  55                  60

Ala Thr Arg Gly Gln Leu Ile Arg Glu Ala Tyr Glu Asp Tyr Arg His
65                  70                  75                  80

Phe Ser Ser Glu Cys Pro Trp Ile Pro Arg Glu Ala Gly Glu Ala Phe
                85                  90                  95

Asp Phe Ile Pro Thr Ser Met Asp Pro Pro Glu Gln Arg Gln Phe Arg
            100                 105                 110

Ala Leu Ala Asn Gln Val Val Gly Met Pro Val Val Asp Lys Leu Glu
        115                 120                 125

Asn Arg Ile Gln Glu Leu Ala Cys Ser Leu Ile Glu Ser Leu Arg Pro
    130                 135                 140

Gln Gly Gln Cys Asn Phe Thr Glu Asp Tyr Ala Glu Pro Phe Pro Ile
145                 150                 155                 160

Arg Ile Phe Met Leu Leu Ala Gly Leu Pro Glu Glu Asp Ile Pro His
                165                 170                 175

Leu Lys Tyr Leu Thr Asp Gln Met Thr Arg Pro Asp Gly Ser Met Thr
            180                 185                 190

Phe Ala Glu Ala Lys Glu Ala Leu Tyr Asp Tyr Leu Ile Pro Ile Ile
        195                 200                 205

Glu Gln Arg Arg Gln Lys Pro Gly Thr Asp Ala Ile Ser Ile Val Ala
    210                 215                 220

Asn Gly Gln Val Asn Gly Arg Pro Ile Thr Ser Asp Glu Ala Lys Arg
225                 230                 235                 240

Met Cys Gly Leu Leu Leu Val Gly Gly Leu Asp Thr Val Val Asn Phe
                245                 250                 255

Leu Ser Phe Ser Met Glu Phe Leu Ala Lys Ser Pro Glu His Arg Gln
            260                 265                 270

Glu Leu Ile Glu Arg Pro Glu Arg Ile Pro Ala Ala Cys Glu Glu Leu
        275                 280                 285

Leu Arg Arg Phe Ser Leu Val Ala Asp Gly Arg Ile Leu Thr Ser Asp
    290                 295                 300
```

```
Tyr Glu Phe His Gly Val Gln Leu Lys Lys Gly Asp Gln Ile Leu Leu
305                 310                 315                 320

Pro Gln Met Leu Ser Gly Leu Asp Glu Arg Glu Asn Ala Cys Pro Met
            325                 330                 335

His Val Asp Phe Ser Arg Gln Lys Val Ser His Thr Thr Phe Gly His
        340                 345                 350

Gly Ser His Leu Cys Leu Gly Gln His Leu Ala Arg Arg Glu Ile Ile
    355                 360                 365

Val Thr Leu Lys Glu Trp Leu Thr Arg Ile Pro Asp Phe Ser Ile Ala
370                 375                 380

Pro Gly Ala Gln Ile Gln His Lys Ser Gly Ile Val Ser Gly Val Gln
385                 390                 395                 400

Ala Leu Pro Leu Val Trp Asp Pro Ala Thr Thr Lys Ala Val
                405                 410
```

<210> SEQ ID NO 68
<211> LENGTH: 414
<212> TYPE: PRT
<213> ORGANISM: Artificial Sequence
<220> FEATURE:
<223> OTHER INFORMATION: Cytochrome P450 variant CYP101A1var2-2

<400> SEQUENCE: 68

```
Thr Thr Glu Thr Ile Gln Ser Asn Ala Asn Leu Ala Pro Leu Pro Pro
1               5                   10                  15

His Val Pro Glu His Leu Val Phe Asp Phe Asp Met Tyr Asn Pro Ser
            20                  25                  30

Asn Leu Ser Ala Gly Val Gln Glu Ala Trp Ala Val Leu Gln Glu Ser
        35                  40                  45

Asn Val Pro Asp Leu Val Trp Thr Arg Cys Asn Gly Gly His Trp Ile
50                  55                  60

Ala Thr Arg Gly Gln Leu Ile Arg Glu Ala Tyr Glu Asp Tyr Arg His
65                  70                  75                  80

Phe Ser Ser Glu Cys Pro Phe Ile Pro Arg Glu Ala Gly Glu Ala Phe
                85                  90                  95

Asp Phe Ile Pro Thr Ser Met Asp Pro Pro Glu Gln Arg Gln Phe Arg
            100                 105                 110

Ala Leu Ala Asn Gln Val Val Gly Met Pro Val Val Asp Lys Leu Glu
        115                 120                 125

Asn Arg Ile Gln Glu Leu Ala Cys Ser Leu Ile Glu Ser Leu Arg Pro
130                 135                 140

Gln Gly Gln Cys Asn Phe Thr Glu Asp Tyr Ala Glu Pro Phe Pro Ile
145                 150                 155                 160

Arg Ile Phe Met Leu Leu Ala Gly Leu Pro Glu Glu Asp Ile Pro His
                165                 170                 175

Leu Lys Tyr Leu Thr Asp Gln Met Thr Arg Pro Asp Gly Ser Met Thr
            180                 185                 190

Phe Ala Glu Ala Lys Glu Ala Leu Tyr Asp Tyr Leu Ile Pro Ile Ile
        195                 200                 205

Glu Gln Arg Arg Gln Lys Pro Gly Thr Asp Ala Ile Ser Ile Val Ala
210                 215                 220

Asn Gly Gln Val Asn Gly Arg Pro Ile Thr Ser Asp Glu Ala Lys Arg
225                 230                 235                 240

Met Cys Gly Leu Leu Leu Leu Gly Gly Leu Asp Thr Val Val Asn Phe
                245                 250                 255

Leu Ser Phe Ser Met Glu Phe Leu Ala Lys Ser Pro Glu His Arg Gln
```

```
                   260                 265                 270
Glu Leu Ile Glu Arg Pro Glu Arg Ile Pro Ala Ala Cys Glu Glu Leu
                275                 280                 285

Leu Arg Arg Phe Ser Leu Val Ala Asp Gly Arg Ile Leu Thr Ser Asp
            290                 295                 300

Tyr Glu Phe His Gly Val Gln Leu Lys Lys Gly Asp Gln Ile Leu Leu
305                 310                 315                 320

Pro Gln Met Leu Ser Gly Leu Asp Glu Arg Glu Asn Ala Cys Pro Met
                325                 330                 335

His Val Asp Phe Ser Arg Gln Lys Val Ser His Thr Thr Phe Gly His
            340                 345                 350

Gly Ser His Leu Cys Leu Gly Gln His Leu Ala Arg Arg Glu Ile Ile
                355                 360                 365

Val Thr Leu Lys Glu Trp Leu Thr Arg Ile Pro Asp Phe Ser Ile Ala
            370                 375                 380

Pro Gly Ala Gln Ile Gln His Lys Ser Gly Ile Val Ser Gly Val Gln
385                 390                 395                 400

Ala Leu Pro Leu Val Trp Asp Pro Ala Thr Thr Lys Ala Val
                405                 410

<210> SEQ ID NO 69
<211> LENGTH: 414
<212> TYPE: PRT
<213> ORGANISM: Artificial Sequence
<220> FEATURE:
<223> OTHER INFORMATION: Cytochrome P450 variant CYP101A1var2-3

<400> SEQUENCE: 69

Thr Thr Glu Thr Ile Gln Ser Asn Ala Asn Leu Ala Pro Leu Pro Pro
1               5                   10                  15

His Val Pro Glu His Leu Val Phe Asp Phe Asp Met Tyr Asn Pro Ser
                20                  25                  30

Asn Leu Ser Ala Gly Val Gln Glu Ala Trp Ala Val Leu Gln Glu Ser
            35                  40                  45

Asn Val Pro Asp Leu Val Trp Thr Arg Cys Asn Gly Gly His Trp Ile
50                  55                  60

Ala Thr Arg Gly Gln Leu Ile Arg Glu Ala Tyr Glu Asp Tyr Arg His
65                  70                  75                  80

Phe Ser Ser Glu Cys Pro Trp Ile Pro Arg Glu Ala Gly Glu Ala Phe
                85                  90                  95

Asp Phe Ile Pro Thr Ser Met Asp Pro Pro Glu Gln Arg Gln Phe Arg
            100                 105                 110

Ala Leu Ala Asn Gln Val Val Gly Met Pro Val Val Asp Lys Leu Glu
        115                 120                 125

Asn Arg Ile Gln Glu Leu Ala Cys Ser Leu Ile Glu Ser Leu Arg Pro
    130                 135                 140

Gln Gly Gln Cys Asn Phe Thr Glu Asp Tyr Ala Glu Pro Phe Pro Ile
145                 150                 155                 160

Arg Ile Phe Met Leu Leu Ala Gly Leu Pro Glu Glu Asp Ile Pro His
                165                 170                 175

Leu Lys Tyr Leu Thr Asp Gln Met Thr Arg Pro Asp Gly Ser Met Thr
            180                 185                 190

Phe Ala Glu Ala Lys Glu Ala Leu Tyr Asp Tyr Leu Ile Pro Ile Ile
        195                 200                 205

Glu Gln Arg Arg Gln Lys Pro Gly Thr Asp Ala Ile Ser Ile Val Ala
    210                 215                 220
```

```
Asn Gly Gln Val Asn Gly Arg Pro Ile Thr Ser Asp Glu Ala Lys Arg
225                 230                 235                 240

Met Cys Gly Leu Leu Leu Gly Gly Leu Asp Thr Val Val Asn Phe
                245                 250                 255

Leu Ser Phe Ser Met Glu Phe Leu Ala Lys Ser Pro Glu His Arg Gln
            260                 265                 270

Glu Leu Ile Glu Arg Pro Glu Arg Ile Pro Ala Ala Cys Glu Glu Leu
            275                 280                 285

Leu Arg Arg Phe Ser Leu Val Ala Asp Gly Arg Ile Leu Thr Ser Asp
        290                 295                 300

Tyr Glu Phe His Gly Val Gln Leu Lys Lys Gly Asp Gln Ile Leu Leu
305                 310                 315                 320

Pro Gln Met Leu Ser Gly Leu Asp Glu Arg Glu Asn Ala Cys Pro Met
                325                 330                 335

His Val Asp Phe Ser Arg Gln Lys Val Ser His Thr Thr Phe Gly His
            340                 345                 350

Gly Ser His Leu Cys Leu Gly Gln His Leu Ala Arg Arg Glu Ile Ile
        355                 360                 365

Val Thr Leu Lys Glu Trp Leu Thr Arg Ile Pro Asp Phe Ser Ile Ala
370                 375                 380

Pro Gly Ala Gln Ile Gln His Lys Ser Gly Ile Val Ser Gly Val Gln
385                 390                 395                 400

Ala Leu Pro Leu Val Trp Asp Pro Ala Thr Thr Lys Ala Val
                405                 410

<210> SEQ ID NO 70
<211> LENGTH: 417
<212> TYPE: PRT
<213> ORGANISM: Bacillus Subtilis
<220> FEATURE:
<221> NAME/KEY: MISC_FEATURE
<222> LOCATION: (1)..(417)
<223> OTHER INFORMATION: Cytochrome P450  enzyme CYP152A1

<400> SEQUENCE: 70

Met Asn Glu Gln Ile Pro His Asp Lys Ser Leu Asp Asn Ser Leu Thr
1               5                   10                  15

Leu Leu Lys Glu Gly Tyr Leu Phe Ile Lys Asn Arg Thr Glu Arg Tyr
            20                  25                  30

Asn Ser Asp Leu Phe Gln Ala Arg Leu Leu Gly Lys Asn Phe Ile Cys
        35                  40                  45

Met Thr Gly Ala Glu Ala Ala Lys Val Phe Tyr Asp Thr Asp Arg Phe
    50                  55                  60

Gln Arg Gln Asn Ala Leu Pro Lys Arg Val Gln Lys Ser Leu Phe Gly
65                  70                  75                  80

Val Asn Ala Ile Gln Gly Met Asp Gly Ser Ala His Ile His Arg Lys
                85                  90                  95

Met Leu Phe Leu Ser Leu Met Thr Pro Pro His Gln Lys Arg Leu Ala
            100                 105                 110

Glu Leu Met Thr Glu Glu Trp Lys Ala Ala Val Thr Arg Trp Glu Lys
        115                 120                 125

Ala Asp Glu Val Val Leu Phe Glu Glu Ala Lys Glu Ile Leu Cys Arg
    130                 135                 140

Val Ala Cys Tyr Trp Ala Gly Val Pro Leu Lys Glu Thr Glu Val Lys
145                 150                 155                 160

Glu Arg Ala Asp Asp Phe Ile Asp Met Val Asp Ala Phe Gly Ala Val
```

```
                         165                 170                 175
Gly Pro Arg His Trp Lys Gly Arg Arg Ala Arg Pro Arg Ala Glu Glu
            180                 185                 190

Trp Ile Glu Val Met Ile Glu Asp Ala Arg Ala Gly Leu Leu Lys Thr
        195                 200                 205

Thr Ser Gly Thr Ala Leu His Glu Met Ala Phe His Thr Gln Glu Asp
    210                 215                 220

Gly Ser Gln Leu Asp Ser Arg Met Ala Ala Ile Glu Leu Ile Asn Val
225                 230                 235                 240

Leu Arg Pro Ile Val Ala Ile Ser Tyr Phe Leu Val Phe Ser Ala Leu
            245                 250                 255

Ala Leu His Glu His Pro Lys Tyr Lys Glu Trp Leu Arg Ser Gly Asn
            260                 265                 270

Ser Arg Glu Arg Glu Met Phe Val Gln Glu Val Arg Arg Tyr Tyr Pro
        275                 280                 285

Phe Gly Pro Phe Leu Gly Ala Leu Val Lys Lys Asp Phe Val Trp Asn
        290                 295                 300

Asn Cys Glu Phe Lys Lys Gly Thr Ser Val Leu Leu Asp Leu Tyr Gly
305                 310                 315                 320

Thr Asn His Asp Pro Arg Leu Trp Asp His Pro Asp Glu Phe Arg Pro
                325                 330                 335

Glu Arg Phe Ala Glu Arg Glu Glu Asn Leu Phe Asp Met Ile Pro Gln
            340                 345                 350

Gly Gly Gly His Ala Glu Lys Gly His Arg Cys Pro Gly Glu Gly Ile
            355                 360                 365

Thr Ile Glu Val Met Lys Ala Ser Leu Asp Phe Leu Val His Gln Ile
    370                 375                 380

Glu Tyr Asp Val Pro Glu Gln Ser Leu His Tyr Ser Leu Ala Arg Met
385                 390                 395                 400

Pro Ser Leu Pro Glu Ser Gly Phe Val Met Ser Gly Ile Arg Arg Lys
            405                 410                 415

Ser
```